United States Patent
Chen et al.

(10) Patent No.: US 11,033,635 B2
(45) Date of Patent: Jun. 15, 2021

(54) ANTIBODY-STING AGONIST CONJUGATES AND THEIR USE IN IMMUNOTHERAPY

(71) Applicants: ImmuneSensor Therapeutics, Inc., Dallas, TX (US); The Board of Regents of the University of Texas System, Austin, TX (US)

(72) Inventors: Zhijian Chen, Dallas, TX (US); Heping Shi, Dallas, TX (US); Qi Wei, Dallas, TX (US); Chuo Chen, Dallas, TX (US); Lijun Sun, Dallas, TX (US); Jian Qiu, Dallas, TX (US); Youtong Wu, Dallas, TX (US)

(73) Assignees: ImmuneSensor Therapeutics, Inc., Dallas, TX (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 16/933,845

(22) Filed: Jul. 20, 2020

(65) Prior Publication Data

US 2021/0015941 A1 Jan. 21, 2021

Related U.S. Application Data

(60) Provisional application No. 63/019,212, filed on May 1, 2020, provisional application No. 62/876,590, filed on Jul. 19, 2019.

(51) Int. Cl.
*A61K 47/68* (2017.01)
*A61P 35/00* (2006.01)

(52) U.S. Cl.
CPC ...... *A61K 47/6807* (2017.08); *A61K 47/6849* (2017.08); *A61K 47/6851* (2017.08); *A61P 35/00* (2018.01)

(58) Field of Classification Search
CPC ............... A61K 47/68; A61K 47/6801; A61K 47/6803; A61K 47/6807; A61K 47/6849; A61K 47/6851
See application file for complete search history.

(56) References Cited

U.S. PATENT DOCUMENTS

| | | |
|---|---|---|
| 10,106,574 B2 | 10/2018 | Altman et al. |
| 10,519,188 B2 | 12/2019 | Zhong et al. |
| 10,738,074 B2 | 8/2020 | Altman et al. |
| 10,759,825 B2 | 9/2020 | Altman et al. |
| 10,766,919 B2 | 9/2020 | Altman et al. |
| 2017/0044206 A1 | 2/2017 | Altman et al. |
| 2017/0158772 A1 | 6/2017 | Thompson et al. |
| 2017/0298139 A1 | 10/2017 | Thompson et al. |
| 2018/0230177 A1 | 8/2018 | Zhong et al. |
| 2018/0230178 A1 | 8/2018 | Altman et al. |
| 2018/0237469 A1 | 8/2018 | Altman et al. |
| 2018/0244712 A1 | 8/2018 | Altman et al. |
| 2019/0328762 A1 | 10/2019 | Cemerski et al. |
| 2020/0010501 A1 | 1/2020 | Zhong et al. |
| 2020/0062798 A1 | 2/2020 | Wu et al. |
| 2020/0113924 A1 | 4/2020 | Cemerski et al. |

FOREIGN PATENT DOCUMENTS

| | | | |
|---|---|---|---|
| WO | 17/027645 A1 | 2/2017 | |
| WO | 17/027646 A1 | 2/2017 | |
| WO | 17/100305 A2 | 6/2017 | |
| WO | 17/161349 A1 | 9/2017 | |
| WO | 18/045058 A1 | 3/2018 | |
| WO | 18/118664 A1 | 6/2018 | |
| WO | 18/118665 A1 | 6/2018 | |
| WO | WO-2018100558 A2 * | 6/2018 | ............. A61P 35/00 |
| WO | 18/140831 A2 | 8/2018 | |
| WO | 18/200812 A1 | 11/2018 | |
| WO | 18/208667 A1 | 11/2018 | |
| WO | 2019/129880 A1 | 7/2019 | |

OTHER PUBLICATIONS

Casi and Neri, Journal of Controlled Release, 2012, vol. 161, pp. 422-428 (Year: 2012).*
Kellog et al (Bioconjugate Chemistry, 2011, vol. 22, pp. 717-727 (Year: 2011).*
Anami et al., "Glutamic acid—valine—citrulline linkers ensure stability and efficacy of antibody—drug conjugates in mice," Nature Communications (2018) 9(1):2512.
Cetinbas et al., "Tumor Targeting of a Sting Agonist with an Antibody-Drug Conjugate Elicits Potent Anti-Tumor Immune Responses," ™P695 Poster, 2019.
Dorywalska et al., "Molecular Basis of Valine-Citrulline-PABC Linker Instability in Site-Specific ADCs and Its Mitigation by Linker Design," Mol Cancer Ther (2016),15(5), 958-970.
Kern et al.,"Novel Phosphate Modified Cathepsin B Linkers: Improving Aqueous Solubility and Enhancing Payload Scope of ADCs," Bioconjugate Chem. (2016) 27, 2081-2088.
Tsuchikama et al., "Antibody-drug conjugates: recent advances in conjugation and linker chemistries," Protein Cell (2018) 9(1), 33-46.
Wei et al., "Discovery of Peptidomimetic Antibody-Drug Conjugate Linkers with Enhanced Protease Specificity," J. Med. Chem. (2018) 61, 989-1000.
International Search Report corresponding to International Application No. PCT/US2020/042815 dated Oct. 15, 2020.
International Written Opinion corresponding to International Application No. PCT/US2020/042815 dated Oct. 15, 2020.

* cited by examiner

*Primary Examiner* — Karen A. Canella
(74) *Attorney, Agent, or Firm* — Carl A. Morales; Seth E. Snyder; Dechert LLP

(57) ABSTRACT

The present disclosure relates to, among other things, antibody-drug conjugates comprising a STING agonist cyclic di-nucleotide conjugated to an antibody, preparation methods therefor, and uses therefor.

28 Claims, 22 Drawing Sheets

Figure 1A:
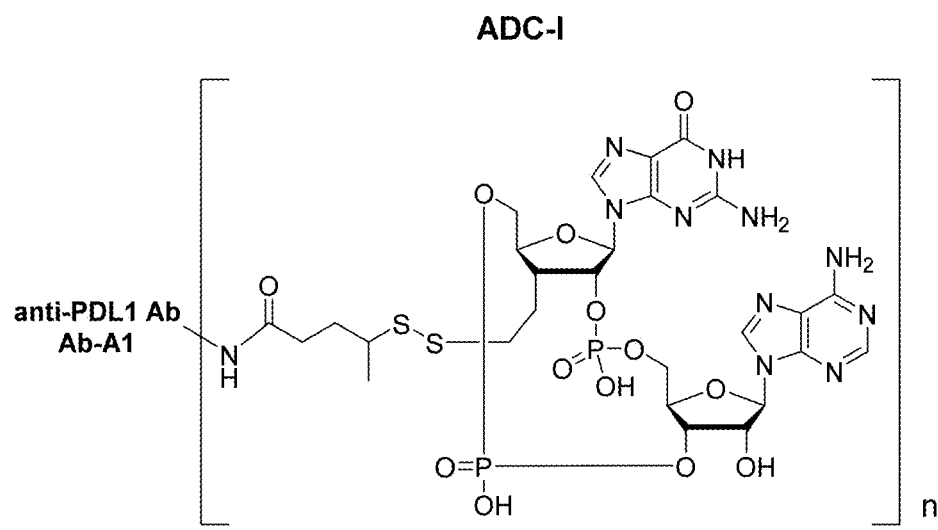

Specification includes a Sequence Listing.

ANTIBODY-STING AGONIST CONJUGATES AND THEIR USE IN IMMUNOTHERAPY

CROSS REFERENCE TO RELATED APPLICATIONS

This application claims benefit under 35 U.S.C. § 119(e) to U.S. Provisional Application No. 63/019,212, filed May 1, 2020, and U.S. Provisional Application No. 62/876,590, filed Jul. 19, 2019. The entire text of each of the above priority documents is specifically incorporated herein by reference.

1. SEQUENCE LISTING

The instant application contains a Sequence Listing which has been submitted electronically in ASCII format and is hereby incorporated by reference in its entirety. Said ASCII copy, created on Jul. 17, 2020, is named 400160_005US_SL_ST25.txt and is 44,502 bytes in size.

FIELD

This disclosure pertains to, among other things, the use of STING agonists in antibody-drug conjugates (ADCs) for immunotherapy; compositions including the ADCs, methods of making the ADCs, and methods of using the ADCs to treat cancers.

BACKGROUND

Cytosolic DNA sensing pathway plays pivotal roles in initiation and maintenance of immune responses against malignancies, in addition to its primary function in host defense against invasion of DNA-containing microbes. Cytosolic DNA from damaged tumor cells triggers activation of an enzyme named cyclic AMP-GMP synthase (cGAS), which synthesizes 2'3'-cyclic AMP-GMP (cGAMP). As an endogenous ligand, cGAMP binds to and activates the ER adaptor protein Stimulator of Interferon Genes (STING), and leads to induction of interferons and inflammatory cytokines, recruitment and maturation of antigen presenting cells, and ultimately anti-tumor immunity carried out by T cells and natural killer (NK) cells. A number of STING agonists, which resemble cGAMP but possess improved therapeutic properties, are under development for cancer immunotherapy. Although these drugs are promising for treatment of a range of solid tumors, they have obvious limitations. These compounds rely on intratumoral administration, due to their potential to induce systemic cytokine response if injected otherwise. Even intratumoral injection could still induce unwanted cytokine response because the rapid leakage to peripheral tissues. The short exposure of these compounds to immune cells in tumor environment also reduces their effect. Therefore, novel therapeutics that can specifically deliver a STING agonist to the tumor environment with prolonged retention time are in urgent need.

4. SUMMARY

The disclosure provides particular cyclic di-nucleotides (CDNs) that can be conjugated to antibodies or antigen-binding fragments targeting specific antigens in the microenvironment of diseased cells or tissue. For instance, the antibodies or antigen-binding fragments thereof can target cancer-related antigens present on cells in the tumor microenvironment, such as tumor cells or immune cells. The CDNs of the disclosure are capable of agonizing STING, hence stimulating the immune system. When the CDNs of the disclosure are conjugated to antibodies targeting antigens in diseased cells or tissue, they provide sufficient exposure of the CDNs in the microenvironment of diseased cells or tissue while reducing concomitant side effects associated with extensive CDN leakage into peripheral tissues.

In one aspect, the disclosure provides antibody-drug conjugates (ADCs) having the structure of Formula I:

Ab-[-L-(D)$_m$]$_n$    (Formula I)

wherein:

"D" represents a CDN (e.g., a CDN as described herein, such as those of Formula II);

"Ab" represents an antibody or binding fragment thereof which binds a target antigen;

"L" represents, independently for each occurrence, a linker linking one or more occurrences of D to Ab;

"m" represents the number of occurrences of D linked to a given linker; and

"n" represents the number of linkers linked to Ab.

In certain embodiments, the disclosure provides ADCs having the structure of Formula Ia:

Ab-[-L-D]$_n$    (Formula Ia)

wherein:

"D" represents a CDN (e.g., a CDN as described herein, such as those of Formula II);

"Ab" represents an antibody or binding fragment thereof which binds a target antigen;

"L" represents, independently for each occurrence, a linker linking D to Ab; and "n" represents the number of occurrences of D linked to Ab via the linker (L).

In another aspect, the disclosure provides specific CDNs (D) that can be administered by themselves or as part of the ADC of Formula I. These CDNs can have the structure of Formula II:

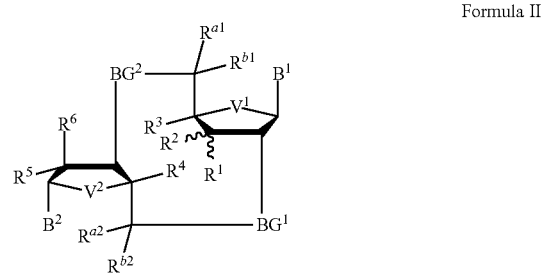

Formula II wherein $R^1$ is $C_{1-6}$alkyl, such as $C_{2-6}$alkyl or $C_{2-3}$alkyl, substituted with a hydroxyl, thiol, amino, $C_{1-6}$alkylamino, or a -PEG-OH group;

$R^3$ and $R^4$ are independently hydrogen, halogen, $C_{1-6}$alkyl, $C_{2-6}$alkenyl, or $C_{2-6}$alkynyl, wherein $C_{1-6}$alkyl, $C_{2-6}$alkenyl, and $C_{2-6}$alkynyl are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido;

$R^2$, $R^5$, and $R^6$ are independently hydrogen, halogen, hydroxyl, azido, amino, $C_{1-6}$alkylamino, di($C_{1-6}$alkyl)

amino, $C_{1-6}$alkyl, $C_{1-6}$alkoxy, $C_{2-6}$alkenyl, $C_{3-6}$alkenyl-O—, $C_{2-6}$alkynyl, or $C_{3-6}$alkynyl-O—, wherein $C_{1-6}$alkyl, $C_{1-6}$alkoxy, $C_{2-6}$alkenyl, $C_{3-6}$alkenyl-O—, $C_{2-6}$alkynyl, and $C_{3-6}$alkynyl-O—, are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or $R^6$ and $R^5$ together are =$CH_2$; or $R^6$ and $R^4$ together form a bridge across the ring containing $V^2$ selected from ethylene, —O—$CH_2$—, and —NH—$CH_2$—;

$V^1$ and $V^2$ are independently O, S, or $CH_2$;

$BG^1$, starting from the carbon in the ring containing $V^1$, and $BG^2$, starting from the carbon in the ring containing $V^2$, are independently —O—P(O)$R^p$—O—, —O—P(S)$R^p$—O—, —O—P(O)$R^p$—S—, —O—P(S)$R^p$—S—, —S—P(O)$R^p$—O—, —S—P(S)$R^p$—O—, —S—P(O)$R^p$—S—, —S—P(S)$R^p$—S—, or —NH—$SO_2$—NH—; wherein $R^p$ is, independently for each occurrence, hydroxyl, thiol, $C_{1-6}$alkyl, $C_{1-6}$alkoxy, $C_{3-6}$alkenyl-O—, $C_{3-6}$alkynyl-O—, -PEG-OH, borano (—$BH_3^-$), or —NR'R", wherein $C_{1-6}$alkyl, $C_{1-6}$alkoxy, $C_{3-6}$alkenyl-O—, and $C_{3-6}$alkynyl-O—, are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; and R' and R" are independently hydrogen or $C_{1-6}$alkyl optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or R' and R" together on the same nitrogen form a $C_{3-5}$heterocyclic ring;

$R^{a1}$, $R^{b1}$, $R^{a2}$, and $R^{b2}$ are independently hydrogen or $C_{1-3}$alkyl; and $B^1$ and $B^2$ are independently selected from:

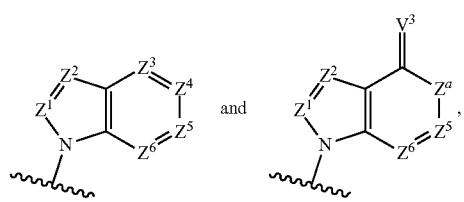

wherein $V^3$ is O or S, particularly O;

$Z^1$, $Z^2$, $Z^3$, $Z^4$, $Z^5$, and $Z^6$ are, independently for each occurrence, $CR^z$ or N;

$Z^a$ is O (except when $Z^5$ is N) or NR'; wherein $R^z$ is, independently for each occurrence, hydrogen, halogen, azido, amino, $C_{1-6}$alkylamino, di($C_{1-6}$alkyl)amino, $C_{1-6}$alkyl, $C_{1-6}$alkoxy, $C_{2-6}$alkenyl, $C_{3-6}$alkenyl-O—, $C_{2-6}$alkynyl, $C_{3-6}$alkynyl-O—, —$NO_2$, —CN, —C(O)$C_{1-6}$alkyl, —$CO_2$H, —$CO_2C_{1-6}$alkyl, —S(O)$C_{1-6}$alkyl, —S(O)$_2C_{1-6}$alkyl, —C(O)NR', —C(O)NR'R", —$SO_2$NR'R", —OC(O)$C_{1-6}$alkyl, —NR'C(O)$C_{1-6}$alkyl, —N(R')C(O)NR'R", —N(R')$SO_2$NR'R", —N(R)$SO_2C_{1-6}$alkyl, or —OC(O)NR'R", wherein $C_{1-6}$alkyl, $C_{1-6}$alkoxy, $C_{2-6}$alkenyl, $C_{3-6}$alkenyl-O—, $C_{2-6}$alkynyl, and $C_{3-6}$alkynyl-O—, are, independently for each occurrence, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; and R' and R" are, independently for each occurrence, hydrogen or $C_{1-6}$alkyl optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or R' and R" on the same nitrogen together form a $C_{3-5}$heterocyclic ring;

or a pharmaceutically acceptable salt thereof.

The disclosure provides methods of making ADCs of formula I by conjugating a CDN of Formula II to an antibody via a linker. The CDN of Formula II can be conjugated to the antibody via a cleavable or non-cleavable linker. In particular embodiments, the CDN is released into a tumor cell, a cancer-related immune cell, or into the tumor microenvironment upon cleavage of the linker.

In the ADCs of Formula I, wherein the CDN (D) is of Formula II, the CDN may be covalently bound to linker (L) at the hydroxyl, thiol, amino, $C_{1-6}$alkylamino, or -PEG-OH group at the $R^1$ position of the CDN of Formula II.

In one embodiment of the disclosure, the CDN of Formula II has the Formula IIe:

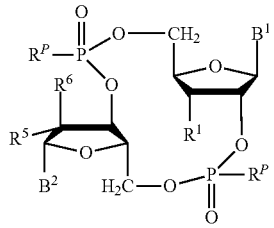

Formula IIe wherein $R^1$, $R^5$, and $R^6$; $R^P$; and $B^1$ and $B^2$ are as defined above for Formula II;

or a pharmaceutically acceptable salt thereof.

In one embodiment of the disclosure, the CDN of Formula II has the Formula IIk:

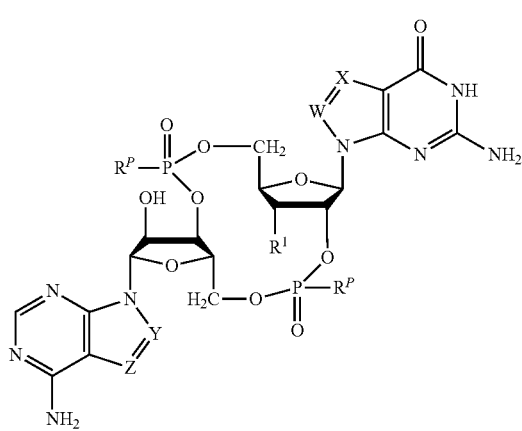

Formula IIk wherein
W, X, Y, and Z are independently CH or N; and
$R^P$, independently for each occurrence, is as defined above for Formula II;
or a pharmaceutically acceptable salt thereof.

In some embodiments, the disclosure provides a composition comprising a CDN and a base, wherein the CDN is a compound of Formula II, such as Formula IIe or IIk above, or Formula IIn or IIo below. In certain of such embodiments, the composition consists of the CDN and the base. In some embodiments, the base is an amine base, such as pyridine. In some of these embodiments, the composition is anhydrous.

In certain embodiments, the disclosure provides a composition comprising a CDN and a linker or a coupling agent, or both a linker and a coupling agent, wherein the CDN is a compound of Formula II, such as Formula IIe or IIk above or Formula IIn or IIo below, and wherein the coupling agent facilitates coupling of the CDN to the linker, for example, by generating an activated ester on the linker. In some embodiments, the composition further comprises an aprotic polar solvent. In certain embodiments, the composition is anhydrous.

In some embodiments, the disclosure provides a compound that is a cyclic dinucleotide (CDN) coupled to a linker (L) of the formula L-CDN. In certain embodiments, the CDN is coupled to a linker L via a thioether, an amide, an ester, a carbamate, a carbonate, a urea, a disulfide, or an ether group, particularly an amide, a carbamate, or a disulfide group. In certain embodiments, the CDN is of Formula II, such as Formula IIe or IIk above, or Formula IIm, IIn or IIo below, and the CDN is coupled to L at the thiol, amino, or $C_{1-6}$alkylamino group of $R^1$ of Formula II, and L includes a site capable of coupling to a complementary site on an antibody.

In one embodiment, the ADC of Formula I has the structure of Formula III:

wherein variables W, X, Y, Z, $R^P$, and n are defined as above for Formulas I and II.

In one embodiment, the ADC of Formula I has the structure of Formula IV:

Formula IV

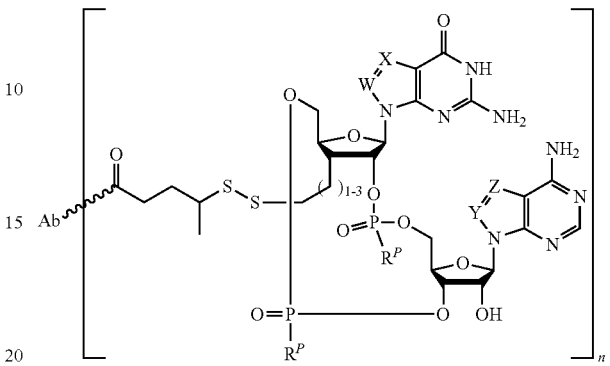

wherein variables W, X, Y, Z, $R^P$, and n are defined as above Formulas I and II.

In one embodiment, the ADC of Formula I or III is derived from a CDN (D) having the following structure (CDN-A):

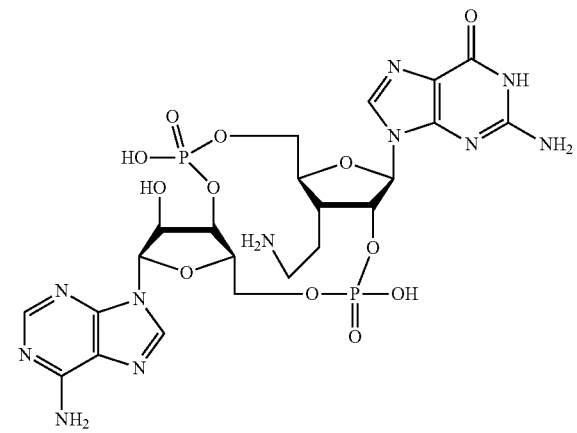

Formula III

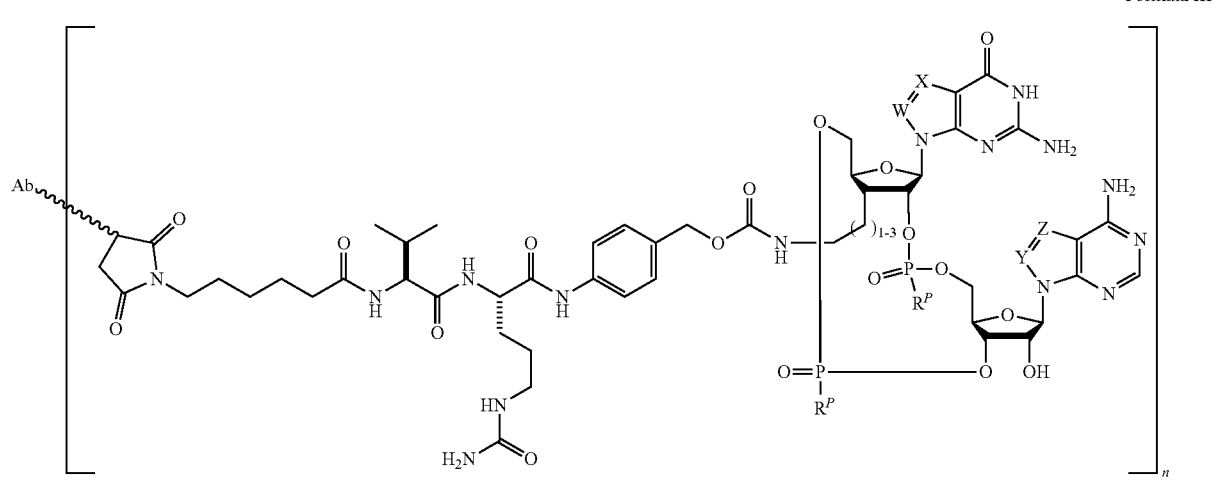

or a pharmaceutically acceptable salt thereof. It will be understood that the phrase "derived from" indicates that the amino (—NH$_2$) functionality at the R$^1$ position of the CDN is covalently bound to a corresponding position in the linker. For instance, in some embodiments, the amino group is covalently bonded to a carbonyl moiety of the linker, hence forming an amide or carbamate bond.

In another embodiment, the ADC of Formula I or IV is derived from a CDN (D) having the following structure (CDN-B):

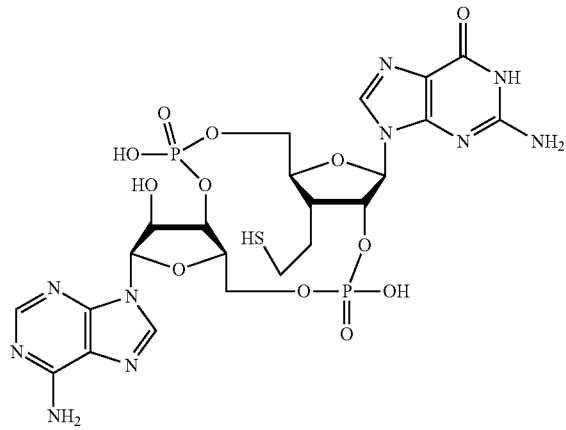

or a pharmaceutically acceptable salt thereof. It will be understood that the phrase "derived from" indicates that the thiol (—SH) functionality at the R$^1$ position of the CDN is covalently bound to a corresponding position in the linker. For instance, in some embodiments, the thiol group of the CDN is covalently bonded to a thiol group of the linker, hence forming a disulfide bond.

In another embodiment, the ADC of Formula I or III is derived from a CDN (D) having the following structure:

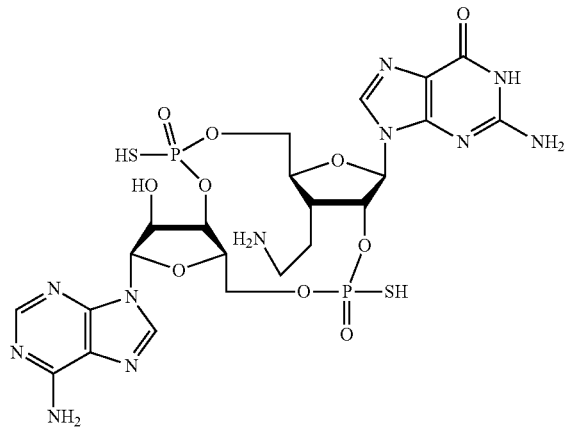

or a pharmaceutically acceptable salt thereof.

In another embodiment, the ADC of Formula I or III is derived from a CDN (D) having the following structure:

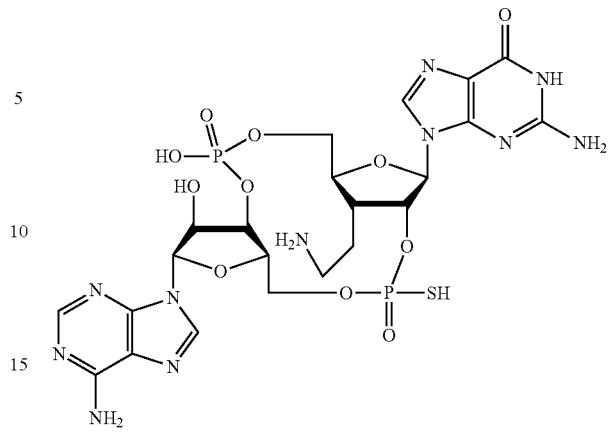

or a pharmaceutically acceptable salt thereof.

In another embodiment, the ADC of Formula I or III is derived from a CDN (D) having the following structure:

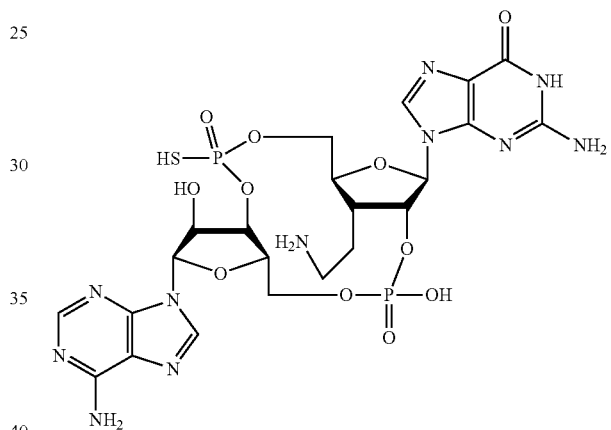

or a pharmaceutically acceptable salt thereof.

In certain embodiments, the antibody or antigen-binding fragment of the ADC of Formula I, III, or IV targets a specific antigen that is expressed on tumor cells or immune cells in the tumor microenvironment. In particular embodiments, the antibody or antigen-binding fragment of the ADC of Formula I, III, or IV targets the receptor PD-L1. In other particular embodiments, the antibody or antigen-binding fragment thereof specifically binds to a cancer related tumor antigen which is a Growth Factor Receptor (GFR). In certain embodiments, the cancer related tumor antigen is an EGFR/ErbB/HER family GFR.

In one aspect, the disclosure provides methods of inducing an immune response in a subject (e.g., a human patient) by administering a therapeutically effective amount of an ADC of Formula I, III, or IV. For instance, an ADC of Formula I, III, or IV can be employed for inducing interferon-β (IFNβ) in a human subject.

The ADC of Formula I, III, or IV can be used in combination with one or more additional therapeutic agents. The additional therapeutic agent(s) can be administered prior to, concurrently or following administration of the additional therapeutic agent(s). In a particular embodiment, the ADC of Formula I, III, or IV can be used in combination with an immune checkpoint inhibitor. For instance, the ADC of Formula I, III, or IV can be administered with an inhibitor of PD-1, PD-L1, or CTLA-4, or a combination thereof.

In another embodiment, the ADC of Formula I, III, or IV can be administered with a free CDN that is not conjugated to the antibody or antigen-binding fragment of Formula I. In such cases, the free CDN may be the same or different than the CDN that is conjugated to the antibody of the ADC of Formula I, III, or IV.

5. BRIEF DESCRIPTION OF THE FIGURES

Figure 1B:
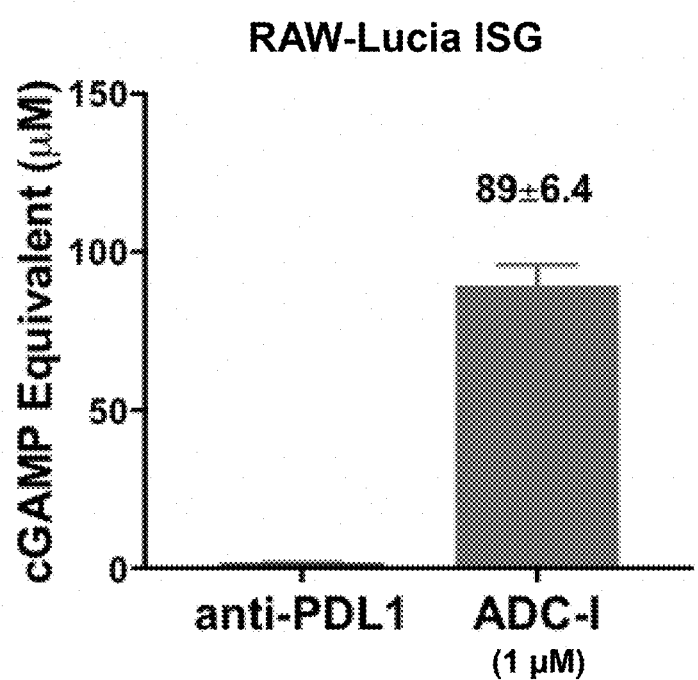
Figure 1C:
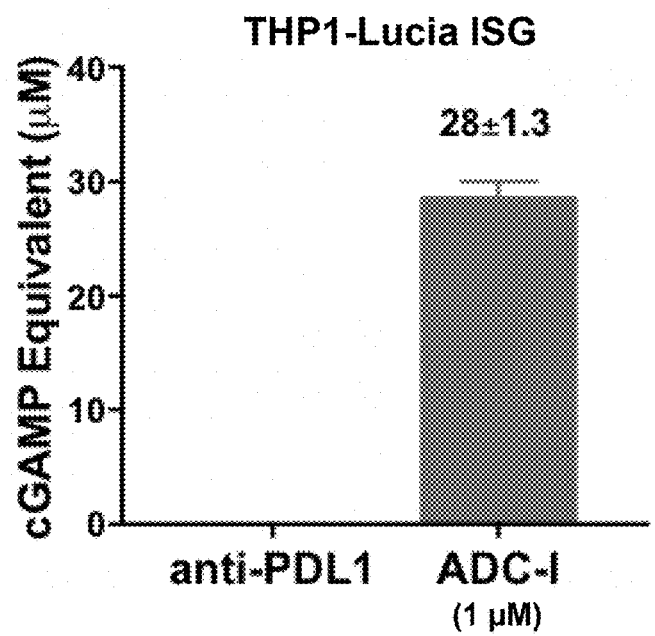
Figure 1D:
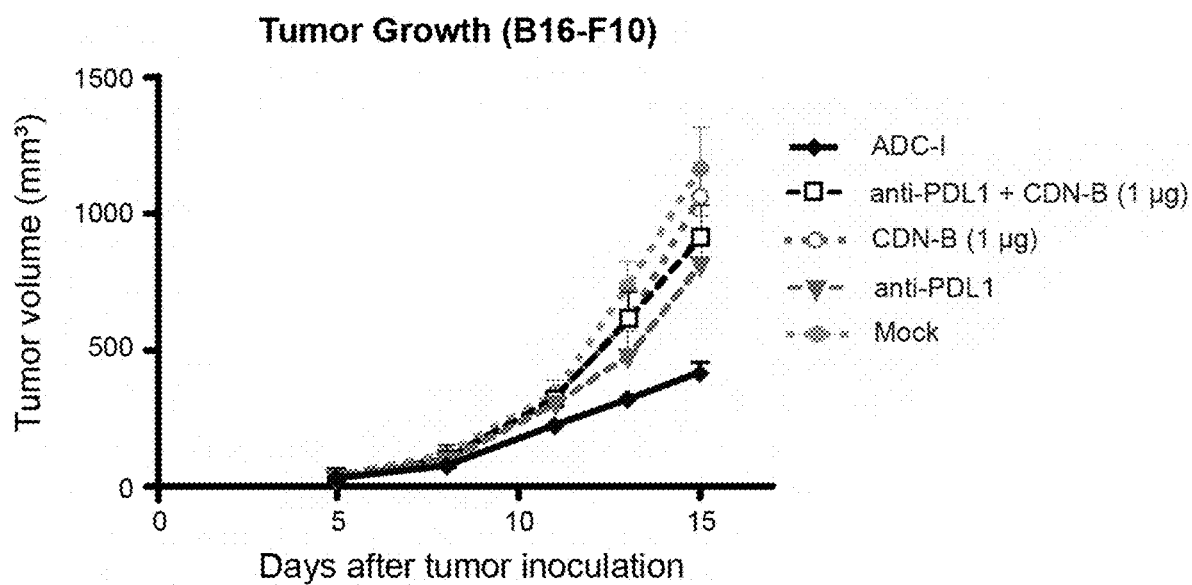

FIGS. 1A-1D show the structural characterization and activity of ADC-I. FIG. 1A shows the chemical structure of ADC-I. FIGS. 1B and 1C show the potency of IFN stimulatory activity in a luciferase reporter assay using mouse RAW-Lucia ISG cells, and human THP1-Lucia ISG cells, respectively. FIG. 1D shows tumor progression in B16-F10 tumor-bearing C57BL6 mice under indicated treatments. The comparator anti-PDL1 antibody is Ab-A1.

Figure 2A:
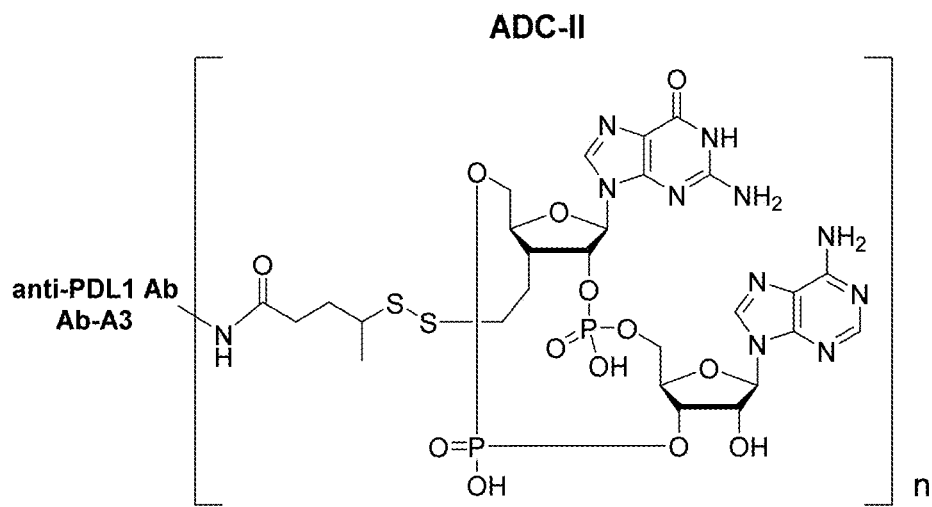
Figure 2B:
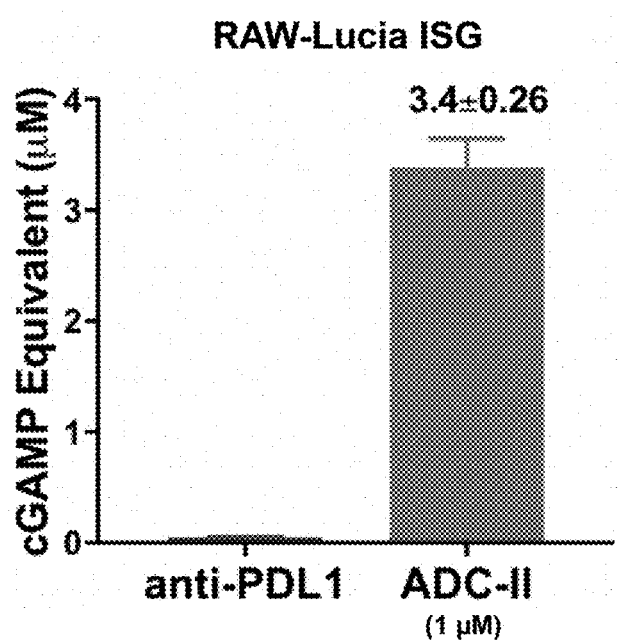
Figure 2C:
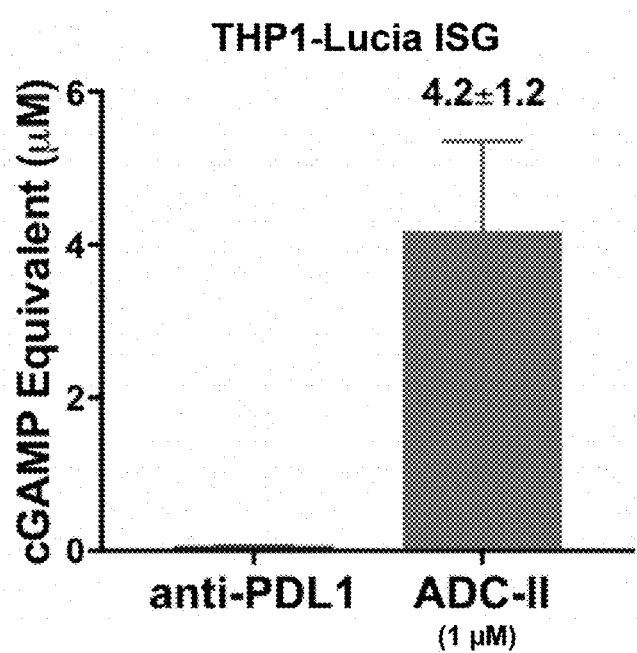

FIGS. 2A-2C show the structural characterization and activity of ADC-II. FIG. 2A shows the chemical structure of ADC-II. FIGS. 2B and 2C show the potency of IFN stimulatory activity in a luciferase reporter assay using mouse RAW-Lucia ISG cells, and human THP1-Lucia ISG cells, respectively.

Figure 3A:
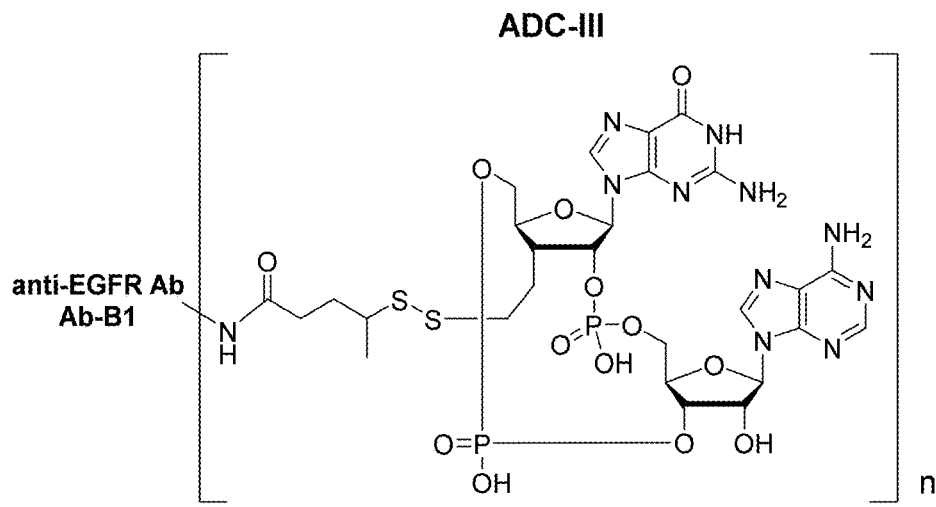
Figure 3B:
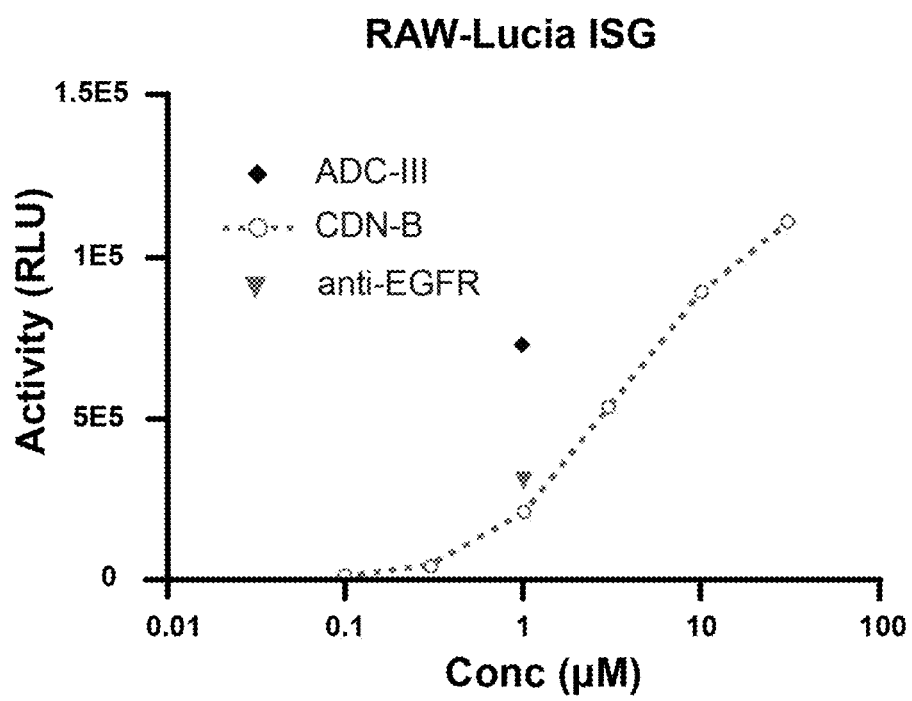

FIGS. 3A-3B show the structural characterization and activity of ADC-III. FIG. 3A shows the chemical structure of ADC-III. FIG. 3B shows the potency of IFN stimulatory activity in a luciferase reporter assay using mouse RAW-Lucia ISG cells. The comparator anti-EGFR antibody is Ab-B1.

Figure 4A:
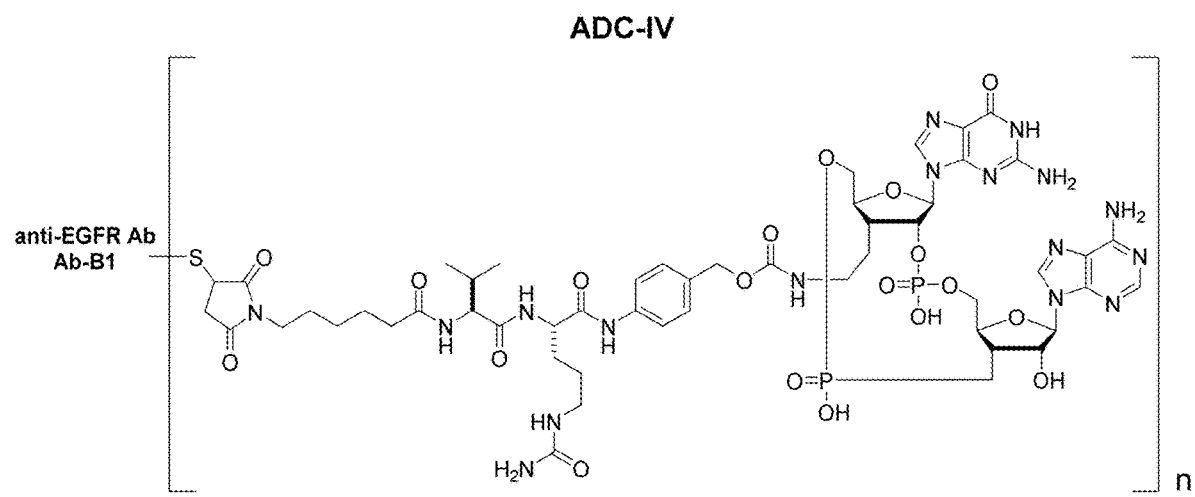
Figure 4B:
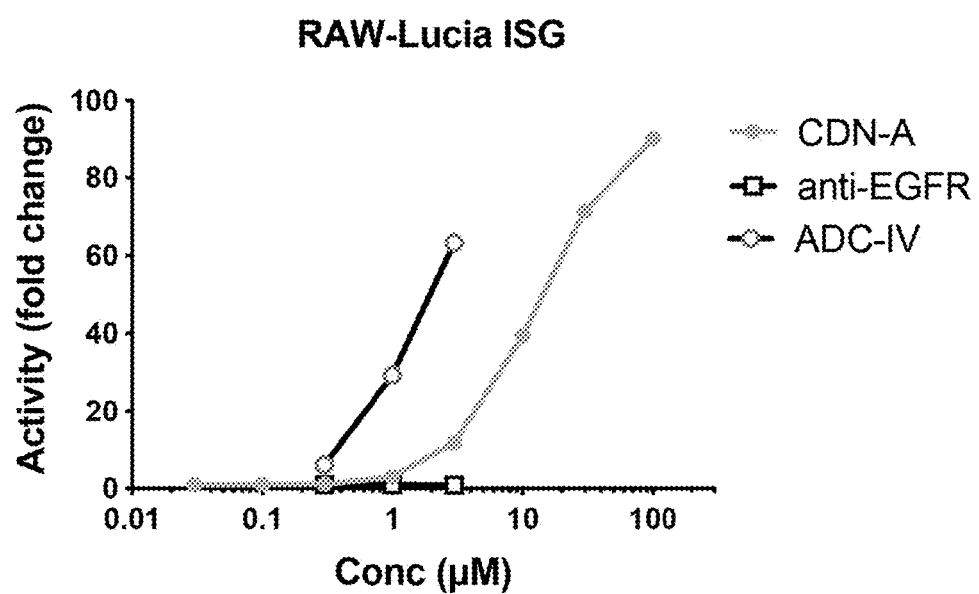
Figure 4C:
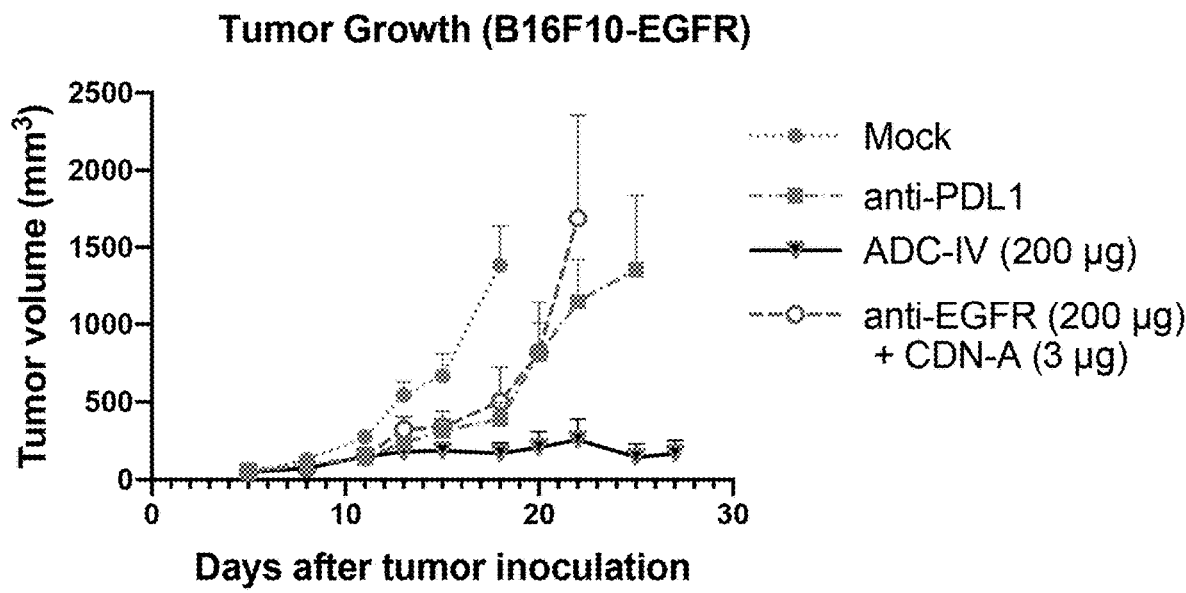
Figure 4D:
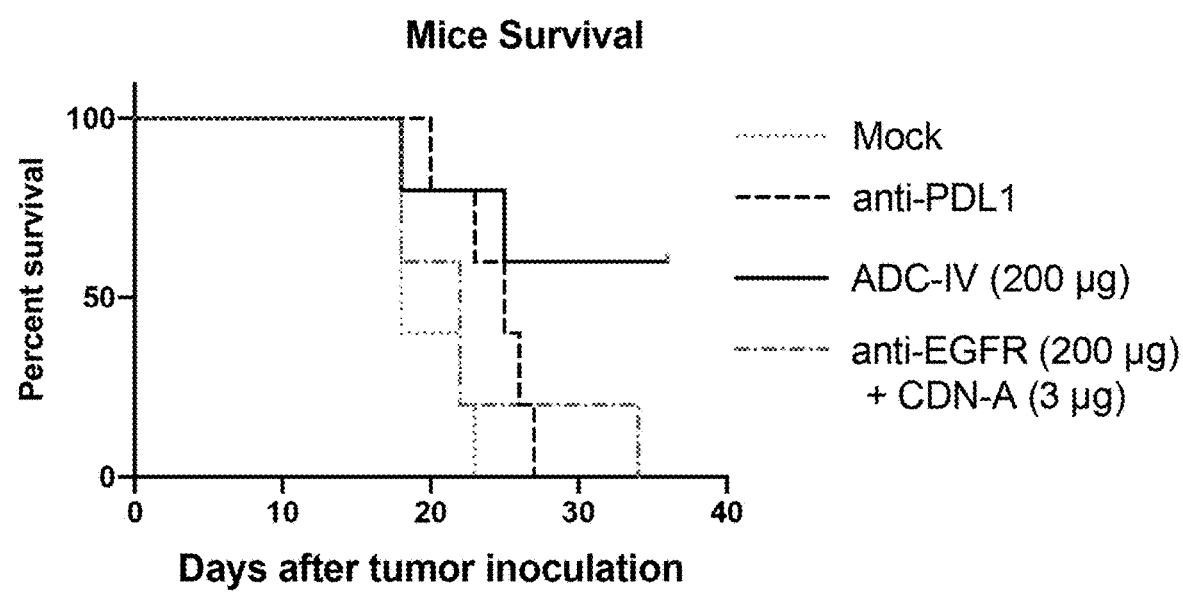
Figure 4E:
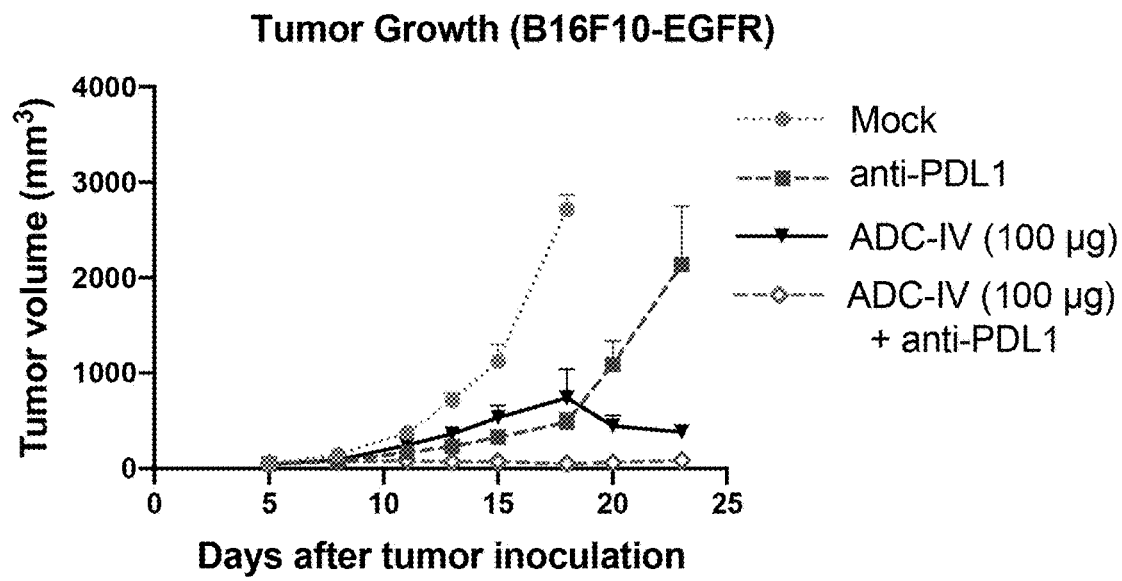
Figure 4F:
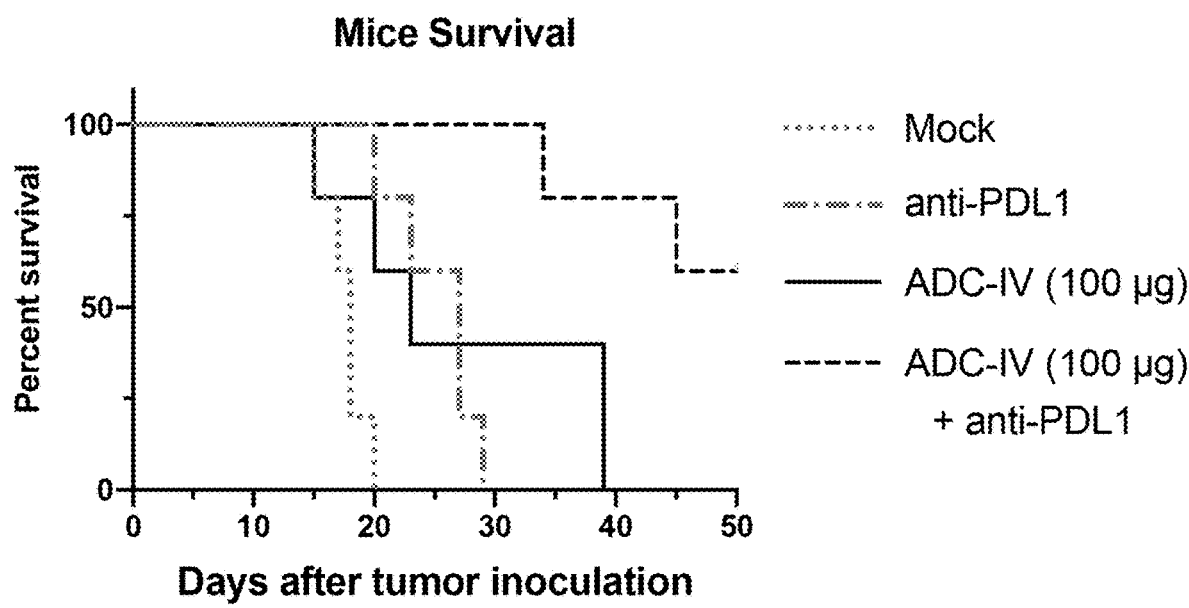

FIGS. 4A-4F show the structural characterization and activity of ADC-IV. FIG. 4A shows the chemical structure of ADC-IV. FIG. 4B shows the potency of IFN stimulatory activity in a luciferase reporter assay using mouse RAW-Lucia ISG cells (fold change versus PBS-stimulated cells). FIGS. 4C and 4D show tumor progression and survival, respectively, in EGFR-expressing B16F10 tumor bearing C57BL6 mice under indicated treatments. FIGS. 4E and 4F show tumor progression and survival, respectively, in EGFR-expressing B16F10 tumor bearing C57BL6 mice under indicated treatments. The comparator anti-EGFR antibody is Ab-B1, and the comparator anti-PDL1 antibody is Ab-A3.

Figure 5A:
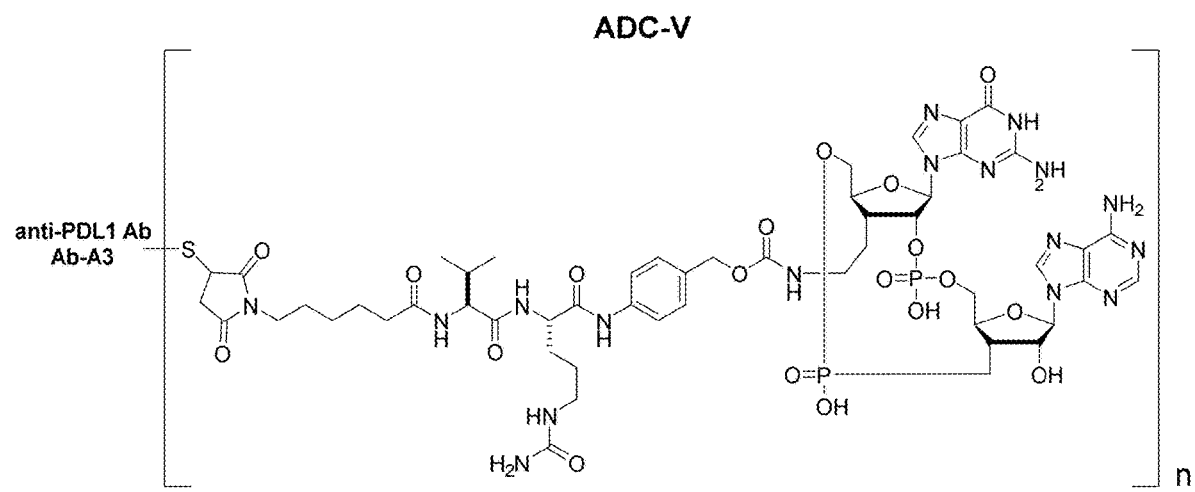
Figure 5B:
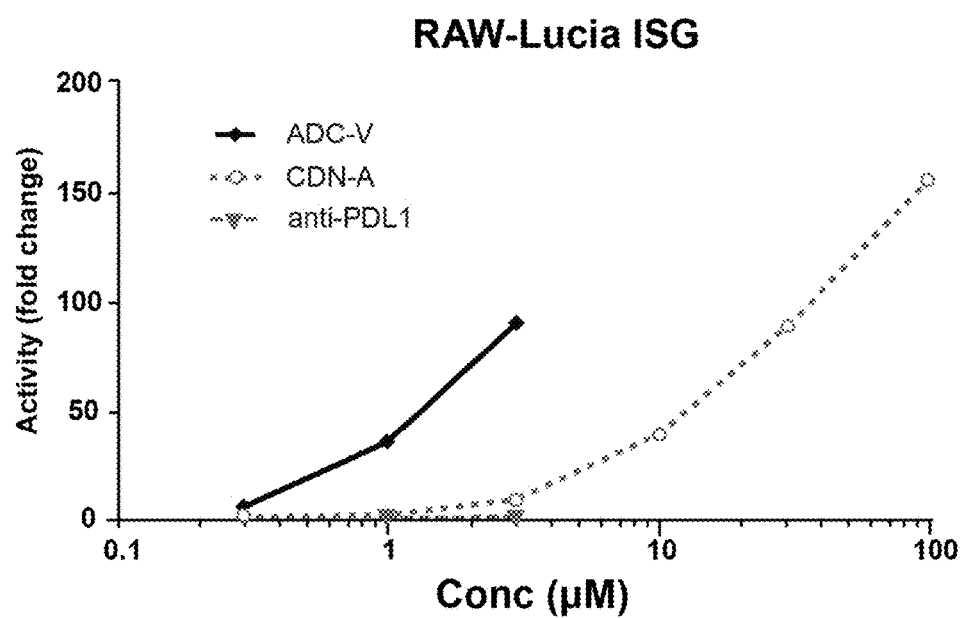

FIGS. 5A-5B show the structural characterization and activity of ADC-V. FIG. 5A shows the chemical structure of ADC-V. FIG. 5B shows the potency of IFN stimulatory activity in a luciferase reporter assay using mouse RAW-Lucia ISG cells. The comparator anti-PDL1 antibody is Ab-A3.

Figure 6A:
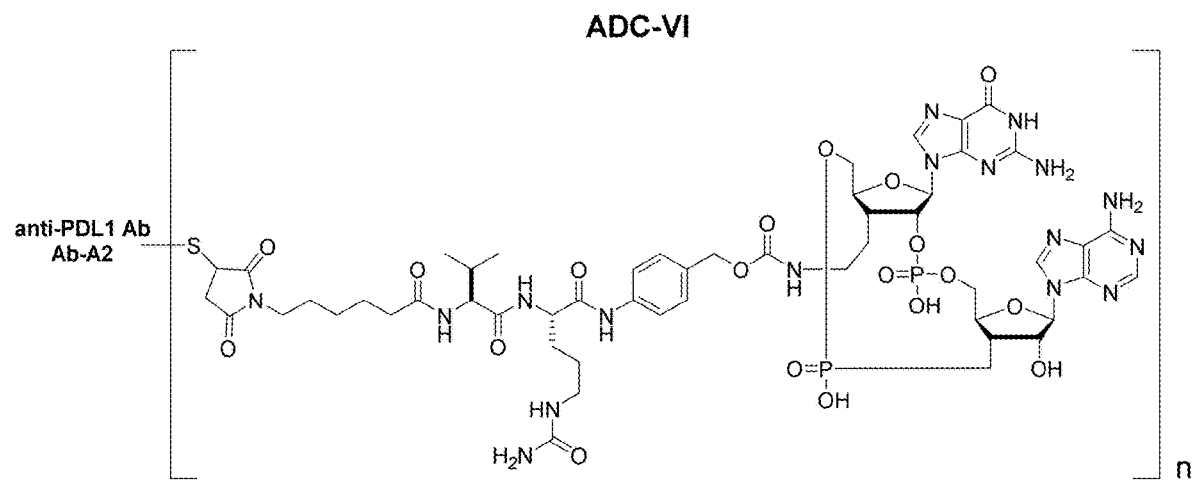
Figure 6B:
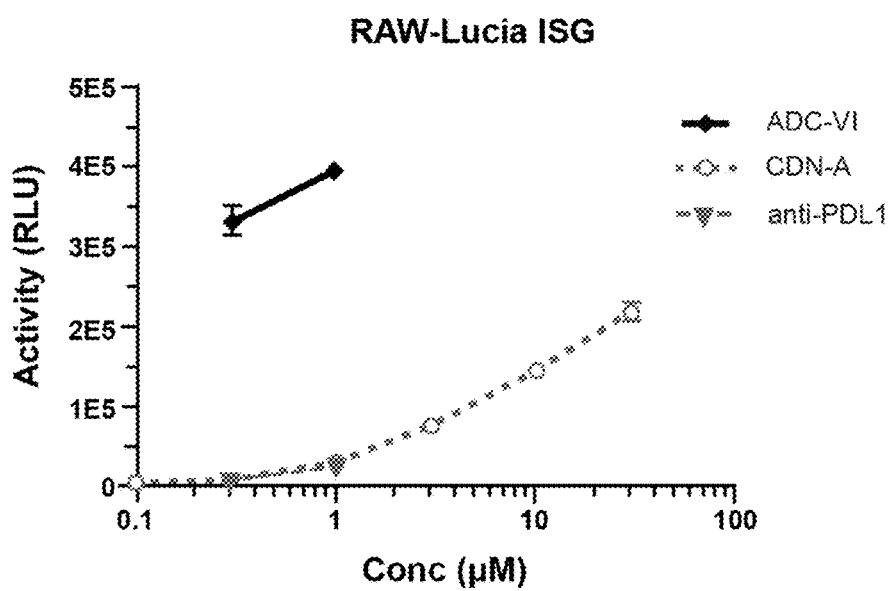
Figure 6C:
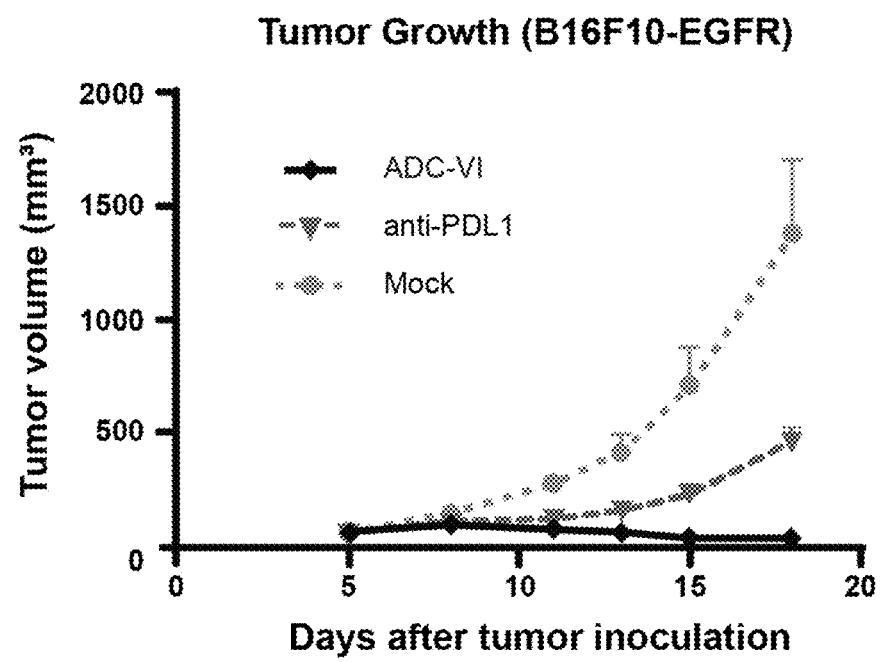
Figure 6D:
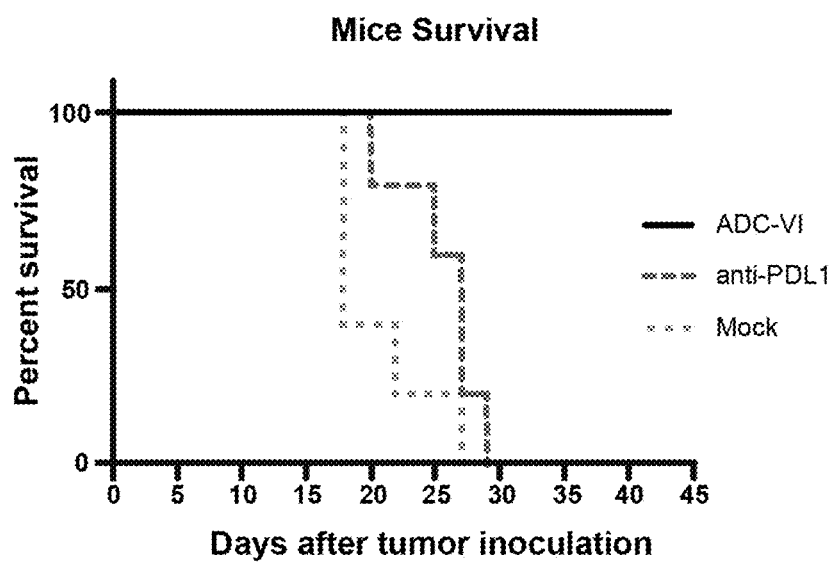
Figure 6E:
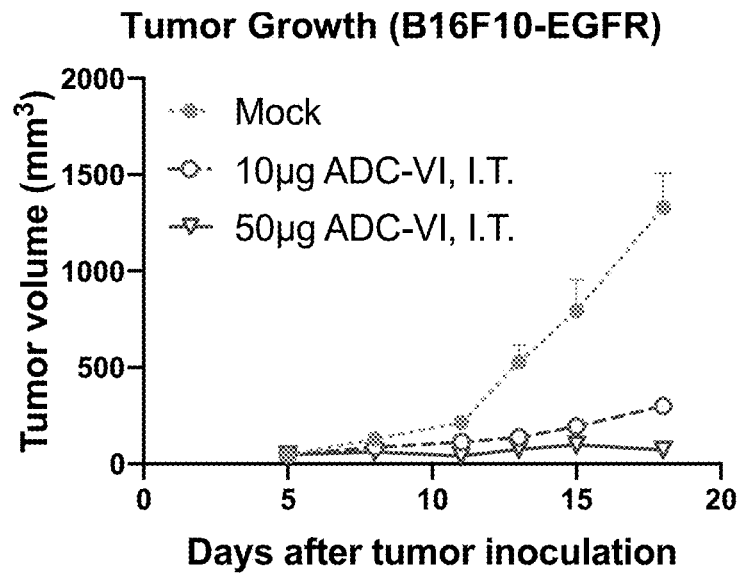
Figure 6F:
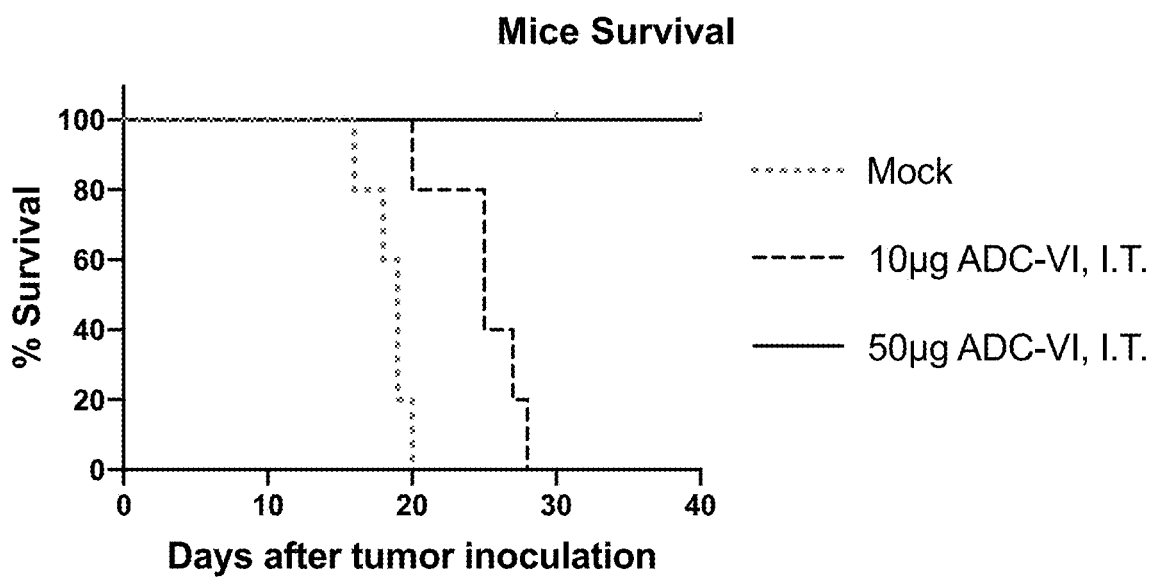

FIGS. 6A-6F show the structural characterization and activity of ADC-VI. FIG. 6A shows the chemical structure of ADC-VI. FIG. 6B shows the potency of IFN stimulatory activity in a luciferase reporter assay using mouse RAW-Lucia ISG cells. FIGS. 6C and 6D show tumor progression and survival, respectively, in EGFR-expressing B16F10 tumor bearing C57BL6 mice under indicated treatments. The comparator anti-PDL1 antibody is Ab-A2. FIGS. 6E and 6F show tumor progression and survival, respectively, in EGFR-expressing B16F10 tumor bearing C57BL6 mice under indicated treatments.

Figure 7A:
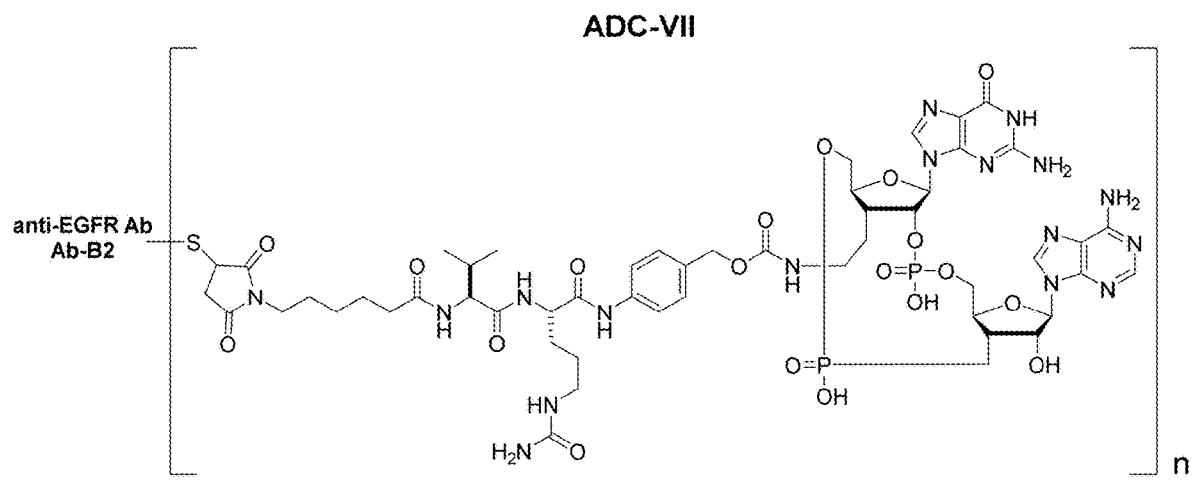
Figure 7B:
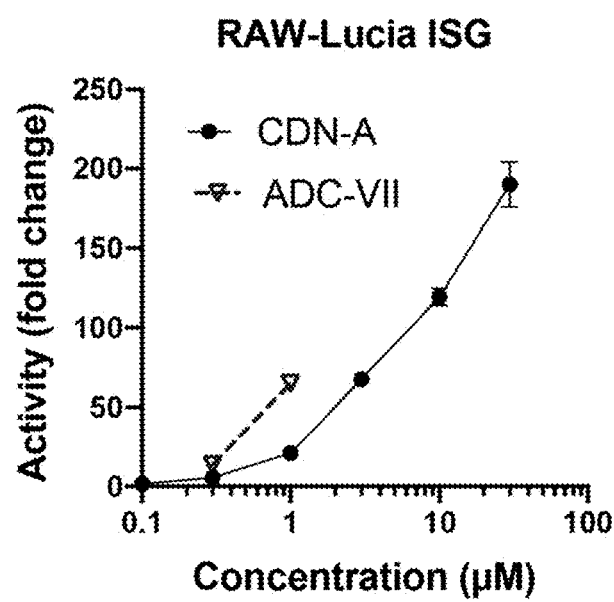
Figure 7C:
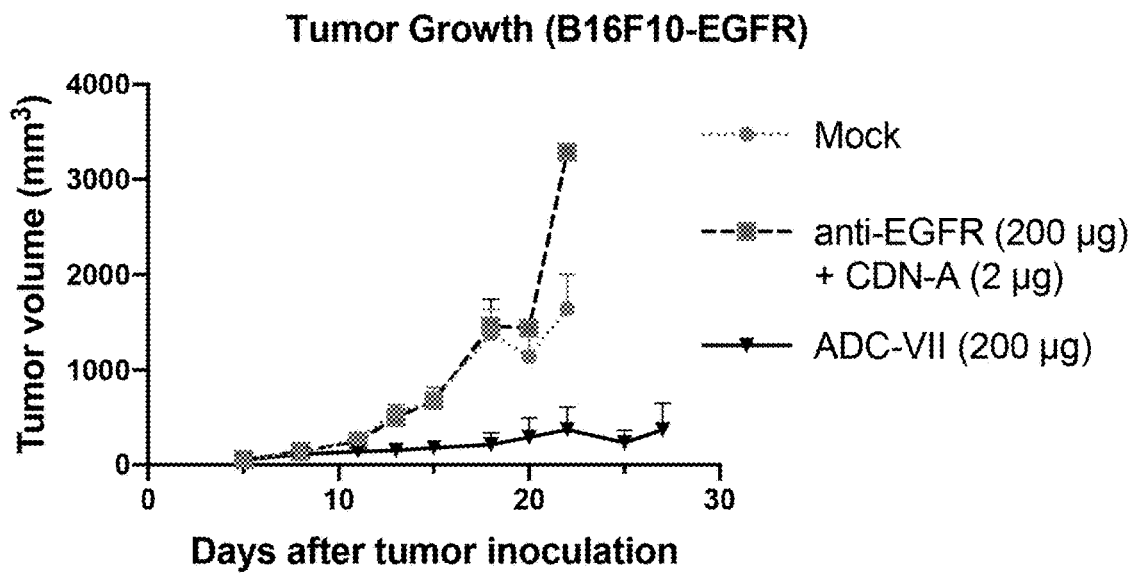
Figure 7D:
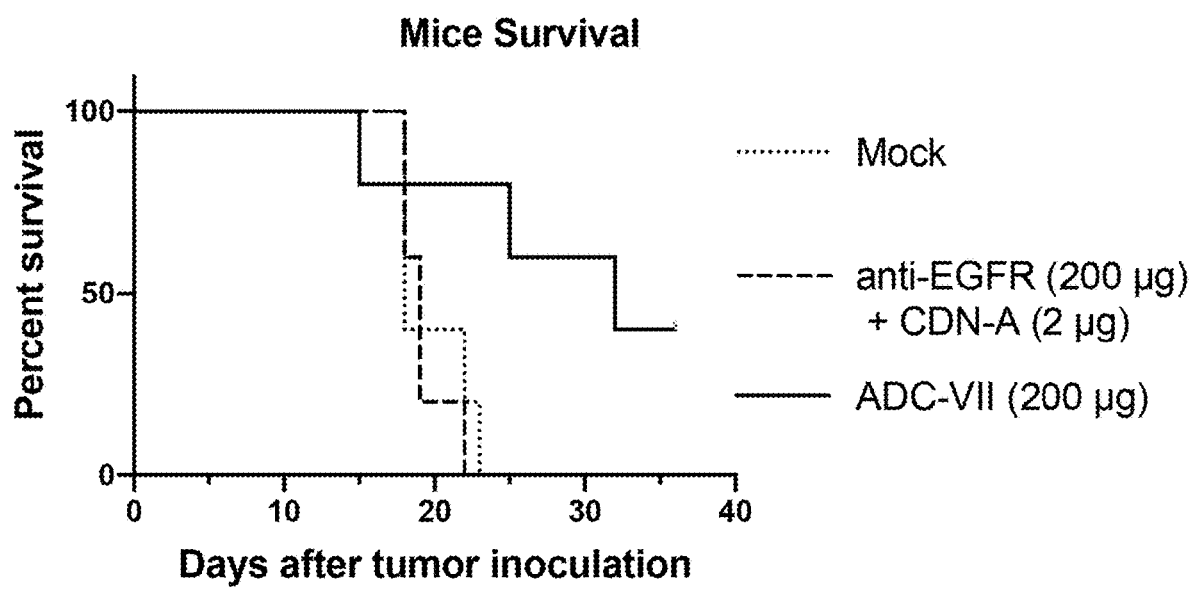
Figure 7E:
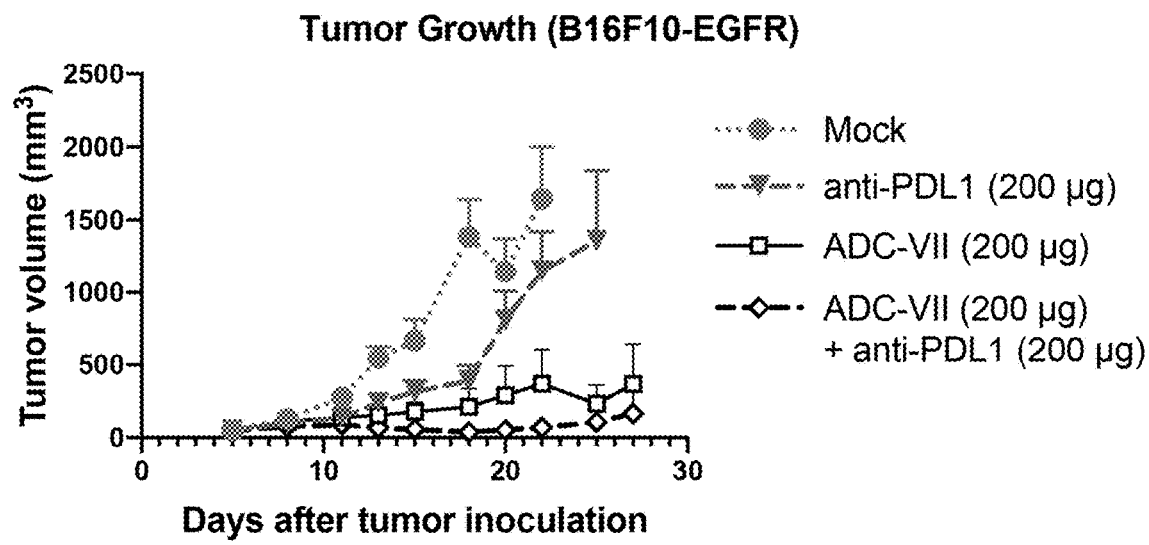
Figure 7F:
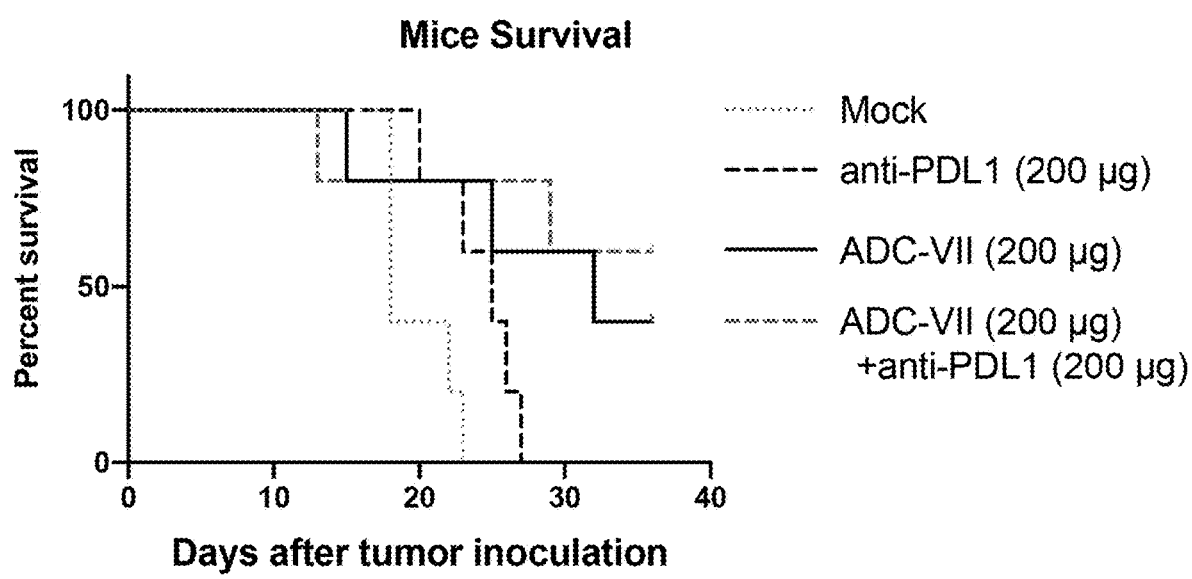

FIGS. 7A-7F show the structural characterization and activity of ADC-VII. FIG. 7A shows the chemical structure of ADC-VII. FIG. 7B shows the potency of IFN stimulatory activity in a luciferase reporter assay using mouse RAW-Lucia ISG cells (fold change versus PBS-stimulated cells). FIGS. 7C and 7D show tumor progression and survival, respectively, in EGFR-expressing B16F10 tumor bearing C57BL6 mice under indicated treatments. I.p. (intraperitoneal) injections occurred on days 7, 11, and 15. FIGS. 7E and 7F show tumor progression and survival, respectively, in EGFR-expressing B16F10 tumor bearing C57BL6 mice under indicated treatments. I.p. injections occurred on days 7, 11, and 15. The comparator anti-EGFR antibody is Ab-B2, and the comparator anti-PDL1 antibody is Ab-A3.

Figure 8A:
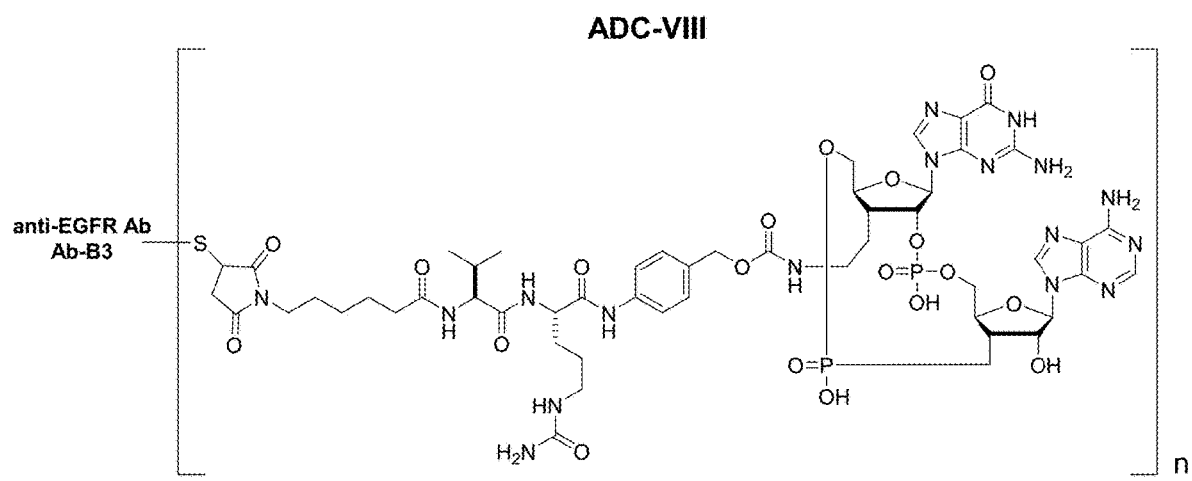
Figure 8B:
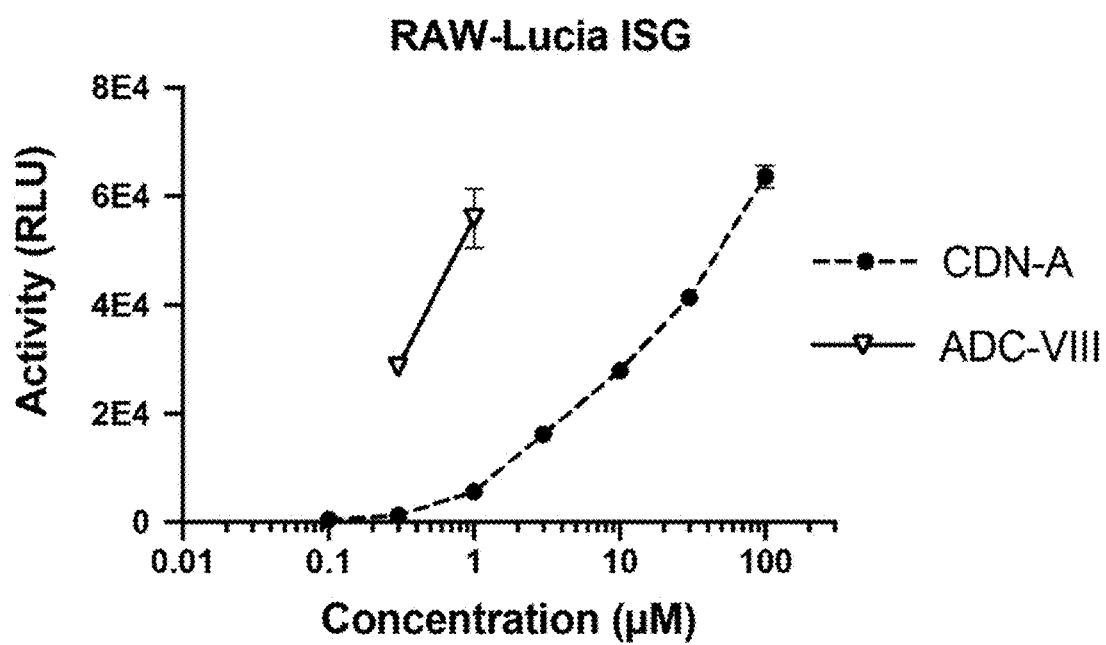
Figure 8C:
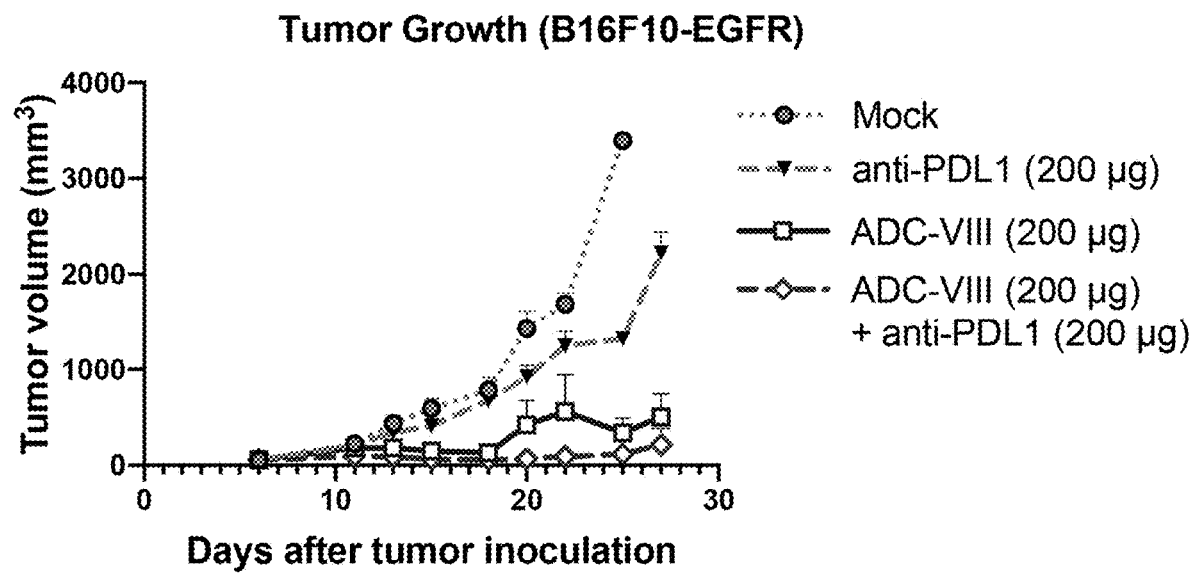
Figure 8D:
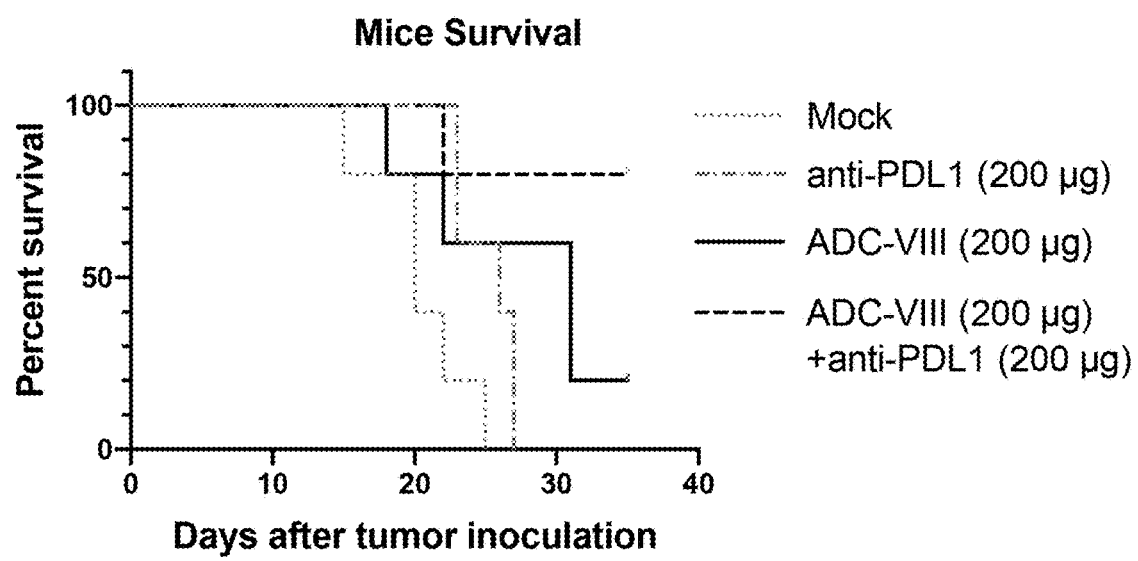

FIGS. 8A-8D show the structural characterization and activity of ADC-VIII. FIG. 8A shows the chemical structure of ADC-VIII. FIG. 8B shows the potency of IFN stimulatory activity in a luciferase reporter assay using mouse RAW-Lucia ISG cells. FIGS. 8C and 8D show tumor progression and survival, respectively, in EGFR-expressing B16F10 tumor bearing C57BL6 mice under indicated treatments. I.p. injections occurred on days 7, 11, and 15. The comparator anti-PDL1 antibody is Ab-A3.

Figure 9A:
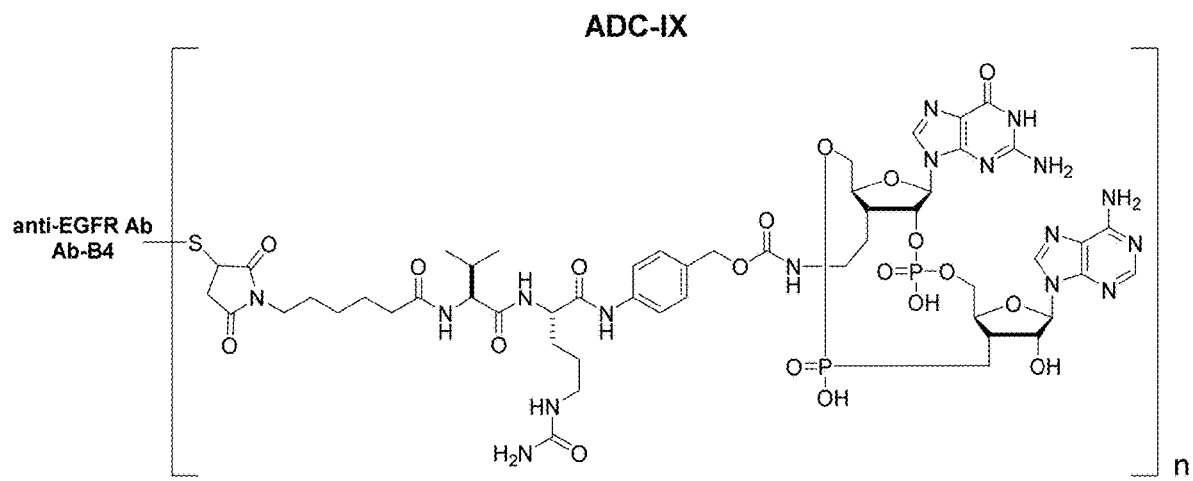
Figure 9B:
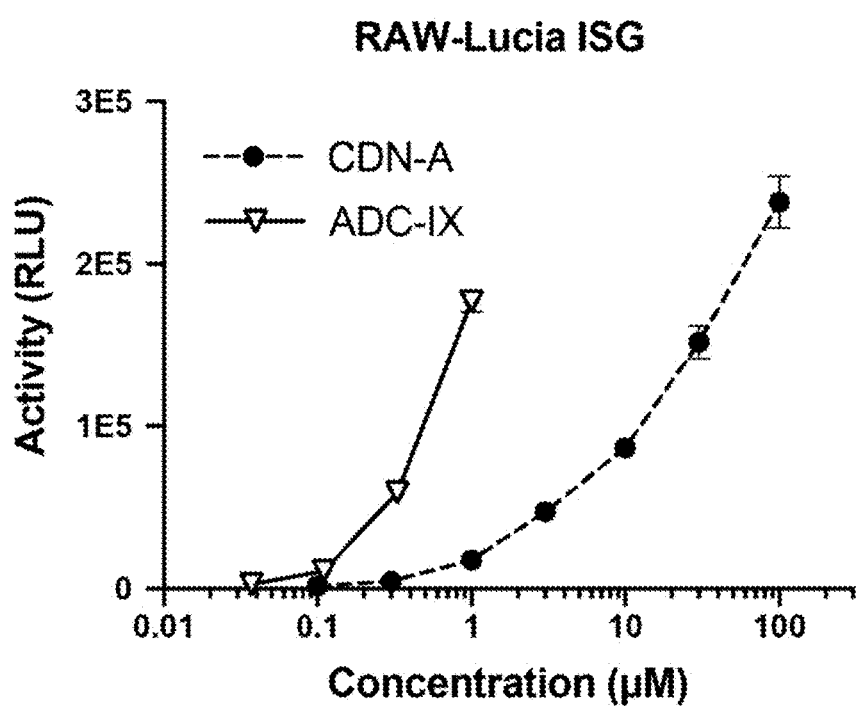
Figure 9C:
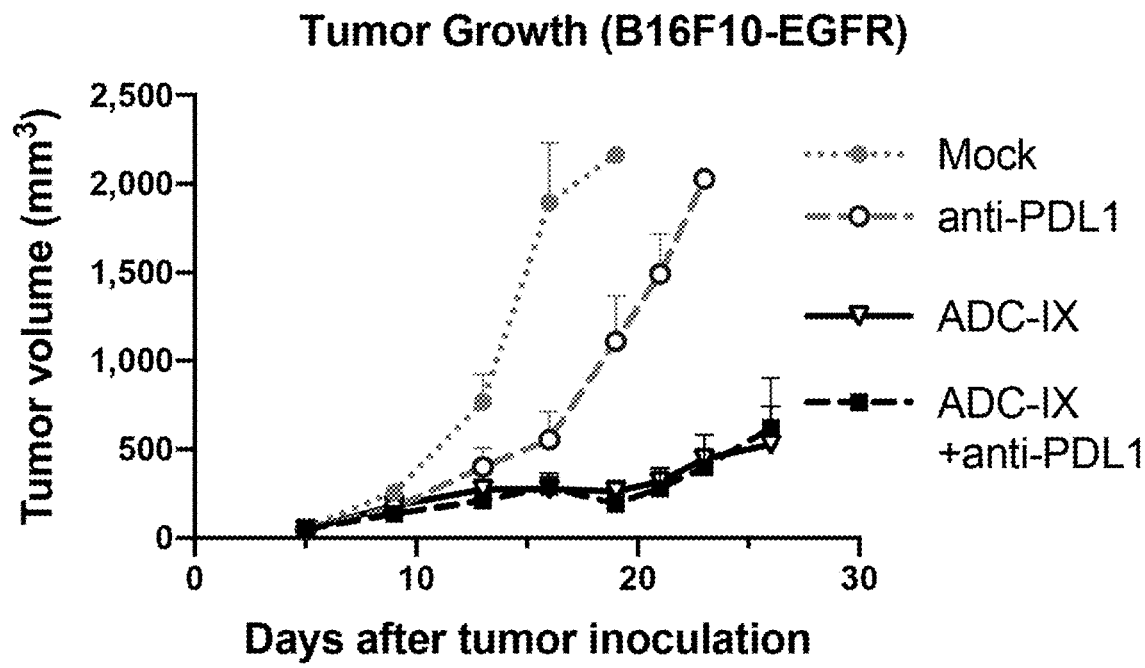
Figure 9D:
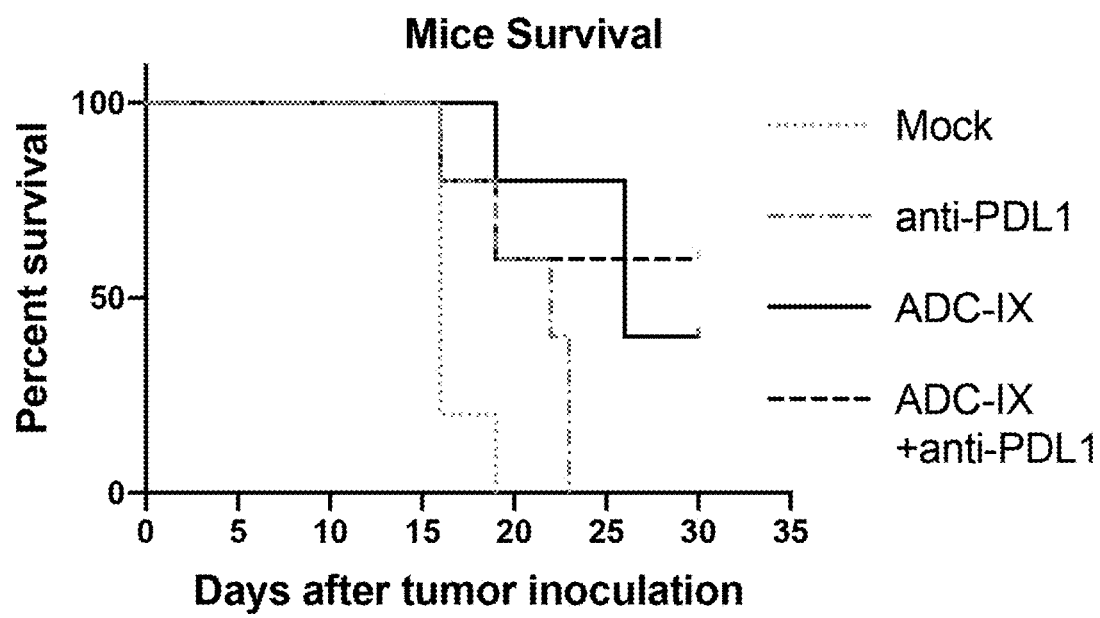

FIGS. 9A-9D show the structural characterization and activity of ADC-IX. FIG. 9A shows the chemical structure of ADC-IX. FIG. 9B shows the potency of IFN stimulatory activity in a luciferase reporter assay using mouse RAW-Lucia ISG cells. FIGS. 9C and 9D show tumor progression and survival, respectively, in EGFR-expressing B16F10 tumor bearing C57BL6 mice under indicated treatments. I.p. injections occurred on days 6, 9, and 13. The comparator anti-PDL1 antibody is Ab-A3.

Figure 10A:
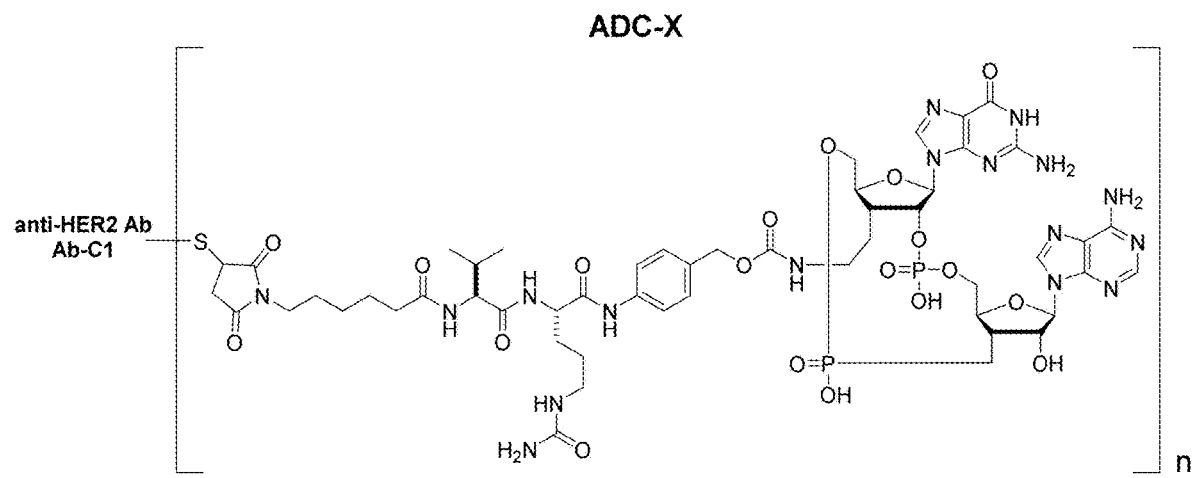
Figure 10B:
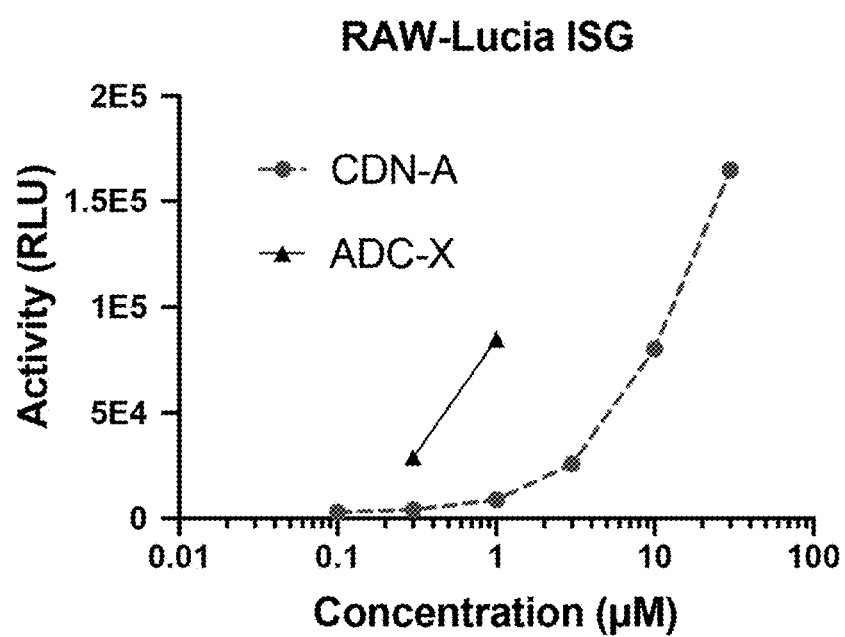
Figure 10C:
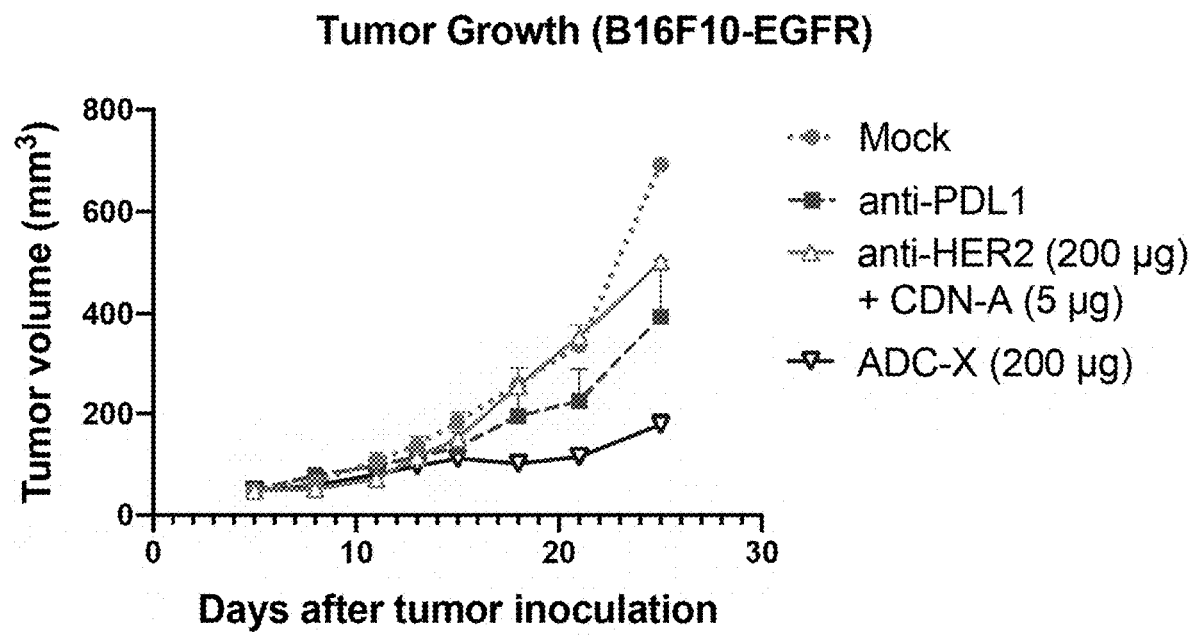
Figure 10D:
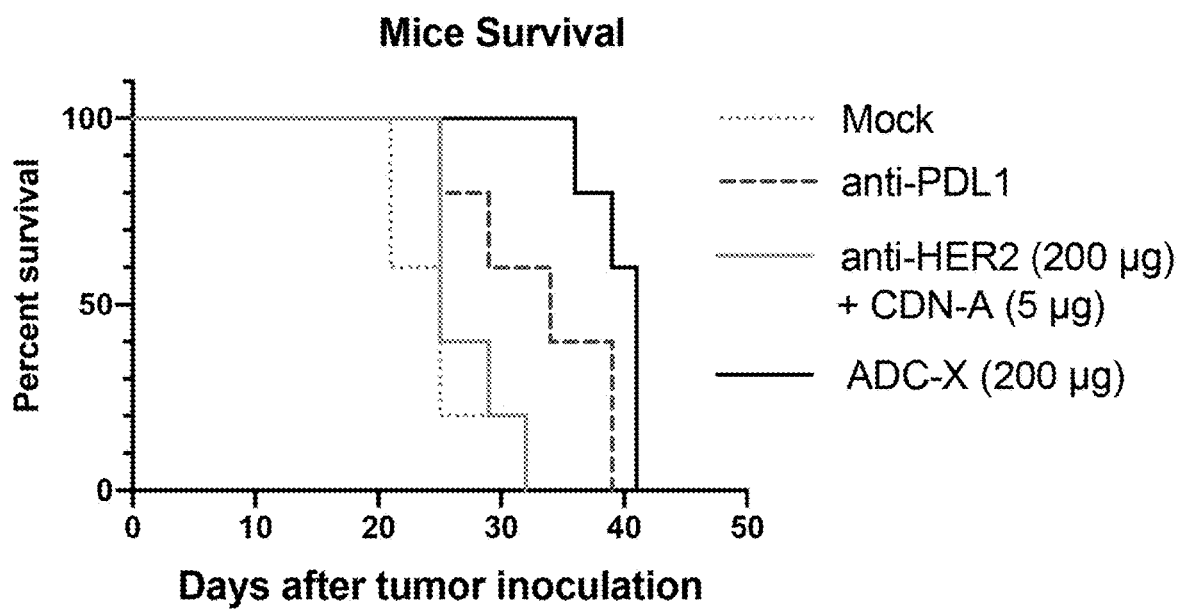
Figure 10E:
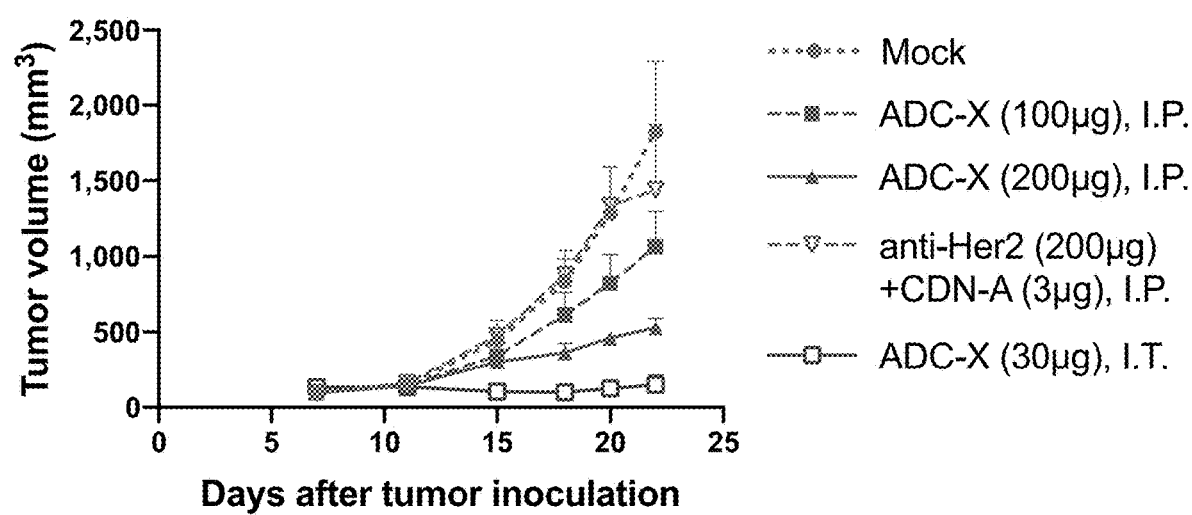

FIGS. 10A-10E show the structural characterization and activity of ADC-X. FIG. 10A shows the chemical structure of ADC-X. FIG. 10B shows the potency of IFN stimulatory activity in a luciferase reporter assay using mouse RAW-Lucia ISG cells. FIGS. 10C and 10D show tumor progression and survival, respectively, in EGFR-expressing B16F10 tumor bearing C57BL6 mice under indicated treatments. I.p. injections occurred on days 6, 10, and 13. The comparator anti-HER2 antibody is Ab-C1 (trastuzumab), and the comparator anti-PDL1 antibody is Ab-A3. FIG. 10E shows tumor progression in EGFR-expressing B16F10 tumor bearing C57BL6 mice under indicated treatments. I.p. and intratumoral (i.t.) injections occurred on days 7 and 11.

6. DETAILED DESCRIPTION

The present disclosure provides antibody-drug conjugates (ADCs), each comprising an antibody, one or more cyclic di-nucleotides (CDNs), and one or more linkers that connect the one or more CDNs to the antibody. The ADCs of the disclosure have the ability to agonize and/or bind STING and promote an immune response.

6.1. Antibody-Drug Conjugates (ADCs)

In certain embodiments, the ADCs of the present disclosure generally have the structure of Formula I

wherein:

"D" represents a CDN (e.g., a CDN as described herein, such as those of Formula II);

"Ab" represents an antibody or binding fragment thereof which binds a target antigen;

"L" represents, independently for each occurrence, a linker linking one or more occurrences of D to Ab;

"m" represents the number of occurrences of D linked to a given linker; and

"n" represents the number of linkers linked to Ab.

In certain embodiments of Formula I, m represents an integer selected from 1 to 10, including 1, 2, 3, 4, 5, 6, 7, 8, 9, or 10. In some instances, m ranges from 1 to 2, 1 to 3, 1 to 4, 1 to 5, 1 to 6, 1 to 7, 1 to 8, 1 to 9, or 1 to 10, such as from 1 to 2, 1 to 3, 1 to 4, 1 to 5, or 1 to 6. In other embodiments, Formula I describes the ADCs in a mixture of ADCs exhibiting a range of values for m, such that m ranges from 1 to 2, 1 to 3, 1 to 4, 1 to 5, 1 to 6, 1 to 7, 1 to 8, 1 to 9, or 1 to 10, such as from 1 to 2, 1 to 3, 1 to 4, 1 to 5, or 1 to 6. In certain embodiments, Formula I describes the ADCs in a mixture of ADCs such that more than 60%, 65%, 70%, 75%, 80%, 85%, 90%, or 95% of the ADCs in the mixture have an m value of 1, 2, 3, 4, 5, 6, 7, 8, 9, or 10. In some embodiments, Formula I describes the ADCs in a mixture of ADCs such that more than 60%, 65%, 70%, 75%, 80%, 85%, 90%, or 95% of the ADCs in the mixture have an m value that ranges from 1 to 2, 1 to 3, 1 to 4, 1 to 5, 1 to 6, 1 to 7, 1 to 8 1, to 9, or 1 to 10, such as from 1 to 2, 1 to 3, 1 to 4, 1 to 5, or 1 to 6.

In other embodiments, Formula I describes the ADCs in a mixture of ADCs and m is replaced by "$m_{ave}$", which represents the average of m values for the mixture, i.e., the average number of CDNs linked to a given linker (L) in the mixture, which can be calculated by dividing the total number of antibody-linked CDNs by the total number of CDN-containing linkers (L) in the mixture. In such embodiments, $m_{ave}$ represents an integer or non-integer value ranging from 1 to 10, such as ranging from 1 to 2, 1 to 3, 1 to 4, 1 to 5, 1 to 6, 1 to 7, 1 to 8, or 1 to 9, such as from 1 to 2, 1 to 3, 1 to 4, 1 to 5, or 1 to 6.

In some embodiments of Formula I, n represents an integer selected from 1 to 20, including 1, 2, 3, 4, 5, 6, 7, 8, 9, 10, 11, 12, 13, 14, 15, 16, 17, 18, 19, or 20. In some instances, n ranges from 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 7, t o 18, 1 to 19, or 1 to 20, such as from 1 to 2, 1 to 3, 1 to 4, 1 to 5, 1 to 6, 1 to 7, or 1 to 8. In other embodiments, Formula I describes the ADCs in a mixture of ADCs exhibiting a range of values for n, such that n ranges from 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, or 1 to 20, such as from 1 to 2, 1 to 3, 1 to 4, 1 to 5, 1 to 6, 1 to 7, 1 to 8, 1 to 9, or 1 to 10. In certain embodiments, Formula I describes the ADCs in a mixture of ADCs such that more than 60%, 65%, 70%, 75%, 80%, 85%, 90%, or 95% of the ADCs in the mixture have an n value of 1, 2, 3, 4, 5, 6, 7, 8, 9, 10, 11, 12, 13, 14, 15, 16, 17, 18, 19, or 20. In some embodiments, Formula I describes the ADCs in a mixture of ADCs such that more than 60%, 65%, 70%, 75%, 80%, 85%, 90%, or 95% of the ADCs in the mixture have an n value that ranges from 1 to 2, 1 to 3, 1 to 4, 1 to 5, 1 to 6, 1 to 7, 1 to 8 1, to 9, 1 to 10, 1 to 11, 1 to 12, 1 to 13, 1 to 14, 1 to 15, 1 to 16, 1 to 17, 1 to 18, 1 to 19, or 1 to 20, such as from 1 to 2, 1 to 3, 1 to 4, 1 to 5, 1 to 6, 1 to 7, 1 to 8, 1 to 9, or 1 to 10.

In other embodiments, Formula I describes the ADCs in a mixture of ADCs and n is replaced by "$n_{ave}$", which represents the average of n values for the mixture, i.e., the average number of linkers (L) linked to a given antibody (Ab) in the mixture, which can be calculated by dividing the total number of antibody-linked linkers (L) by the total number of linker-containing antibodies (Ab) in the mixture. In such embodiments, $n_{ave}$ represents an integer or non-integer value ranging from 1 to 20, such as ranging from 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, or 1 to 20, such as from 1 to 2, 1 to 3, 1 to 4, 1 to 5, 1 to 6, 1 to 7, 1 to 8, 1 to 9, or 1 to 10.

In certain embodiments, m is 1, in which case the ADC has a 1:1 ratio of linker to CDN and can be represented by Formula Ia:

Ab-[-L-D]$_n$                                        (Formula Ia)

wherein:

"D" represents a CDN (e.g., a CDN as described herein, such as those of Formula II);

"Ab" represents an antibody or binding fragment thereof which binds a target antigen;

"L" represents, independently for each occurrence, a linker linking one or more occurrences of D to Ab; and "n" represents the number of occurrences of D linked to Ab via the linker (L).

In some embodiments of Formula Ia, n represents an integer selected from 1 to 20, including 1, 2, 3, 4, 5, 6, 7, 8, 9, 10, 11, 12, 13, 14, 15, 16, 17, 18, 19, or 20. In some instances, n ranges from 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 7, t o 18, 1 to 19, or 1 to 20, such as from 1 to 2, 1 to 3, 1 to 4, 1 to 5, 1 to 6, 1 to 7, or 1 to 8. In other embodiments, Formula Ia describes the ADCs in a mixture of ADCs exhibiting a range of values for n, such that n ranges from 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, or 1 to 20, such as from 1 to 2, 1 to 3, 1 to 4, 1 to 5, 1 to 6, t o 7, or 1 to 8. In certain embodiments, Formula Ia describes the ADCs in a mixture of ADCs such that more than 60%, 65%, 70%, 75%, 80%, 85%, 90%, or 95% of the ADCs in the mixture have an n value of 1, 2, 3, 4, 5, 6, 7, 8, 9, 10, 11, 12, 13, 14, 15, 16, 17, 18, 19, or 20. In some embodiments, Formula Ia describes the ADCs in a mixture of ADCs such that more than 60%, 65%, 70%, 75%, 80%, 85%, 90%, or 95% of the ADCs in the mixture have an n value that ranges from 1 to 2, 1 to 3, 1 to 4, 1 to 5, 1 to 6, 1 to 7, 1 to 8 1, to 9, 1 to 10, 1 to 11, 1 to 12, 1 to 13, 1 to 14, 1 to 15, 1 to 16, 1 to 17, 1 to 18, 1 to 19, or 1 to 20, such as from 1 to 2, 1 to 3, 1 to 4, 1 to 5, 1 to 6, 1 to 7, or 1 to 8.

In other embodiments, Formula Ia describes the ADCs in a mixture of ADCs and n is replaced by "$n_{ave}$", which represents the average of n values for the mixture, i.e., the average number of linkers (L) linked to a given antibody (Ab) in the mixture, which can be calculated by dividing the total number of antibody-linked linkers (L) by the total number of linker-containing antibodies (Ab) in the mixture. In such embodiments, $n_{ave}$ represents an integer or non-integer value ranging from 1 to 20, such as ranging from 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, or 1 to 20, such as from 1 to 2, 1 to 3, 1 to 4, 1 to 5, 1 to 6, 1 to 7, 1 to 8, 1 to 9, or 1 to 10.

The ADCs disclosed herein are "modular" in nature in that each has the above modular components Ab, L, and D. Throughout the present disclosure, various specific non-limiting embodiments and examples of these modular components are described. It is intended that the modules of all of the specific embodiments described may be combined with each other as though each specific combination were explicitly described individually.

It will also be appreciated by skilled artisans that the various ADCs described herein may be in the form of salts, and in some specific embodiments, pharmaceutically acceptable salts.

6.2. Cyclic Di-Nucleotides (CDNs)

The CDNs used herein comprise two nucleosides joined by two bridge groups. In certain embodiments, the CDNs are 2'3'-CDNs, meaning that each nucleoside includes a cyclic 5-carbon sugar (a pentose), wherein the first nucleoside is linked at the 2'-position of its sugar to the 5'-position of the second nucleoside's sugar, e.g., by an intervening bridge group, to form a 2'-5' linkage, and the second nucleoside is linked at the 3'-position of its sugar to the 5'-position of the first nucleoside's sugar, e.g., by an intervening bridge group, to form a 3'-5' linkage. Examples of suitable 2'3'-CDNs include 2'3'-cGAMP and analogs or derivatives thereof, including pharmaceutically acceptable salts. CDNs of Formula II below are 2'3'-CDNs.

In other embodiments, the CDNs are 3'3'-CDNs, wherein the first nucleotide is linked to the second nucleotide, e.g., by an intervening bridge group, by a 3'-5' linkage in analogous fashion as described above, and the second nucleotide is linked to the first nucleotide, e.g., by an intervening bridge group, also by a 3'-5' linkage in analogous fashion as described above. Examples of suitable 3'3'-CDNs include 3'3'-cGAMP and analogs or derivatives thereof, including pharmaceutically acceptable salts.

In other embodiments, the CDNs are 2'2'-CDNs, wherein the first nucleotide is linked to the second nucleotide, e.g., by an intervening bridge group, by a 2'-5' linkage in analogous fashion as described above, and the second nucleotide is linked to the first nucleotide, e.g., by an intervening bridge group, also by a 2'-5' linkage in analogous fashion as described above. Examples of suitable 2'2'-CDNs include 2'2'-cGAMP and analogs or derivatives thereof, including pharmaceutically acceptable salts.

In other embodiments, the CDNs are 3'2'-CDNs, wherein the first nucleotide is linked to the second nucleotide, e.g., by an intervening bridge group, by a 3'-5' linkage in analogous fashion as described above, and the second nucleotide is linked to the first nucleotide, e.g., by an intervening bridge group, by a 2'-5' linkage in analogous fashion as described above. Examples of suitable 3'2'-CDNs include 3'2'-cGAMP and analogs or derivatives thereof, including pharmaceutically acceptable salts.

6.2.1. Nucleosides

In some instances, each nucleoside of the CDN includes a nucleobase that can be, independently from the other, a pyrimidine base or a purine base. For instance, each nucleobase can be a canonical nucleobase (such as adenine, guanine, thymine, uracil, or cytosine) or a non-canonical, modified, non-natural nucleobase (such as xanthine, hypoxanthine, 7-methylguanine, 5,6-dihydrouracil, 5-methylcytosine, 5-hydroxymethylcytosine, 1-methylcytosine, 2,6-diaminopurine, 6,8-diaminopurine, 2-aminoimidazo[1,2a][1,3,5]triazin-4(1H)-one, 6-amino-5-nitropyridin-2-one, iso-guanine, iso-cytosine, 5-(2,4-diaminopyrimindine), 4-thiouracil, pseudouracil, etc.). Suitable nucleobases include those described below for variables $B^1$ and $B^2$.

In certain instances, the CDN comprises two nucleosides that comprise two pyrimidine bases or two purine bases, or one pyrimidine base and one purine base. In some embodiments, the two nucleosides comprise two purine bases, such as an adenine and a guanine, two adenines, or two guanines, particularly an adenine and a guanine or two adenines. It is understood that recitation of the indefinite article "a" or "an" before a particular nucleobase or other defined chemical structure (e.g., "an adenine") indicates that both the canonical nucleobase and modified variants thereof are contemplated.

In some embodiments, the CDN comprises two nucleosides that each include a cyclic 5-carbon sugar (a pentose), such as D- or L-ribose or deoxyribose, D- or L-arabinose, D- or L-lyxose, D- or L-xylose, or modified forms thereof. In certain instances, one of the pentoses of the CDN (e.g., a ribose) connects to the linker (L) at the 3'-position of the sugar, such as via a $C_{1-6}$alkyl group (e.g., a $C_{2-6}$alkyl group) at the 3' position, the $C_{1-6}$alkyl group being optionally substituted with a hydroxyl, thiol, amino, $C_{1-6}$alkylamino, or -PEG-OH group; with a hydroxyl, thiol, amino, or $C_{1-6}$alkylamino group; with a thiol, amino, or $C_{1-6}$alkylamino group; or with a thiol or amino group. In other embodiments, one of the pentoses of the CDN (e.g., a ribose) connects to the linker (L) at the 2'-position of the sugar, such as via a $C_{1-6}$alkyl group (e.g., a $C_{2-6}$alkyl group) at the 2' position, the $C_{1-6}$alkyl group being optionally substituted with a hydroxyl, thiol, amino, $C_{1-6}$alkylamino, or -PEG-OH group; with a hydroxyl, thiol, amino, or $C_{1-6}$alkylamino group; with a thiol, amino, or $C_{1-6}$alkylamino group; or with a thiol or amino group. In some embodiments, the linker (L) is connected to the CDN by substituting for a proton of the hydroxyl, thiol, amino, $C_{1-6}$alkylamino, or -PEG-OH group.

The following descriptions of the group at the 3'-position of the pentose can also apply to the group at the 2'-position of the pentose.

In certain instances, the group at the 3'-position of the pentose (e.g., a ribose) is a $C_{1-6}$alkyl group, such as a $C_{2-6}$alkyl group, substituted with a hydroxyl, such as -ethylene-OH, -propylene-OH, -butylene-OH, or -pentylene-OH. In some embodiments, the linker (L) is connected by substituting for the proton of the hydroxyl in one of the above groups.

In some instances, the group at the 3'-position of the pentose (e.g., a ribose) is a $C_{1-6}$alkyl group, such as a $C_{2-6}$alkyl group, substituted with a thiol, such as -ethylene-SH, -propylene-SH, -butylene-SH, or -pentylene-SH. In some embodiments, the linker (L) is connected by substituting for the proton of the thiol in one of the above groups.

In certain instances, the group at the 3'-position of the pentose (e.g., a ribose) is a $C_{1-6}$alkyl group, such as a $C_{2-6}$alkyl group, substituted with an amino, such as -ethylene-$NH_2$, -propylene-$NH_2$, -butylene-$NH_2$, or -pentylene-$NH_2$. In some embodiments, the linker (L) is connected by substituting for a proton of the amino in one of the above groups.

In some instances, the group at the 3'-position of the pentose (e.g., a ribose) is a $C_{1-6}$alkyl group, such as a $C_{2-6}$alkyl group, substituted with a $C_{1-6}$alkylamino, such as -ethylene-N($C_{1-6}$alkyl)H, -propylene-N($C_{1-6}$alkyl)H, -butylene-N($C_{1-6}$alkyl)H, or -pentylene-N($C_{1-6}$alkyl)H. In some embodiments, the linker (L) is connected by substituting for a proton of the $C_{1-6}$alkylamino in one of the above groups.

In certain embodiments, the group at the 3'-position of the pentose (e.g., a ribose) is a $C_{1-6}$alkyl group, such as a $C_{2-6}$alkyl group, substituted with a -PEG-OH group, such as -ethylene-PEG-OH, -propylene-PEG-OH, -butylene-PEG-OH, or -pentylene-PEG-OH. In some embodiments, the linker (L) is connected by substituting for a proton of the terminal hydroxyl of the -PEG-OH group. It is understood that "PEG" refers to the polymer polyethylene glycol, polyethylene oxide, or polyoxyethylene and having the repeating structure —(O—$CH_2$—$CH_2$)$_x$— and average molecular weights ranging from 200 to 10000 g/mol, such as from 200, 400, 800, 1000, 2000, or 4000 to 5000, 6000 8000 or 10000 g/mol, including from 400 to 8,000 g/mol, 400 to 2000 g/mol, 5000 to 10000 g/mol, 1000 to 4000 g/mol, 1000 to 6000 g/mol, or 2000 to 6000 g/mol, including less than 4000, 5000, or 6000 g/mol.

In some instances, the group at the 3'-position of the pentose (e.g., a ribose) is a $C_{2-3}$alkyl group substituted with hydroxyl, thiol, amino, a $C_{1-6}$alkylamino, or -PEG-OH group, such as -ethylene-OH, -propylene-OH, -ethylene-SH, -propylene-SH, -ethylene-NH$_2$, -propylene-NH$_2$, -ethylene-N(C$_{1-6}$alkyl)H, -propylene-N(C$_{1-6}$alkyl)H, -ethylene-PEG-OH, or -propylene-PEG-OH. In some embodiments, the linker (L) is connected by substituting for a proton of the hydroxyl, thiol, amino, or C$_{1-6}$alkylamino or -PEG-OH group in one of the above groups.

In some instances, the group at the 3'-position of the pentose (e.g., a ribose) is a C$_2$alkyl group (an ethyl group) substituted with hydroxyl, thiol, amino, a C$_{1-6}$alkylamino, or -PEG-OH group, such as -ethylene-OH, -ethylene-SH, -ethylene-NH$_2$, -ethylene-N(C$_{1-6}$alkyl)H, or -ethylene-PEG-OH. In some embodiments, the linker (L) is connected by substituting for a proton of the hydroxyl, thiol, amino, or C$_{1-6}$alkylamino or -PEG-OH group in one of the above groups.

In some instances, the group at the 3'-position of the pentose (e.g., a ribose) is a C$_3$alkyl group (a propyl group) substituted with hydroxyl, thiol, amino, a C$_{1-6}$alkylamino, or -PEG-OH group, such as -propylene-OH, -propylene-SH, -propylene-NH$_2$, -propylene-N(C$_{1-6}$alkyl)H, or -propylene-PEG-OH. In some embodiments, the linker (L) is connected by substituting for a proton of the hydroxyl, thiol, amino, or C$_{1-6}$alkylamino or -PEG-OH group in one of the above groups.

In certain embodiments, one of the pentoses of the CDN (e.g., a ribose) connects to the linker (L) at the 3'-position of the sugar via a substituted methyl group at the 3' position, the methyl group being substituted, for example, with a hydroxyl, thiol, amino, C$_{1-6}$alkylamino, or -PEG-OH group; with a hydroxyl, thiol, amino, or C$_{1-6}$alkylamino group; with a thiol, amino, or C$_{1-6}$alkylamino group; with a thiol or amino group; or with a thiol group. In some embodiments, the linker (L) is connected to the CDN by substituting for a proton of the hydroxyl, thiol, amino, C$_{1-6}$alkylamino, or -PEG-OH group.

In certain embodiments, the CDN comprises two nucleosides that each include a ribose, wherein one of the riboses connects to the linker (L) via a C$_{2-6}$alkyl group (such as a C$_2$alkyl, C$_3$alkyl, or C$_{2-3}$alkyl group) at the 3'-position of the ribose ring, the C$_{2-6}$alkyl group being optionally substituted with a hydroxyl, thiol, amino, C$_{1-6}$alkylamino, or -PEG-OH group; with a hydroxyl, thiol, amino, or C$_{1-6}$alkylamino group; with a thiol, amino, or C$_{1-6}$alkylamino group; or with a thiol or amino group; wherein the linker (L) is connected to the CDN by substituting for a proton of the hydroxyl, thiol, amino, C$_{1-6}$alkylamino, or -PEG-OH group.

In certain embodiments, the CDN comprises two nucleosides that each include a ribose, wherein one of the riboses connects to the linker (L) via a substituted ethyl group at the 3'-position of the ribose ring, the ethyl group being substituted, for example, with a hydroxyl, thiol, amino, C$_{1-6}$alkylamino, or -PEG-OH group; with a hydroxyl, thiol, amino, or C$_{1-6}$alkylamino group; with a thiol, amino, or C$_{1-6}$alkylamino group; or with a thiol or amino group; wherein the linker (L) is connected to the CDN by substituting for a proton of the hydroxyl, thiol, amino, C$_{1-6}$alkylamino, or -PEG-OH group.

In certain embodiments, the CDN comprises two nucleosides that each include a ribose, wherein one of the riboses connects to the linker (L) via a substituted ethyl group at the 3'-position of the ribose ring selected from —CH$_2$CH$_2$—OH, —CH$_2$CH$_2$—SH, and —CH$_2$CH$_2$—NH$_2$, particularly from —CH$_2$CH$_2$—SH and —CH$_2$CH$_2$—NH$_2$; wherein the linker (L) is connected to the CDN by substituting for a proton of the hydroxyl, thiol, or amino group.

6.2.2. Bridge Groups

Due to their cyclic structure, CDNs include two bridge groups that join the nucleosides described above to form the CDN macrocycle. In certain embodiments, the bridge groups, independently, include 2 to 5 atoms in the bridge between the two sugars of the nucleosides, such as 3 atoms. For instance, —O—P(=O)(OH)—O— may be a bridge group, where it is understood that the sugars are bonded at the terminal oxygen atoms, and there are three atoms in the bridge. The bridge groups, independently, may include only heteroatoms in the bridge, both heteroatoms and carbon atoms in the bridge, or only carbon atoms in the bridge.

In certain instances the bridge groups are divalent phosphate or thiophosphate groups or modified variants thereof, e.g., —O—P(=O)(OH)—O— or —O—P(=O)(SH)—O—. For example, the two bridge groups can be independently selected from —O—P(O)R$^p$—O—, —O—P(S)R$^p$—O—, —O—P(O)R$^p$—S—, —O—P(S)R$^p$—S—, —S—P(O)R$^p$—O—, —S—P(S)R$^p$—O—, —S—P(O)R$^p$—S—, or —S—P(S)R$^p$—S—, wherein R$^p$ is defined further below. In some embodiments, R$^p$ in the above bridge groups independently for each occurrence selected from hydroxyl or thiol.

It is understood that when both bridge groups are phosphate groups or modified variants thereof, then each bridge group in combination with a nucleoside described above represents a nucleotide, with both sets of bridge groups and nucleosides providing a cyclic dinucleotide. Nevertheless, CDNs disclose herein are not necessarily limited to bridge groups that are phosphate groups.

6.2.3. Specific CDNs

The present disclosure provides CDNs (D) that can be administered by themselves or as part of the ADC of Formula I. In certain instances, the CDN has the structure of Formula II below. It is understood that reference to Formula I also includes reference to sub Formula Ia. Likewise, reference to Formula II also includes references to its sub formulas, such as Formula IIa, IIb, etc. Formula II has the structure:

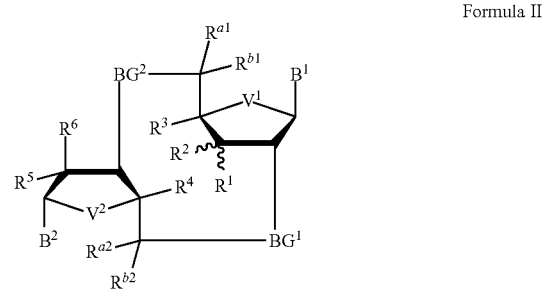

Formula II wherein

R$^1$ is C$_{1-6}$alkyl, such as C$_{2-6}$alkyl or C$_{2-3}$alkyl, substituted with a hydroxyl, thiol, amino, C$_{1-6}$alkylamino, or a -PEG-OH group;

R$^3$ and R$^4$ are independently hydrogen, halogen, C$_{1-6}$alkyl, C$_{2-6}$alkenyl, or C$_{2-6}$alkynyl, wherein C$_{1-6}$alkyl, C$_{2-6}$alkenyl, and C$_{2-6}$alkynyl are, independently, optionally substituted with one or more groups selected from halogen, thiol, hydroxyl, carboxyl, C$_{1-6}$alkoxy, C$_{1-6}$hydroxyalkoxy, —OC(O)C$_{1-6}$alkyl, —N(H)C(O)C$_{1-6}$alkyl, —N(C$_{1-3}$alkyl)C(O)C$_{1-6}$alkyl, amino, C$_{1-6}$alkylamino, di(C$_{1-6}$alkyl)amino, oxo, and azido;

R$^2$, R$^5$, and R$^6$ are independently hydrogen, halogen, hydroxyl, azido, amino, C$_{1-6}$alkylamino, di(C$_{1-6}$alkyl)amino, C$_{1-6}$alkyl, C$_{1-6}$alkoxy, C$_{2-6}$alkenyl, C$_{3-6}$alkenyl-O—, $C_{2-6}$alkynyl, or $C_{3-6}$alkynyl-O—, wherein $C_{1-6}$alkyl, $C_{1-6}$alkoxy, $C_{2-6}$alkenyl, $C_{3-6}$alkenyl-O—, $C_{2-6}$alkynyl, and $C_{3-6}$alkynyl-O—, are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or $R^6$ and $R^5$ together are =CH$_2$; or $R^6$ and $R^4$ together form a bridge across the ring containing $V^2$ selected from ethylene, —O—CH$_2$—, and —NH—CH$_2$—;

$V^1$ and $V^2$ are independently O, S, or CH$_2$;

BG$^1$, starting from the carbon in the ring containing $V^1$, and BG$^2$, starting from the carbon in the ring containing $V^2$, are independently —O—P(O)R$^p$—O—, —O—P(S)R$^p$—O—, —O—P(O)R$^p$—S—, —O—P(S)R$^p$—S—, —S—P(O)R$^p$—O—, —S—P(S)R$^p$—O—, —S—P(O)R$^p$—S—, —S—P(S)R$^p$—S—, —NH—P(O)R$^p$—O—, —O—P(O)R$^p$—NH—, —NH—P(S)R$^p$—O—, —O—P(S)R$^p$—NH—, or —NH—SO$_2$—NH—; wherein R$^p$ is, independently for each occurrence, hydroxyl, thiol, $C_{1-6}$alkyl, $C_{1-6}$alkoxy, $C_{3-6}$alkenyl-O—, $C_{3-6}$alkynyl-O—, -PEG-OH, borano (—BH$_3^-$), or —NR'R", wherein $C_{1-6}$alkyl, $C_{1-6}$alkoxy, $C_{3-6}$alkenyl-O—, and $C_{3-6}$alkynyl-O—, are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; and R' and R" are independently hydrogen or $C_{1-6}$alkyl optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or R' and R" on the same nitrogen together form a $C_{3-5}$heterocyclic ring;

$R^{a1}$, $R^{b1}$, $R^{a2}$, and $R^{b2}$ are independently hydrogen or $C_{1-3}$alkyl; and $B^1$ and $B^2$ are independently selected from:

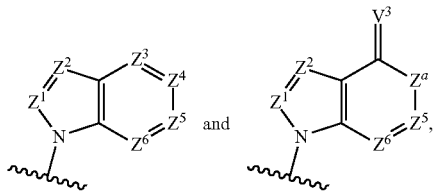

wherein $V^3$ is O or S, particularly O;

$Z^1$, $Z^2$, $Z^3$, $Z^4$, $Z^5$, and $Z^6$ are, independently for each occurrence, CR$^z$ or N;

$Z^a$ is O (except when $Z^5$ is N) or NR'; wherein

R$^z$ is, independently for each occurrence, hydrogen, halogen, azido, amino, $C_{1-6}$alkylamino, di($C_{1-6}$alkyl)amino, $C_{1-6}$alkyl, $C_{1-6}$alkoxy, $C_{2-6}$alkenyl, $C_{3-6}$alkenyl-O—, $C_{2-6}$alkynyl, $C_{3-6}$alkynyl-O—, —NO$_2$, —CN, —C(O)$C_{1-6}$alkyl, —CO$_2$H, —CO$_2C_{1-6}$alkyl, —S(O)$C_{1-6}$alkyl, —S(O)$_2C_{1-6}$alkyl, —C(O)NR', —C(O)NR'R", —SO$_2$NR'R", —OC(O)$C_{1-6}$alkyl, —NR'C(O)$C_{1-6}$alkyl, —N(R')C(O)NR'R", —N(R')SO$_2$NR'R", —N(R)SO$_2C_{1-6}$alkyl, or —OC(O)NR'R", wherein $C_{1-6}$alkyl, $C_{1-6}$alkoxy, $C_{2-6}$alkenyl, $C_{3-6}$alkenyl-O—, $C_{2-6}$alkynyl, and $C_{3-6}$alkynyl-O—, are, independently for each occurrence, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; and R' and R" are, independently for each occurrence, hydrogen or $C_{1-6}$alkyl optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or R' and R" on the same nitrogen together form a $C_{3-5}$heterocyclic ring;

or a pharmaceutically acceptable salt thereof.

In some instances, when the CDN (D) of Formula II is covalently bound to linker (L) in an ADC of Formula I or Ia, the CDN is covalently bound to the linker at the hydroxyl, thiol, amino, $C_{1-6}$alkylamino, or -PEG-OH group of the $R^1$ position.

In certain embodiments, $R^1$ is $C_{2-6}$alkyl substituted with a hydroxyl, thiol, amino, $C_{1-6}$alkylamino, or a -PEG-OH group. In some embodiments, $R^1$ is $C_{2-6}$alkyl substituted with a hydroxyl, thiol, amino, or $C_{1-6}$alkylamino. In certain embodiments, $R^1$ is $C_{2-6}$alkyl substituted with a thiol, amino, or $C_{1-6}$alkylamino. In some embodiments, $R^1$ is $C_{2-6}$alkyl substituted with a thiol or amino. In certain embodiments, $R^1$ is $C_{2-6}$alkyl substituted with a thiol. In some embodiments, $R^1$ is $C_{2-6}$alkyl substituted with an amino. For any of these embodiments, $R^1$ can be $C_{2-4}$alkyl, such as $C_{2-3}$alkyl, substituted with hydroxyl, thiol, amino, or $C_{1-6}$alkylamino, such as ethyl substituted with hydroxyl, thiol, amino, or $C_{1-6}$alkylamino.

In some embodiments, $R^1$ is $C_{2-4}$alkyl substituted with a hydroxyl group. In some such embodiments, $R^1$ is a $C_2$alkyl substituted with a hydroxyl. In other such embodiments, $R^1$ is a $C_3$alkyl substituted with a hydroxyl. In yet other such embodiments, $R^1$ is a $C_4$alkyl substituted with a hydroxyl.

In some embodiments, $R^1$ is $C_{2-4}$alkyl substituted with an amino (—NH$_2$) group. In some such embodiments, $R^1$ is a $C_2$alkyl substituted with an amino group. In other such embodiments, $R^1$ is a $C_3$alkyl substituted with an amino group. In yet other such embodiments, $R^1$ is a $C_4$alkyl substituted with an amino group.

In some embodiments, $R^1$ is $C_{2-4}$alkyl substituted with a thiol (—SH) group. In some such embodiments, $R^1$ is a $C_2$alkyl substituted with a thiol group. In other such embodiments, $R^1$ is a $C_3$alkyl substituted with a thiol group. In yet other such embodiments, $R^1$ is a $C_4$alkyl substituted with a thiol group.

In some embodiments, $R^1$ is a $C_{2-4}$alkyl substituted with a $C_{1-6}$alkylamino group. In some such embodiments, $R^1$ is a $C_2$alkyl substituted with a methylamino group. In other such embodiments, $R^1$ is a $C_3$alkyl substituted with a methylamino group. In yet other such embodiments, $R^1$ is a $C_3$alkyl substituted with a methylamino group.

In some embodiments, $R^3$ and $R^4$ are independently hydrogen, halogen, $C_{1-6}$alkyl, $C_{2-6}$alkenyl, or $C_{2-6}$alkynyl, wherein $C_{1-6}$alkyl, $C_{2-6}$alkenyl, and $C_{2-6}$alkynyl are unsubstituted. In certain embodiments, $R^3$ and $R^4$ are independently hydrogen, $C_{1-6}$alkyl, or $C_{2-6}$alkynyl, wherein $C_{1-6}$alkyl and $C_{2-6}$alkynyl are unsubstituted.

In some embodiments, one of $R^3$ and $R^4$ is hydrogen and the other is halogen, $C_{1-6}$alkyl, $C_{2-6}$alkenyl, or $C_{2-6}$alkynyl, wherein $C_{1-6}$alkyl, $C_{2-6}$alkenyl, and $C_{2-6}$alkynyl are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido. In some embodiments, one of $R^3$ and $R^4$ is hydrogen and the other is halogen, $C_{1-6}$alkyl, $C_{2-6}$alkenyl, or $C_{2-6}$alkynyl, wherein $C_{1-6}$alkyl, $C_{2-6}$alkenyl, and $C_{2-6}$alkynyl are unsubstituted. In certain embodiments, one of $R^3$ and $R^4$ is hydrogen and the other is $C_{1-6}$alkyl or $C_{2-6}$alkynyl, wherein $C_{1-6}$alkyl and $C_{2-6}$alkynyl are unsubstituted. In some embodiments, both $R^3$ and $R^4$ are hydrogen.

In certain embodiments, $R^2$ is hydrogen, halogen, hydroxyl, azido, amino, $C_{1-6}$alkyl, or $C_{1-6}$alkoxy, wherein $C_{1-6}$alkyl and $C_{1-6}$alkoxy are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido. In some embodiments, $R^2$ is hydrogen, halogen, hydroxyl, azido, amino, $C_{1-6}$alkyl, or $C_{1-6}$alkoxy, wherein $C_{1-6}$alkyl and $C_{1-6}$alkoxy are unsubstituted. In certain embodiments, $R^2$ is hydrogen or halogen, such as fluorine. In instances, $R^2$ is hydrogen.

In some embodiments, $R^5$ and $R^6$ are independently hydrogen, halogen, hydroxyl, azido, amino, $C_{1-6}$alkyl, or $C_{1-6}$alkoxy, wherein $C_{1-6}$alkyl and $C_{1-6}$alkoxy are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido. In certain embodiments, $R^5$ and $R^6$ are independently hydrogen, halogen, hydroxyl, azido, amino, $C_{1-6}$alkyl, or $C_{1-6}$alkoxy, wherein $C_{1-6}$alkyl and $C_{1-6}$alkoxy are unsubstituted. In some embodiments, $R^5$ and $R^6$ are independently hydrogen, halogen, or hydroxyl. In certain embodiments, $R^5$ and $R^6$ together are =$CH_2$.

In certain embodiments, $R^5$ is hydrogen and $R^6$ is hydrogen, halogen, hydroxyl, azido, amino, $C_{1-6}$alkylamino, di($C_{1-6}$alkyl)amino, $C_{1-6}$alkyl, $C_{1-6}$alkoxy, $C_{2-6}$alkenyl, $C_{3-6}$alkenyl-O—, $C_{2-6}$alkynyl, or $C_{3-6}$alkynyl-O—, wherein $C_{1-6}$alkyl, $C_{1-6}$alkoxy, $C_{2-6}$alkenyl, $C_{3-6}$alkenyl-O—, $C_{2-6}$alkynyl, and $C_{3-6}$alkynyl-O—, are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido. In some embodiments, $R^5$ is hydrogen and $R^6$ is hydrogen, halogen, hydroxyl, azido, amino, $C_{1-6}$alkyl, or $C_{1-6}$alkoxy, wherein $C_{1-6}$alkyl and $C_{1-6}$alkoxy are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido. In certain embodiments, $R^5$ is hydrogen and $R^6$ is hydrogen, halogen, hydroxyl, azido, amino, $C_{1-6}$alkyl, or $C_{1-6}$alkoxy, wherein $C_{1-6}$alkyl and $C_{1-6}$alkoxy are unsubstituted. In some embodiments, $R^5$ is hydrogen and $R^6$ is hydrogen, halogen (such as fluorine or chlorine), hydroxyl, or unsubstituted $C_{1-6}$alkoxy (such as methoxy). In some embodiments, $R^5$ is hydrogen and $R^6$ is halogen, such as fluorine or chlorine. In certain instances, $R^5$ is hydrogen and $R^6$ is hydroxyl. In other embodiments, $R^5$ is hydrogen and $R^6$ is unsubstituted $C_{1-6}$alkoxy, such as methoxy.

In certain embodiments, $R^6$ is hydrogen and $R^5$ is hydrogen, halogen, hydroxyl, azido, amino, $C_{1-6}$alkylamino, di($C_{1-6}$alkyl)amino, $C_{1-6}$alkyl, $C_{1-6}$alkoxy, $C_{2-6}$alkenyl, $C_{3-6}$alkenyl-O—, $C_{2-6}$alkynyl, or $C_{3-6}$alkynyl-O—, wherein $C_{1-6}$alkyl, $C_{1-6}$alkoxy, $C_{2-6}$alkenyl, $C_{3-6}$alkenyl-O—, $C_{2-6}$alkynyl, and $C_{3-6}$alkynyl-O—, are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido. In some embodiments, $R^6$ is hydrogen and $R^5$ is hydrogen, halogen, hydroxyl, azido, amino, $C_{1-6}$alkyl, or $C_{1-6}$alkoxy, wherein $C_{1-6}$alkyl and $C_{1-6}$alkoxy are, independently, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido. In certain embodiments, $R^6$ is hydrogen and $R^5$ is hydrogen, halogen, hydroxyl, azido, amino, $C_{1-6}$alkyl, or $C_{1-6}$alkoxy, wherein $C_{1-6}$alkyl and $C_{1-6}$alkoxy are unsubstituted. In some embodiments, $R^6$ is hydrogen and $R^5$ is hydrogen, halogen (such as fluorine or chlorine), hydroxyl, or unsubstituted $C_{1-6}$alkoxy (such as methoxy). In some embodiments, $R^6$ is hydrogen and $R^5$ is halogen, such as fluorine or chlorine. In certain instances, $R^6$ is hydrogen and $R^5$ is hydroxyl. In other embodiments, $R^5$ is hydrogen and $R^6$ is unsubstituted $C_{1-6}$alkoxy, such as methoxy.

In some embodiments, one of $R^5$ and $R^6$ is hydrogen and the other is halogen, such as fluorine. In certain embodiments, $R^5$ is hydrogen and $R^6$ is halogen, such as fluorine. In certain embodiments, $R^6$ is hydrogen and $R^5$ is halogen, such as fluorine.

In certain instances, both $R^5$ and $R^6$ are hydrogen or halogen, such as both $R^5$ and $R^6$ are hydrogen, or both $R^5$ and $R^6$ are halogen, such as fluorine.

In some embodiments, $R^5$ is hydrogen. In other embodiments, $R^5$ is hydroxyl. In other embodiments, $R^5$ is halogen. For instance, $R^5$ can be fluorine, bromine, or chlorine.

In some embodiments, $R^6$ is hydrogen. In other embodiments, $R^6$ is hydroxyl. In other embodiments, $R^6$ is methoxy. In other embodiments, $R^6$ is halogen. For instance, $R^6$ can be fluorine, bromine, or chlorine.

In certain embodiments, $V^1$ and $V^2$ are independently O or S. In some embodiments, $V^1$ and $V^2$ are independently O or $CH_2$. In some embodiments, $V^1$ and $V^2$ are both O. In certain embodiments, $V^1$ and $V^2$ are both S. In certain embodiments, at least one of $V^1$ and $V^2$ is O. In some embodiments, at least one of $V^1$ and $V^2$ is S. In certain embodiments, at least one of $V^1$ and $V^2$ is $CH_2$.

In some embodiments, $BG^1$ and $BG^2$ are independently —O—P(O)$R^p$—O— or —P(S)$R^p$—O—. In certain embodiments, at least one of $BG^1$ and $BG^2$ is —O—P(O)$R^p$—O—. In some embodiments, at least one of $BG^1$ and $BG^2$ is —O—P(S)$R^p$—O—. In certain embodiments, $BG^1$ is —O—P(O)$R^p$—O— and $BG^2$ is —O—P(S)$R^p$—O—. In some embodiments, $BG^1$ is —O—P(O)$R^p$—O— and $BG^2$ is —O—P(S)$R^p$—O—. In certain embodiments, both $BG^1$ and $BG^2$ are —O—P(O)$R^p$—O—.

In certain embodiments, $R^p$ is, independently for each occurrence, hydroxyl, thiol, $C_{1-6}$alkyl, borano (—$BH_3^-$), or —NR'R". In some embodiments, $R^p$ is, independently for each occurrence, hydroxyl or thiol. In certain embodiments, $R^p$ is hydroxyl. In some embodiments, $R^p$ is thiol. In some embodiments, one $R^p$ is hydroxyl and the other is thiol.

In some embodiments, both $BG^1$ and $BG^2$ are —O—P(O)$R^p$—O— and $R^p$ is, independently for each occurrence, hydroxyl, thiol, $C_{1-6}$alkyl, borano (—$BH_3^-$), or —NR'R". In certain embodiments, both $BG^1$ and $BG^2$ are —O—P(O)$R^p$—O— and $R^p$ is, independently for each occurrence, hydroxyl or thiol. In some embodiments, both $BG^1$ and $BG^2$ are —O—P(O)$R^p$—O— and $R^p$ is hydroxyl. In other embodiments, both $BG^1$ and $BG^2$ are —O—P(O)$R^p$—O— and $R^p$ is thiol. In some embodiments, $BG^1$ is —O—P(O)$R^p$—O—, wherein $R^p$ is hydroxyl, and $BG^2$ is —O—P(O)$R^p$—O—, wherein $R^p$ is thiol. In other embodiments, $BG^1$ is —O—P(O)$R^p$—O—, wherein $R^p$ is thiol, and $BG^2$ is —O—P(O)$R^p$—O—, wherein $R^p$ is hydroxyl.

In certain instances, at least one of $BG^1$ and $BG^2$ is —NH—P(O)$R^p$—O—, —O—P(O)$R^p$—NH—, —NH—P(S)$R^p$—O—, or —O—P(S)$R^p$—NH—. In some instances, at least one of $BG^1$ and $BG^2$ is —NH—P(O)$R^p$—O—, or —O—P(O)$R^p$—NH—. In certain embodiments, both $BG^1$ and $BG^2$ are —NH—P(O)$R^p$—O— or —O—P(O)$R^p$—NH—. In certain instances, at least one of $BG^1$ and $BG^2$ is —NH—P(O)$R^p$—O—, —O—P(O)$R^p$—NH—, —NH—P(S)$R^p$—O—, or —O—P(S)$R^p$—NH—; and $R^p$ is, independently for each occurrence, hydroxyl or thiol. In some instances, at least one of $BG^1$ and $BG^2$ is —NH—P(O)$R^p$—O—, or —O—P(O)$R^p$—NH—; and $R^p$ is, independently for each occurrence, hydroxyl or thiol. In certain embodiments, both $BG^1$ and $BG^2$ are —NH—P(O)$R^p$—O— or —O—P(O)$R^p$—NH—; and $R^p$ is, independently for each occurrence, hydroxyl or thiol. In some embodiments, both $BG^1$ and $BG^2$ are —NH—P(O)$R^p$—O— or —O—P(O)$R^p$—NH—; and $R^p$ is hydroxyl. In other embodiments, both $BG^1$ and $BG^2$ are —NH—P(O)$R^p$—O— or —O—P(O)$R^p$—NH—; and $R^p$ is thiol.

In certain embodiments, when $R^p$ is —NR'R", R' and R" are independently hydrogen or unsubstituted $C_{1-6}$alkyl, or R' and R" together on the same nitrogen form a $C_{3-5}$heterocyclic ring, such as morpholine, pyrrolidine, or piperazine.

In certain embodiments, $B^1$ and $B^2$ are the same nucleobase. In other embodiments, $B^1$ and $B^2$ are different nucleobases. In some embodiments, $B^1$ and $B^2$ are both a purine nucleobase. In certain embodiments, $B^1$ and $B^2$ are both a pyrimidine nucleobase. In some embodiments, $B^1$ is a purine nucleobase, and $B^2$ is a pyrimidine nucleobase. In certain embodiments, $B^1$ is a pyrimidine nucleobase, and $B^2$ is a purine nucleobase.

In some instances, $B^1$ and $B^2$ are independently selected from adenine, guanine, thymine, uracil, and cytosine and modified variants of these. In certain embodiments, both $B^1$ and $B^2$ are adenine or a modified variant thereof. In some embodiments, both $B^1$ and $B^2$ are guanine or a modified variant thereof. In certain embodiments, $B^1$ is guanine or a modified variant thereof, and $B^2$ is adenine or a modified variant thereof. In certain embodiments, $B^1$ is adenine or a modified variant thereof, and $B^2$ is guanine or a modified variant thereof.

In some embodiments, $B^1$ and $B^2$ are independently selected from:

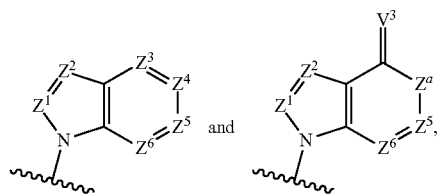

wherein $Z^1$, $Z^2$, $Z^3$, $Z^4$, $Z^5$, and $Z^6$ are, independently for each occurrence, $CR^z$ or N;

$Z^a$ is O (except when $Z^5$ is N) or NR'; wherein $R^z$ is, independently for each occurrence, hydrogen, halogen, azido, amino, $C_{1-6}$alkylamino, di($C_{1-6}$alkyl)amino, $C_{1-6}$alkyl, $C_{1-6}$alkoxy, —C(O)$C_{1-6}$alkyl, —$CO_2$H, —$CO_2C_{1-6}$alkyl, —C(O)NR', —C(O)NR'R", —OC(O)$C_{1-6}$alkyl, —NR'C(O)$C_{1-6}$alkyl, —N(R')C(O)NR'R", or —OC(O)NR'R", wherein $C_{1-6}$alkyl and $C_{1-6}$alkoxy are, independently for each occurrence, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; and R' and R" are, independently for each occurrence, hydrogen or $C_{1-6}$alkyl optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_6$alkyl, —N($C_{1-3}$alkyl)C(O)$C_{1-6}$alkyl, amino, $C_{1-6}$alkylamino, di($C_{1-6}$alkyl)amino, oxo, and azido; or R' and R" on the same nitrogen together form a $C_{3-5}$heterocyclic ring.

In some embodiments, for $B^1$ and $B^2$, one or both occurrences of $Z^1$ are $CR^z$ (such as CH or $CNH_2$). In certain embodiments, one or both occurrences of $Z^5$ are $CR^z$ (such as CH or $CNH_2$). In some embodiments, one or both occurrences of $Z^1$ are $CR^z$ (such as CH or $CNH_2$), and one or both occurrences of $Z^5$ are $CR^z$ (such as CH or $CNH_2$). In certain embodiments, both occurrences of $Z^1$ are $CR^z$ (such as CH or $CNH_2$), and both occurrences of $Z^5$ are $CR^z$ (such as CH or $CNH_2$).

In certain instances, for $B^1$ and $B^2$, $Z^3$ is $CR^z$ (such as CH or $CNH_2$). In certain embodiments, $Z^3$ is $CR^z$ (such as CH or $CNH_2$), and one or both occurrences of $Z^1$ are $CR^z$(such as CH or $CNH_2$). In certain embodiments, $Z^3$ is $CR^z$ (such as CH or $CNH_2$), and one or both occurrences of $Z^5$ are $CR^z$ (such as CH or $CNH_2$). In certain embodiments, $Z^3$ is $CR^z$(such as CH or $CNH_2$), both occurrences of $Z^1$ are $CR^z$ (such as CH or $CNH_2$), and both occurrences of $Z^5$ are $CR^z$ (such as CH or $CNH_2$).

In some instances, for $B^1$ and $B^2$, $Z^a$ is NR', such as NH or $NC_{1-6}$alkyl. In other embodiments, $Z^a$ is O.

In embodiments instances, one or both occurrences of $Z^2$ are N. In certain embodiments, $Z^4$ is N. In some embodiments, one or both occurrences of $Z^2$ are N, and $Z^4$ is N. In certain embodiments, both occurrences of $Z^2$ are N, and $Z^4$ is N.

In embodiments instances, one or both occurrences of $Z^6$ are N. In certain embodiments, $Z^4$ is N. In some embodiments, one or both occurrences of $Z^6$ are N, and $Z^4$ is N. In certain embodiments, both occurrences of $Z^6$ are N, and $Z^4$ is N. In some embodiments, one or both occurrences of $Z^6$ are N, and one or both occurrences of $Z^2$ are N. In some embodiments, both occurrences of $Z^6$ are N, and both occurrences of $Z^2$ are N.

In some embodiments, $B^1$ and $B^2$ are independently selected from:

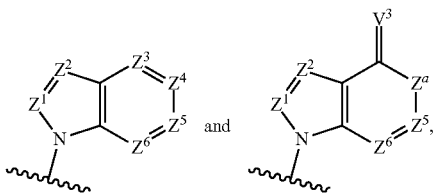

wherein $Z^1$, $Z^3$, and $Z^5$ are, independently for each occurrence, $CR^z$ or N;

$Z^a$ is O (except when $Z^5$ is N) or NR'; wherein $R^z$ is, independently for each occurrence, hydrogen, halogen, azido, amino, $C_{1-6}$alkylamino, di($C_{1-6}$alkyl) amino, $C_{1-6}$alkyl, $C_{1-6}$alkoxy, —C(O)$C_{1-6}$alkyl, —CO$_2$H, —CO$_2$$C_{1-6}$alkyl, —C(O)NR', —C(O)NR'R", —OC(O)$C_{1-6}$alkyl, —NR'C(O)$C_{1-6}$alkyl, —N(R')C(O)NR'R", or —OC(O)NR'R", wherein $C_{1-6}$alkyl and $C_{1-6}$alkoxy are, independently for each occurrence, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; and R' and R" are, independently for each occurrence, hydrogen or $C_{1-6}$alkyl optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or R' and R" on the same nitrogen together form a $C_{3-5}$heterocyclic ring.

In some embodiments, $B^1$ and $B^2$ are independently selected from:

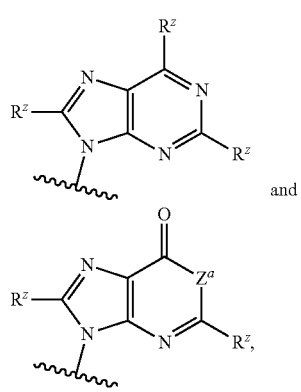

wherein $Z^a$ is NR'; wherein $R^z$ is, independently for each occurrence, hydrogen, halogen, azido, amino, $C_{1-6}$alkylamino, di($C_{1-6}$alkyl) amino, $C_{1-6}$alkyl, $C_{1-6}$alkoxy, —C(O)$C_{1-6}$alkyl, —CO$_2$H, —CO$_2$$C_{1-6}$alkyl, —C(O)NR', —C(O)NR'R", —OC(O)$C_{1-6}$alkyl, —NR'C(O)$C_{1-6}$alkyl, —N(R')C(O)NR'R", or —OC(O)NR'R", wherein $C_{1-6}$alkyl and $C_{1-6}$alkoxy are, independently for each occurrence, optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; and R' and R" are, independently for each occurrence, hydrogen or $C_{1-6}$alkyl optionally substituted with one or more groups selected from halogen, thiol, hydroxyl, carboxyl, $C_{1-6}$alkoxy, $C_{1-6}$hydroxyalkoxy, —OC(O)$C_{1-6}$alkyl, —N(H)C(O)$C_{1-6}$alkyl, —N($C_{1-3}$alkyl)C(O)$C_{1-6}$alkyl, amino, $C_{1-6}$alkylamino, di($C_{1-6}$alkyl)amino, oxo, and azido; or R' and R" on the same nitrogen together form a $C_{3-5}$heterocyclic ring.

In certain embodiments, $B^1$ and $B^2$ are independently selected from:

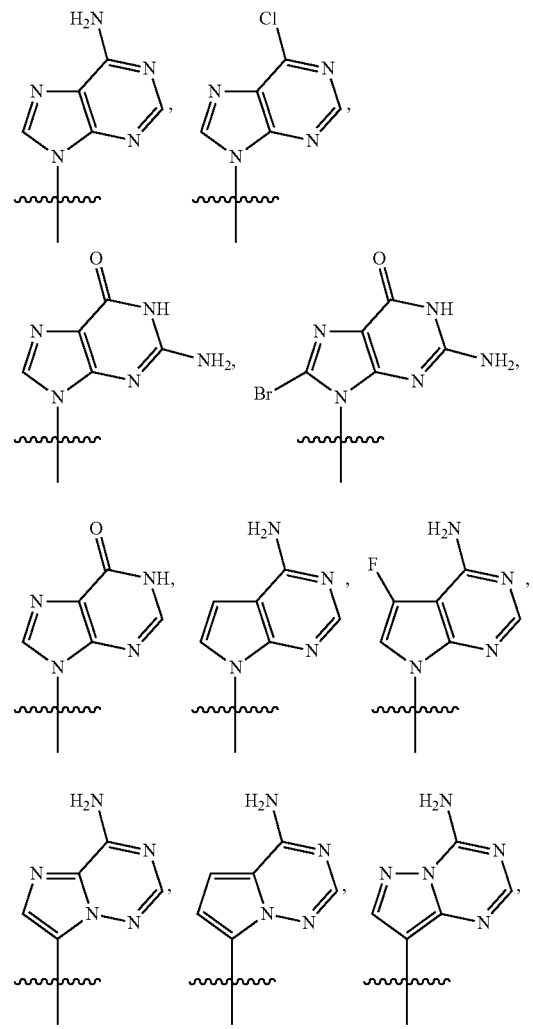

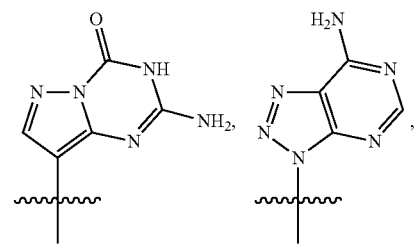

25
-continued
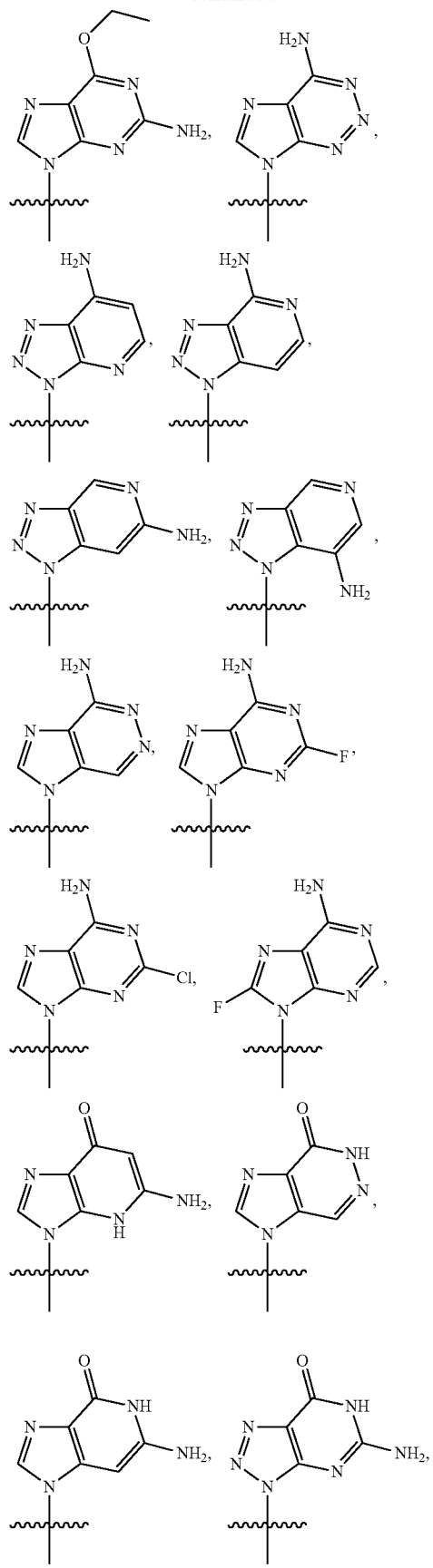
26
-continued
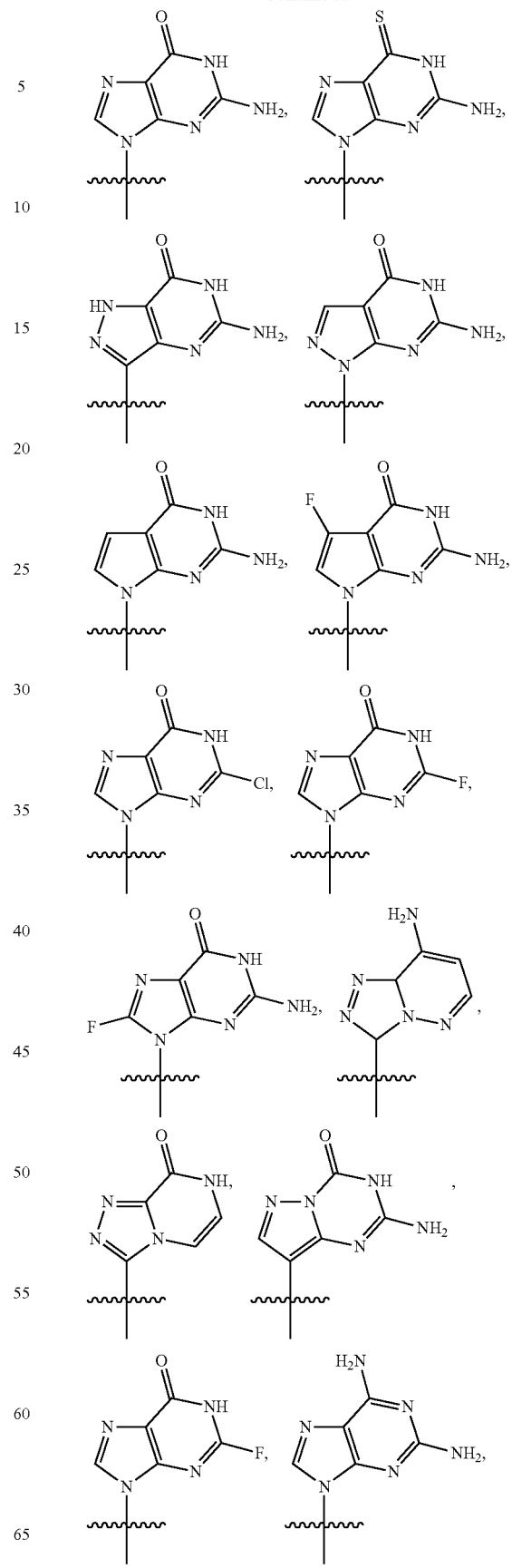

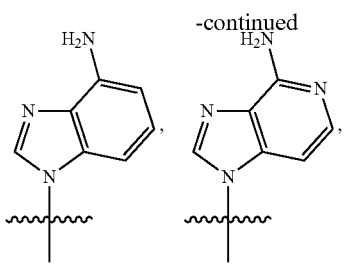

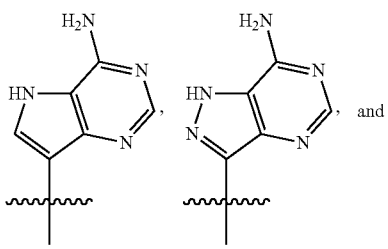

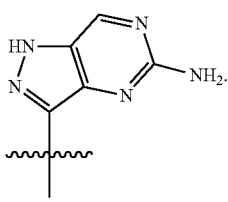 [SMILES: *c1n[nH]c2cnc(N)nc12]

In certain embodiments, $R^{a1}$, $R^{b1}$, $R^{a2}$, and $R^{b2}$ are all hydrogen. In some embodiments, at least one of $R^{a1}$, $R^{b1}$, $R^{a2}$, and $R^{b2}$ is $C_{1-3}$alkyl, such as methyl. In certain instances, $R^{a1}$ and $R^{a2}$ are $C_{1-3}$alkyl, such as methyl. In some embodiments, one of $R^{a1}$, $R^{b1}$, $R^{a2}$, and $R^{b2}$ is $C_{1-3}$alkyl, such as methyl.

In certain instances, the CDN has the structure of Formula IIa:

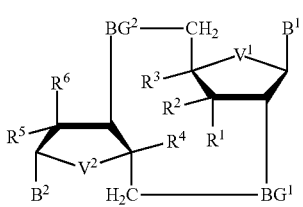

Formula IIa wherein $R^1$, $R^2$, $R^3$, $R^4$, $R^5$, and $R^6$; $V^1$ and $V^2$; $BG^1$ and $BG^2$; and $B^1$ and $B^2$ are as defined above for Formula II;

or a pharmaceutically acceptable salt thereof.

In some embodiments, of Formula IIa, $R^1$ is $C_{2-4}$alkyl, such as ethyl, substituted with hydroxyl, thiol, or amino. In certain embodiments, of Formula IIa, $R^1$ is $C_{2-4}$alkyl, such as ethyl, substituted with thiol or amino.

In certain instances, the CDN has the structure of Formula IIb:

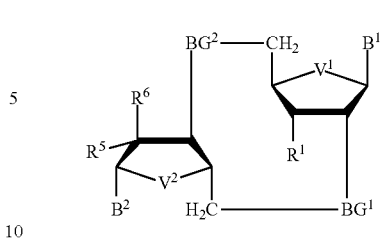

Formula IIb wherein $R^1$, $R^5$, and $R^6$; $V^1$ and $V^2$; $BG^1$ and $BG^2$; and $B^1$ and $B^2$ are as defined above for Formula II;

or a pharmaceutically acceptable salt thereof.

In some embodiments, of Formula IIb, $R^1$ is $C_{2-4}$alkyl, such as ethyl, substituted with hydroxyl, thiol, or amino. In certain embodiments, of Formula IIb, $R^1$ is $C_{2-4}$alkyl, such as ethyl, substituted with thiol or amino.

In certain instances, the CDN has the structure of Formula IIc:

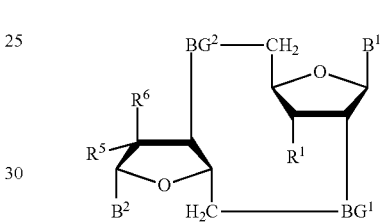

Formula IIc wherein $R^1$, $R^5$, and $R^6$; $BG^1$ and $BG^2$; and $B^1$ and $B^2$ are as defined above for Formula II;

or a pharmaceutically acceptable salt thereof.

In some embodiments, of Formula IIc, $R^1$ is $C_{2-4}$alkyl, such as ethyl, substituted with hydroxyl, thiol, or amino. In certain embodiments, of Formula IIc, $R^1$ is $C_{2-4}$alkyl, such as ethyl, substituted with thiol or amino.

In certain instances, the CDN has the structure of Formula IId:

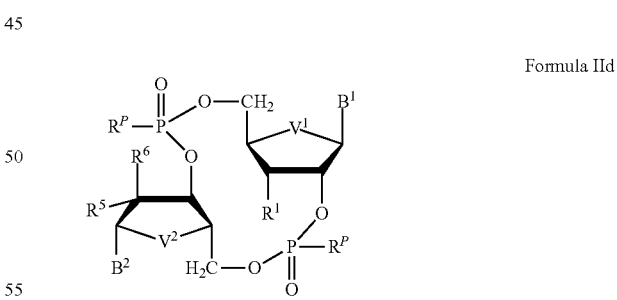

Formula IId wherein $R^1$, $R^5$, $R^6$, and $R^P$; $V^1$ and $V^2$; and $B^1$ and $B^2$ are as defined above for Formula II;

or a pharmaceutically acceptable salt thereof.

In some embodiments, of Formula IId, $R^1$ is $C_{2-4}$alkyl, such as ethyl, substituted with hydroxyl, thiol, or amino. In certain embodiments, of Formula IId, $R^1$ is $C_{2-4}$alkyl, such as ethyl, substituted with thiol or amino.

In certain instances, the CDN has the structure of Formula IIe:

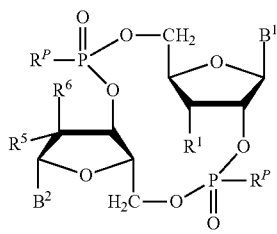

Formula IIe wherein $R^1$, $R^5$, $R^6$, and $R^P$; and $B^1$ and $B^2$ are as defined above for Formula II;
or a pharmaceutically acceptable salt thereof.

In some embodiments, of Formula IIe, $R^1$ is $C_{2-4}$alkyl, such as ethyl, substituted with hydroxyl, thiol, or amino. In certain embodiments, of Formula IIe, $R^1$ is $C_{2-4}$alkyl, such as ethyl, substituted with thiol or amino.

In certain instances, the CDN has the structure of Formula IIf:

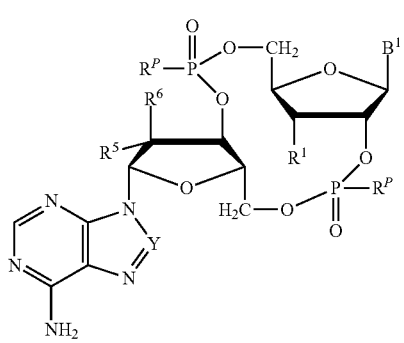

Formula IIf wherein
Y and Z are independently CH or N; and
$R^1$, $R^5$, $R^6$, $R^P$, and $B^1$ are as defined above for Formula II;
or a pharmaceutically acceptable salt thereof.

In some embodiments, of Formula IIf, $R^1$ is $C_{2-4}$alkyl, such as ethyl, substituted with hydroxyl, thiol, or amino. In certain embodiments, of Formula IIf, $R^1$ is $C_{2-4}$alkyl, such as ethyl, substituted with thiol or amino.

In certain instances, the CDN has the structure of Formula IIg:

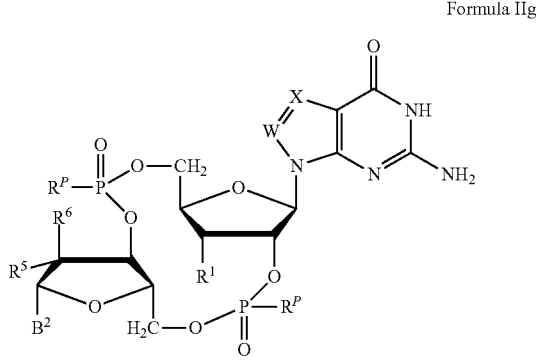

Formula IIg wherein
W and X are independently CH or N; and
$R^1$, $R^5$, $R^6$, $R^P$, and $B^2$ are as defined above for Formula II;
or a pharmaceutically acceptable salt thereof.

In some embodiments, of Formula IIg, $R^1$ is $C_{2-4}$alkyl, such as ethyl, substituted with hydroxyl, thiol, or amino. In certain embodiments, of Formula IIg, $R^1$ is $C_{2-4}$alkyl, such as ethyl, substituted with thiol or amino.

In certain instances, the CDN has the structure of Formula IIh:

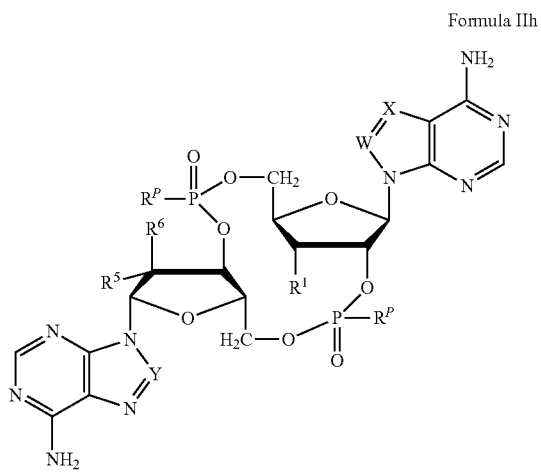

Formula IIh wherein
W, X, Y, and Z are independently CH or N; and
$R^1$, $R^5$, $R^6$, and $R^P$ are as defined above for Formula II;
or a pharmaceutically acceptable salt thereof.

In some embodiments, of Formula IIh, $R^1$ is $C_{2-4}$alkyl, such as ethyl, substituted with hydroxyl, thiol, or amino. In certain embodiments, of Formula IIh, $R^1$ is $C_{2-4}$alkyl, such as ethyl, substituted with thiol or amino.

In certain instances, the CDN has the structure of Formula IIi:

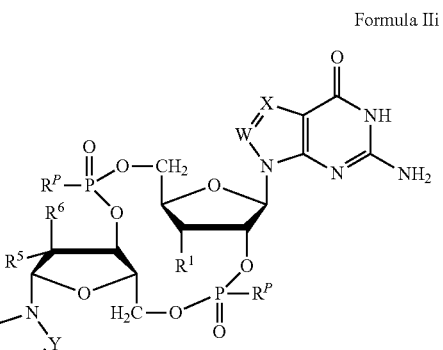

Formula IIi wherein
W, X, Y, and Z are independently CH or N; and
$R^1$, $R^5$, $R^6$, and $R^P$ are as defined above for Formula II;
or a pharmaceutically acceptable salt thereof.

In some embodiments, of Formula IIi, $R^1$ is $C_{2-4}$alkyl, such as ethyl, substituted with hydroxyl, thiol, or amino. In certain embodiments, of Formula IIi, $R^1$ is $C_{2-4}$alkyl, such as ethyl, substituted with thiol or amino.

In certain instances, the CDN has the structure of Formula IIj:

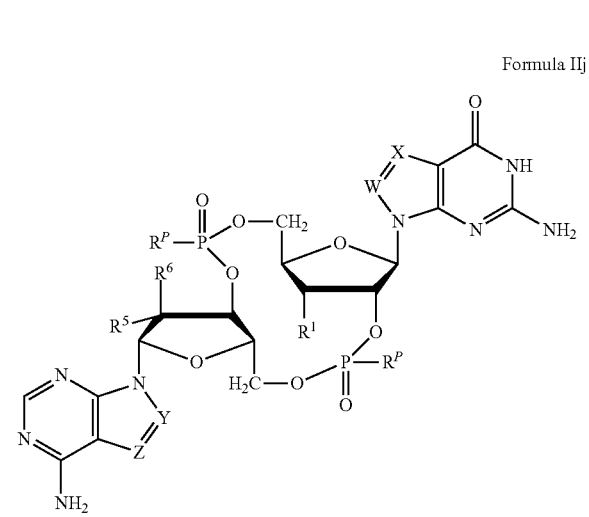

Formula IIj wherein

W, X, Y, and Z are independently CH or N; and $R^1$, $R^5$, $R^6$, and $R^P$ are as defined above for Formula II;

or a pharmaceutically acceptable salt thereof.

In some embodiments, of Formula IIj, $R^1$ is $C_{2-4}$alkyl, such as ethyl, substituted with hydroxyl, thiol, or amino. In certain embodiments, of Formula IIj, $R^1$ is $C_{2-4}$alkyl, such as ethyl, substituted with thiol or amino.

In certain instances, the CDN has the structure of Formula IIk:

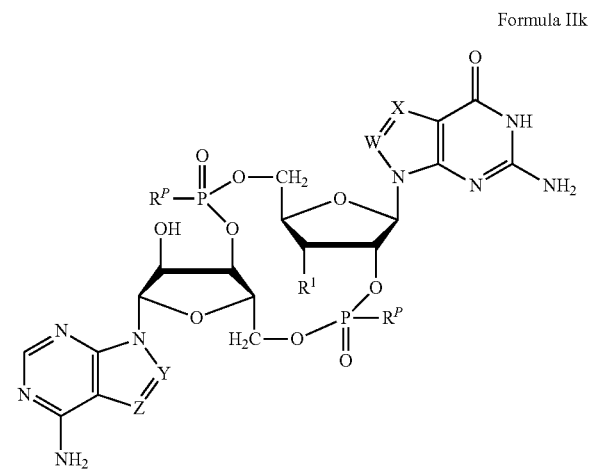

Formula IIk wherein

W, X, Y, and Z are independently CH or N; and $R^1$ and $R^P$ are as defined above for Formula II;

or a pharmaceutically acceptable salt thereof.

In some embodiments, of Formula IIk, $R^1$ is $C_{2-4}$alkyl, such as ethyl, substituted with hydroxyl, thiol, or amino. In certain embodiments, of Formula IIk, $R^1$ is $C_{2-4}$alkyl, such as ethyl, substituted with thiol or amino.

In certain instances, the CDN has the structure of Formula IIm:

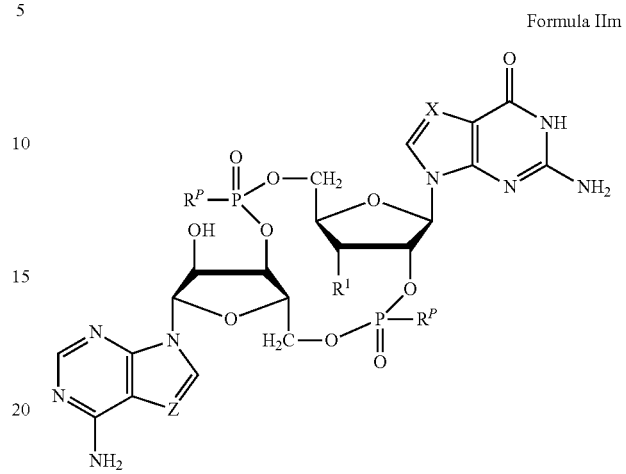

Formula IIm wherein $R^1$ is $C_{2-4}$alkyl, such as ethyl, substituted with a thiol or amino group;

X and Z are independently CH or N;

$R^P$, independently for each occurrence, is hydroxyl or thiol;

or a pharmaceutically acceptable salt thereof.

In some embodiments, the CDN has the structure of Formula IIn:

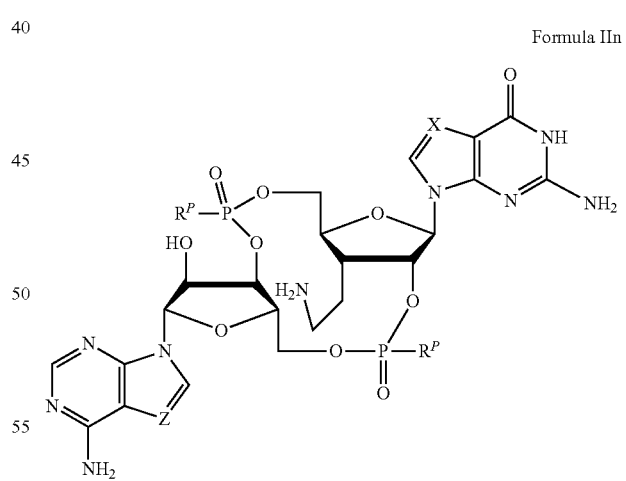

Formula IIn wherein

X and Z are independently CH or N; and $R^P$, independently for each occurrence, is hydroxyl or thiol;

or a pharmaceutically acceptable salt thereof.

In some embodiments, the CDN has the structure of Formula IIo:

Formula IIo

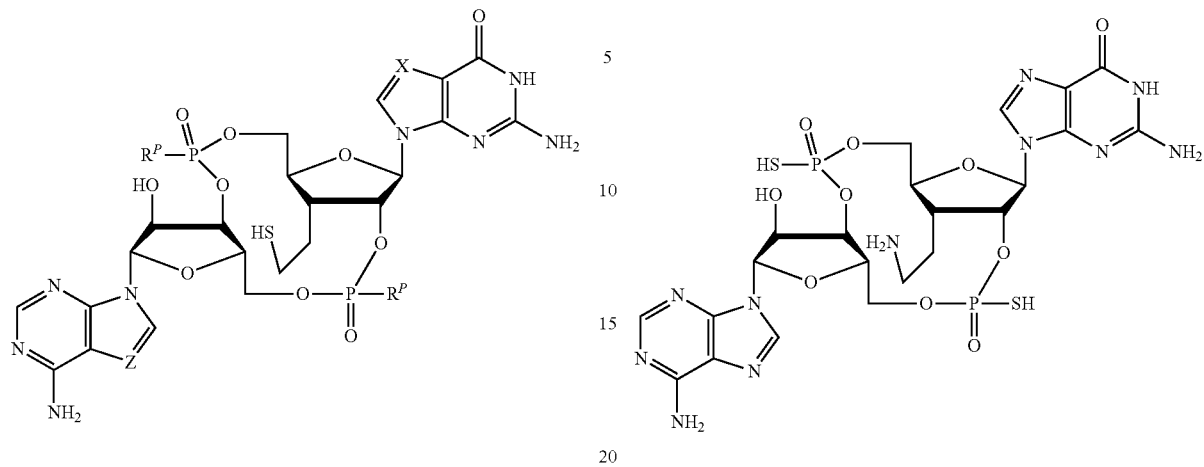

wherein

X and Z are independently CH or N; and $R^P$, independently for each occurrence, is hydroxyl or thiol;

or a pharmaceutically acceptable salt thereof.

In some embodiments, in Formulas IId-k and IIm-o, both occurrences of $R^P$ are hydroxyl. In certain embodiments, in Formulas IId-k and IIm-o, both occurrences of $R^P$ are thiol. In some embodiments, in Formulas IId-k and IIm-o, the occurrence of $R^P$ that corresponds with $BG^1$ (the upper left $R^P$) is hydroxyl and the occurrence of $R^P$ that corresponds with $BG^2$ (the lower right $R^P$) is thiol. In certain embodiments, in Formulas IId-k and IIm-o, the occurrence of $R^P$ that corresponds with $B^{G1}$ is thiol and the occurrence of $R^P$ that corresponds with $BG^2$ is hydroxyl.

In one embodiment, the CDN has the following structure (CDN-A):

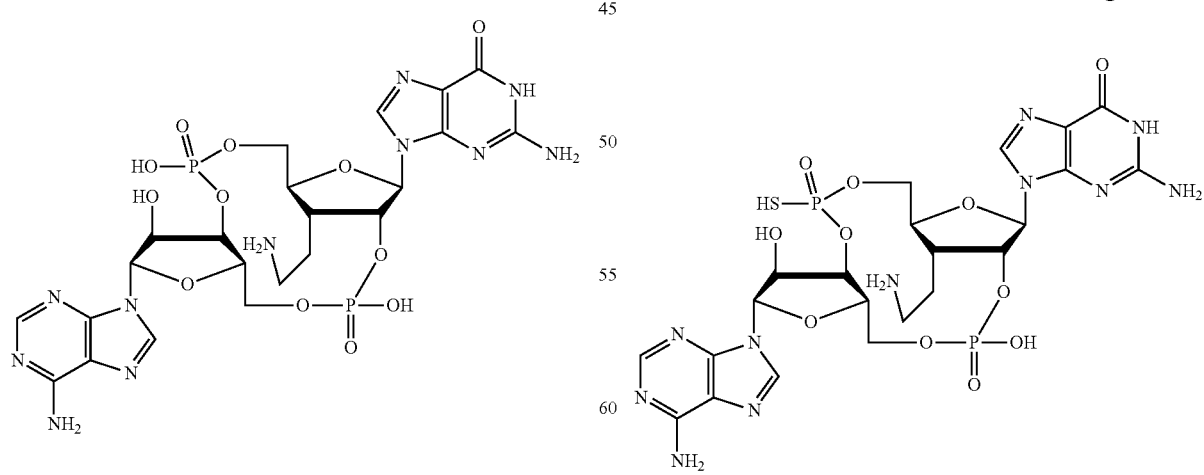

or a pharmaceutically acceptable salt thereof.

In one embodiment, the CDN has the following structure:

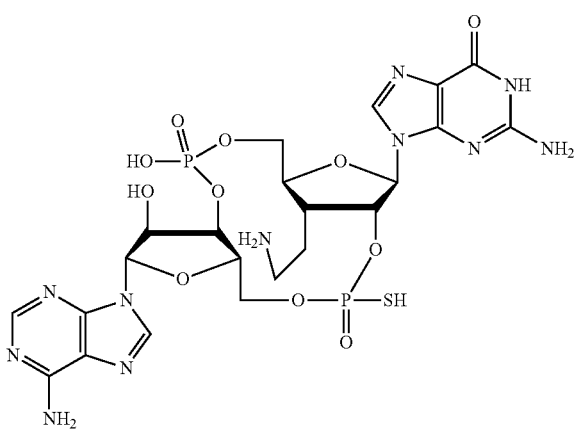

or a pharmaceutically acceptable salt thereof.

In one embodiment, the CDN has the following structure:

or a pharmaceutically acceptable salt thereof.

In one embodiment, the CDN has the following structure or a pharmaceutically acceptable salt thereof.

In one embodiment, the CDN has the following structure (CDN-B):

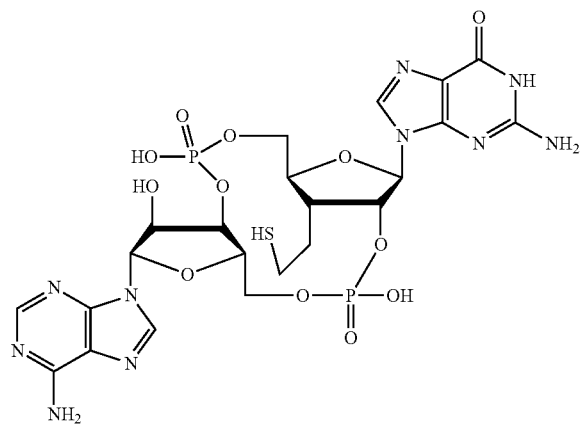

or a pharmaceutically acceptable salt thereof.

In one embodiment, the CDN has the following structure:

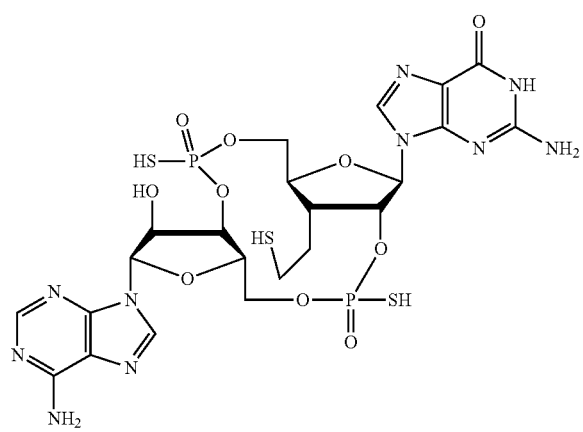

or a pharmaceutically acceptable salt thereof.

In one embodiment, the CDN has the following structure:

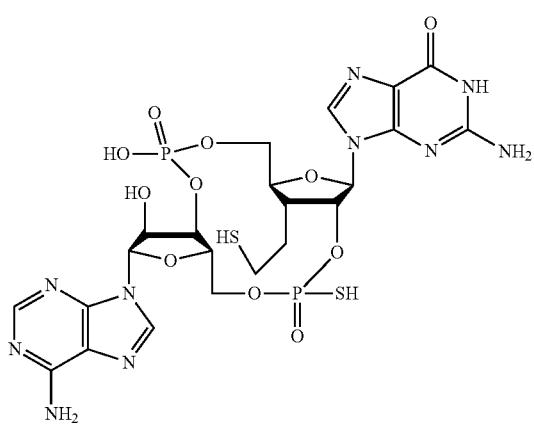

or a pharmaceutically acceptable salt thereof.

In one embodiment, the CDN has the following structure

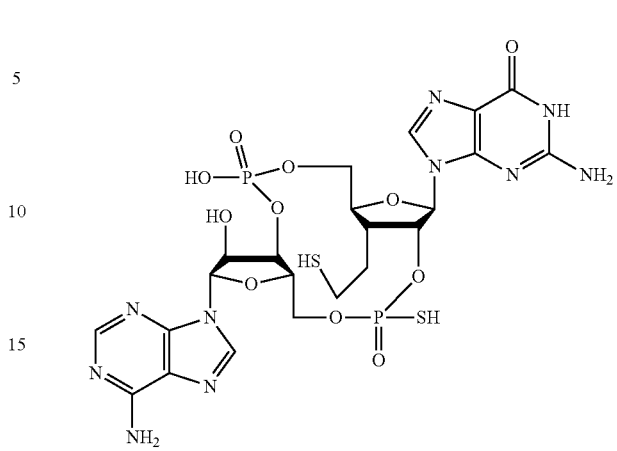

or a pharmaceutically acceptable salt thereof.

The present disclosure provides methods of making ADCs of Formula I by conjugating a CDN of Formula II (e.g., CDN-A or CDN-B) to an antibody via a linker. The CDN of Formula II can be conjugated to the antibody via a cleavable or non-cleavable linker. In particular embodiments, the CDN is released into a tumor cell, a cancer-related immune cell, or the tumor microenvironment upon cleavage of the linker.

In the ADCs of Formula I, wherein the CDN (D) is of Formula II (e.g., CDN-A or CDN-B), the CDN may be covalently bound to linker (L) at the hydroxyl, thiol, amino, $C_{1-6}$alkylamino, or -PEG-OH group of $R^1$ of the CDN of Formula II. It is understood that the CDN of Formulas II, may also not be bound to a linker (L) or ADC and maybe be administered in the methods described herein, either alone, in combination with the ADCs described herein, in combination with other active agents (such as immuno-oncology agents, such as immune checkpoint inhibitors, including anti-PD1, anti-PD-L1, and anti-CTLA-4 antibodies), or in combination both with the ADCs described herein and in combination with other active agents (such as immuno-oncology agents).

The CDNs of Formula II (e.g., CDN-A or CDN-B), are capable of agonizing STING when used alone or as a component of an ADC of Formula I. In particular embodiments, the CDNs may be conjugated to an antibody or antigen-binding fragment via a linker. As disclosed herein, the CDNs can be covalently bonded to a linker via a chemical reaction between the hydroxyl, amino, thiol, $C_{1-6}$alkylamino, or -PEG-OH group of $R^1$ of the CDN of Formula II and a corresponding group in the linker. Put differently, in some embodiments, the CDN is connected to the linker (L) by one of the following linkages occurring at $R^1$ of the CDN: $R^1$—O-L, $R^1$—NH-L, $R^1$—S-L, $R^1$—N($C_{1-6}$alkyl)-L, or $R^1$-PEG-O-L, where $R^1$ represents the remainder of the $R^1$ moiety excluding the hydroxyl, amino, thiol, $C_{1-6}$alkylamino, or -PEG-OH group of $R^1$. Particular antibodies, antigen-binding fragments, and linkers are described below.

6.3. Antibodies and Antigen-Binding Fragments

As used herein, the term "antibody" refers to an immunoglobulin molecule that specifically binds to a particular target antigen. Antibodies may be of human or non-human origin. Antibodies may be conjugated to CDNs described in Section 6.2 via a linker. The antibodies may be polyclonal, monoclonal, genetically engineered, and/or otherwise modified in nature. The antibodies composing the ADCs of the disclosure are suitable for administration to humans, for example, as humanized antibodies or fully human antibodies.

Antibodies comprise heavy and light chains having hypervariable regions known as complementarity determining regions (CDRs) that mediate binding of the antibody with the target antigen. Antibodies generally comprise a heavy chain comprising a variable region ($V_H$) having three CDRs, namely, $V_H$ CDR #1, $V_H$ CDR #2, and $V_H$ CDR #3, and a light chain comprising a variable region ($V_L$) having three CDRs, namely, $V_L$ CDR #1, $V_L$ CDR #2, and $V_L$ CDR #3. Specific embodiments of the ADCs of the disclosure include, but are not limited to, those that comprise antibodies and/or antigen-binding fragments that include these exemplary CDRs and/or $V_H$ and/or $V_L$ sequences.

Antibodies composing ADCs of the disclosure may be in the form of full-length antibodies that may be of, or derived from any antibody isotype, including for example, IgA, IgD, IgE, IgG, IgM, or IgY. In some embodiments, the antibody composing the ADCs is an IgG (e.g., $IgG_1$, $IgG_2$, $IgG_3$, or $IgG_4$). In some embodiments, the antibodies comprise all or a portion of a constant region of an antibody.

Antibodies composing ADCs of the disclosure may be bispecific antibodies, dual variable domain antibodies, multiple chain or single chain antibodies, single domain antibodies, camelized antibodies, scFv-Fc antibodies, surrobodies (including surrogate light chain construct) and the like.

The ADCs of the disclosure may comprise full-length (intact) antibody molecules, as well as antigen-binding fragments. As used herein, the term "fragment" refers to a portion of an intact antibody that comprises fewer amino acid residues than the intact antibody. As used herein, the term "antigen-binding fragment" refers to a polypeptide fragment of an antibody that mediates binding to an antigen, or competes with intact antibody for antigen-binding. Suitable exemplary antigen-binding fragments include Fab, Fab', F(ab')2, Fv, scFv, dAb, Fd, or an isolated complementarity determining region (CDR) having sufficient framework to bind. As would be appreciated by a skilled artisan, fragments can be obtained by molecular engineering or via chemical or enzymatic treatment of an intact antibody or antibody chain or by recombinant means.

Antibodies or antigen-binding fragments thereof are not limited to a particular method of generation or production, and can be prepared using well known techniques such as hybridoma techniques, recombinant techniques, phage display technologies, transgenic animals, or some combination thereof.

6.4. Target Antigens and Antibodies

The antibodies or antigen-binding fragments thereof composing the ADCs as contemplated in the present disclosure specifically bind to one or more cancer related tumor or immune cell associated antigens.

In certain embodiments, the cancer related tumor or immune cell associated antigen is a T-cell co-inhibitory molecule. In some embodiments, the antibody or antigen-binding fragment thereof specifically binds to a tumor associated antigen selected from PD-L1, PD-L2, CD47, CD80, CD86, HVEM, UL144, CD155, CD112, CD113, galectin-1, galectin-3, galectin-9, CD48, LIGHT, BTLA, and CD160. In some embodiments, the tumor associated antigen is a molecule that binds to a T-cell molecule selected from BTLA, Tim-3, PD-1, CTLA-4, TIGIT, CD244, and CD223.

In some embodiments, the antibody is an anti-PD-L1 antibody, such as atezolizumab, durvalumab, avelumab, or antigen-binding fragment thereof or an antibody or antigen-binding fragment thereof having an amino sequence equivalent thereto.

In some embodiments, the antibody is an anti-CD47 antibody, such as Hu5F9-G4, IBI88, CC-90002, ZL1201, TTI-621, AO-176, the antibody of SGN-CD47M, the antigen binding domain of ALX148, or antigen-binding fragment thereof or an antibody or antigen-binding fragment thereof having an amino acid sequence equivalent thereto.

In other embodiments, the antibody or antigen-binding fragment thereof specifically binds to a cancer related tumor antigen which is a Growth Factor Receptor (GFR). In certain embodiments, the cancer related tumor antigen is an EGFR/ErbB/HER family GFR. In some embodiments, the cancer related tumor antigen is selected from an EGFR/HER1 (ErbB1), HER2/c-Neu (ErbB2), Her3 (ErbB3), and Her4 (ErbB4) receptor. In certain embodiments, the cancer related tumor antigen is an IGFR family GFR. In some embodiments, the cancer related tumor antigen is an IGF1R or IGF2R receptor. In certain embodiments, the cancer related tumor antigen is a TGF-βR (TβR) family GFR. In some embodiments, the cancer related tumor antigen is a TβR I or TβR II receptor. In certain embodiments, the cancer related tumor antigen is a VEGFR family GFR. In some embodiments, the cancer related tumor antigen is a VEGFR1, VEGFR2, or VEGFR3 receptor. In certain embodiments, the cancer related tumor antigen is a PDGFR family GFR. In some embodiments, the cancer related tumor antigen is a PDGFR-α, or PDGFR-β receptor. In certain embodiments, the cancer related tumor antigen is a FGFR family GFR. In some embodiments, the cancer related tumor antigen is a FGFR1, FGFR2, FGFR3, or FGFR4 receptor.

In some embodiments, the antibody is an anti-EGFR/IER1 (ErbB1) antibody, such as cetuximab, panitumumab, necitumumab, or antigen-binding fragment thereof or an antibody or antigen-binding fragment thereof having an amino sequence equivalent thereto. In some embodiments, the antibody is an anti-HER2 (ErbB2) antibody, such as trastuzumab, pertuzumab, or antigen-binding fragment thereof or an antibody or antigen-binding fragment thereof having an amino sequence equivalent thereto. In some embodiments, the antibody is an anti-VEGFR2 antibody, such as ramucirumab, or antigen-binding fragment thereof or an antibody or antigen-binding fragment thereof having an amino sequence equivalent thereto. In some embodiments, the antibody is an anti-PDGFR-α antibody, such as olaratumab, or antigen-binding fragment thereof or an antibody or antigen-binding fragment thereof having an amino sequence equivalent thereto.

In other embodiments, the antibody or antigen-binding fragment thereof specifically binds to lymphoma related antigen. In certain embodiments, the lymphoma related antigen is CD20, CD30, CD19/CD3, CD22, or CD33.

In some embodiments, the antibody is an anti-CD20 antibody, such as rituximab, ibritumomab, ofatumumab, obinutuzumab, or antigen-binding fragment thereof or an antibody or antigen-binding fragment thereof having an amino sequence equivalent thereto. In some embodiments, the antibody is an anti-CD30 antibody, such as brentuximab or antigen-binding fragment thereof or an antibody or antigen-binding fragment thereof having an amino sequence equivalent thereto. In some embodiments, the antibody is an anti-CD19/CD3 antibody, such as blinatumomab, or antigen-binding fragment thereof or an antibody or antigen-binding fragment thereof having an amino sequence equivalent thereto. In some embodiments, the antibody is an anti-CD22 antibody, such as inotuzumab, or antigen-binding fragment thereof or an antibody or antigen-binding fragment thereof having an amino sequence equivalent thereto. In some embodiments, the antibody is an anti-CD33 antibody, such as gemtuzumab, or antigen-binding fragment thereof or an antibody or antigen-binding fragment thereof having an amino sequence equivalent thereto.

In other embodiments, the antibody or antigen-binding fragment thereof specifically binds to myeloma related antigen. In certain embodiments, the lymphoma related antigen is SLAMF7 or CD38.

In some embodiments, the antibody is an anti-SLAMF7 antibody, such as elotuzumab or antigen-binding fragment thereof or an antibody or antigen-binding fragment thereof having an amino sequence equivalent thereto. In some embodiments, the antibody is an anti-CD38 antibody, such as daratumumab or antigen-binding fragment thereof or an antibody or antigen-binding fragment thereof having an amino sequence equivalent thereto.

In other embodiments, the antibody or antigen-binding fragment thereof specifically binds to blastoma related antigen. In certain embodiments, the blastoma related antigen is GD2.

In some embodiments, the antibody is an anti-GD2 antibody, such as dinutuximab, or antigen-binding fragment thereof or an antibody or antigen-binding fragment thereof having an amino sequence equivalent thereto.

In other embodiments, the antibody or antigen-binding fragment thereof specifically binds to RANK Ligand.

In some embodiments, the antibody is an anti-RANK Ligand antibody, such as denosumab, or antigen-binding fragment thereof or an antibody or antigen-binding fragment thereof having an amino sequence equivalent thereto.

In certain embodiments, the antibody is an antibody that binds to an antigen preferentially expressed or overexpressed in cancer cells, such as PD-L1 and EGFR.

In some embodiments, the antibody is an antibody that binds to an antigen derived from a microbe that infects human cells.

As used herein, "α" and "anti" are used interchangeably, for example as when describing an "anti-PD-L1" antibody or "α-PD-L" antibody.

As used herein, protein names having hyphenation are used interchangeably with their non-hyphenated form (i.e., "PD-L1" and "PDL1" are used interchangeably).

As used herein, numbering of immunoglobulin amino acid residues is done according to the Eu numbering system, unless otherwise indicated.

6.5. Linkers

In the ADCs described herein, the CDN is linked to the antibody or antigen-binding fragment by way of a multi-atom linker. The linkers link the CDN to the antibody or the antigen-binding fragment by forming a covalent linkage to CDN at one location on the linker and a covalent linkage to the antibody or antigen-binding fragment at another location on the linker. The linkers may be monovalent with respect to the CDN (e.g., in Formula Ia), such that they covalently link a single CDN to a single site on the antibody or fragment thereof. The linkers may also be polyvalent with respect to the CDN (e.g., in Formula I when m>1), such that they covalently link more than one CDN to a single site on the antibody or fragment thereof. As used herein, the expression "linker" is intended to include unconjugated, partially conjugated (i.e., to the CDN or Ab only), and fully conjugated forms of the linker (i.e., to both the CDN and Ab). In specific embodiments, moieties comprising functional groups on the antibody and linker which form the covalent linkage between the antibody and the linker are specifically illustrated as $R^X$ and $R^Y$, respectively.

The linkers linking the CDN to the antibody or fragment thereof may be long, short, flexible, rigid, hydrophilic, or hydrophobic in nature, or may comprise segments that have different characteristics. A wide variety of linkers useful for linking drugs to antibodies or fragments thereof in the context of ADCs are known in the art. These linkers, as well as other linkers, may be used to link the CDN to the antibody of antigen-binding fragment of the ADCs described herein.

In certain embodiments, linkers include from 2-100, 2-75, 2-50, 2-25, 2-10, 5-100, 5-75, 5-50, 5-25, 5-10, 10-100, 10-75, 10-50, or 10-25 atoms in the chain that connects the CDN to the antibody or antigen-binding fragment (including any atoms at the ends of the linker that may derive from the CDN or antibody or antigen-binding fragment). Likewise, linkers used in CDN-coupled linkers (as discussed below), also may include from 2-100, 2-75, 2-50, 2-25, 2-10, 5-100, 5-75, 5-50, 5-25, 5-10, 10-100, 10-75, 10-50, or 10-25 atoms in the chain that connects the CDN to a site on the linker capable of coupling to a complementary site on an antibody or antigen-binding fragment.

The linker may be chemically stable to extracellular environment and serum, or may include linkages that are intentionally unstable and can release the CDN in the extracellular milieu or tumor microenvironment.

In some embodiments, the linkers include linkages that are designed to release the CDN upon internalization of the ADC within a cell. In some specific embodiments, the linkers include linkages designed to cleave and/or immolate or otherwise specifically or non-specifically degrade inside cells.

The number of CDNs linked to the antibody or antigen-binding fragment thereof of an ADC can vary (called the "drug-to-antibody ratio," or "DAR") and will be limited by the number of available attachments sites on the antibody or antigen-binding fragment thereof and the number of CDNs linked to a single linker. In ADCs that include more than one CDN, each CDN may be the same or different. As long as the CDN does not exhibit unacceptable levels of aggregation under the conditions of use and/or storage, ADCs with DARs of 10, or even higher, are contemplated. In some embodiments, the ADCs described herein may have a DAR in the range of 1 to 10, 1 to 9, 1 to 8, 1 to 7, 1 to 6, 1 to 5, or 1 to 4. In some embodiments, the ADCs described herein may have a DAR in the range of 2 to 10, 2 to 9, 2 to 8, 2 to 7, 2 to 6, 2 to 5, or 2 to 4. In certain specific embodiments, the ADCs may have a DAR of 1, 2, 3, or 4. In other specific embodiments, the ADCs may have a DAR of 5, 6, 7, or 8. In some specific embodiments, the ADCs may have a DAR of 1.

By way of example and not limitation, some cleavable and non-cleavable linkers that may be included in the ADCs described herein are described below.

6.5.1. Cleavable Linkers

In certain embodiments, the linker is cleavable in vivo by chemical or enzymatic processes to liberate the CDN. In certain instances, the CDN is cleaved from the linker to regenerate the same CDN prior to coupling with the linker. In other embodiments, the liberated CDN is a CDN modified from the CDN that was originally coupled to the linker, the modified CDN having a residual functional group from the linker but retaining efficacy or even exhibiting enhanced efficacy over the original CDN. Generally, cleavable linkers incorporate one or more chemical bonds that are either chemically or enzymatically cleavable, while the remainder of the linker is non-cleavable.

In certain embodiments, the cleavable linker comprises a chemically labile group. Chemically labile groups exploit differential properties between the plasma and some cytoplasmic compartments, for example the acidic environment of endosomes and lysosomes, or the high thiol concentrations in the cytosol (e.g., glutathione). In certain embodiments, the plasma stability of a linker comprising a chemically labile group may be increased or decreased by altering steric hindrance near the chemically labile group using substituents.

In some embodiments, the chemically labile group of the cleavable linker is an acid labile group. Acid labile groups can remain intact during circulation in the blood's neutral pH and undergo hydrolysis under acidic conditions to release the CDN, such as within an acidic tumor microenvironment or upon internalization into endosomal (pH 5.0-6.5) and lysosomal (pH 4.5-5.0) cellular compartments. This pH-dependent release mechanism of the cleavable linker can be optimized by chemical modification, e.g., substitution, to tune release of CDN to a particular pH. In some embodiments, the cleavable linker comprises an acid-labile group, such as a hydrazone, hydrazine, cis-aconityl, acetal, orthoester, or an imine group. In some embodiments, the acid-labile group undergoes cleavage in the tumor microenvironment, in an endosome of the tumor or immune cell, in a lysosome of the tumor or immune cell, in an acidic intracellular compartment of the tumor or immune cell, or any combination thereof. In some embodiments, the acid-labile group does not undergo cleavage in the tumor microenvironment, in an endosome of the tumor or immune cell, in a lysosome of the tumor or immune cell, and/or in an acidic intracellular compartment of the tumor or immune cell. As contemplated herein, cleavability of the acid-labile group may be determined by pH sensitivity of the fully conjugated linker in the ADC. Acid labile linkers may contain additional cleavage sites, such as additional acid-labile cleavage sites and/or enzymatically labile cleavage sites.

In certain embodiments, the cleavable linker comprises a disulfide group. Disulfides are designed to release the drug upon internalization into cells, where the cytosol provides a more reducing environment compared to the extracellular environment. Scission of disulfide bonds generally requires the presence of a cytosolic thiol cofactor, such as (reduced) glutathione (GSH), such that disulfide-containing linkers are reasonably stable in circulation and selectively release the drug in the cytosol. The intracellular enzyme protein disulfide isomerase, or similar enzymes capable of cleaving disulfide bonds, may also contribute to disulfide cleavage. Tumor cells may induce a hypoxic state due to irregular blood flow, resulting in enhanced reductive enzyme activity and even higher glutathione concentrations.

ADCs including exemplary disulfide-containing linkers include the following formulas:

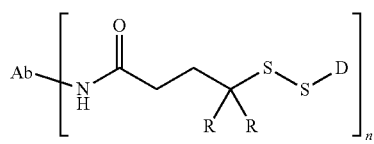

(V)

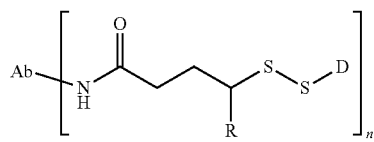

(VI)

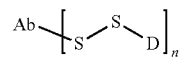

(VII)

wherein
D represents the CDN (e.g., CDN-A or CDN-B);
S of S-D is from the CDN, NH of Ab-NH is from the Ab, S of Ab-S is from the Ab;
Ab represents the antibody or binding fragment thereof;
"n" represents the number of number of occurrences of D linked to Ab via the linker; and
R is, independently for each occurrence, hydrogen or $C_{1-3}$alkyl.

In certain embodiments, the linker comprises the structure

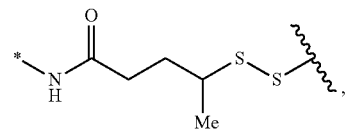 [SMILES: *NC(=O)CCC(C)SS*]

where the NH of *—NH may be from the Ab, and $⸸$ represents the point of attachment of the linker directly or indirectly to the CDN (e.g., at the hydroxyl, amino, thiol, etc. of $R^1$ of the CDN, e.g., CDN-A or CDN-B). In certain embodiments, represents a direct point of attachment of the linker to a thiol of the $R^1$ group of the CDN, $⸸$ wherein the S adjacent $⸸$ is part of the thiol of the $R^1$ group.

Another type of cleavable linker contemplated for the disclosed ADCs is an enzymatically cleavable linker. Such linkers are typically peptide-based or include peptidic regions, and can be more stable in plasma and extracellular milieu than chemically labile linkers. Peptide bonds are generally stable in serum due to a higher pH value compared to lysosomes and the presence of endogenous inhibitors of lysosomal proteolytic enzymes. Release of a CDN from the ADC can occur by action of lysosomal proteases, e.g., cathepsin and plasmin, which may be present at elevated levels in certain tumor cells. In some embodiments, the cleavable peptide is cleaved by a lysosomal enzyme. In certain embodiments, the cleavable peptide is cleaved by a cathepsin (e.g. Cathepsin B) or plasmin.

As a skilled artisan would recognize, proteolytic cleavage of a peptide linker that is directly attached to a CDN can produce an amino acid adduct of the CDN upon amide bond hydrolysis. Thus, also contemplated for ADCs of the disclosure is an enzymatically cleavable linker that comprises a self-immolative spacer to spatially separate the CDN from the cleavage site. The use of a self-immolative spacer allows for the elimination of the fully active, chemically unmodified CDN of Formula II upon amide bond hydrolysis.

One contemplated self-immolative spacer is the bifunctional para-aminobenzyl alcohol group, which on one end is linked at the benzylic hydroxyl group to an amine group on the CDN functionalized with a carbamate, and on the other end is linked at the amino group to form an amide bond with the peptide (i.e., a PABC group). Upon protease-mediated cleavage of the peptide, the resulting CDN is activated, leading to a 1,6-elimination reaction that releases the unmodified CDN, carbon dioxide, and remnants of the linker. In some embodiments, the cleavable linker comprises a PABC group. Additionally contemplated self-immolative spacers are heterocyclic variants of PABC that have been described (see for example, U.S. Pat. No. 7,989,434, which is incorporated herein by reference).

In some embodiments, the enzymatically cleavable linker is a non-peptidic linker. In certain embodiments, the non-peptidic linker is peptidomimetic. In certain embodiments, the non-peptidic linker is cleaved by tumor-specific proteases. In certain embodiments, the non-peptidic linker is cleaved by tumor-specific proteases having increased abundance in tumors and/or the tumor microenvironment). In certain embodiments, the non-peptidic linker is cleaved by cathepsin B. In certain embodiments, the non-peptidic linker is cyclobutane-1,1-dicarboxamide.

In some embodiments, the enzymatically cleavable linker is a ß-glucuronic acid-based linker. Cleavage of the ß-glucuronide glycosidic bond can occurs via the lysosomal enzyme ß-glucuronidase, which is abundantly present within lysosomes and is overexpressed in some tumor types, while having low activity outside cells.

Cleavable linkers may include non-cleavable portions or segments, and/or cleavable segments or portions may be included in an otherwise non-cleavable linker to render it cleavable. By way of example only, polyethylene glycol (PEG) and related polymers may include cleavable groups in the polymer backbone. For example, a polyethylene glycol or polymer linker may include one or more cleavable groups such as a disulfide, a hydrazine, a hydrazone, a dipeptide, or a cyclobutane-1,1-dicarboxamide.

In certain embodiments, the linker comprises an enzymatically cleavable peptide moiety, for example, a linker comprising Formula VIIIa, VIIIb, VIIIc, VIIId, VIIIe, VIIIf, or VIIIg:

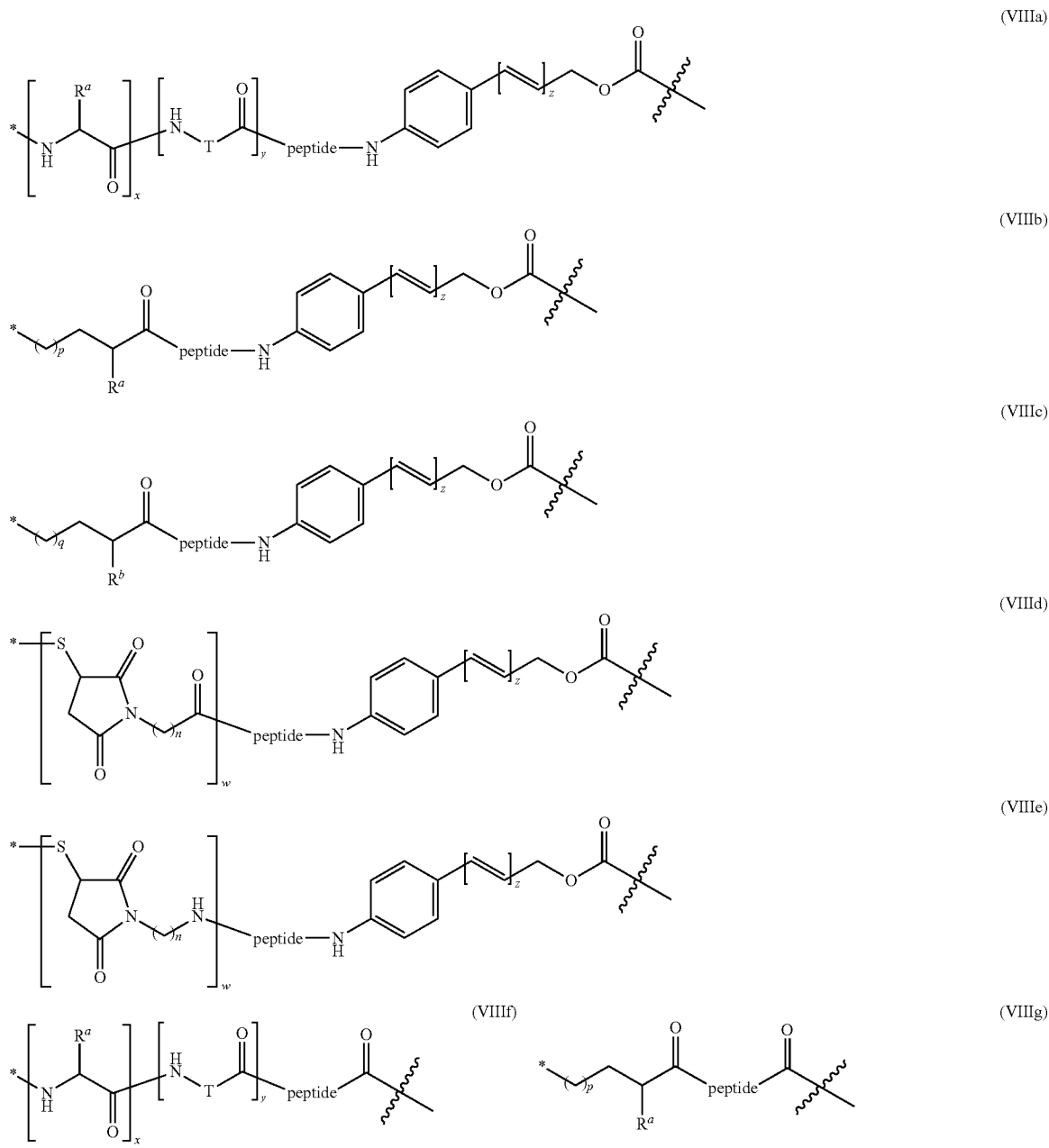

wherein:

"peptide" represents a peptide or peptidomimetic chain (illustrated N→C and not showing the carboxyl and amino "termini") cleavable by a lysosomal enzyme;

T represents a chain (e.g., a polymer chain) comprising one or more ethylene glycol units or an alkylene chain, or combinations thereof;

$R^a$ is selected from hydrogen, $C_{1-6}$alkyl, sulfonate, and methyl sulfonate;

$R^b$ is selected from hydrogen,

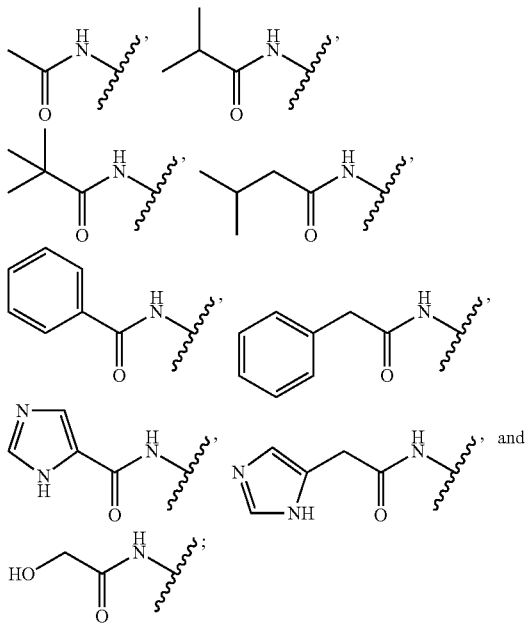

n is an integer ranging from 2 to 10, such as 3 to 6, particularly 5;

p is an integer ranging from 0 to 5;

q is an integer ranging from 0 to 5, particularly 3;

w is 0 or 1, and the —S— of *—S— may be from the Ab;

x is 0 or 1, and the NH of *—NH may be from the Ab;

y is 0 or 1; and the NH of *—NH may be from the Ab;

z is 0 or 1;

ʄ represents the point of attachment of the linker directly or indirectly to the CDN (e.g., at the hydroxyl, amino, thiol, etc. of $R^1$ of the CDN, e.g., CDN-A or CDN-B); and

* represents the point of attachment to the remainder of the linker or directly or indirectly to the antibody; or a salt thereof.

In some embodiments, the cleavable peptide moiety or "peptide" in Formulas VIIIa-d comprise the following structure:

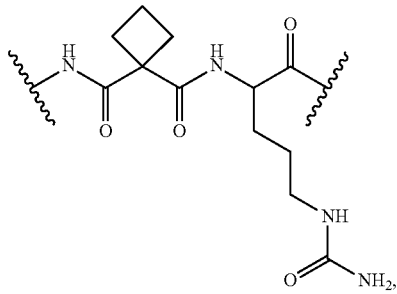 [SMILES: *NC(=O)C1(C(=O)NC(CCCNC(N)=O)C(*)=O)CCC1]

where the terminal —NH— may be from the Ab if x, y, and w are 0.

In some embodiments, the cleavable peptide moiety or "peptide" in Formula VIIIe comprises the following structure:

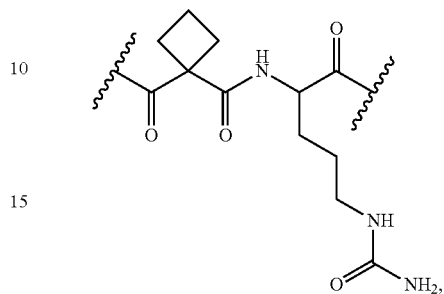

where w is 1.

In certain embodiments, the cleavable peptide moiety or "peptide" in Formulas VIIIa-g comprises from 2-20 amino acid residues, such as 2-15, 2-10, 2-7, or 2-5 residues, including a tetrapeptide, a tripeptide, or a dipeptide. In particular embodiments, the cleavable peptide moiety or "peptide" comprises a dipeptide, such as a dipeptide selected from: Ala-Ala, Ala-(D)Asp, Ala.-Cit, Ala-Lys, Ala-Val, Asn-Cit, Asp-Cit, Asn-Lys, Asn-(D)Lys, Asp-Val, Cit-Ala, Cit-Asn, Cit-Asp, Cit-Cit, Cit-Lys, Cit-Ser, Cit-Val, Glu-Val, PhenylGly-(D)Lys, His-Val, Ile-Cit, Ile-Pro, Ile-Val, Leu-Cit, Lys-Cit, Me3Lys-Pro, Met-Lys, Met-(D)Lys, Phe-Arg, Phe-Cit, Phe-Lys, Pro-(D)Lys, Ser-Cit, Trp-Cit, Val-Ala, Val-(D)Asp, NorVal-(D)Asp, Val-Cit, Val-Glu, Val-Lys, and salts thereof. In certain embodiments, the dipeptide is Val-Cit. In certain embodiments, the cleavable peptide moiety or "peptide" comprises a tripeptide, such as Glu-Val-Cit. In certain embodiments, the cleavable peptide moiety or "peptide" comprises a tetrapeptide, such as Gly-Phe-Leu-Gly or Ala-Leu-Ala-Leu.

In certain embodiments, the linker is of Formula VIIIa and comprises the following structure:

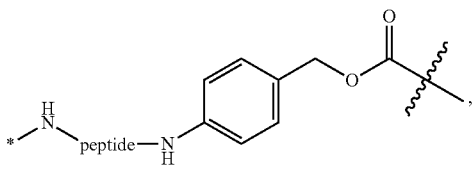

where "peptide" is Glu-Val-Cit.

In certain embodiments, the linker is of Formula VIIIc and comprises the following structure:

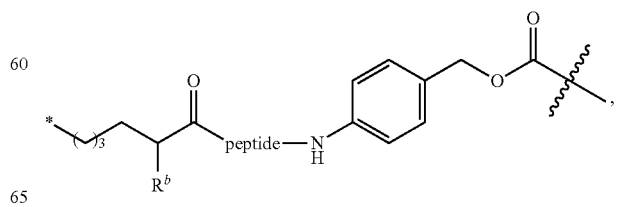

where "peptide" is Val-Cit.

In certain embodiments, the cleavable peptide moiety or "peptide" in Formula VIIId comprises dipeptide, such as a dipeptide selected from: Ala-Ala, Ala-(D)Asp, Ala-Cit, Ala-Lys, Ala-Val, Asn-Cit, Asp-Cit, Asn-Lys, Asn-(D)Lys, Asp-Val, Cit-Ala, Cit-Asn, Cit-Asp, Cit-Cit, Cit-Lys, Cit-Ser, Cit-Val, Glu-Val, PhenylGly-(D)Lys, His-Val, Ile-Cit, Ile-Pro, Ile-Val, Leu-Cit, Lys-Cit, Me3Lys-Pro, Met-Lys, Met-(D)Lys, Phe-Arg, Phe-Cit, Phe-Lys, Pro-(D)Lys, Ser-Cit, Trp-Cit, Val-Ala, Val-(D)Asp, NorVal-(D)Asp, Val-Cit, Val-Glu, Val-Lys, and salts thereof. In certain embodiments, the dipeptide in Formula VIIId is Val-Cit. In certain embodiments, the cleavable peptide moiety or "peptide" in Formula VIIId comprises a tripeptide, such as Glu-Val-Cit. In certain embodiments, the cleavable peptide moiety or "peptide" in Formula VIIId comprises a tetrapeptide, such as Gly-Phe-Leu-Gly or Ala-Leu-Ala-Leu.

In certain embodiments, the linker is of Formula VIIId and comprises the following structure:

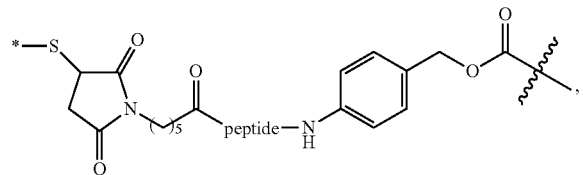

where "peptide" is Val-Cit.

In certain embodiments, the linker is of Formula VIIIe and comprises the following structure:

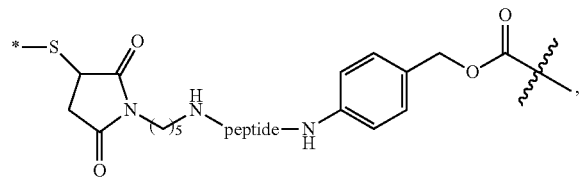

where "peptide" is

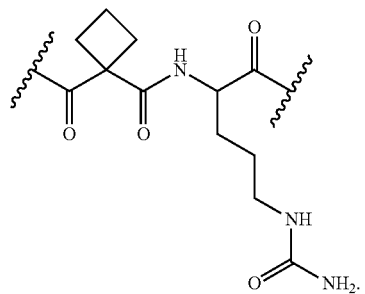 [SMILES: *C(=O)C(CCCNC(N)=O)NC(=O)C1(C(*)=O)CCC1]

6.5.2. Groups Used to Attach Linkers to Antibodies

A variety of attachment groups may be used to attach linker-CDN synthons to antibodies to produce ADCs. Attachment groups on the linker-CDN synthon are generally electrophilic in nature. In some embodiments, the attachment group is selected from a maleimide group; an activated disulfide such as DSDM, SPDB, or sulfo-SPDB; an active ester such as an NHS ester or a HOBt ester; a haloformate, an acid halide, and an alkyl or benzyl halide such as a haloacetamide. In certain embodiments, the resulting linkage between the linker (L) and the antibody (Ab) is a thioether, an amide, an ester, a carbamate, a carbonate, a urea, a disulfide, or an ether.

Also contemplated for the disclosed ADCs are "self-stabilizing" maleimides and "bridging disulfides". An example of a "self-stabilizing" maleimide group is provided for in US 2013/0309256, hereby incorporated by reference. Examples of "bridging disulfides" are provided for in Badescu et al., 2014, Bioconjugate Chem. 25:1124-1136, and WO 2013/085925, each of which are hereby incorporated by reference.

6.5.3. ADCs with Cathepsin Cleavable Linkers

As set forth above, in some embodiments of the disclosure, the CDN (e.g., CDN-A or CDN-B) and the antibodies comprising the ADCs of the disclosure are linked via a cathepsin cleavable linker. In one such embodiment, the ADC has the structure of Formula III:

Formula III

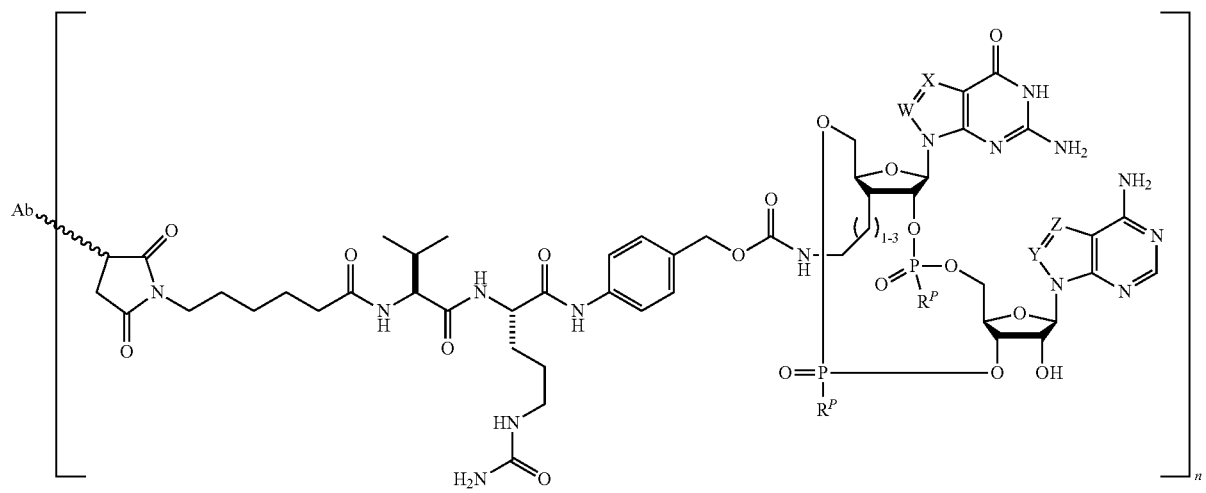

wherein variables W, X, Y, Z, $R^P$, and n are defined as above for Formulas I and II. In the schematic above, ∿∿ represents covalent linkage of the cathepsin cleavable linker to the antibody or antigen-binding fragment thereof (Ab).

In one embodiment, the pyrrolidine-2,5-dione group of the linker of Formula III is linked at its 3-position to the antibody (Ab) by a thiol group. For instance, the pyrrolidine-2,5-dione can be covalently linked at its 3-position to the antibody via a cysteine residue on the antibody. The resultant ADC has the structure of Formula IIIa:

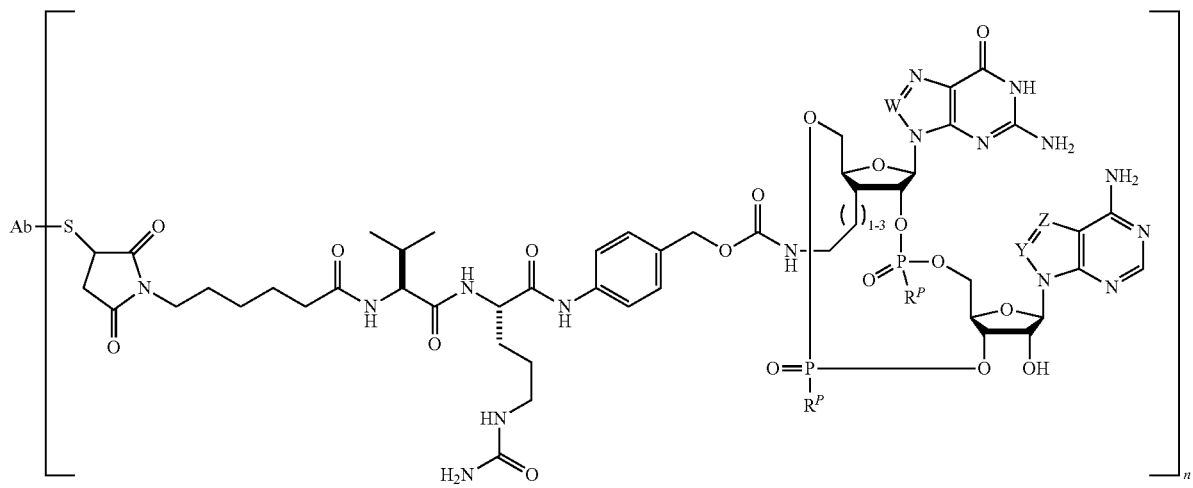

Formula IIIa wherein variables W, X, Y, Z, $R^P$, and n are defined as above for Formulas I and II.

In one embodiment, the ADC has the following structure:

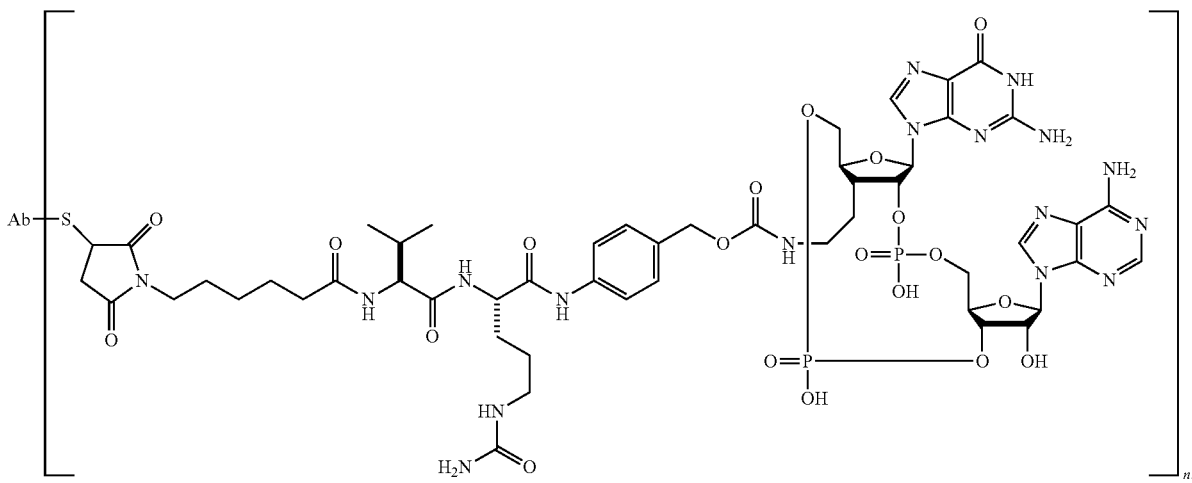

6.5.4. ADCs with Glutathione Cleavable Linkers

As set forth above, in some embodiments of the disclosure, the CDN (e.g., CDN-A or CDN-B) and the antibodies comprising the ADCs of the disclosure are linked via a glutathione cleavable linker. In one such embodiment, the ADC has the structure of Formula IV:

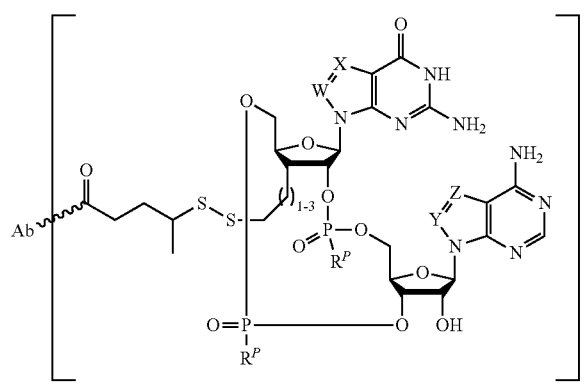

Formula IV wherein variables W, X, Y, Z, $R^P$, and n are defined as above in Formulas I and II. In the schematic above, ⁓ represents covalent linkage of the glutathione cleavable linker to the antibody (Ab).

In one embodiment, the carbonyl group of the linker in Formula IV can be covalently linked to the antibody via a lysine or other amino acid residue on the antibody bearing an amino group-containing sidechain, such as by forming an amide bond with the amino group at the ⁓ bond attached to the carbonyl group. The resultant ADC has the structure of Formula IVa:

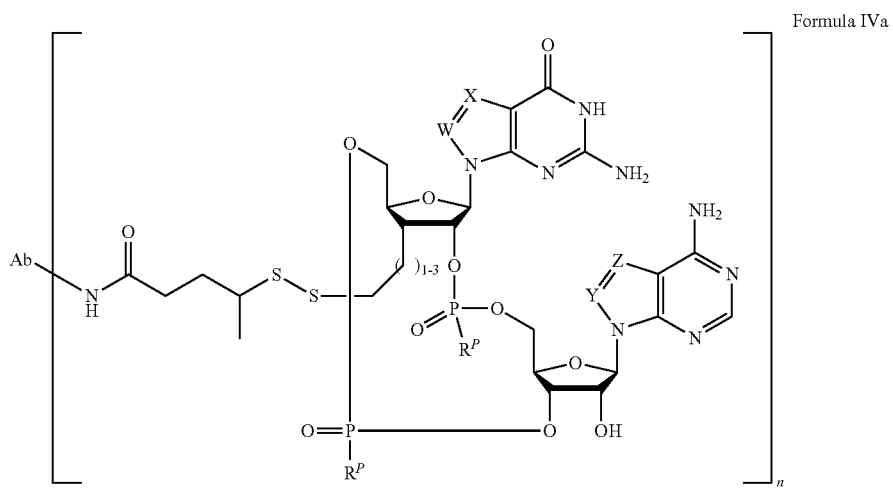

Formula IVa wherein variables W, X, Y, Z, $R^P$, and n are defined as above in Formulas I and II.

In one embodiment, the ADC has the following structure:

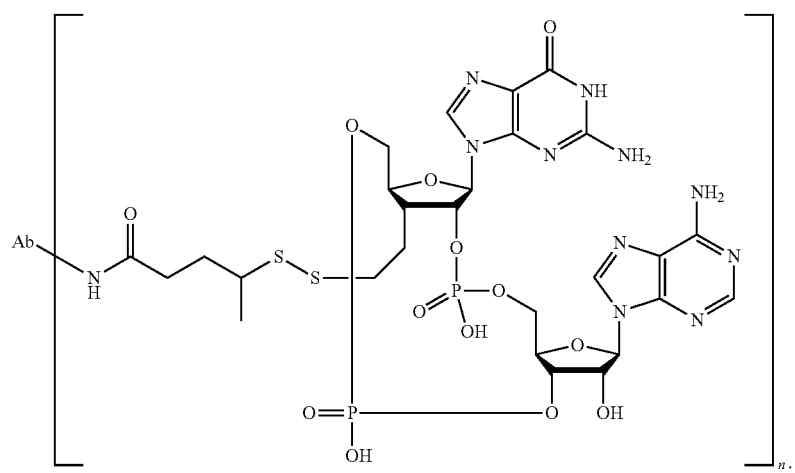

6.6. Methods of Making Antibody-Drug Conjugates

Generally, ADCs according to Formula I may be prepared according to the following scheme:

$$\text{Ab-R}^X + \text{R}^Y\text{-L-(D)}_m \rightarrow \text{Ab-[-L-(D)}_m]_n \quad \text{(Formula I)}$$

wherein Ab, L, D, m, and n are as previously defined for Formula I, and $R^X$ and $R^Y$ represent complementary groups capable of forming covalent linkages with one another.

Relatedly, ADCs according to Formula Ia may be prepared according to the following scheme:

$$\text{Ab-R}^X + \text{R}^Y\text{-L-D} \rightarrow \text{Ab-[-L-D]}_n \quad \text{(Formula Ia)}$$

wherein Ab, L, D, and n are as previously defined for Formula I, and $R^X$ and $R^Y$ represent complementary groups capable of forming covalent linkages with one another, as described above.

The identities of groups $R^X$ and $R^Y$ will depend upon the chemistry used to link synthon $R^Y$-L-(D)$_m$ or $R^Y$-L-D to the antibody. The synthons are typically linked to the side chains of amino acid residues of the antibody, including, for example, a free thiol group of an accessible cysteine residue or a primary amino group of an accessible lysine residue. In some embodiments, $R^X$ is a group on a side chain of an amino acid of the antibody, such as an amino or thiol group. In certain embodiments, $R^X$ is an amino group on a side chain of an amino acid, such as lysine, 5-hydroxylysine, ornithine, or statine, particularly lysine. In some embodiments, $R^X$ is a thiol group on a side chain of an amino acid, such as cysteine or homocysteine, particularly cysteine. In such linkages, free thiol groups may be obtained by first fully or partially reducing the antibody to disrupt interchain disulfide bridges between cysteine residues. A number of functional groups $R^Y$ and chemistries may be used to form linkages with thiol groups, and include by way of example and not limitation maleimides and haloacetyls.

Also contemplated for the disclosed ADCs are engineered antibodies having mutations to or more codons to disrupt one or more disulfide bridges, and includes by way of example and not limitation the mutation of a single cysteine residue of an interchain disulfide bridge to a serine residue to produce a free thiol from the unpaired cysteine. Also contemplated for the disclosed ADCs are engineered antibodies having mutations to or more codons to introduce a residue having a thiol for linker conjugation, and includes by way of example and not limitation the mutation of one or more residues to a cysteine residue, or incorporation of additional cysteine residues into the amino acid sequence of the antibody or antigen-binding fragment thereof.

In certain embodiments, $R^X$ is a thiol, such as from a cysteine residue on the antibody, and $R^Y$ is a group selected from a haloacetyl, maleimide, aziridine, acryloyl, vinylsulfone, pyridyl disulfide, TNB-thiol, and an alkylating or arylating agent. In some embodiments, $R^X$ is a thiol group, such as from a cysteine residue on the antibody, and $R^Y$ is a maleimide group. In some embodiments, $R^X$ is a primary amino group of a lysine residue. A number of functional groups $R^X$ and chemistries may be used for lysine linkages, and include by way of example and not limitation NHS-esters and isothiocyanates.

In certain embodiments, $R^X$ is an amine, such as from a lysine residue on the antibody, and $R^Y$ is a group capable of alkylating or acylating the amine. In some embodiments, $R^X$ is an amine, such as from a lysine residue on the antibody, and $R^Y$ is a group selected from an isothiocyanate, isocyanate, acyl azide, NHS ester, sulfonyl chloride, aldehyde, glyoxal, epoxide, oxirane, carbonate, aryl halide, imidoestes, carbodiimide, anhydride, and a fluorophenyl ester.

In certain embodiments, $R^X$ is an amine, such as from a lysine residue on the antibody, and $R^Y$ is an NHS ester.

As contemplated for ADCs of the disclosure, conjugation chemistries are not limited to available side chain groups. An antibody may also be engineered to include amino acid residues for conjugation, and includes by way of example and not limitation the conversion of side chains such as amines to other useful groups, such as a thiol, by linking an appropriate small molecule to the amine. For instance, a primary amine-containing side chain of an amino acid may be converted to a thiol-containing side chain, such as —NH—$C_{1-6}$alkyl-SH, including —NH—CH$_2$—CH$_2$—SH, where —NH— is from the primary amine.

As will be appreciated by skilled artisans, the number of CDNs linked to an antibody molecule may vary, resulting in a heterogeneous ADC preparation in which some antibodies contain one linked CDN, some two, some three, etc. (and some none). The degree of heterogeneity will depend upon, among other things, the chemistry used for linking the CDN. For example, when an IgG1 antibody is reduced to yield thiol groups for attachment, heterogeneous mixtures of antibodies having zero, 1, 2, 3, 4, 5, 6, 7, or 8 linked CDNs per molecule are often produced. Furthermore, by adjusting the molar ratio of $R^X$ to $R^Y$, ADCs having 0, 1, 2, 3, 4, 5, 6, 7, or 8 linked CDNs per molecule can be produced. Thus, it will be understood that depending upon context, stated drug-to-antibody ratios (DARs) may be averages for a collection of ADCs. For example, "DAR3" refers to a heterogeneous ADC preparation in which the average drug-to-antibody ratio is 3, e.g., a mixture of ADCs having equal numbers of DAR2 and DAR4.

Purity may be assessed by a variety of methods, as is known in the art. As a specific example, an ADC preparation may be analyzed via HPLC, hydrophobic exchange, ion exchange, size exclusion, or other chromatography and the purity assessed by analyzing areas under the curves of the resultant peaks.

In some embodiments, the present disclosure is directed to a method of making an ADC comprising (a) coupling one or more CDNs of the disclosure (i.e., a CDN of Formula II) to a linker (e.g., L as described herein) to generate one or more CDN-coupled linkers; and (b) coupling one or more of the CDN-coupled linkers to an antibody or antigen-binding fragment thereof (e.g., Ab as described herein) to generate the ADC.

In certain embodiments, the present disclosure is directed to a method of making an ADC comprising (b) coupling one or more of CDN-coupled linkers (i.e., a CDN of Formula II and, e.g., L as described herein) to an antibody or antigen-binding fragment thereof (e.g., Ab as described herein) to generate the ADC.

In certain embodiments, the present disclosure is directed to a method of making one or more CDN-coupled linkers comprising (a) coupling one or more CDNs of the disclosure (i.e., a CDN of Formula II) to a linker (e.g., L as described herein) to generate one or more CDN-coupled linkers.

In other embodiments, the present disclosure is directed to a method of making an ADC comprising (a) coupling one or more linkers (e.g., L as described herein) to an antibody or antigen-binding fragment thereof (e.g., Ab as described herein) to generate a linker-coupled antibody; and (b) coupling one or more CDNs of the disclosure (i.e., a CDN of Formula II) to the linker-coupled antibody to generate the ADC.

In certain embodiments, the present disclosure is directed to a method of making an ADC comprising (b) coupling one or more CDNs of the disclosure (i.e., a CDN of Formula II)

to a linker-coupled antibody or antigen-binding fragment thereof (e.g., one or more L as described herein and, e.g., Ab as described herein) to generate the ADC.

In certain embodiments, the present disclosure is directed to a method of making a linker-coupled antibody comprising (a) coupling one or more linkers (e.g., L as described herein) to an antibody or antigen-binding fragment thereof (e.g., Ab as described herein) to generate the linker-coupled antibody.

In some embodiments, the present disclosure is directed to a method of making an ADC comprising (a) coupling a CDN of the disclosure (i.e., a CDN of Formula II) to a linker (e.g., L as described herein) to generate a CDN-coupled linker; and (b) coupling a plurality of the CDN-coupled linkers to an antibody or antigen-binding fragment thereof (e.g., Ab as described herein) to generate the ADC.

In other embodiments, the present disclosure is directed to a method of making an ADC comprising (a) coupling a plurality of linkers (e.g., L as described herein) to an antibody or antigen-binding fragment thereof (e.g., Ab as described herein) to generate a linker-coupled antibody; and (b) coupling a plurality of one or more CDNs of the disclosure (i.e., a CDN of Formula II) to the linker-coupled antibody to generate the ADC.

6.6.1. CDN Compositions for Handling CDNs to Prior to Coupling

As described above, CDNs of the disclosure (i.e., a CDN of Formula II, such as CDN-A or CDN-B) may be coupled to a linker (e.g., L as described herein) to generate one or more CDN-coupled linkers, or may be coupled to a linker-coupled antibody (e.g., one or more L as described herein and, e.g., Ab as described herein) to generate an ADC. Therefore, the present disclosure provides CDN compositions that facilitate the purification, drying, or handling of the CDNs that are used in these coupling steps.

In that context, the present disclosure provides a CDN composition comprising a CDN of Formula II (including sub formulas of Formula II, such as Formula IIa, IIb, etc.), and a base, such as an amine base. In some embodiments, the amine base is a liquid at room temperature and pressure, such as pyridine, piperidine, pyrrolidine, morpholine, lutidine (e.g., 2,6-lutidine), triethylamine (TEA), or diisopropylethylamine (DIPEA), particularly pyridine. In certain embodiments, the CDN composition comprising the CDN and the base is an anhydrous composition having less than 100, 50, 25, or 10 ppm of water. The CDN composition comprising the CDN and the base can be dried by concentration under high vacuum prior to use in a coupling step.

In some embodiments, the CDN composition comprises a CDN of Formula II, such as Formula IIk, IIm, IIn, or IIo, and an amine base, such as pyridine. In certain embodiments, the CDN composition comprises a CDN of Formula II that has an amino group at the $R^1$ position, and an amine base, such as pyridine. In certain embodiments, the CDN composition comprises a CDN of Formula IIn or IIo (and optionally that has an amino group at the $R^1$ position), and an amine base, such as pyridine. In some embodiments, the CDN composition comprises CDN-A as described herein, or a pharmaceutically acceptable salt thereof, and an amine base, such as pyridine, and is optionally anhydrous. In some embodiments, the CDN composition comprises CDN-B as described herein, or a pharmaceutically acceptable salt thereof, and an amine base, such as pyridine, and is optionally anhydrous.

The present disclosure also provides a CDN composition that is an aqueous solution comprising a CDN of Formula II (including sub formulas of Formula II, such as Formula IIa, IIb, etc.), and a buffer suitable to achieve a pH in the range of 5 to 10, including 5 to 8, such as a pH of 5, 5.5, 5.8, 6, 6.2, 6.5, 7, 7.5 or 8, including any pH ranges created by using these pH values as end points, such as 5 to 7. In certain embodiments, the buffer is suitable to achieve a pH of 6+/−0.2. In some embodiments, the buffer is a phosphate buffer. In some embodiments, the CDN composition is an aqueous solution comprising a CDN of Formula II that has a thiol group at the $R^1$ position, such as Formula IIo, and a buffer suitable to achieve a pH of 6+/−0.2, such as a phosphate buffer. In particular embodiments, the CDN composition is an aqueous solution comprising a CDN of Formula IIo and a buffer suitable to achieve a pH of 6+/−0.2, such as a phosphate buffer. In one embodiment, the CDN composition is an aqueous solution comprising CDN-B or a pharmaceutically acceptable salt thereof and a buffer suitable to achieve a pH of 6+/−0.2, particularly a phosphate buffer.

6.6.2. CDN Compositions for Coupling CDNs to Linkers

Preparation of a CDN-coupled linker, as described above (i.e., comprising a CDN of Formula II, such as CDN-A or CDN-B, coupled to a linker, e.g., L as described herein), may include preparation of one or more CDN compositions for coupling the CDN to the linker.

In that context, the present disclosure provides a CDN composition comprising a CDN of Formula II (including sub formulas of Formula II, such as Formula IIa, IIb, etc.) and either a linker (e.g., L as described herein) or a coupling agent, or both a linker and a coupling agent, wherein the coupling agent facilitates coupling of the CDN to the linker. In some embodiments, the coupling agent is capable of activating the linker for coupling with the CDN, such as by generating an activated ester on the linker such that the CDN is then capable of reacting with the activated ester of the linker to couple the CDN to the linker. Examples of suitable coupling agents include hydroxybenzotriazole (HOBt), N-hydroxysuccinimide (NHS), dicyclohexylcarbodiimide (DCC), diisopropylcarbodiimide (DIC), 1-ethyl-3-(3-dimethylaminopropyl)carbodiimide (EDC), and hexafluorophosphate azabenzotriazole tetramethyl uranium (HATU). In certain embodiments, the CDN composition further comprises an aprotic polar solvent, such as dimethylformamide (DMF), dimethylacetamide (DMA), acetonitrile, or tetrahydrofuran (THF), particularly DMF. In certain embodiments, the CDN composition comprising the CDN and either or both of the linker and the coupling agent is an anhydrous composition having less than 100, 50, 25, or 10 ppm of water.

In certain embodiments, the CDN composition comprises a CDN of Formula II, such as Formula IIk, IIm, IIn, or IIo (and has an amino or thiol group at the $R^1$ position), and either a linker (e.g., L as described herein) or a coupling agent or both a linker and a coupling agent. In some embodiments, the CDN composition comprises a CDN of Formula II that has an amino or thiol group at the $R^1$ position, and either a linker or a coupling agent or both a linker and a coupling agent. In certain embodiments, the CDN composition comprises a CDN of Formula IIn or IIo (and optionally that has an amino or thiol group at the $R^1$ position), and either a linker or a coupling agent or both a linker and a coupling agent. In certain embodiments, the CDN composition comprises CDN-A or CDN-B as described herein, or a pharmaceutically acceptable salt of either, and either a linker or a coupling agent, or both a linker and a coupling agent, and optionally an aprotic polar solvent as described above. In certain embodiments, the CDN composition comprises CDN-A or CDN-B or a pharmaceutically acceptable salt of either, a linker, and an aprotic polar solvent. In certain embodiments, the CDN composition comprises CDN-A or CDN-B or a pharmaceutically acceptable salt of either, a coupling agent, and an aprotic polar solvent.

6.6.3. CDN-Coupled Linkers

As discussed above, CDN-coupled linkers may be useful intermediates in the preparation of ADCs described herein. In some embodiments, a CDN-coupled linker comprises a CDN of Formula II (e.g., CDN-A or CDN-B) coupled to a linker, e.g., L as described herein. For example, a CDN-coupled linker may have the formula L-CDN, wherein L includes a site capable of coupling to a complementary site on an antibody or antigen-binding fragment, wherein the CDN is of Formula II (including sub formulas, such as Formulas IIk, IIm, IIn, and IIo), and wherein the CDN is covalently bound to the linker at the hydroxyl, thiol, amino, $C_{1-6}$alkylamino, or -PEG-OH group of the $R^1$ position of Formula II.

In certain embodiments, the CDN and the linker of a CDN-coupled linker are coupled via a thioether, an amide, an ester, a carbamate, a carbonate, a urea, a disulfide, or an ether group, particularly an amide, carbamate, or disulfide group. For example, in certain embodiments, the CDN and the linker of a CDN-coupled linker are coupled via an amide group. In such embodiments, the CDN-coupled linker may have the formula L-C(O)NH-CDN or L-C(O)N($C_{1-6}$alkyl)-CDN, wherein the CDN is of Formula II (including sub formulas, such as Formulas IIk, IIm, and IIn), wherein $R^1$ of Formula II is $C_{1-6}$alkyl, such as $C_{2-6}$alkyl or $C_{2-3}$alkyl, substituted with an amino or a $C_{1-6}$alkylamino group, either of which form the amine portion of the amide group in the formula. In one such embodiment, the CDN-coupled linker has the formula L-C(O)NH-CDN, wherein the CDN is of Formula II (including sub formulas, such as Formulas IIk, IIm, and IIn), wherein $R^1$ of Formula II is $C_{2-3}$alkyl, such as ethyl, substituted with an amino group, which forms the amine portion of the amide group in the formula.

In some embodiments, the CDN-coupled linker has the structure of Formula IXa:

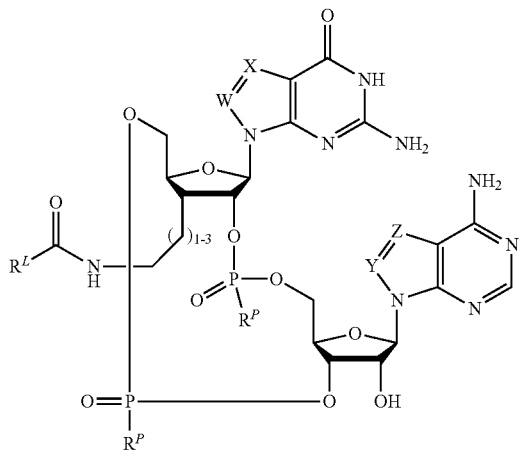

Formula IXa wherein $R^L$ represents the remainder of the linker L, and variables W, X, Y, Z, and $R^P$ are defined as above for Formulas I and II.

In other embodiments, the CDN and the linker of a CDN-coupled linker are coupled via a carbamate group. In such embodiments, the CDN-coupled linker may have the formula L-OC(O)NH-CDN or L-OC(O)N($C_{1-6}$alkyl)-CDN, wherein the CDN is of Formula II (including sub formulas, such as Formulas IIk, IIm, and IIn), wherein $R^1$ of Formula II is $C_{1-6}$alkyl, such as $C_{2-6}$alkyl or $C_{2-3}$alkyl, substituted with an amino or a $C_{1-6}$alkylamino group, either of which form the amine portion of the carbamate group in the formula. In one such embodiment, the CDN-coupled linker has the formula L-OC(O)NH-CDN, wherein the CDN is of Formula II (including sub formulas, such as Formulas IIk, IIm, and IIn), wherein $R^1$ of Formula II is $C_{2-3}$alkyl, such as ethyl, substituted with an amino group, which forms the amine portion of the carbamate group in the formula.

In some embodiments, the CDN-coupled linker has the structure of Formula IXb:

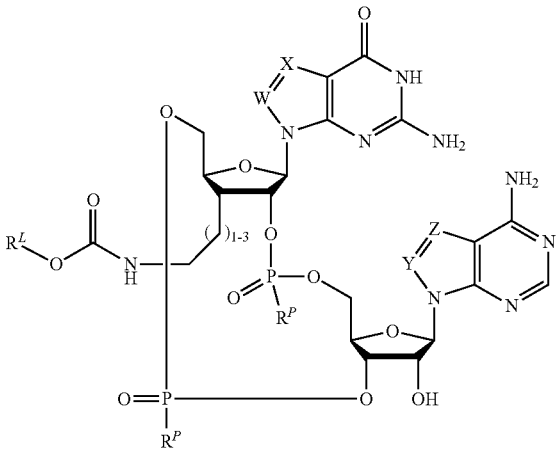

Formula IXb wherein $R^L$ represents the remainder of the linker L, and variables W, X, Y, Z, and $R^P$ are defined as above for Formulas I and II.

In some embodiments, the CDN-coupled linker has the following structure:

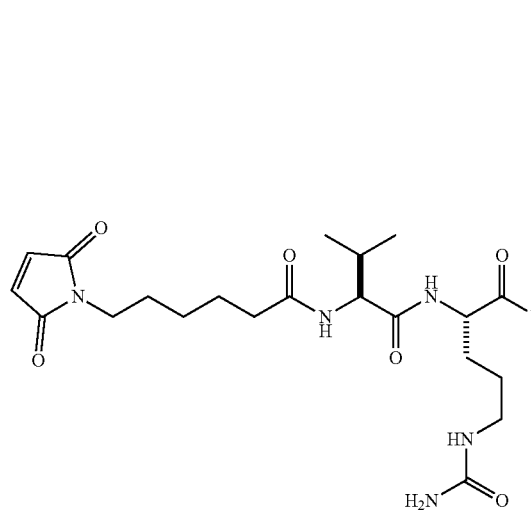

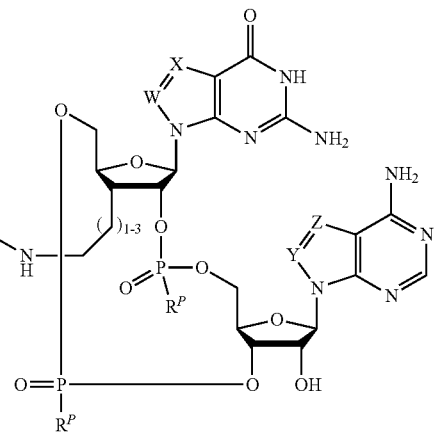

wherein variables W, X, Y, Z, and $R^P$ are defined as above for Formulas I and II.

In other embodiments, the CDN and the linker of a CDN-coupled linker are coupled via a urea group. In such embodiments, the CDN-coupled linker may have the formula L-NHC(O)NH-CDN or L-NHC(O)N($C_{1-6}$alkyl)-CDN, wherein the CDN is of Formula II (including sub formulas, such as Formulas IIk, IIm, and IIn), wherein $R^1$ of Formula II is $C_{1-6}$alkyl, such as $C_{2-6}$alkyl or $C_{2-3}$alkyl, substituted with an amino or a $C_{1-6}$alkylamino group, either of which form the rightmost amine portion of the urea group in the formula. In one such embodiment, the CDN-coupled linker has the formula L-NHC(O)NH-CDN, wherein the CDN is of Formula II (including sub formulas, such as Formulas IIk, IIm, and IIn), wherein $R^1$ of Formula II is $C_{2-3}$alkyl, such as ethyl, substituted with an amino group, which forms the rightmost amine portion of the urea group in the formula.

In some embodiments, the CDN-coupled linker has the structure of Formula IXc:

Formula IXc

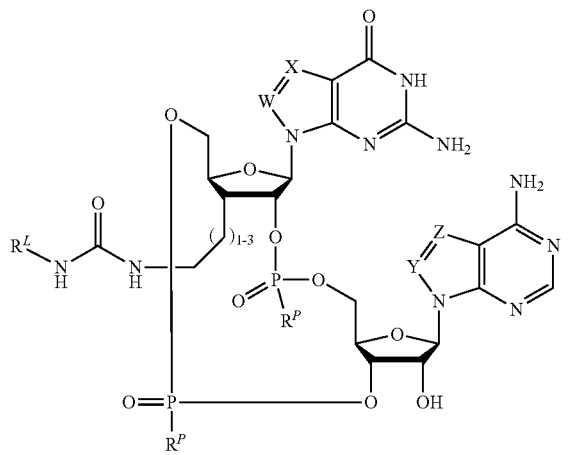

wherein $R^L$ represents the remainder of the linker L, and variables W, X, Y, Z, and $R^P$ are defined as above for Formulas I and II.

In other embodiments, the CDN and the linker of a CDN-coupled linker are coupled via an ester group. In such embodiments, the CDN-coupled linker may have the formula L-C(O)O-CDN, wherein the CDN is of Formula II (including sub formulas, such as Formulas IIk, IIm, and IIn), wherein $R^1$ of Formula II is $C_{1-6}$alkyl, such as $C_{2-6}$alkyl or $C_{2-3}$alkyl, substituted with a hydroxyl or a -PEG-OH group, either of which form the alcohol portion of the ester group in the formula. In one such embodiment, the CDN-coupled linker has the formula L-C(O)O-CDN, wherein the CDN is of Formula II (including sub formulas, such as Formulas IIk, IIm, and IIn), wherein $R^1$ of Formula II is $C_{2-3}$alkyl, such as ethyl, substituted with a hydroxyl group, which forms the alcohol portion of the ester group in the formula.

In some embodiments, the CDN-coupled linker has the structure of Formula IXd:

Formula IXd

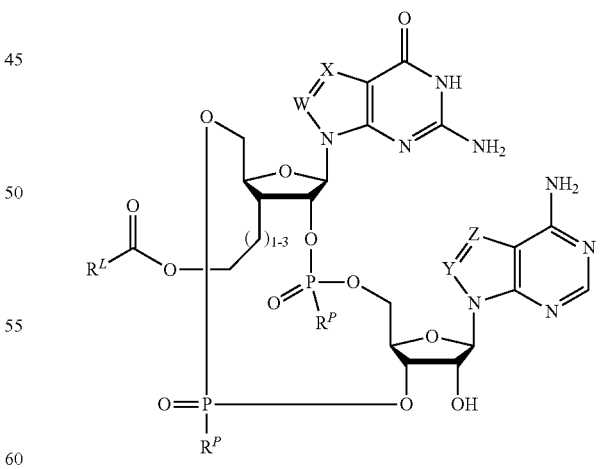

wherein $R^L$ represents the remainder of the linker L, and variables W, X, Y, Z, and $R^P$ are defined as above for Formulas I and II.

In other embodiments, the CDN and the linker of a CDN-coupled linker are coupled via a carbonate group. In such embodiments, the CDN-coupled linker may have the formula L-OC(O)O-CDN, wherein the CDN is of Formula II (including sub formulas, such as Formulas IIk, IIm, and IIn), wherein $R^1$ of Formula II is $C_{1-6}$alkyl, such as $C_{2-6}$alkyl or $C_{2-3}$alkyl, substituted with a hydroxyl or a -PEG-OH group, either of which form the rightmost alcohol portion of the carbonate group in the formula. In one such embodiment, the CDN-coupled linker has the formula L-OC(O)O-CDN, wherein the CDN is of Formula II (including sub formulas, such as Formulas IIk, IIm, and IIn), wherein $R^1$ of Formula II is $C_{2-3}$alkyl, such as ethyl, substituted with a hydroxyl group, which forms the rightmost alcohol portion of the carbonate group in the formula.

In some embodiments, the CDN-coupled linker has the structure of Formula IXe:

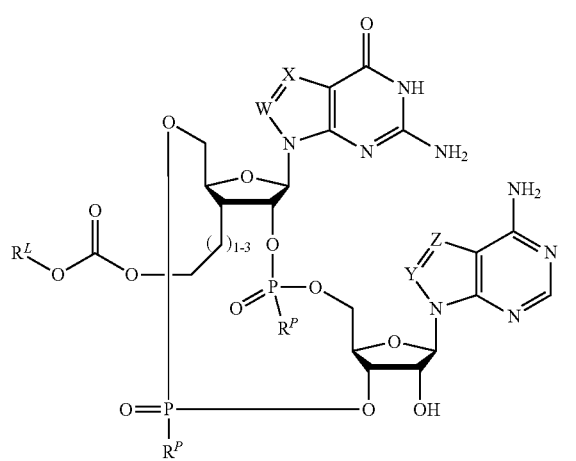

Formula IXe wherein $R^L$ represents the remainder of the linker L, and variables W, X, Y, Z, and $R^P$ are defined as above for Formulas I and II.

In other embodiments, the CDN and the linker of a CDN-coupled linker are coupled via a disulfide group. In such embodiments, the CDN-coupled linker may have the formula L-S-S-CDN, wherein the CDN is of Formula II (including sub formulas, such as Formulas IIk, IIm, and IIo), wherein $R^1$ of Formula II is $C_{1-6}$alkyl, such as $C_{2-6}$alkyl or $C_{2-3}$alkyl, substituted with a thiol group, which forms the rightmost portion of the disulfide group in the formula. In one such embodiment, the CDN-coupled linker has the formula L-S-S-CDN, wherein the CDN is of Formula II (including sub formulas, such as Formulas IIk, IIm, and IIo), wherein $R^1$ of Formula II is $C_{2-3}$alkyl, such as ethyl, substituted with a thiol group, which forms the rightmost portion of the disulfide group in the formula.

In some embodiments, the CDN-coupled linker has the structure of Formula IXf:

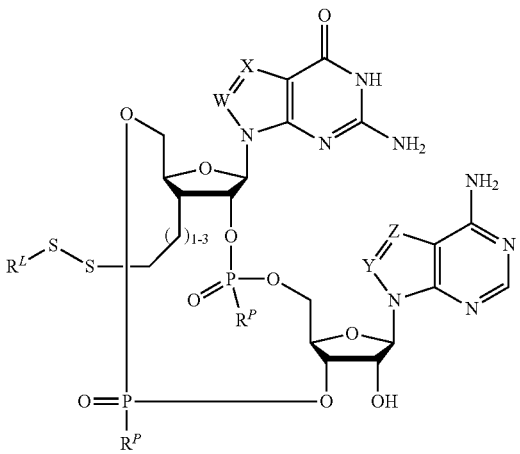

Formula IXf wherein $R^L$ represents the remainder of the linker L, and variables W, X, Y, Z, and $R^P$ are defined as above for Formulas I and II.

In some embodiments, the CDN-coupled linker has the following structure:

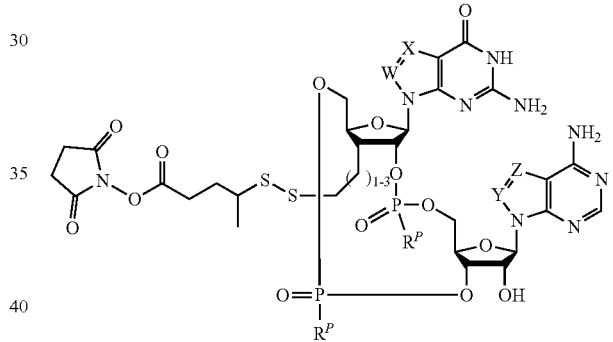

wherein variables W, X, Y, Z, and $R^P$ are defined as above for Formulas I and II.

6.7. Pharmaceutical Compositions and Medicaments

The ADCs and/or or CDNs described herein may be in the form of pharmaceutical compositions comprising the ADC or CDN and one or more carriers, excipients and/or diluents. The compositions may be formulated for pharmaceutical use in humans, and may include a pharmaceutically acceptable carrier, such as an aqueous, optionally buffered, solution, suspension, or dispersion. The compositions may also be lyophilized solid compositions, which may be reconstituted prior to use.

The present pharmaceutical compositions can be in any suitable form, and can be administered to a patient by a variety of routes such as intravenously, intratumorally, subcutaneously, intramuscularly, orally, intranasally, intrathecally, transdermally, topically, or locally. The route for administration in any given case may depend on the particular antibody and/or ADC, the subject, and the nature and severity of the disease and the physical condition of the subject. In certain embodiments, the pharmaceutical composition will be administered intravenously, intratumorally, subcutaneously, or intramuscularly in the form of a liquid formulation.

In some embodiments, the ADCs and/or CDN's described herein, including their pharmaceutical compositions, are administered systemically, such as subcutaneously, intraperitoneally, intramuscularly, or intravenously, particularly intravenously. In other embodiments, the ADCs and/or CDN's described herein, including their pharmaceutical compositions, are administered locally at a tumor site, such as intratumorally or in the microenvironment of the tumor.

The present disclosure also provides CDNs of Formula II (including sub formulas of Formula II, such as Formula IIa, IIb, etc.) for use in the manufacture of medicaments for therapy, such as for promoting an immune response and/or for treating cancer in a subject, including one or more of the various cancers described below, and in combination with one or more additional therapeutic agents as described below.

6.8. Methods of Treatment

In certain embodiments, an ADC of the disclosure (i.e., an ADC of Formula I) or a CDN of the disclosure (i.e., a CDN of Formula II, such as CDN-A or CDN-B) may be used in therapy. In some embodiments, the present disclosure is directed to pharmaceutical compositions described herein comprising an ADC of the disclosure (i.e., an ADC of Formula I) or a CDN of the disclosure (i.e., a CDN of Formula II) for use in therapy.

The ADCs and/or CDNs disclosed herein may be employed alone or in combination with each other and/or with other therapeutic agents. As shown in the examples discussed below, the ADCs and CDNs are capable of promoting an immune response when delivered to a subject. For instance, the ADCs and CDNs of the disclosure, either alone or in combination are capable of inducing interferon-β (IFNβ) in a human subject. The ability of the ADCs and CDNs of the disclosure to promote an immune response is attributed, in part, to their ability to agonize STING. The ADCs are capable of delivering CDNs of the disclosure (e.g., a compound of Formula II) to target tumor or cancer-related immune cells, or the tumor microenvironment to trigger activation of STING and the resultant immune response. Conjugation of the CDNs to an antibody or antigen-binding fragment thereof that binds to a cancer-related tumor or immune cell antigen targets delivery of the CDN and prolongs and enhances the immune response.

The ADCs of the disclosure are capable of promoting an immune response that is greater than either the unconjugated CDN or the antibody that comprises the ADC. Surprisingly, it has been found that the ADCs of the disclosure can promote an immune response that is greater than the additive immune response of the unconjugated CDN and the antibody comprising the ADC. In other words, by conjugating a CDN of the disclosure with a specific immunotherapeutic antibody, a synergistic effect can be achieved. In other embodiments, as discussed herein, the CDNs of the disclosure may also be administered not as part of an ADC.

Accordingly, in one aspect, the disclosure provides methods of inducing or promoting an immune response in a subject comprising administering an effective amount of an ADC of the disclosure (i.e., an ADC of Formula I). In another aspect, the disclosure provides methods of inducing or promoting an immune response in a subject comprising administering an effective amount of a CDN of the disclosure (i.e., a CDN of Formula II). And in another aspect, the disclosure provides methods of inducing or promoting an immune response in a subject comprising administering an effective amount of an ADC of the disclosure in combination with a CDN of the disclosure. In some embodiments, the ADC and/or CDN are administered to mammals in need thereof. In particular embodiments, the ADC and/or CDN are administered to humans in need thereof.

In particular embodiments, the ADCs or CDNs of the present disclosure are used to treat cancer. For instance, the ADCs or CDNs of the disclosure can be used to treat cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver. Further cancers treatable by the ADCs or CDNs of the present disclosure include rectal cancer; cancer of the anal region; carcinomas of the fallopian tubes, endometrium, cervix, vagina, vulva, renal pelvis, and renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease; or a combination of one or more of the foregoing cancers.

Accordingly, in one aspect, the disclosure provides methods of treating cancer in a subject comprising administering a pharmaceutical composition comprising a pharmaceutically acceptable amount of an ADC of the disclosure (i.e., an ADC of Formula I). In another aspect, the disclosure provides methods of treating cancer in a subject comprising administering a pharmaceutical composition comprising a pharmaceutically acceptable amount of a CDN of the disclosure (i.e., a CDN of Formula II). In some embodiments, the pharmaceutical compositions are administered to mammals in need thereof. In particular embodiments, the pharmaceutical compositions are administered to humans in need thereof.

In another aspect, the disclosure provides methods of treating cancer in a subject by administering a pharmaceutical composition comprising a pharmaceutically acceptable amount of an ADC of the disclosure (i.e., an ADC of Formula I) with at least one additional anti-cancer agent to a subject (e.g., a human). The ADC and the one or more additional anti-cancer agents may be administered together or separately and, when administered separately, administration may occur simultaneously or sequentially, in any order, by any convenient route in separate or combined pharmaceutical compositions. In some embodiments, the additional anti-cancer agent enhances expression of the target antigen of the antibody or antigen-binding fragment thereof of the ADC of Formula I. The amounts of the ADC and the other pharmaceutically active anti-cancer agent(s) and the relative timings of administration will be selected in order to achieve the desired combined therapeutic effect.

In some instances, the disclosure provides methods of treating cancer in a subject by administering a pharmaceutical composition comprising a pharmaceutically acceptable amount of a CDN of the disclosure (i.e., a CDN of Formula II) with at least one additional anti-cancer agent to a subject (e.g., a human). The CDN and the one or more additional anti-cancer agents may be administered together or separately and, when administered separately, administration may occur simultaneously or sequentially, in any order, by any convenient route in separate or combined pharmaceutical compositions. The amounts of the CDN and the other anti-cancer agent(s) and the relative timings of administration will be selected in order to achieve the desired combined therapeutic effect.

The combination of an ADC or CDN of the disclosure and one or more anti-cancer agents may be administered together in a single pharmaceutical composition. Alternatively, the ADC or CDN and the one or more anti-cancer agents may be formulated separately. When formulated separately they may be provided in any convenient composition, conveniently, in such a manner as known for such compounds in the art.

Accordingly, an ADC or CDN of the disclosure may be employed with other therapeutic methods of cancer treatment, e.g., in anti-neoplastic therapy, combination therapy with immune checkpoint inhibitors, other chemotherapeutic, hormonal, antibody agents as well as surgical and/or radiation treatments, particularly radiation.

In one embodiment, an ADC of the disclosure (i.e., an ADC of Formula I) or a CDN of the disclosure (i.e., a CDN of Formula II) is—or both an ADC and a CDN of the disclosure are—employed in combination with an immune checkpoint inhibitor to treat cancer. Immune checkpoint inhibitors, such as humanized antibodies against PD-1, PD-L1, and CTLA4, have recently been shown to be highly successful in treating several types of metastatic cancer, including melanoma, non-small cell lung cancers, renal cell carcinoma and bladder cancer (Sharma and Allison, 2015, Science 348, 56). However, still only a small percentage of cancer patients benefit from the checkpoint inhibitor therapies, in part because insufficient number of anti-tumor immune cells, such as CD8 T cells, are generated and/or infiltrated into the tumors. As shown in examples described herein, the combination of an ADC and/or CDN of the disclosure and an immune checkpoint inhibitor is capable of functioning synergistically to treat cancers that are refractory to monotherapy with the immune checkpoint inhibitor.

In one embodiment, the disclosure provides methods of treating cancer in a subject by administering a pharmaceutical composition comprising a pharmaceutically acceptable amount of an ADC of the disclosure (i.e., an ADC of Formula I) or a CDN of the disclosure (i.e., a CDN of Formula II) or both an ADC and CDN of the disclosure in combination with a PD-L1 inhibitor. Examples of PD-L1 inhibitors that can be used in combination with ADCs of the disclosure include, but are not limited to, atezolizumab (Tecentriq®), avelumab (Bavencio®), durvalumab (Imfinzi®), BMS-936559, and CK-301. In certain embodiments, the ADC and/or CDN of the disclosure is not administered in combination with a PD-L1 inhibitor, including those mentioned above.

In one embodiment, the disclosure provides methods of treating cancer in a subject by administering a pharmaceutical composition comprising a pharmaceutically acceptable amount of an ADC of the disclosure (i.e., an ADC of Formula I) or a CDN of the disclosure (i.e., a CDN of Formula II) or both an ADC and CDN of the disclosure in combination with a PD-1 inhibitor. Examples of PD-1 inhibitors that can be used in combination with ADCs of the disclosure include, but are not limited to, pembrolizumab (Keytruda®), nivolumab (Opdivo®), cemiplimab (Libtayo®), AMP-224, AMP-514, and PDR001. In certain embodiments, the ADC and/or CDN of the disclosure is not administered in combination with a PD-1 inhibitor, including those mentioned above.

In one embodiment, the disclosure provides methods of treating cancer in a subject by administering a pharmaceutical composition comprising a pharmaceutically acceptable amount of an ADC of the disclosure (i.e., an ADC of Formula I) or a CDN of the disclosure (i.e., a CDN of Formula II) or both an ADC and CDN of the disclosure in combination with a CTLA-4 inhibitor. Examples of CTLA-4 inhibitors that can be used in combination with ADCs of the disclosure include, but are not limited to, ipilmumab (Yervoy®) and tremelimumab. In certain embodiments, the ADC and/or CDN of the disclosure is not administered in combination with a CTLA-4 inhibitor, including those mentioned above.

In another embodiment, the disclosure provides methods of treating cancer in a subject by administering a pharmaceutical composition comprising a pharmaceutically acceptable amount of an ADC of the disclosure (i.e., an ADC of Formula I) or a CDN of the disclosure (i.e., a CDN of Formula II) or both an ADC and CDN of the disclosure with one or more anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; and or cell cycle signaling inhibitors.

The ADCs of Formula I can be used, e.g., for treating cancer or for inducing or promoting an immune response, in combination with a STING agonist that is not conjugated to an antibody or antigen-binding fragment. In certain embodiments, the STING agonist that is not conjugated to an antibody or antigen-binding fragment is a CDN, such as one of those described herein, i.e., 2'3'-CDNs. In other embodiments, the STING agonist is a 3'3'-CDN, a 2'2'-CDN, or a 3'2'-CDN. In some embodiments, the STING agonist is a benzophenone analog. In further embodiments, the STING agonist is a dimeric amidobenzimidazole. Examples of STING agonists that are not conjugated to an antibody or antigen-binding fragment that can be used in combination with ADCs of the disclosure include, IMSA101, ADU-S100 (MIW815), BMS-986301, CRD5500, CMA (10-carboxymethyl-9-acridanone), diABZI STING agonist-1 (e.g., CAS No.: 2138299-34-8), DMXAA (ASA404/vadimezan), E7766, GSK-532, GSK-3745417, MK-1454, MK-2118, SB-11285, SRCB-0074, TAK-676, and TTI-10001. The STING agonist can be administered prior to, concurrently with or following administration of the ADC of Formula I.

The ADCs of Formula I can be used, e.g., for treating cancer or for inducing or promoting an immune response, in combination with a "free" CDN that is not conjugated to the antibody or antigen-binding fragment of Formula I. The free CDN can be administered prior to, concurrently with or following administration of the ADC of Formula I. In such cases, the free CDN may be the same or different than the CDN that is conjugated to the antibody of the ADC of Formula I. The free CDN may be a cGAMP, e.g., 2'3'-cGAMP or an analog or derivative thereof or a pharmaceutically acceptable salt thereof. In other embodiments, the free CDN is a 3'3'-cGAMP, 2'2'-cGAMP, 3'2'-cGAMP or an analog or derivative of any of these or a pharmaceutically acceptable salt thereof.

Accordingly, the disclosure provides methods of treating cancer in a subject by administering a pharmaceutical composition comprising a pharmaceutically acceptable amount of an ADC of the disclosure (i.e., an ADC of Formula I) with at least one CDN that is not conjugated to an antibody ("free CDN"). The ADCs of Formula I and the free CDN may be administered together or separately and, when administered separately, administration may occur simultaneously or sequentially, in any order, by any convenient route in separate or combined In one embodiment, the free CDN administered in combination with the ADC of Formula I is the following compound, or a pharmaceutically acceptable salt thereof:

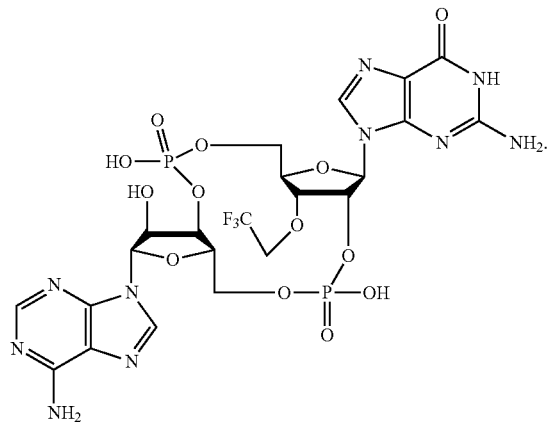

In another embodiment, the free CDN administered in combination with the ADC of Formula I is the following compound, or a pharmaceutically acceptable salt thereof:

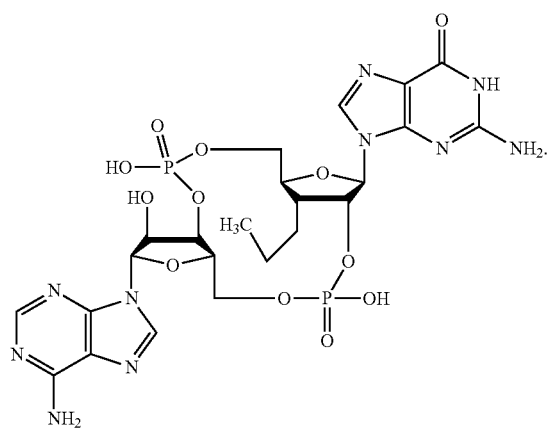

In another embodiment, the free CDN administered in combination with the ADC of Formula I is the following compound, or a pharmaceutically acceptable salt thereof:

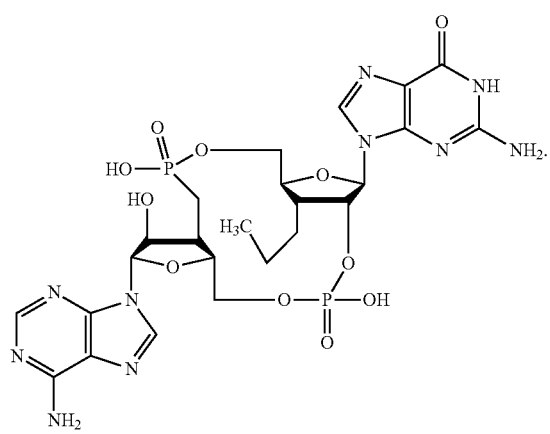

In another embodiment, the free CDN administered in combination with the ADC of Formula I is the following compound, or a pharmaceutically acceptable salt thereof:

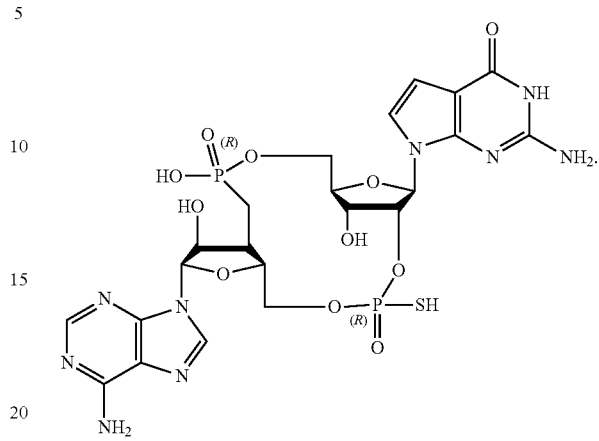

In another embodiment, the free CDN administered in combination with the ADC of Formula I is the following compound, or a pharmaceutically acceptable salt thereof:

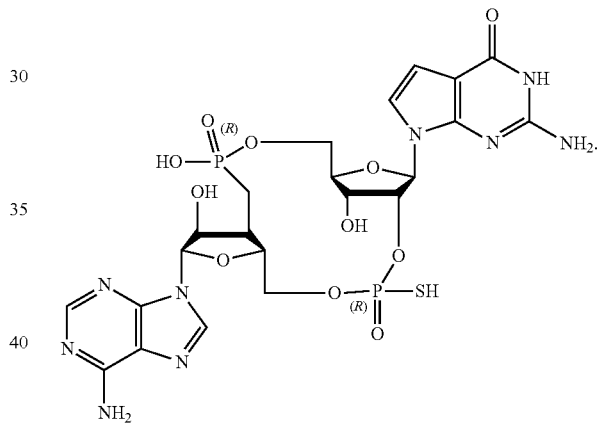

In another embodiment, the free CDN administered in combination with the ADC of Formula I is the following compound, or a pharmaceutically acceptable salt thereof:

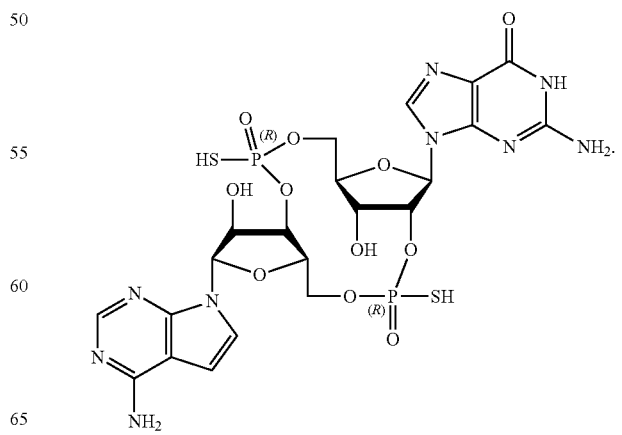

In another embodiment, the free CDN administered in combination with the ADC of Formula I is the following compound, or a pharmaceutically acceptable salt thereof:

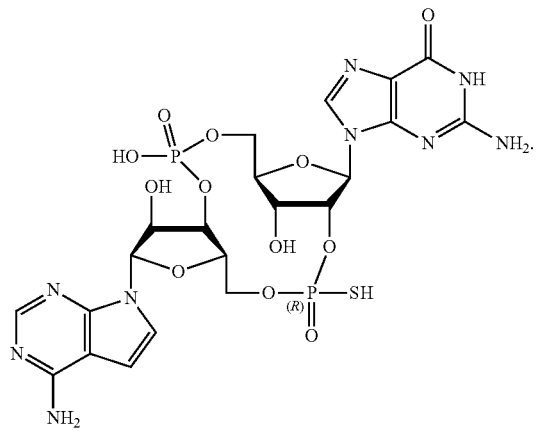

In another embodiment, the free CDN administered in combination with the ADC of Formula I is the following compound, or a pharmaceutically acceptable salt thereof:

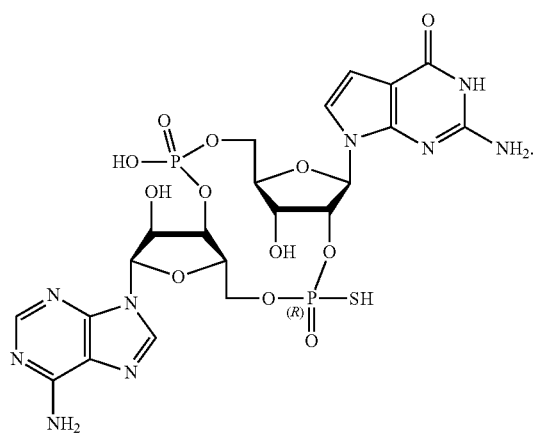

In another embodiment, the free CDN administered in combination with the ADC of Formula I is the following compound, or a pharmaceutically acceptable salt thereof:

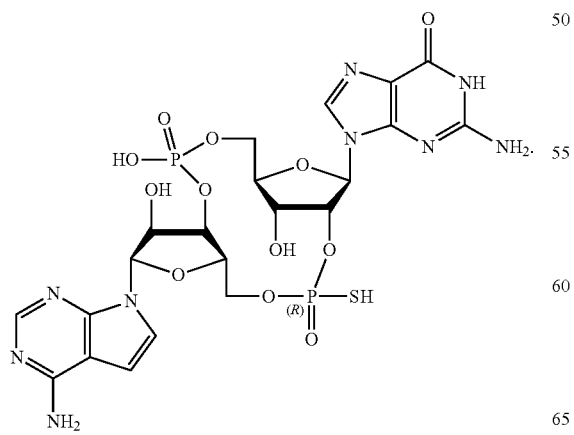

In another embodiment, the free CDN administered in combination with the ADC of Formula I is the following compound, or a pharmaceutically acceptable salt thereof:

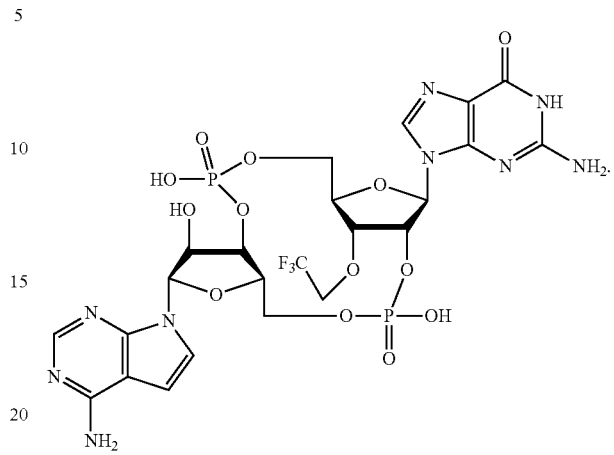

In another embodiment, the free CDN administered in combination with the ADC of Formula I is the following compound, or a pharmaceutically acceptable salt thereof:

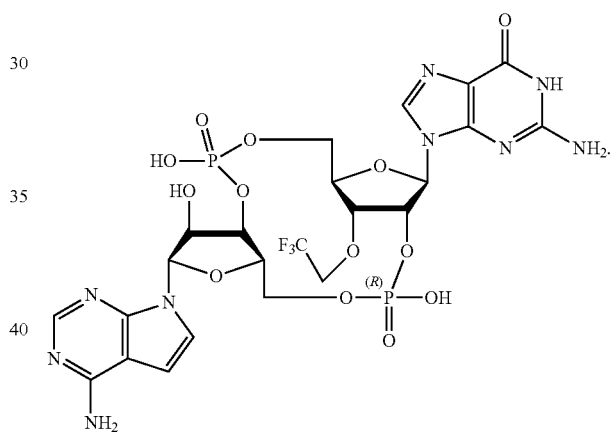

In another embodiment, the free CDN administered in combination with the ADC of Formula I is the following compound, or a pharmaceutically acceptable salt thereof:

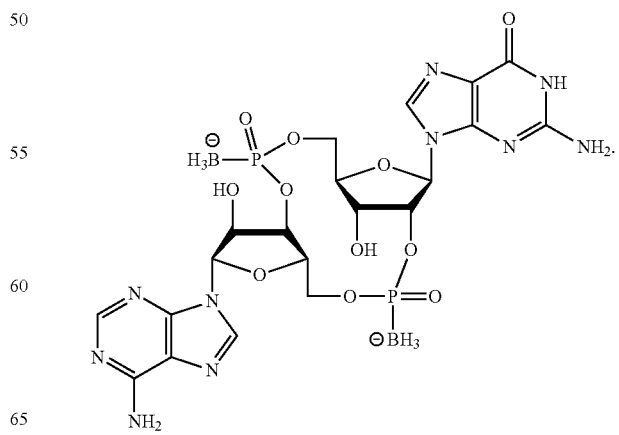

In another embodiment, the free CDN administered in combination with the ADC of Formula I is the following compound, or a pharmaceutically acceptable salt thereof:

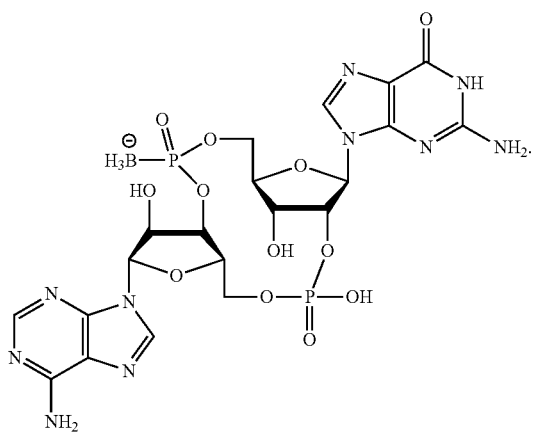

In another embodiment, the free CDN administered in combination with the ADC of Formula I is the following compound, or a pharmaceutically acceptable salt thereof:

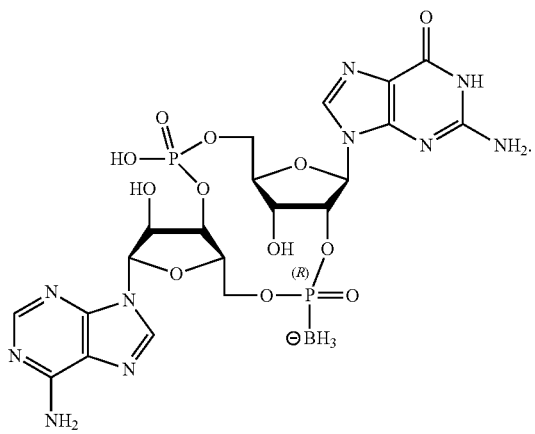

In another embodiment, the free CDN administered in combination with the ADC of Formula I is the following compound, or a pharmaceutically acceptable salt thereof.

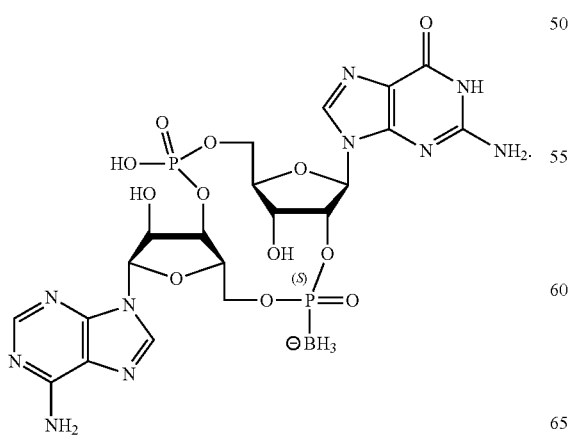

In another embodiment, the free CDN administered in combination with the ADC of Formula I is the following compound, or a pharmaceutically acceptable salt thereof:

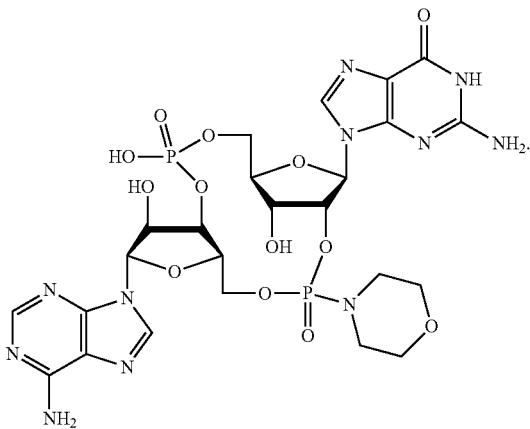

In another embodiment, the free CDN administered in combination with the ADC of Formula I is the following compound, or a pharmaceutically acceptable salt thereof:

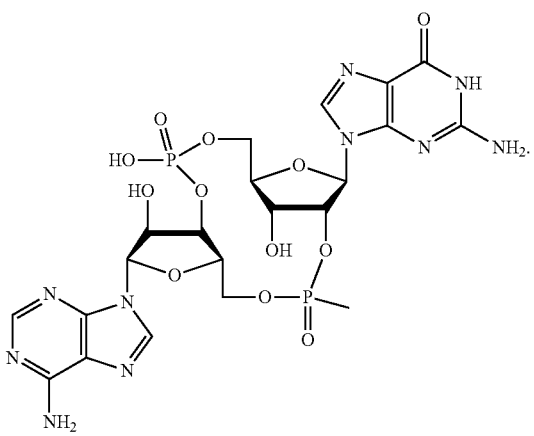

In another embodiment, the free CDN administered in combination with the ADC of Formula I is the following compound, or a pharmaceutically acceptable salt thereof:

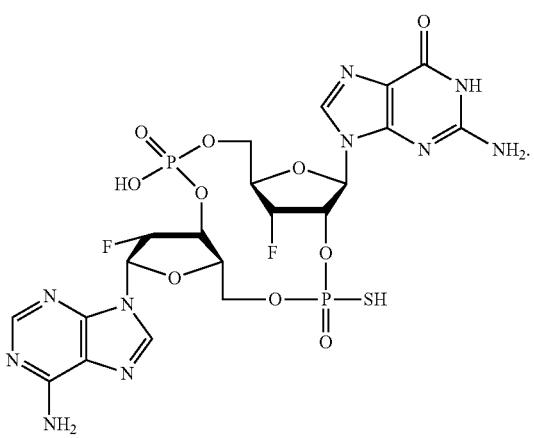

In another embodiment, the free CDN administered in combination with the ADC of Formula I is the following compound, or a pharmaceutically acceptable salt thereof:

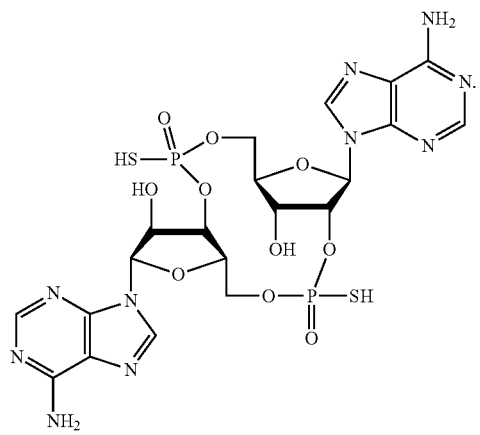

7. EXAMPLES

The following Examples, which highlight certain features and properties of exemplary embodiments of CDNs, ADCs, and methods of using these ADCs to treat patients are provided for purposes of illustration, and not limitation.

Abbreviations $^1$H-NMR Proton nuclear magnetic resonance spectroscopy
$^{19}$F-NMR $^{19}$F nuclear magnetic resonance spectroscopy
$^{31}$P-NMR $^{31}$P nuclear magnetic resonance spectroscopy
G Guanine
A Adenine
$A^{Bz}$ 6N-benzoyladenine
Gib 2N-isobutyryl
Bz Benzoyl
DCA Dichloroacetic acid
DCM Dichloromethane
DMOCP 2-chloro-5,5-dimethyl-1,3,2-dioxaphosphineane 2-oxide
DMT 4,4'-dimethoxytrityl
DMTCI 4,4'-dimethoxytrityl chloride
PBS Phosphate-buffered saline
Py. Pyridine
TBS t-Butyldimethylsilyl
TrCl Tris(hydroxymethyl)aminomethane hydrochloride
IBX 2-Iodoxybenzoic acid
LAH Lithium aluminum hydride
DMF Dimethylformamide
NMM N-Methylmorpholine
Et$_3$N Triethylamine Example 1. Preparation of CDN-A Schemes A1 and A2 below depict the synthesis of a CDN ("CDN-A") disclosed herein. The synthesis and characterization of the CDN and the synthetic intermediates are described below.

Synthesis of Intermediate 19 from 1

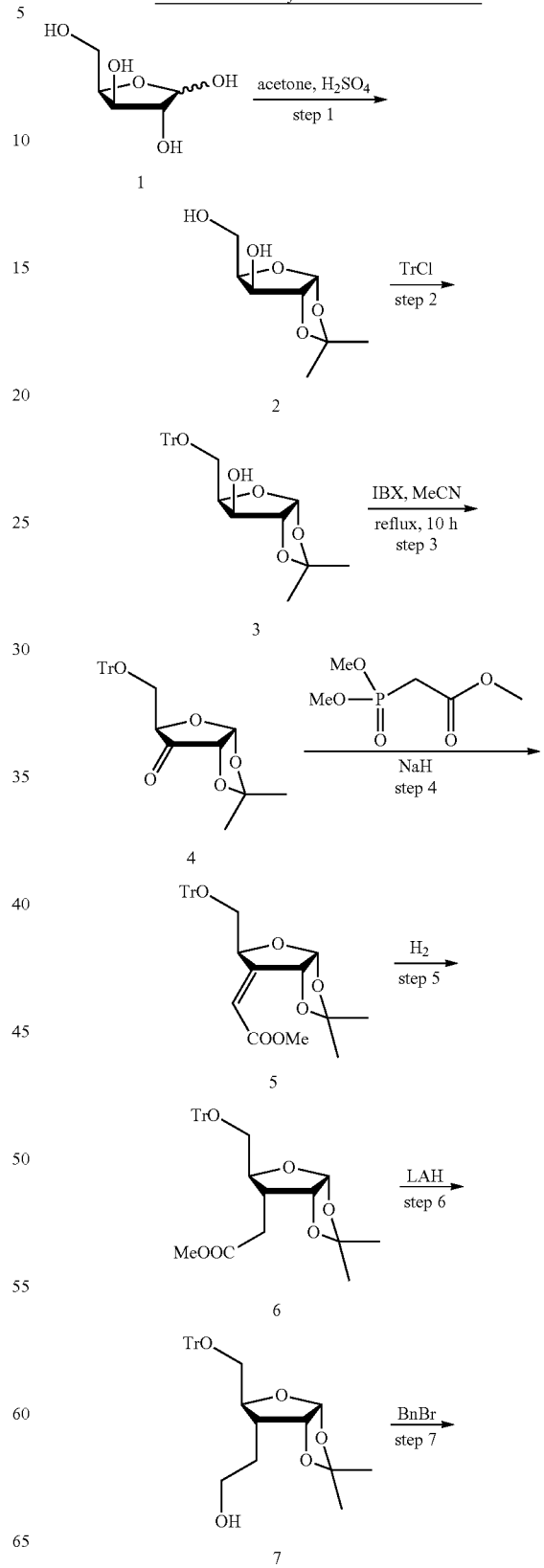

Scheme A1. The synthesis of intermediate 19

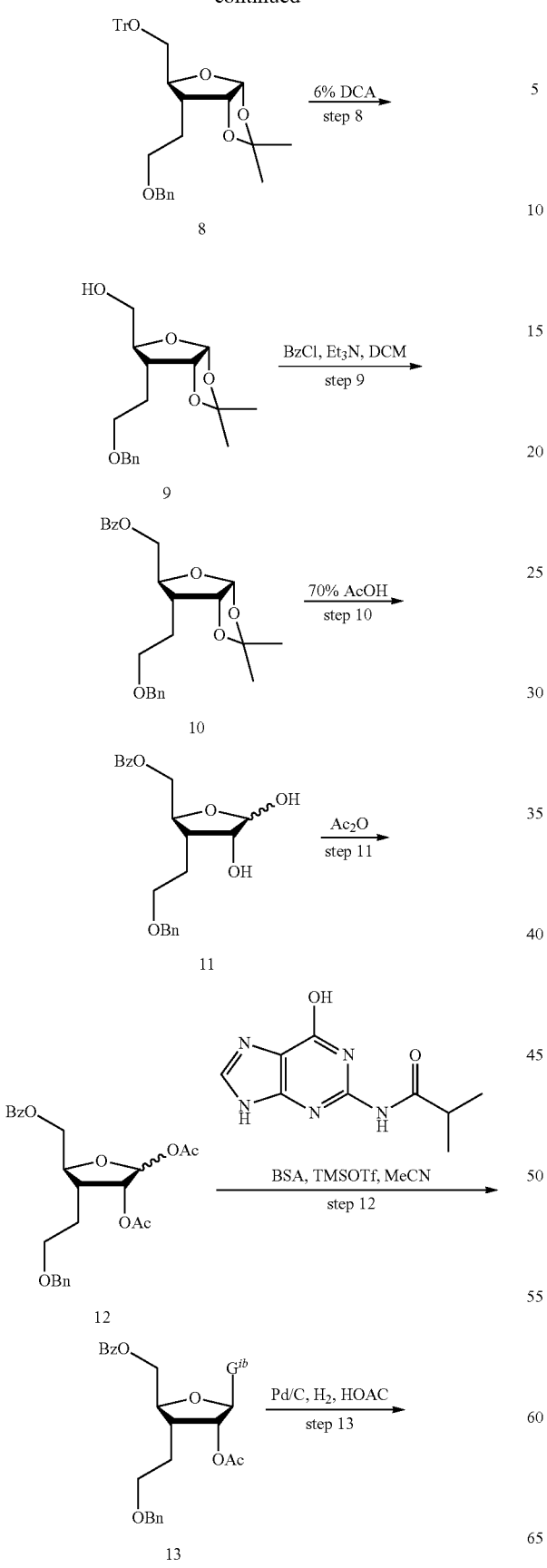
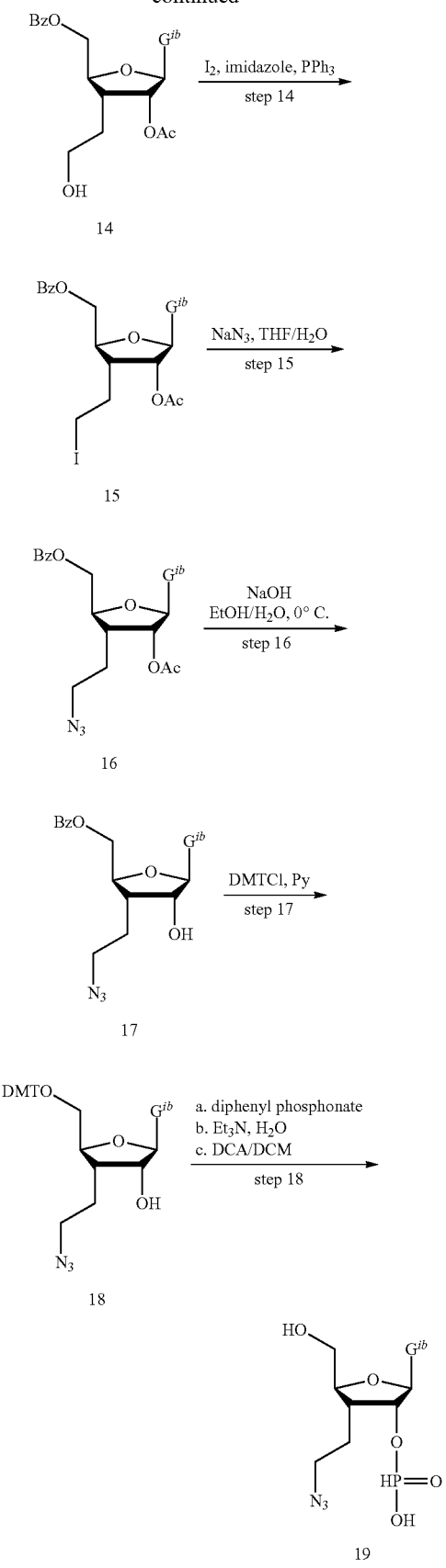

Step 1: Synthesis of (3aR,5R,6S,6aR)-5-(hydroxymethyl)-2,2-dimethyltetrahydrofuro[2,3-d][1,3]dioxol-6-ol

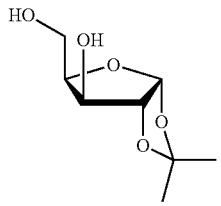

A solution of (2R,4S,5R)-5-(hydroxymethyl)tetrahydrofuran-2,3,4-triol (100 g, 0.67 mol) in acetone (2.6 L) containing $H_2SO_4$ (con., 184.00 g, 1.88 mol, 100 mL, 2.8 eq.) is stirred at 20° C. for 1 h. A solution of $Na_2CO_3$ (130 g, 1.23 mol, 1.8 eq.) in $H_2O$ (600 mL) is carefully added at 0° C. The mixture is stirred for a further 2.5 h before a second batch of $Na_2CO_3$ (70 g, 0.66 mol) is added. After 0.5 h, the precipitate is collected by filtration and washed by acetone (0.5 L×3). The filtrate is concentrated and purified by column chromatography ($SiO_2$, DCM:MeOH=10:1 to 5:1) to give (3aR,5R,6R)-5-(hydroxymethyl)-2,2-dimethyl-3a,5,6,6a-tetrahydrofuro[2,3-d][1,3]dioxol-6-ol (53.5 g, 0.28 mol, 85% yield) as yellow oil. (MS: [M+Na]$^+$ 213.0).

Step 2: Synthesis of 3aR,5R,6S,6aR)-2,2-dimethyl-5-((trityloxy)methyl)tetrahydrofuro[2,3-d][1,3]dioxol-6-ol

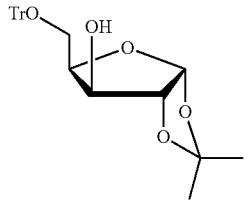

To a solution of (3aR,5R,6R)-5-(hydroxymethyl)-2,2-dimethyl-3a,5,6,6a-tetrahydrofuro[2,3-d][1,3]dioxol-6-ol (125 g, 0.66 mol) in pyridine (600 mL) is added TrCl (219.9 g, 0.79 mol, 1.2 eq.). After 16 h at 60° C., the mixture is cooled down and concentrated. The residue is partitioned between $CH_2Cl_2$ (400 mL) and aq. $NaHCO_3$ (sat., 800 mL). The aqueous phase is extracted with $CH_2Cl_2$ (600 mL×2). The combined organic layers are dried over $Na_2SO_4$, filtered, concentrated and purified by column chromatography ($SiO_2$, petroleum ether/ethyl acetate=10:1 to 5:1) to give (3aR,5R,6R)-2,2-dimethyl-5-(trityloxymethyl)-3a,5,6,6a-tetrahydrofuro[2,3-d][1,3]dioxol-6-ol (250 g, 0.58 mol, 88% yield) as white solid. (MS: [M+Na]$^+$ 455.0).

Step 3: Synthesis of (3aR,5R,6aS)-2,2-dimethyl-5-((trityloxy)methyl)dihydrofuro[2,3-d][1,3]dioxol-6(3aH)-one

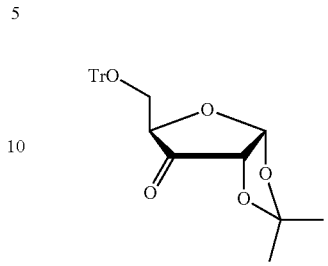

To a solution of (3aR,5R,6R)-2,2-dimethyl-5-(trityloxymethyl)-3a,5,6,6a-tetrahydrofuro[2,3-d][1,3]dioxol-6-ol (250 g, 0.58 mol) in $CH_3CN$ (1.5 L) is added IBX (323 g, 1.2 mol, 2.00 eq.). The mixture is stirred at 90° C. for 6 h. After cooling down, the mixture is filtered. The filtrate is concentrated and give (3aR,5R,6aS)-2,2-dimethyl-5-(trityloxymethyl)-3a,6a-dihydrofuro[2,3-d][1,3]dioxol-6-one (240 g, 0.56 mol, 96.5% yield) as light yellow oil. (MS: [M+Na]$^+$ 453.0).

Step 4: Synthesis of (E)-methyl-2-((3aR,5S,6aR)-2,2-dimethyl-5-((trityloxy)methyl)furo[2,3-d][1,3]dioxol-6(3aH,5H,6aH)-ylidene)acetate

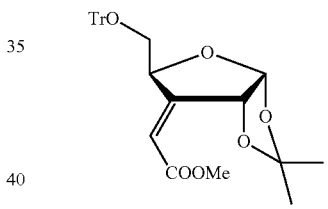

To a mixture of NaH (14.5 g, 0.36 mol, 60% in oil, 1.3 eq.) and THF (1.00 L) is added methyl 2-dimethoxyphosphorylacetate (66 g, 0.36 mol, 52.4 mL, 1.3 eq.) dropwise at 0° C. over 15 min. The mixture is stirred at the same temperature for 45 min before a solution of (3aR,5R,6aS)-2,2-dimethyl-5-(trityloxymethyl)-3a,6a-dihydrofuro[2,3-d][1,3]dioxol-6-one (120 g, 0.28 mol, 1 eq.) in THF (500 mL) is added dropwise. After 15 h at 25° C., the reaction is quenched by $NH_4Cl$ (sat., 50 mL) at 0° C. The mixture is concentrated and partitioned between brine (500 mL) and $CH_2Cl_2$ (500 mL×3). The combined organic layers are dried over $Na_2SO_4$, filtered, concentrated and purified by column chromatography ($SiO_2$, petroleum ether/ethyl acetate=15:1 to 5:1) to give methyl (2E)-2-[(3aR,5S,6aR)-2,2-dimethyl-5-(trityloxymethyl)-3a,6a-dihydrofuro[2,3-d][1,3]dioxol-6-ylidene]acetate (65 g, 0.53 mol, 96% yield) as light yellow oil. (MS: [M+Na]$^+$ 509.0).

Step 5: Synthesis of methyl 2-((3aR,5S,6R,6aR)-2,2-dimethyl-5-((trityloxy)methyl)tetrahydrofuro[2,3-d][1,3]dioxol-6-yl)acetate

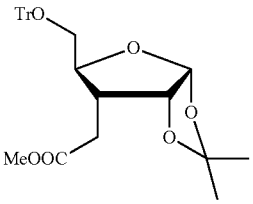

To a solution of methyl (2E)-2-[(3aR,5S,6aR)-2,2-dimethyl-5-(trityloxymethyl)-3a,6a-dihydrofuro[2,3-d][1,3]dioxol-6-ylidene]acetate (260 g, 0.53 mol) in EtOAc (700 mL) is added Pd/C (10% on carbon, 10 g) under $N_2$ atmosphere. The suspension is degassed and purged with $H_2$ for 3 times. The mixture is stirred under $H_2$ (20 psi) at 25° C. for 16 h. The catalyst is removed by filtration. The filtrate is concentrated and purified by column chromatography ($SiO_2$, petroleum ether/ethyl acetate=15:1 to 10:1) to give methyl 2-[(3aR,5S,6S)-2,2-dimethyl-5-(trityloxymethyl)-3a,5,6,6a-tetrahydrofuro[2,3-d][1,3]dioxol-6-yl]acetate (210 g, 0.43 mol, 80.4% yield) as white solid. (MS: [M+Na]$^+$ 511.1).

Step 6: Synthesis of 2-((3aR,5S,6R,6aR)-2,2-dimethyl-5-((trityloxy)methyl)tetrahydrofuro[2,3-d][1,3]dioxol-6-yl)ethanol

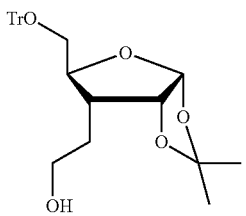

To a mixture of $LiAlH_4$ (15.5 g, 0.41 mol, 2 eq.) and THF (500 mL) is slowly added a solution of methyl 2-[(3aR,5S,6S)-2,2-dimethyl-5-(trityloxymethyl)-3a,5,6,6a-tetrahydrofuro[2,3-d][1,3]dioxol-6-yl]acetate (100 g, 0.20 mol) in THF (20 mL) at 0° C. After being stirred for 2.5 h at 25° C., the reaction is quenched by water (15 mL) and NaOH (aq., 15%, 15 mL) at 0° C. The crude is dried over $Na_2SO_4$, filtered, concentrated and purified by column chromatography ($SiO_2$, petroleum ether/ethyl acetate=5:1 to 2:1) to give 2-[(3aR,5S,6S)-2,2-dimethyl-5-(trityloxymethyl)-3a,5,6,6a-tetrahydrofuro[2,3-d][1,3]dioxol-6-yl]ethanol (80 g, 0.35 mol, 85% yield) as light yellow oil.

$^1$HNMR (400 MHz, CDCl$_3$) δ=7.43-7.35 (m, 6H), 7.25-7.18 (m, 6H), 7.18-7.11 (m, 3H), 5.82 (d, J=3.8 Hz, 1H), 4.62 (t, J=4.2 Hz, 1H), 3.86 (td, J=3.5, 10.2 Hz, 1H), 3.61-3.47 (m, 2H), 3.37 (dd, J=2.8, 10.7 Hz, 1H), 3.02 (dd, J=4.1, 10.7 Hz, 1H), 2.13 (tt, J=4.8, 9.9 Hz, 1H), 1.73-1.62 (m, 2H), 1.42 (s, 3H), 1.40-1.31 (m, 1H), 1.26 (s, 3H). MS: [M+Na]$^+$ 483.2

Step 7: Synthesis of (3aR,5S,6R,6aR)-6-(2-(benzyloxy)ethyl)-2,2-dimethyl-5-((trityloxy)methyl)tetrahydrofuro[2,3-d][1,3]dioxole

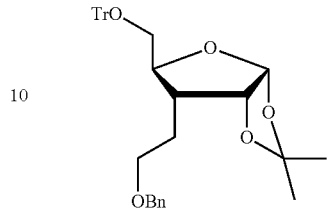

To a mixture of NaH (27.1 g, 0.68 mol, 60% in oil, 4.00 eq.) and THF (500 mL) is added dropwise a solution of 2-[(3aR,5S,6S)-2,2-dimethyl-5-(trityloxymethyl)-3a,5,6,6a-tetrahydrofuro[2,3-d][1,3]dioxol-6-yl]ethanol (78 g, 0.17 mol) in THF (200 mL) at −20° C. over 5 min. After addition, the mixture is stirred at 25° C. for 2 h. BnBr (60.3 mL, 0.51 mol, 3.00 eq.) is added dropwise. The mixture is stirred at 80° C. for 14 h. After cooling down to 0° C., the reaction is quenched by aq. $NH_4Cl$ (sat., 20 mL), diluted with $H_2O$ (400 mL) and extracted with $CH_2Cl_2$ (400 mL×3). The combined organic layers are dried over $Na_2SO_4$, filtered, concentrated and purified by column chromatography ($SiO_2$, petroleum ether/ethyl acetate=15:1 to 5:1) to give (3aR,5S,6S)-6-(2-benzyloxyethyl)-2,2-dimethyl-5-(trityloxymethyl)-3a,5,6,6a-tetrahydrofuro[2,3-d][1,3]dioxole (90 g, 0.16 mol, 97% yield) as white solid. (MS: [M+Na]$^+$=573.1).

Step 8: Synthesis of (3aR,5S,6R,6aR)-6-(2-(benzyloxy)ethyl)-2,2-dimethyltetrahydrofuro[2,3-d][1,3]dioxol-5-yl)methanol

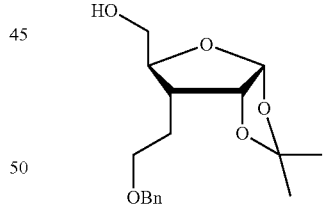

To a solution of (3aR,5S,6S)-6-(2-benzyloxyethyl)-2,2-dimethyl-5-(trityloxymethyl)-3a,5,6,6a-tetrahydrofuro[2,3-d][1,3]dioxole (90 g, 0.16 mol) in $CH_2Cl_2$ (300 mL) is added $CHCl_2COOH$ (30 mL, 0.16 mol, 1.00 eq.). After 3 h at 25° C., the reaction mixture is neutralized with aq. $NaHCO_3$ (sat., 500 mL) to pH-7.0 at 0° C. The crude is extracted with $CH_2Cl_2$ (100 mL×3). The combined organic layers are dried over $MgSO_4$, filtered, concentrated and purified by column chromatography ($SiO_2$, petroleum ether/ethyl acetate=5:1 to 2:1) to give [(3aR,5S,6S)-6-(2-benzyloxyethyl)-2,2-dimethyl-3a,5,6,6a-tetrahydrofuro[2,3-d][1,3]dioxol-5-yl]methanol (44 g, 0.14 mol, 87% yield) as yellow oil.

Step 9: Synthesis of (3aR,5S,6R,6aR)-6-(2-(benzyloxy)ethyl)-2,2-dimethyltetrahydrofuro[2,3-d][1,3]dioxol-5-yl)methyl benzoate

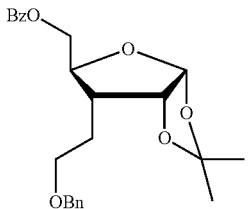

To a solution of [(3aR,5S,6S)-6-(2-benzyloxyethyl)-2,2-dimethyl-3a,5,6,6a-tetrahydrofuro[2,3-d][1,3]dioxol-5-yl]methanol (62 g, 0.2 mol) in CH$_2$Cl$_2$ (200 mL) is added BzCl (35 mL, 0.3 mol, 1.50 eq.) and Et$_3$N (55.7 mL, 0.4 mol, 2 eq.). After 1 h at 25° C., the reaction mixture is concentrated and purified by column chromatography (SiO$_2$, petroleum ether/ethyl acetate=15:1 to 10:1) to give [(3aR,5S,6S)-6-(2-benzyloxyethyl)-2,2-dimethyl-3a,5,6,6a-tetrahydrofuro[2,3-d][1,3]dioxol-5-yl]methyl benzoate (80 g, 0.19 mol, 97% yield) as light yellow oil. (MS: [M+Na]$^+$ 435.1).

Step 10: Synthesis of ((2S,3S,4R)-3-(2-(benzyloxy)ethyl)-4,5-dihydroxytetrahydrofuran-2-yl)methylbenzoate

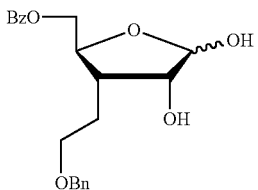

To a mixture of [(3aR,5S,6S)-6-(2-benzyloxyethyl)-2,2-dimethyl-3a,5,6,6a-tetrahydrofuro[2,3-d][1,3]dioxol-5-yl]methyl benzoate (20 g, 49 mmol) and H$_2$O (6 mL) is added HOAc (28 mL, 10 eq.). The mixture is stirred at 100° C. for 5 h. After cooling down, the reaction mixture is neutralized with aq. NaHCO$_3$ (sat., 2 L) and extracted with CH$_2$Cl$_2$ (400 mL×3). The combined organic layers are concentrated and give [(2S,3R,5R)-3-(2-benzyloxyethyl)-4,5-dihydroxy-tetrahydrofuran-2-yl]methyl benzoate (17.5 g, 47 mmol, 96% yield) as light yellow oil, which is used for the next step without purification. (MS: [M+Na]$^+$ 395.1).

Step 11: Synthesis of (3R,4R,5S)-5-((benzoyloxy)methyl)-4-(2-(benzyloxy)ethyl)tetrahydrofuran-2,3-diyliacetate

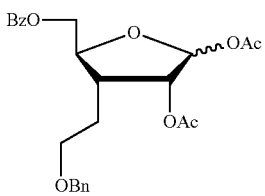

To a solution of [(2S,3R,5R)-3-(2-benzyloxyethyl)-4,5-dihydroxy-tetrahydrofuran-2-yl]methyl benzoate (70 g, 0.19 mol) in pyridine (300 mL) is added Ac$_2$O (0.75 mol, 70.4 mL, 4.0 eq.). The mixture is stirred at 60° C. for 4 h. After cooling to 25° C., the reaction mixture is neutralized with aq. NaHCO$_3$ (sat.) to pH-7 and extracted with CH$_2$Cl$_2$ (300 mL×3). The organic layers are concentrated and purified by column chromatography (SiO$_2$, petroleum ether/ethyl acetate=10:1 to 5:1) to give [(2S,3S,5S)-4,5-diacetoxy-3-(2-benzyloxyethyl)tetrahydrofuran-2-yl]methyl benzoate (80 g, 93% yield) as white solid. (MS: [M+Na]$^+$ 479.1).

Step 12: Synthesis of ((2S,3R,4R,5R)-4-acetoxy-3-(2-(benzyloxy)ethyl)-5-(2-isobutyramido-6-oxo-1H-purin-9(6H)-yl)tetrahydrofuran-2-yl)methylbenzoate

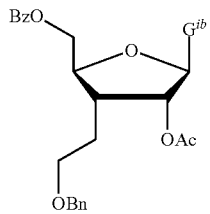

To a solution of 2-methyl-N-(6-oxo-1,9-dihydropurin-2-yl)propanamide (18.9 g, 85.4 mmol, 1.30 eq.) in CH$_3$CN (300 mL) is added BSA (84.5 mL, 341.7 mmol, 5.2 eq.) at 20° C. After stirring at 65° C. for 0.5 h, the mixture is cooled down and concentrated. The residue is dissolved in MeCN (600 mL) followed by addition of a solution of [(2S,3S,5S)-4,5-diacetoxy-3-(2-benzyloxyethyl)tetrahydrofuran-2-yl]methyl benzoate (30 g, 65.7 mmol) in MeCN (150 mL) and TMSOTf (17.8 mL, 98.6 mmol, 1.5 eq.) at −15° C. The mixture is stirred at 65° C. for 15 h. After cooling down, the mixture is concentrated and purified by column chromatography (SiO$_2$, petroleum ether/ethyl acetate=5:1 to 1:1) to give ((2S,3R,4R,5R)-4-acetoxy-3-(2-(benzyloxy)ethyl)-5-(2-isobutyramido-6-oxo-1H-purin-9(6H)-yl)tetrahydrofuran-2-yl)methyl benzoate (30 g, 48.6 mmol, 74% yield) as white solid. (MS: [M+1]$^+$ 618.1).

$^1$HNMR (400 MHz, CHLOROFORM-d) δ=12.00 (s, 1H), 9.11 (s, 1H), 7.92-7.84 (m, 2H), 7.82-7.76 (m, 1H), 7.58 (t, J=7.1 Hz, 1H), 7.46-7.37 (m, 2H), 7.27-7.16 (m, 5H), 5.90-5.85 (m, 1H), 5.74 (d, J=5.3 Hz, 1H), 4.78-4.61 (m, 2H), 4.55-4.38 (m, 3H), 3.55 (t, J=5.8 Hz, 2H), 3.23-3.14 (m, 1H), 2.47 (spt, J=6.9 Hz, 1H), 2.22-2.10 (m, 3H), 1.83 (q, J=6.1 Hz, 2H), 1.17 (dd, J=6.9, 8.9 Hz, 6H).

Step 13: Synthesis of ((2S,3R,4R,5R)-4-acetoxy-3-(2-hydroxyethyl)-5-(2-isobutyramido-6-oxo-1H-purin-9(6H)-yl)tetrahydrofuran-2-yl)methylbenzoate

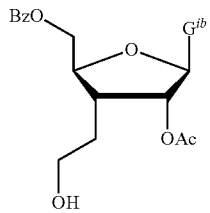

To a solution of [(2S,3S,5R)-4-acetoxy-3-(2-benzyloxy-ethyl)-5-[2-(2-methylpropanoylamino)-6-oxo-1H-purin-9-yl]tetrahydrofuran-2-yl]methyl benzoate (25 g, 40.5 mmol) in EtOH (500 mL) is added Pd/C (38 g, 10% on carbon) and HOAc (25.00 mL, 437.1 mmol, 11 eq.) under $N_2$. The suspension is purged with $H_2$ for 3 times and stirred under $H_2$ (40 Psi) for 48 h at 50° C. After cooling down, the reaction mixture is filtered. The filtrate is concentrated and purified by column chromatography (SiO$_2$, petroleum ether/ ethyl acetate=5:1 to 2:1) to give [(2S,3S,5R)-4-acetoxy-3-(2-hydroxyethyl)-5-[2-(2-methylpropanoylamino)-6-oxo-1H-purin-9-yl]tetrahydrofuran-2-yl]methyl benzoate (20 g, 37.9 mmol, 94% yield) as white solid. (MS: [M+1]$^+$ 528.3).

Step 14: Synthesis of [(2S,3R,5R)-4-acetoxy-3-(2-iodoethyl)-5-[2-(2-methylpropanoylamino)-6-oxo-1H-purin-9-yl]tetrahydrofuran-2-yl]methylbenzoate

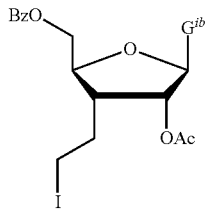

To a solution of [(2S,3R,5R)-4-acetoxy-3-(2-hydroxy-ethyl)-5-[2-(2-methylpropanoylamino)-6-oxo-1H-purin-9-yl]tetrahydrofuran-2-yl]methyl benzoate (3 g, 5.69 mmol, 1 eq.) in THF (90 mL) is added imidazole (1.16 g, 17.06 mmol, 3 eq.) and triphenylphosphine (4.47 g, 17.06 mmol, 3 eq.) in one portion, then a solution of 12 (2.60 g, 10.24 mmol, 1.8 eq.) in THF (10 mL) is added slowly. The reaction mixture is stirred at 25° C. for 16 h, quenched with saturated Na$_2$SO$_3$ aq. solution (8 mL) and evaporated to give the residue. The residue is dissolved in ethyl acetate (80 mL) and washed by water (80 mL). The aqueous layer is extracted with EtOAc (150 mL×3). The combined organic layers are dried over anhydrous Na$_2$SO$_4$ and concentrated under reduced pressure. The residue is purified by column chromatography (SiO$_2$, petroleum ether/ethyl acetate=1:1 to 1:3) to afford [(2S,3R,5R)-4-acetoxy-3-(2-iodoethyl)-5-[2-(2-methylpropanoylamino)-6-oxo-1H-purin-9-yl]tetrahydrofuran-2-yl]methyl benzoate (2.3 g, 64% yield) as yellow solid. (MS: [M+1]$^+$ 638.2).

Step 15: Synthesis of [(2S,3R,4R,5R)-4-acetoxy-3-(2-azidoethyl)-5-[2-(2-methylpropanoylamino)-6-oxo-1H-purin-9-yl]tetrahydrofuran-2-yl]methylbenzoate

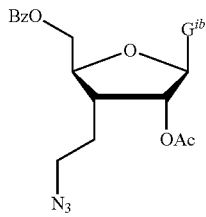

To a solution of [(2S,3R,4R,5R)-4-acetoxy-3-(2-iodo-ethyl)-5-[2-(2-methylpropanoylamino)-6-oxo-1H-purin-9-yl]tetrahydrofuran-2-yl]methyl benzoate (3.8 g, 5.96 mmol, 1 eq.) in THF (40 mL) is added NaN$_3$ (2.52 g, 38.75 mmol, 6.5 eq.) and H$_2$O (10 mL). The mixture is stirred at 50° C. for 2 h. The mixture is quenched with saturated aq. Na$_2$CO$_3$ solution (50 mL), and extracted with EtOAc (100 mL×3). The combined organic layers are dried over anhydrous Na$_2$SO$_4$ and concentrated under reduced pressure to afford [(2S,3R,4R,5R)-4-acetoxy-3-(2-azidoethyl)-5-[2-(2-methylpropanoylamino)-6-oxo-1H-purin-9-yl]tetrahydrofuran-2-yl]methyl benzoate (2 g, 61% yield) as yellow solid. (MS: [M+1]$^+$ 553.1).

Step 16: Synthesis of N-[9-[(2R,3R,4S,5S)-4-(2-azidoethyl)-3-hydroxy-5-(hydroxymethyl)tetrahydrofuran-2-yl]-6-oxo-1H-purin-2-yl]-2-methyl-propanamide

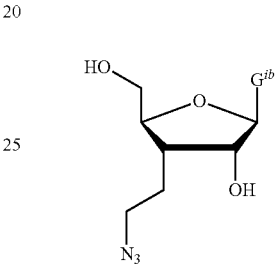

To a solution of [(2S,3R,5R)-4-acetoxy-3-(2-azidoethyl)-5-[2-(2-methylpropanoylamino)-6-oxo-1H-purin-9-yl]tetrahydrofuran-2-yl]methyl benzoate (2.55 g, 4.62 mmol, 1 eq.) in EtOH (220 mL) is added aq. NaOH (2M, 23 mL, 10 eq.) at 0° C. The resulting mixture is stirred at ambient temperature for 0.5 h. To the reaction mixture is added HCOOH to adjust pH=7~8 at 0° C., and the mixture is concentrated under reduced pressure to give a residue. The residue is purified by prep-HPLC (0.1% FA in MeCN and water, 0%~70%) to afford N-[9-[(2R, 3R,4S,5S)-4-(2-azidoethyl)-3-hydroxy-5-(hydroxymethyl)tetrahydrofuran-2-yl]-6-oxo-1H-purin-2-yl]-2-methyl-propanamide (1.6 g, 3.94 mmol, 85% yield) as white solid. (MS: [M+1]$^+$ 407.1).

Step 17: Synthesis of N-[9-[(2R,3R,4S,5S)-4-(2-azidoethyl)-5-[[bis(4-methoxyphenyl)-phenyl-methoxy]methyl]-3-hydroxy-tetrahydrofuran-2-yl]-6-oxo-1H-purin-2-yl]-2-methyl-propanamide

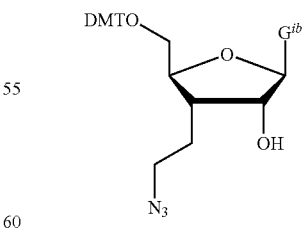

To a solution of N-[9-[(2R,3R,4S,5S)-4-(2-azidoethyl)-3-hydroxy-5-(hydroxymethyl)tetra hydrofuran-2-yl]-6-oxo-1H-purin-2-yl]-2-methyl-propanamide (1.6 g, 3.94 mmol) in pyridine (15 mL) is added DMTCl (1.60 g, 4.72 mmol, 1.2 eq.). The mixture is stirred at 25° C. for 3 h. The reaction mixture is quenched by addition of MeOH (10 mL) at 25° C.

The mixture is concentrated under reduced pressure to give a residue as yellow oil. The residue is purified by column chromatography (SiO$_2$, petroleum ether/ethyl acetate=1/1 to EtOH/ethyl acetate=1:250) to give N-[9-[(2R,3R,4S,5S)-4-(2-azidoethyl)-5-[[bis(4-methoxyphenyl)-phenyl-methoxy]methyl]-3-hydroxy-tetrahydrofuran-2-yl]-6-oxo-1H-purin-2-yl]-2-methyl-propanamide (950 mg, 1.34 mmol, 34% yield) as yellow solid. (MS: [M+1]$^+$ 709.4).

Step 18: Synthesis of [(2R,3R,4R,5S)-4-(2-azidoethyl)-5-(hydroxymethyl)-2-[2-(2-methylpropanoylamino)-6-oxo-1H-purin-9-yl]tetrahydrofuran-3-yl] oxyphosphinic acid

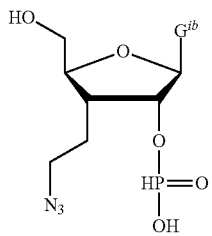

To a solution of N-[9-[(2R,3R,4S,5S)-4-(2-azidoethyl)-5-[[bis(4-methoxyphenyl)-phenyl-methoxy]methyl]-3-hydroxytetrahydrofuran-2-yl]-6-oxo-1H-purin-2-yl]-2-methyl-propanamide (700 mg, 988 µmol) in pyridine (6 mL) is added diphenyl phosphite (809.5 mg, 3.46 mmol, 664 µL, 3.5 eq.). After 1 h at 25° C., DCM (5 mL) and Et$_3$N (3 mL) are added and the mixture is stirred at 25° C. for another 1.5 h. The mixture is concentrated and the residue is partitioned between DCM (20 mL) and aq. NaHCO$_3$ solution (5%, 20 mL). The organic phase is evaporated to give the crude intermediate, which is re-dissolved in a mixture of H$_2$O (3 mL) and 2,2-dichloroacetic acid (382 mg, 2.96 mmol, 243 µL, 3 eq.) in DCM (10 mL). The mixture is stirred at 25° C. for 0.5 h. The reaction is quenched with Et$_3$N (3.0 mL), then the mixture is evaporated to give the residue. The residue is purified by reversed-phase column (0.1% TEA in MeCN and water, 0%~70%) to give [(2R,3R,4R,5S)-4-(2-azidoethyl)-5-(hydroxymethyl)-2-[2-(2-methylpropanoylamino)-6-oxo-1H-purin-9-yl]tetrahydrofuran-3-yl]oxyphosphinic acid (400 mg, 82% yield, 95% purity) as white solid. (MS: [M+1]$^+$ 471.0).

Synthesis of CDN-A from Intermediate 19

Scheme A2. The synthesis of CDN-A

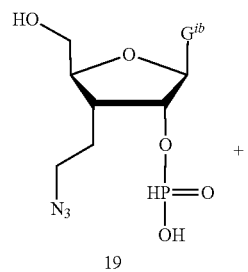

19

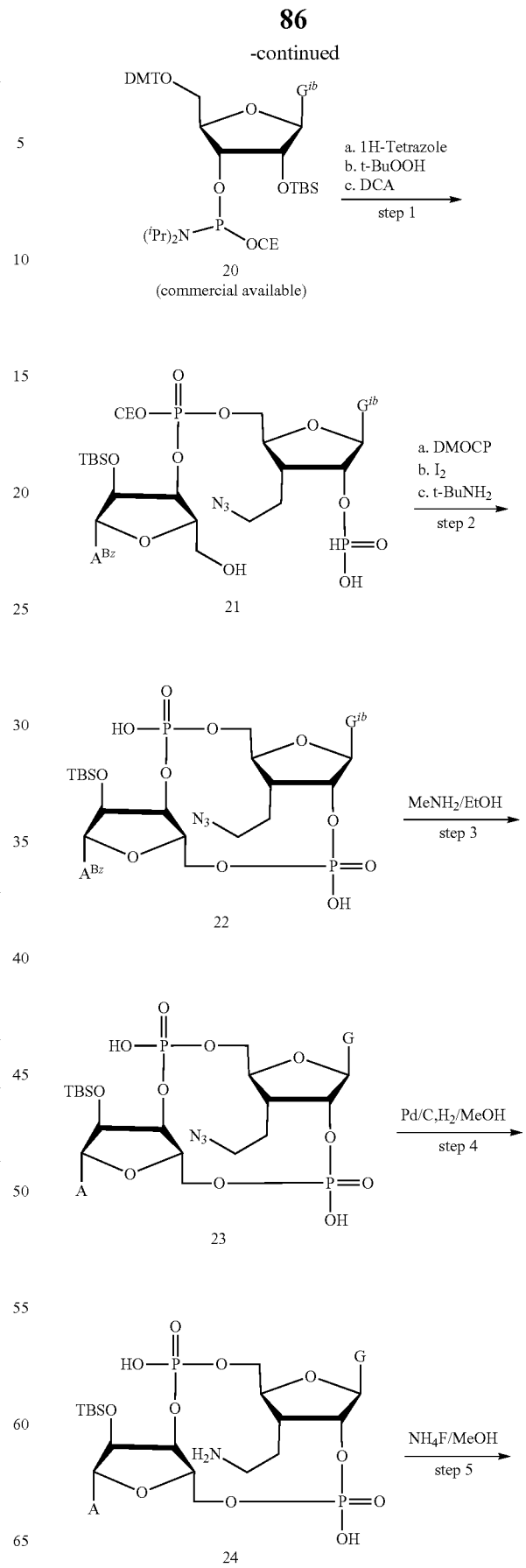

-continued

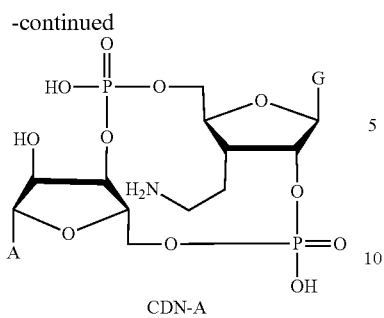

CDN-A

Step 1: Synthesis of [(2R,3R,4R,5R)-2-[[[(2R,3R,
4R,5S)-4-(2-azidoethyl)-5-(hydroxymethyl)-2-[2-(2-
methylpropanoylamino)-6-oxo-1H-purin-9-yl]tetra-
hydrofuran-3-yl]oxy-(2-cyanoethoxy)phosphoryl]
oxymethyl]-5-(6-benzamidopurin-9-yl)-4-[tertbutyl
(dimethyl)silyl]oxy-tetrahydrofuran-3-yl]
oxyphosphinicacid

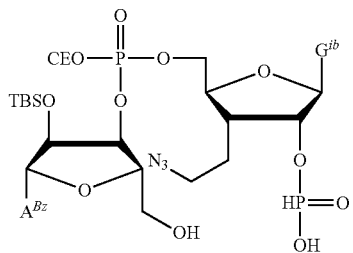

To a solution of [(2R,3R,4R,5R)-5-(6-benzamidopurin-9-yl)-4-[tert-butyl(dimethyl)silyl]oxy-2-(hydroxymethyl)tetrahydrofuran-3-yl]oxyphosphinic acid (400 mg, 727.8 µmol) in CH$_3$CN (3 mL) is added tetrazole solution (0.45M in MeCN, 6.47 mL, 4 eq.). The mixture is stirred at 25° C. for 5 min. N-[9-[(2R,3R,4R,5S)-4-(2-azidoethyl)-5-[[bis(4-methoxyphenyl)-phenyl-methoxy]methyl]-3-[2-cyanoethoxy-(diisopropylamino)phosphanyl]oxytetrahydrofuran-2-yl]-6-oxo-1H-purin-2-yl]-2-methyl-propanamide (595 mg, 655 µmol, 0.9 eq.) is added. After 0.5 h at 25° C., 2-hydroperoxy-2-methyl-propane (197 mg, 2.18 mmol, 209 µL, 3 eq.) is added and the mixture is stirred at 25° C. for 0.5 h. Then 2,2-dichloroacetic acid (938 mg, 7.28 mmol, 598 µL, 10 eq.) in DCM (10 mL) is added. The mixture is stirred at 25° C. for 25 min and quenched with sat. aq. Na$_2$SO$_3$ (2.0 mL) followed by pyridine (2.0 mL) for neutralization. The mixture is evaporated to give the residue. The residue is purified by reversed-phase column (0.1% TEA in MeCN and water, 0%~70%) to afford [(2R,3R,4R,5R)-2-[[[(2R,3R,4R,5S)-4-(2-azidoethyl)-5-(hydroxyl-methyl)-2-[2-(2-methyl-propanoylamino)-6-oxo-1H-purin-9-yl]tetrahydrofuran-3-yl]oxy-(2-cyanoethoxy)phosphoryl]oxymethyl]-5-(6-benzamidopurin-9-yl)-4-[tertbutyl(dimethyl)silyl]oxy-tetrahydrofuran-3-yl]oxyphosphinic acid (600 mg, 62% yield, 80% purity) as white solid. (MS: [M+1]$^+$ 1071.5).

Step 2: Synthesis of N-[9-[(27S,28R,29R,30R,31R,
32R,33R,34R)-29-(2-azidoethyl)-32-[tert-butyl(dimethyl)silyl]oxy-67,68-dihydroxy-33-[2-(2-methyl-
propanoylamino)-6-oxo-1H-purin-9-yl]-67,68-
dioxo-59,60,61,62,63,64-hexaoxa-67,68-
diphosphatricyclooctadecan-34-yl]purin-6-yl]
benzamide

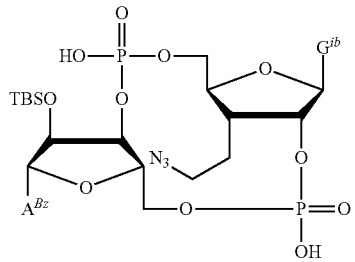

To a solution of [(2R,3R,4R,5S)-4-(2-azidoethyl)-5-[[[(2R,3R,4R,5R)-5-(6-benzamidopurin-9-yl)-4-[tertbutyl(dimethyl)silyl]oxy-2-(hydroxymethyl)tetrahydrofuran-3-yl]oxy-(2-cyanoethoxy)phosphoryl]oxymethyl]-2-[2-(2-methylpropanoylamino)-6-oxo-1H-purin-9-yl]tetrahydrofuran-3-yl]oxyphosphinic acid (400 mg, 373.48 µmol) in pyridine (9 mL) is added 2-chloro-5,5-dimethyl-1,3,2-dioxaphosphinane 2-oxide (345 mg, 1.87 mmol, 5 eq.). After 15 min at 25° C., 12 (379 mg, 1.49 mmol, 4 eq.) and H$_2$O (13.5 mg, 747.0 µmol, 13.5 µL, 2 eq.) are added and the mixture is stirred at 25° C. for 0.5 h. The reaction is quenched with saturated aq. NaHCO$_3$ solution (2.0 mL) and saturated aq. Na$_2$SO$_3$ solution (2.0 mL). After evaporation, the residue is dissolved in CH$_3$CN (10 mL) and added with 2-methylpropan-2-amine (10 mL). The mixture is stirred at 25° C. for 1 h. The reaction mixture is evaporated to give a residue. The residue is purified by reversed-phase column (0.1% TEA in MeCN and water, 0%~70%) to afford N-[9-[(27S,28R,29R,30R,31R,32R,33R,34R)-29-(2-azidoethyl)-32-[tert-butyl(dimethyl)silyl]oxy-67,68-dihydroxy-33-[2-(2-methylpropanoylamino)-6-oxo-1H-purin-9-yl]-67,68-dioxo-59,60,61,62,63,64-hexaoxa-67,68diphosphatricyclooctadecan-34-yl]purin-6-yl]benzamide (350 mg, 310 µmol, 83% yield, 90% purity) as white solid. (MS: [M+1]$^+$ 1016.4).

Step 3: Synthesis of 2-amino-9-[(19S,20R,21R,22R,
23R,24R,25R,26R)-26-(6-aminopurin-9-yl)-21-(2-
azidoethyl)-24-[tert-butyl(dimethyl)silyl]oxy-54,55-
dihydroxy-54,55-dioxo-46,47,48,49,50,51-hexaoxa-
54,55-diphosphatricyclooctadecan-25-yl]-1H-purin-
6-one

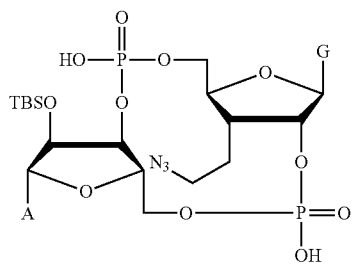

N-[9-[(27S,28R,29R,30R,31R,32R,33R,34R)-29-(2-azidoethyl)-32-[tert-butyl(dimethyl)silyl]oxy-67,68-dihydroxy-33-[2-(2-methylpropanoylamino)-6-oxo-1H-purin-9-yl]-67,68-dioxo-59,60,61,62,63,64-hexaoxa-67,68diphosphatricyclooctadecan-34-yl]purin-6-yl]benzamide (300 mg, 295 mol) is dissolved in MeNH₂/EtOH (5M, 2.95 mL) and the mixture is stirred at 25° C. for 2 h. The mixture is evaporated to give a residue. The residue is purified by reversed-phase column (0.1% TEA in MeCN and water, 0%~35%) to afford 2-amino-9-[(19S,20R,21R,22R,23R,24R,25R,26R)-26-(6-aminopurin-9-yl)-21-(2-azidoethyl)-24-[tert-butyl(dimethyl)silyl]oxy-54,55-dihydroxy-54,55-dioxo-46,47,48,49,50,51-hexaoxa-54,55diphosphatricyclooctadecan-25-yl]-1H-purin-6-one (160 mg, 52% yield, 80% purity) as white solid. (MS: [M+1]⁺ 842.3).

Step 4: Synthesis of 2-amino-9-[(19S,20R,21R,22R,23R,24R,25R,26R)-21-(2-aminoethyl)-26-(6-aminopurin-9-yl)-24-[tert-butyl(dimethyl)silyl]oxy-52,53-dihydroxy-52,53-dioxo-44,45,46,47,48,49-hexaoxa-52,53-diphosphatricyclooctadecan-25-yl]-1H-purin-6-one

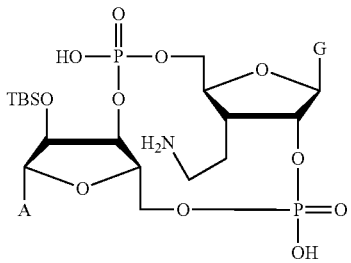

To the solution of 2-amino-9-[(19S,20R,21R,22R,23R,24R,25R,26R)-26-(6-aminopurin-9-yl)-21-(2-azidoethyl)-24-[tertbutyl(dimethyl)silyl]oxy-54,55-dihydroxy-54,55-dioxo-46,47,48,49,50,51-hexaoxa-54,55diphosphatricyclooctadecan-25-yl]-1Hpurin-6-one (100 mg, 118.8 µmol) in MeOH (8 mL) is added Pd/C (30 mg, 10% purity) in one portion, and the mixture is stirred at 25° C. under H₂ (10 psi) for 5 h. The mixture is filtered and the filtrate is evaporated to give a residue. The residue is purified by reversed-phase column (0.1% TEA in MeCN and water, 0%~30%) to afford 2-amino-9-[(19S,20R,21R,22R,23R,24R,25R,26R)-21-(2-aminoethyl)-26-(6-aminopurin-9-yl)-24-[tert-butyl(dimethyl)silyl]oxy-52,53-dihydroxy-52,53-dioxo-44,45,46,47,48,49-hexaoxa-52,53diphosphatricyclooctadecan-25-yl]-1H-purin-6-one (70 mg, 77.2 µmol, 65% yield, 90% purity) as white solid. (MS: [M+1]⁺ 816.5).

Step 5: Synthesis of 2-amino-9-[(14S,15R,16R,17R,18S,19R,20R,21R)-16-(2-aminoethyl)-20-(6-aminopurin-9-yl)-17,45,46-trihydroxy-45,46-dioxo-39,40,41,42,43,44-hexaoxa-45,46-diphosphatricyclooctadecan-21-yl]-1H-purin-6-one (CDN-A)

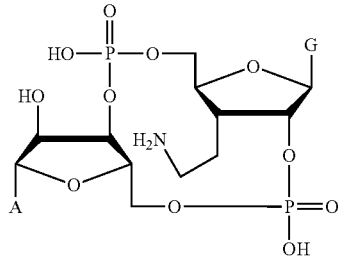

To the solution of 2-amino-9-[(19S,20R,21R,22R,23R,24R,25R,26R)-21-(2-aminoethyl)-26-(6-aminopurin-9-yl)-24-[tertbutyl(dimethyl)silyl]oxy-52,53-dihydroxy-52,53-dioxo-44,45,46,47,48,49-hexaoxa-52,53diphosphatricyclooctadecan-25-yl]-1Hpurin-6-one (35 mg, 42.9 µmol) in MeOH (3 mL) is added NH₄F (127 mg, 3.43 mmol, 80 eq.) in one portion, and the mixture is stirred at 70° C. for 0.25 h. After cooling down to room temperature, the mixture is evaporated to give a residue. The residue is purified by reversed-phase column (0.1% HCOOH in MeCN and water, 0%~30%) to afford 2-amino-9-[(14S,15R,16R,17R,18S,19R,20R,21R)-16-(2-aminoethyl)-20-(6-aminopurin-9-yl)-17,45,46-trihydroxy-45,46-dioxo-39,40,41,42,43,44-hexaoxa-45,46diphosphatricyclooctadecan-21-yl]-1H-purin-6-one (CDN-A, 8.6 mg, 11.9 µmol, 28% yield, 97% purity) as white solid. (MS: [M+1]⁺ 702.0).

¹H NMR (D₂O+buffer, 400 MHz): δ (ppm) 8.19 (s, 1H), 8.18 (s, 1H), 7.76 (s, 1H), 6.08 (s, 1H), 5.83-5.81 (m, 1H), 5.71-5.67 (m, 1H), 5.03-5.01 (m, 1H), 4.42-4.37 (m, 2H), 4.30-4.28 (m, 1H), 4.18-4.16 (m, 1H), 4.07-4.01 (m, 2H), 3.13-3.11 (m, 2H), 2.68-2.66 (m, 1H), 2.33-2.30 (m, 1H), 1.85-1.83 (m, 1H). ³¹P NMR (D₂O+buffer): δ (ppm) −1.15, −2.47

Example 2. Preparation of CDN-B

Schemes B1 and B2 below depict the synthesis of a CDN ("CDN-B") disclosed herein. The synthesis and characterization of this CDN and the synthetic intermediates employed are described below.

Synthesis of Intermediate 29 from Intermediate 14

Scheme B1: The synthesis of intermediate 29

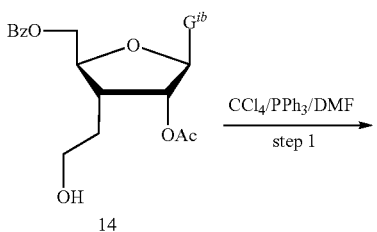

-continued

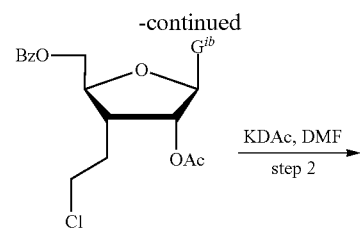
25

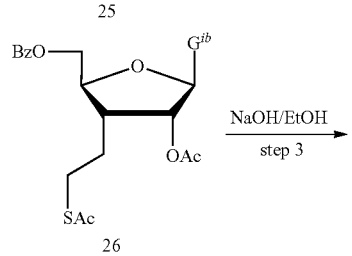
26

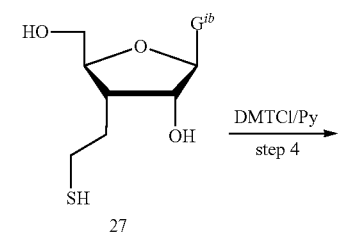
27

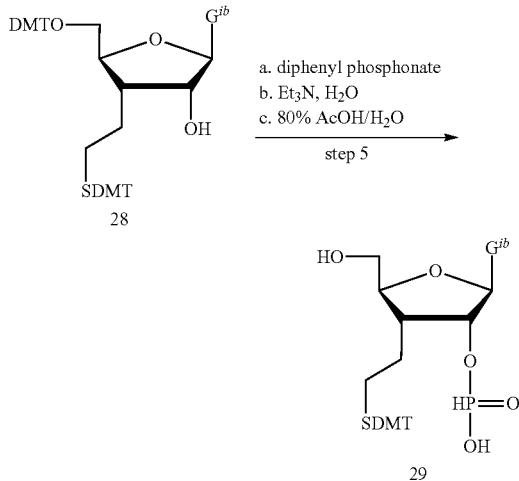
28

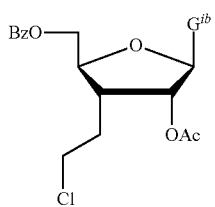
29

Step 1: Synthesis of [(2S,3R,4R,5R)-4-acetoxy-3-(2-chloroethyl)-5-[2-(2-methylpropanoylamino)-6-oxo-1H-purin-9-yl]tetrahydrofuran-2-yl]methyl benzoate To a solution of [(2S,3R,4R,5R)-4-acetoxy-3-(2-hydroxyethyl)-5-[2-(2-methylpropanoylamino)-6-oxo-1H-purin-9-yl]tetrahydrofuran-2-yl]methyl benzoate (19 g, 36.0 mmol) in DMF (100 mL) is added PPh$_3$ (23.6 g, 90.0 mmol, 2.5 eq.) and CCl$_4$ (17.3 mL, 180.1 mmol, 5 eq.). After being stirred for 16 h at 25° C., the reaction is quenched by sat. aq. NaHCO$_3$ (150 mL) and extracted with EtOAc (80 mL×2). The combined organic layers are concentrated and purified by column chromatography (SiO$_2$, petroleum ether/ethyl acetate=10:1 to 1:1) to give [(2S,3R,4R,5R)-4-acetoxy-3-(2-chloroethyl)-5-[2-(2-methylpropanoylamino)-6-oxo-1H-purin-9-yl]tetrahydrofuran-2-yl]methyl benzoate (13 g, 23.8 mmol, 66% yield) as light yellow solid. (MS: [M+1]$^+$ 546.2).

Step 2: Synthesis of [(2S,3R,4R,5R)-4-acetoxy-3-(2-acetylsulfanylethyl)-5-[2-(2-methylpropanoylamino)-6-oxo-1H-purin-9-yl]tetrahydrofuran-2-yl]methyl benzoate

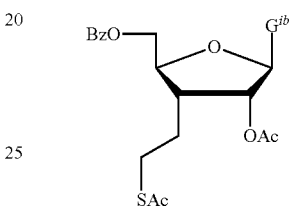

To a solution of [(2S,3R,4R,5R)-4-acetoxy-3-(2-chloroethyl)-5-[2-(2-methylpropanoylamino)-6-oxo-1H-purin-9-yl]tetrahydrofuran-2-yl]methyl benzoate (15 g, 27.5 mmol) in DMF (100 mL) is added AcSK (7.84 g, 68.7 mmol, 2.5 eq.). The reaction mixture is stirred at 50° C. for 16 h. After cooling down, the reaction mixture is diluted with DCM (200 mL) and washed with aq. NaHCO$_3$ (sat., 200 mL). The organic layer is concentrated to give [(2S,3R,4R,5R)-4-acetoxy-3-(2-acetylsulfanylethyl)-5-[2-(2-methylpropanoylamino)-6-oxo-1H-purin-9-yl]tetrahydrofuran-2-yl]methyl benzoate (16 g) as light yellow oil which is used for the next step without purification. (MS: [M+1]$^+$ 586.3).

Step 3: Synthesis of N-[9-[(2R,3R,4S,5S)-3-hydroxy-5-(hydroxymethyl)-4-(2-sulfanylethyl)tetrahydrofuran-2-yl]-6-oxo-1H-purin-2-yl]-2-methyl-propanamide

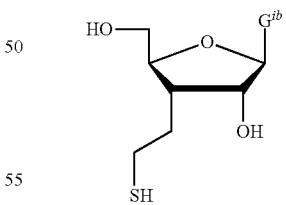

To a solution of [(2S,3R,4R,5R)-4-acetoxy-3-(2-acetylsulfanylethyl)-5-[2-(2-methylpropanoylamino)-6-oxo-1H-purin-9-yl]tetrahydrofuran-2-yl]methyl benzoate (16 g, 27.3 mmol) in EtOH (160 mL) is added NaOH (2 M, 68.3 mL, 5 eq.) at 0° C. The reaction mixture is stirred at 0° C. for 0.5 h. The pH is adjusted to 7 by HOAc. The mixture is concentrated in vacuum to remove most of solvent. The brown precipitate is collected and treated with DCM/TBME (1/100, V/V, 200 mL). After filtration, the filtrate is concentrated to give N-[9-[(2R,3R,4S,5S)-3-hydroxy-5-(hydroxymethyl)-4-(2-sulfanylethyl)tetrahydrofuran-2-yl]-6-oxo-1H-purin-2-yl]-2-methyl-propanamide (11 g, crude, ~10% disulfide) as brown solid which is used for the next step without further purification. (MS: [M+1]$^+$ 398.1).

Step 4: Synthesis of N-[9-[(2R,3R,4S,5S)-3-hydroxy-5-[[(3-methoxyphenyl)-(4-methoxyphenyl)-phenyl-methoxy]methyl]-4-[2-[(3-methoxyphenyl)-(4-methoxyphenyl)-phenyl-methyl]sulfanylethyl]tetrahydrofuran-2-yl]-6-oxo-1H-purin-2-yl]-2-methyl-propanamide

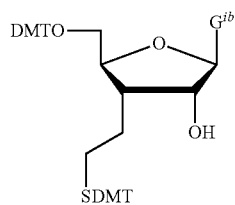

To a solution of N-[9-[(2R,3R,4S,5S)-3-hydroxy-5-(hydroxymethyl)-4-(2-sulfanylethyl)tetrahydrofuran-2-yl]-6-oxo-1H-purin-2-yl]-2-methyl-propanamide (11 g, 27.7 mmol) in py. (110 mL) is added DMTCl (28.1 g, 83.0 mmol, 3 eq.). After 16 h at 25° C., the reaction is quenched with aq. NaHCO$_3$ (sat., 200 mL) and extracted with EtOAc (200 mL×2). The organic phase is dried over Na$_2$SO$_4$, filtered and purified by silica gel chromatography PE:EE(EA:EtOH=3:1)=10:1~2:1 to give compound N-[9-[(2R,3R,4S,5S)-3-hydroxy-5-[[(3-methoxyphenyl)-(4-methoxyphenyl)-phenyl-methoxy]methyl]-4-[2-[(3-methoxyphenyl)-(4-methoxyphenyl)-phenyl-methyl]sulfanylethyl]tetrahydrofuran-2-yl]-6-oxo-1H-purin-2-yl]-2-methyl-propanamide (14 g, 47.0% yield, 93% purity) as light yellow solid. (MS: [M+1]$^+$ 1002.5).

Step 5: Synthesis of [(2R,3R,4R,5S)-5-(hydroxymethyl)-4-[2-[(3-methoxyphenyl)-(4-methoxyphenyl)-phenyl-methyl]sulfanylethyl]-2-[2-(2-methylpropanoylamino)-6-oxo-1H-purin-9-yl]tetrahydrofuran-3-yl]oxyphosphinicacid

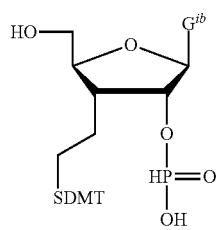

To a solution of N-[9-[(2R,3R,4S,5S)-3-hydroxy-5-[[(3-methoxyphenyl)-(4-methoxyphenyl)-phenyl-methoxy]methyl]-4-[2-[(3-methoxyphenyl)-(4-methoxyphenyl)-phenyl-methyl]sulfanylethyl]tetrahydrofuran-2-yl]-6-oxo-1H-purin-2-yl]-2-methyl-propanamide (12 g, 8.4 mmol) in py. (120 mL) is added phenoxyphosphonoyloxybenzene (7.51 mL, 29.3 mmol, 3.5 eq.) at 25° C. After 1 h, Et$_3$N/H$_2$O (100 mL, 1:1) is added. After 0.5 h, the mixture is extracted with EtOAc (200 mL×2). The organic phase is concentrated and then dissolved in aqueous AcOH (80%, 120 mL). The mixture is stirred at 25° C. for 1 h. The reaction mixture is neutralized by addition of saturated aq. Na$_2$CO$_3$ at 0° C. till pH-7. The mixture is directly purified by reverse phase column (CH$_3$CN/H$_2$O, 0~60%) and give [(2R,3R,4R,5S)-5-(hydroxymethyl)-4-[2-[(3-methoxyphenyl)-(4-methoxyphenyl)-phenyl-methyl]sulfanylethyl]-2-[2-(2-methylpropanoylamino)-6-oxo-1H-purin-9-yl]tetrahydrofuran-3-yl]oxyphosphinic acid (4.2 g, 5.5 mmol, 65% yield) as a white solid. (MS: [M+1]$^+$ 764.4).

Synthesis of CDN-B from Intermediate 29

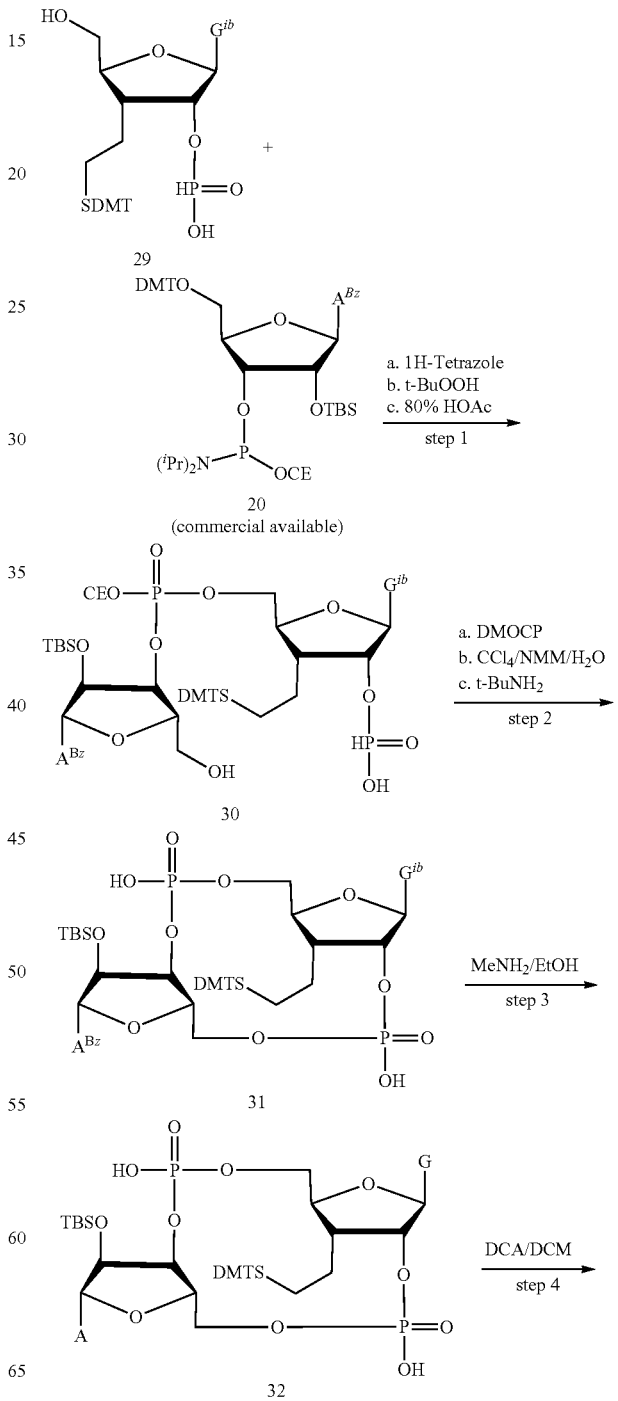

Scheme B2. The synthesis of CDN-B

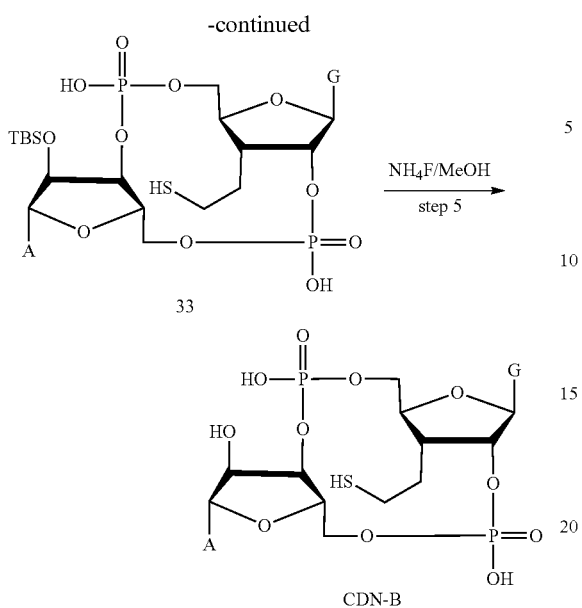

33

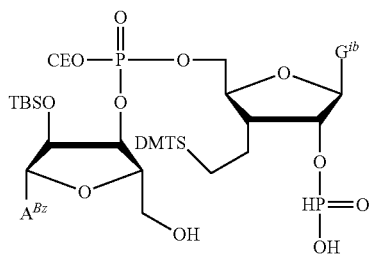

CDN-B

Step 1: Synthesis of [(2R,3R,4R,5S)-5-[[[(2R,3R, 4R,5R)-5-(6-benzamidopurin-9-yl)-4-[tert-butyl(dimethyl)silyl]oxy-2-(hydroxymethyl)tetrahydrofuran-3-yl]oxy-(2-cyanoethoxy)phosphoryl]oxymethyl]-4-[2-[bis(4-methoxyphenyl)-phenyl-methyl]sulfanylethyl]-2-[2-(2-methylpropanoylamino)-6-oxo-1H-purin-9-yl]tetrahydrofuran-3-yl]oxyphosphinic acid To a solution of [(2R,5S)-4-[2-[bis(4-methoxyphenyl)-phenyl-methyl]sulfanylethyl]-5-(hydroxymethyl)-2-[2-(2-methylpropanoylamino)-6-oxo-1H-purin-9-yl]tetrahydrofuran-3-yl]oxyphosphinic acid (0.75 g, 0.98 mmol) in 1H-tetrazole (0.45 M in MeCN, 22.50 mL, 10 eq.) is added N-[9-[(2R,3R,4R,5R)-5-[[bis(4-methoxyphenyl)-phenyl-methoxy]methyl]-3-[tert-butyl(dimethyl)silyl]oxy-4-[2-cyanoethoxy-(diisopropylamino)phosphanyl]oxy-tetrahydrofuran-2-yl]purin-6-yl]benzamide (1.1 g, 1.1 mmol, 1.1 eq.). After 1 h, TBHP (0.43 ml, 65% in decane, 3 eq.) is added. The reaction mixture is stirred at 25° C. for 0.5 h. The reaction is quenched by aq. sodium bisulfite solution (33%, 4 mL) at 0° C. and extracted with EtOAc (100 mL×2). The organic phase is concentrated and dissolved in aq. AcOH (80%, 20 mL). After 1 h, the reaction mixture is neutralized by aq. $Na_2CO_3$ (sat.) at 0° C. The mixture is purified by reverse phase column ($CH_3CN/H_2O$, neutral condition, 0~60%) to give [(2R,3R,4R,5S)-5-[[[(2R,3R,4R,5R)-5-(6-benzamidopurin-9-yl)-4-[tert-butyl(dimethyl)silyl]oxy-2-(hydroxymethyl)tetrahydrofuran-3-yl]oxy-(2-cyanoethoxy)phosphoryl]oxymethyl]-4-[2-[bis(4-methoxyphenyl)-phenyl-methyl]sulfanylethyl]-2-[2-(2-methylpropanoylamino)-6-oxo-1H-purin-9-yl]tetrahydrofuran-3-yl]oxyphosphinic acid (0.79 g, 48% yield, 80% purity) as white solid. (MS: [M+1]$^+$ 1364.0).

Step 2: Synthesis of N-[9-[(47S,48R,49R,50R,51R, 52R,53R,54R)-49-[2-[bis(4-methoxyphenyl)-phenyl-methyl]sulfanylethyl]-52-[tert-butyl(dimethyl)silyl]oxy-87,88-dihydroxy-53-[2-(2-methylpropanoylamino)-6-oxo-1H-purin-9-yl]-87,88-dioxo-77,78,79,80,81,82-hexaoxa-87,88-diphosphatricyclooctadecan-54-yl]purin-6-yl]benzamide

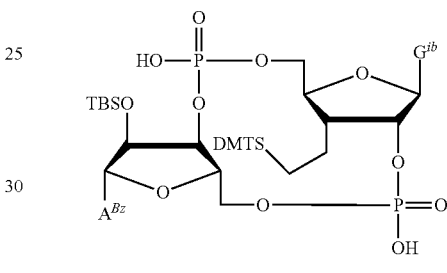

To a solution of [(2R,3R,4R,5S)-5-[[[(2R,3R,4R,5R)-5-(6-benzamidopurin-9-yl)-4-[tert-butyl(dimethyl)silyl]oxy-2-(hydroxymethyl)tetrahydrofuran-3-yl]oxy-(2-cyanoethoxy)phosphoryl]oxymethyl]-4-[2-[bis(4-methoxyphenyl)-phenyl-methyl]sulfanylethyl]-2-[2-(2-methylpropanoylamino)-6-oxo-1H-purin-9-yl]tetrahydrofuran-3-yl]oxyphosphinic acid (0.79 g, 0.58 mmol) in pyridine (16 mL) is added 2-chloro-5,5-dimethyl-1,3,2-dioxaphosphinane 2-oxide (0.7 g, 3.8 mmol, 6.5 eq.). After 0.5 h, $CCl_4$ (3.2 g, 20.6 mmol, 1.98 mL, 35.5 eq.), $H_2O$ (0.16 mL, 8.79 mmol) and NMM (0.79 mL) is added. The reaction mixture is stirred at 25° C. for 0.5 h before pouring into aq. $NaHSO_3$ (sat., 10 mL). After 5 min, aq. $NaHCO_3$ (sat., 20 mL) is added slowly. The mixture is extracted with EtOAc (30 mL×2). The organic phase is concentrated and dissolved in $CH_3CN$ (8 mL) and t-$BuNH_2$ (8 mL). After 0.5 h, the mixture is concentrated and purified by reverse phase column ($CH_3CN/H_2O$, neutral condition, 0~40%) to give N-[9-[(47S,48R, 49R,50R,51R,52R,53R,54R)-49-[2-[bis(4-methoxyphenyl)-phenyl-methyl]sulfanylethyl]-52-[tert-butyl(dimethyl)silyl]oxy-87,88-dihydroxy-53-[2-(2-methylpropanoylamino)-6-oxo-1H-purin-9-yl]-87,88-dioxo-77,78,79,80,81,82-hexaoxa-87,88diphosphatricyclooctadecan-54-yl]purin-6-yl]benzamide (0.5 g, 60% yield, 90.8% purity) as white solid. (MS: [M+1]$^+$ 1309.8).

Step 3: Synthesis of 2-amino-9-[(39S,40R,41R,42R, 43R,44R,45R,46R)-46-(6-aminopurin-9-yl)-41-[2-[bis(4-methoxyphenyl)-phenyl-methyl]sulfanyl-ethyl]-44-[tert-butyl(dimethyl)silyl]oxy-74,75-dihydroxy-74,75-dioxo-64,65,66,67,68,69-hexaoxa-74,75-diphosphatricyclooctadecan-45-yl]-1H-purin-6-one

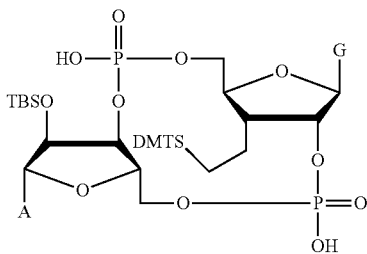

The mixture of N-[9-[(47S,48R,49R,50R,51R,52R,53R, 54R)-49-[2-[bis(4-methoxyphenyl)-phenyl-methyl]sulfanylethyl]-52-[tert-butyl(dimethyl)silyl]oxy-87,88-dihydroxy-53-[2-(2-methylpropanoylamino)-6-oxo-1H-purin-9-yl]-87, 88-dioxo-77,78,79,80,81,82-hexaoxa-87,88diphosphatricyclooctadecan-54-yl]purin-6-yl]benzamide (500 mg, 0.38 mmol) and methylamine alcohol solution (10 mL, 30%) is stirred at 25° C. for 4 h. The reaction mixture is concentrated in vacuum. The residue is purified by reverse phase column (CH$_3$CN/H$_2$O, neutral condition, 0-30%) to give 2-amino-9-[(39S,40R,41R,42R,43R,44R,45R,46R)-46-(6-aminopurin-9-yl)-41-[2-[bis(4-methoxyphenyl)-phenyl-methyl]sulfanylethyl]-44-[tert-butyl(dimethyl)silyl]oxy-74,75-dihydroxy-74,75-dioxo-64,65,66,67,68,69-hexaoxa-74, 75diphosphatricyclooctadecan-45-yl]-1H-purin-6-one (220 mg, 48% yield, 95% purity) as white solid.

Step 4: Synthesis of: 2-amino-9-[(19S,20R,21R, 22R,23R,24R,25R,26R)-26-(6-aminopurin-9-yl)-24-[tert-butyl(dimethyl)silyl]oxy-51,52-dihydroxy-51, 52-dioxo-21-(2-sulfanylethyl)-43,44,45,46,47,48-hexaoxa-51,52-diphosphatricyclooctadecan-25-yl]-1H-purin-6-one

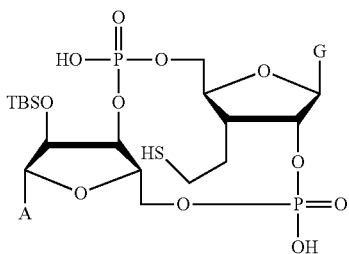

To a solution of 2-amino-9-[(39S,40R,41R,42R,43R,44R, 45R,46R)-46-(6-aminopurin-9-yl)-41-[2-[bis(4-methoxyphenyl)-phenyl-methyl]sulfanylethyl]-44-[tert-butyl(dimethyl)silyl]oxy-74,75-dihydroxy-74,75-dioxo-64,65,66,67, 68,69-hexaoxa-74,75diphosphatricyclooctadecan-45-yl]-1H-purin-6-one (190 mg, 0.17 mmol) in DCM (4 mL) is added 2,2-dichloroacetic acid (0.8 mL, 9.74 mmol, 58 eq.). The mixture is stirred at 25° C. for 2 h and neutralized by water/Et$_3$N (1:1, V/V, 3 mL) at 0° C. The mixture is concentrated and purified by reverse phase column (CH$_3$CN/H$_2$O, contains 0.05% TEA, 0% to 40%) to give 2-amino-9-[(19S,20R,21R,22R,23R,24R,25R,26R)-26-(6-aminopurin-9-yl)-24-[tert-butyl(dimethyl)silyl]oxy-51,52-dihydroxy-51,52-dioxo-21-(2-sulfanylethyl)-43,44,45,46, 47,48-hexaoxa-51,52diphosphatricyclooctadecan-25-yl]-1H-purin-6-one (36 mg, 25% yield, 98% purity, TEA salt) as white solid. (MS: [M+1]$^+$ 833.3).

Step 5: Synthesis of 2-amino-9-[(14S,15R,16R,17R, 18S,19R,20R,21R)-20-(6-aminopurin-9-yl)-17,44, 45-trihydroxy-44,45-dioxo-16-(2-sulfanylethyl)-38, 39,40,41,42, 43-hexaoxa-44,45-diphosphatricyclooctadecan-21-yl]-1H-purin-6-one (CDN-B)

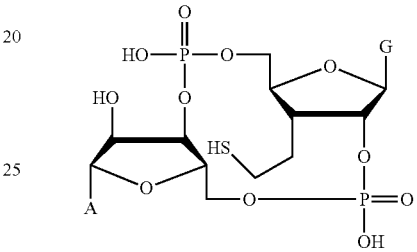

To a solution of 2-amino-9-[(19S,20R,21R,22R,23R,24R, 25R,26R)-26-(6-aminopurin-9-yl)-24-[tert-butyl(dimethyl) silyl]oxy-51,52-dihydroxy-51,52-dioxo-21-(2-sulfanylethyl)-43,44,45,46,47,48-hexaoxa-51,52diphosphatricyclooctadecan-25-yl]-1H-purin-6-one (36 mg, 0.043 mmol) in MeOH (4 mL) is added NH$_4$F (0.16 g, 4.32 mmol, 100 eq.). The mixture is stirred at 70° C. for 1 h, concentrated and purified by reverse phase column (CH$_3$CN/H$_2$O, contains 0.05% FA, 0% to 30%) to give 2-amino-9-[(14S, 15R,16R,17R,18S,19R,20R,21R)-20-(6-aminopurin-9-yl)-17,44,45-trihydroxy-44,45-dioxo-16-(2-sulfanylethyl)-38, 39,40,41,42,43-hexaoxa-44,45diphosphatricyclooctadecan-21-yl]-1H-purin-6-one (CDN-B, 7 mg, 22.5% yield, 99.8% purity) as white solid.

$^1$H NMR (400 MHz, D$_2$O) δ=8.25 (s, 1H), 8.19 (s, 1H), 7.77 (s, 1H), 6.10 (s, 1H), 5.80 (d, J=8.3 Hz, 1H), 5.67 (q, J=8.2 Hz, 1H), 5.05-4.98 (m, 1H), 4.43 (d, J=9.0 Hz, 1H), 4.36 (d, J=12.1 Hz, 1H), 4.31 (brs, 1H), 4.18 (d, J=11.7 Hz, 1H), 4.08-3.97 (m, 2H), 3.11 (q, J=7.2 Hz, 1H), 2.79-2.66 (m, 2H), 2.62-2.51 (m, 1H), 2.28-2.13 (m, 1H), 1.84-1.73 (m, 1H), 1.19 (t, J=7.3 Hz, 1H). $^{31}$P NMR: −0.951, −2.201. MS: [M+1]$^+$ 718.9.

Example 3. Preparation of Target-Binding Antibodies

Anti-PD-L1 Antibodies
Ab-A1 (mu-Anti-PDL1):
Expression vectors encoding a murine anti-human PD-L1 antibody Ab-A1 (mu-anti-PDL1) having a heavy chain of SEQ ID NO:3 and a light chain of SEQ ID NO:5 were prepared by cloning cDNAs encoding a variable heavy (VH) chain of SEQ ID NO:1 and variable light (VL) chain of SEQ ID NO:2 into separate pFUSEss-CHIg-mG2a (mouse IgG2a heavy chain constant region) and pFUSE2ss-CLIg-mk (mouse kappa light chain constant region) expression vectors, respectively. The VH and VL of Ab-A1 are based on atezolizumab.

Ab-A2 (mu-Anti-PDL1-cys):

Expression vectors encoding a murine anti-human PD-L1 antibody Ab-A2 (mu-anti-PDL1-cys) having a heavy chain of SEQ ID NO:4 and a light chain of SEQ ID NO:5 were prepared using analogous techniques as Ab-A1. The VH and VL sequences of Ab-A2 are based on atezolizumab. The heavy chain constant region of Ab-A2 has two mutations relative to wild-type mouse IgG2a, the first being a leucine to phenylalanine substitution at position 234 in the CH2 domain (i.e. L234F, numbered in accordance to the wild-type mouse IgG2a sequence aligned with the human IgG1 sequence, using Eu numbering), and the second being a serine to cysteine substitution at position 239 in the CH2 domain to present an additional cysteine for conjugation (i.e. S239C, using the same numbering).

The sequences of heavy chains of anti-human PD-L1 antibodies Ab-A1 and Ab-A2 are shown below as SEQ ID NOS:3 and 4, respectively. The heavy chain variable region is underlined in each sequence, which is the same for both, and corresponds to SEQ ID NO:1. The L234F and S239C CH2 domain mutations in SEQ ID NO:4 for Ab-A2 are shown in bold.

```
Heavy chain for Ab-A1
                                              (SEQ ID NO: 3)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSAAKTTAPSVYPLAPVCGDTTGSSVTLGCLVKGY

FPEPVTLTWNSGSLSSGVHTFPAVLQSDLYTLSSSVTVTSSTWPSQSITC

NVAHPASSTKVDKKIEPRGPTIKPCPPCKCPAPNLLGGPSVFIFPPKIKD

VLMISLSPIVTCVVVDVSEDDPDVQISWFVNNVEVHTAQTQTHREDYNST

LRVVSALPIQHQDWMSGKEFKCKVNNKDLPAPIERTISKPKGSVRAPQVY

VLPPPEEEMTKKQVILTCMVIDFMPEDIYVEWTNNGKTELNYKNTEPVLD

SDGSYFMYSKLRVEKKNWVERNSYSCSVVHEGLHNHHTTKSFSRTPGK

Heavy chain for Ab-A2
                                              (SEQ ID NO: 4)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSAAKTTAPSVYPLAPVCGDTTGSSVTLGCLVKGY

FPEPVTLTWNSGSLSSGVHTFPAVLQSDLYTLSSSVTVTSSTWPSQSITC

NVAHPASSTKVDKKIEPRGPTIKPCPPCKCPAPNFLGGPCVFIFPPKIKD

VLMISLSPIVTCVVVDVSEDDPDVQISWFVNNVEVHTAQTQTHREDYNST

LRVVSALPIQHQDWMSGKEFKCKVNNKDLPAPIERTISKPKGSVRAPQVY

VLPPPEEEMTKKQVILTCMVIDFMPEDIYVEWTNNGKTELNYKNTEPVLD

SDGSYFMYSKLRVEKKNWVERNSYSCSVVHEGLHNHHTTKSFSRTPGK
```

The sequence of the light chains of anti-human PD-L1 antibodies Ab-A1 and Ab-A2 is shown below as SEQ ID NO:5. The light chain variable region is underlined in the sequence and corresponds to SEQ ID NO:2.

```
Light chain for Ab-A1 and Ab-A2
                                              (SEQ ID NO: 5)
DIQMTQSPSSLSASVGDRVTITCRASQDVSTAVAWYQQKPGKAPKLLIYS

SAFLYSGVPSRFSGSGSGTDFTLTISSLQPEDFATYYCQQYLYHPATFGQ

GTKVEIKRADAAPTVSIFPPSSEQLTSGGASVVCFLNNEYPKDINVKWKI

DGSERQNGVLNSWTDQDSKDSTYSMSSTLTLTKDEYERHNSYTCEATHKT

STSPIVKSFNRNEC
```

Ab-A3 (rt-Anti-PDL1):

A rat anti-mouse PD-L1 antibody Ab-A3 having a rat IgG2b heavy chain constant region was sourced commercially from BioXcell (BE0101).

Anti-EGFR Antibodies

Ab-B1 (mu-Anti-EGFR):

A murine anti-human EGFR antibody Ab-B1 having a mouse IgG2a heavy chain constant region was sourced commercially from BioXcell (BE0279).

Ab-B2 (mu-Anti-EGFR-cys):

Expression vectors encoding a murine anti-human EGFR antibody Ab-B2 having a heavy chain of SEQ ID NO:8 and a light chain of SEQ ID NO:9 were prepared by cloning cDNAs encoding a variable heavy (VH) chain of SEQ ID NO:6 and variable light (VL) chain of SEQ ID NO:7 into separate pFUSEss-CHIg-mG2a (mouse IgG2a heavy chain constant region) and pFUSE2ss-CLIg-mk (mouse kappa light chain constant region) expression vectors, respectively. The VH and VL sequences of Ab-B2 are based on cetuximab. The CH2 domain of the heavy chain of Ab-B2 features mutations L234F and S239C relative to wild-type mouse IgG2a, as described previously for Ab-A2.

The sequence of the heavy chain of anti-human EGFR antibody Ab-B2 is shown below as SEQ ID NO:8. The heavy chain variable region is underlined and corresponds to SEQ ID NO:6. The L234F and S239C mutations in the CH2 domain are shown in bold.

```
Heavy chain for Ab-B2
                                              (SEQ ID NO: 8)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAAKTTAPSVYPLAPVCGDTTGSSVTLGCLVKG

YFPEPVTLTWNSGSLSSGVHTFPAVLQSDLYTLSSSVTVTSSTWPSQSIT

CNVAHPASSTKVDKKIEPRGPTIKPCPPCKCPAPNFLGGPCVFIFPPKIK

DVLMISLSPIVTCVVVDVSEDDPDVQISWFVNNVEVHTAQTQTHREDYNS

TLRVVSALPIQHQDWMSGKEFKCKVNNKDLPAPIERTISKPKGSVRAPQV

YVLPPPEEEMTKKQVILTCMVTDFMPEDIYVEWTNNGKTELNYKNTEPVL

DSDGSYFMYSKLRVEKKNWVERNSYSCSVVHEGLHNHHTTKSFSRTPGK
```

The sequence of the light chain of Ab-B2 is shown below as SEQ ID NO:9. The variable region is underlined and corresponds to SEQ ID NO:7.

```
Light chain for Ab-B2
                                              (SEQ ID NO: 9)
DILLTQSPVILSVSPGERVSFSCRASQSIGTNIHWYQQRTNGSPRLLIKY

ASESISGIPSRFSGSGSGTDFILSINSVESEDIADYYCQQNNNWPTTFGA

GTKLELKRADAAPTVSIFPPSSEQLTSGGASVVCFLNNEYPKDINVKWKI

DGSERQNGVLNSWTDQDSKDSTYSMSSTLTLTKDEYERHNSYTCEATHKT

STSPIVKSFNRNEC
```

Ab-B3 (hu-Anti-EGFR):

Expression vectors encoding a murine-human chimeric anti-human EGFR antibody Ab-B3 having a heavy chain of SEQ ID NO:12 and a light chain of SEQ ID NO:13 were prepared by cloning cDNAs encoding a variable heavy (VH) chain of SEQ ID NO:10 plus a human IgG1 heavy chain constant region, and a variable light (VL) chain of SEQ ID NO:11 plus a human Ig kappa light chain constant region into separate pcDNA3.4 expression vectors. The full length heavy and light chain sequences of Ab-B2 are based on cetuximab.

The sequence of the heavy chain of anti-human EGFR antibody Ab-B3 is shown below as SEQ ID NO:12. The heavy chain variable region is underlined and corresponds to SEQ ID NO:10.

```
Heavy chain for Ab-B3
                                       (SEQ ID NO: 12)
QVQLKQSGPGLVQPSQSLSITCTVSGFSLTNYGVHWVRQSPGKGLEWLGV

IWSGGNITYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVICVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

The sequence of the light chain of Ab-B3 is shown below as SEQ ID NO:13. The variable region is underlined and corresponds to SEQ ID NO:11.

```
Light chain for Ab-B3
                                       (SEQ ID NO: 13)
DILLTQSPVILSVSPGERVSFSCRASQSIGTNIHWYQQRTNGSPRLLIKY

ASESISGIPSRFSGSGSGTDFILSINSVESEDIADYYCQQNNNWPTTFGA

GTKLELKRTVAAPSVFIFPPSDEQLKSGTASVVCLLNNFYPREAKVONKV

DNALQSGNSQESVTEQDSKDSTYSLSSILTLSKADYEKHKVYACEVTHQG

LSSPVTKSFNRGEC
```

Ab-B4 (hu-Anti-EGFR-A/C,V/C):

An expression vector encoding a human anti-human EGFR antibody Ab-B4 having a heavy chain of SEQ ID NO:16 and a light chain of SEQ ID NO:17 was prepared by cloning cDNAs encoding a variable heavy (VH) chain of SEQ ID NO:14 plus a human IgG1 heavy chain constant region, and a variable light (VL) chain of SEQ ID NO:15 plus a modified human Ig kappa light chain constant region into separate pcDNA3.4 expression vectors. The VH and VL of Ab-B4 are based on cetuximab, with VH having an alanine to cysteine mutation at position 109 adjacent to the CH1 domain (i.e., A109C). The light chain of Ab-B4 features a valine to cysteine mutation at position 205 (i.e., V205C).

The sequence of the heavy chain of anti-human EGFR antibody Ab-B4 is shown below as SEQ ID NO:16. The heavy chain variable region is underlined and corresponds to SEQ ID NO:14. The A109C mutation is shown in bold.

```
Heavy chain for Ab-B4
                                       (SEQ ID NO: 16)
QVQLKQSGPGLVQPSQSLSITCTVSGESLTNYGVHWVRQSPGKGLEWLG

VIWSGGNIDYNTPFTSRLSINKDNSKSQVFFKMNSLQSNDTAIYYCARA

LTYYDYEFAYWGQGTLVTVSCASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVICVVVDVSHEDPEVKFMNYVDGVEVHNAKTKPR

EEQYNSTYRVVSVLTVLHQDWLNGKEYKCKVSNKALPAPIEKTISKAKG

QPREPQVYTLPPSRDELTKNQVSLICLVKGFYPSDIAVEWESNGQPENN

YKTIPPVLDSDGSFFLYSKLTVDKSRTNQQGNVFSCSVMHEALHNHYTQ

KSLSLSPGK
```

The sequence of the light chain of Ab-B4 is shown below as SEQ ID NO:17. The variable region is underlined and corresponds to SEQ ID NO:15. The V205C mutation is shown in bold.

```
Light chain for Ab-B4
                                       (SEQ ID NO: 17)
DILLTQSPVILSVSPGERVSFSCRASQSIGTNIHWYQQRTNGSPRLLIK

YASESISGIPSRFSGSGSGTDFILSINSVESEDIADYYCQQNNNWPTTF

GAGTKLELKRTVAAPSVFIFPPSDEQLKSGTASVVCLLNNFYPREAKVQ

NKVDNALQSGNSQESVTEQDSKDSTYSLSSILTLSKADYEKHKVYACEV

THQGLSSPCTKSFNRGEC
```

Anti-HER2 Antibodies

Ab-C1 (Anti-HER2):

A humanized anti-human HER2 antibody Ab-C1 was sourced commercially as trastuzumab (Herceptin®).

The sequence of the heavy chain of anti-human HER2 antibody Ab-C1 is shown below as SEQ ID NO:20. The heavy chain variable region is underlined and corresponds to SEQ ID NO:18.

```
Heavy chain for Ab-C1
                                       (SEQ ID NO: 20)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRIPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK
```

The sequence of the light chain of Ab-C1 is shown below as SEQ ID NO:21. The variable region is underlined and corresponds to SEQ ID NO:19.

Light chain for Ab-C1

(SEQ ID NO: 21)
DIQMTQSPSSLSASVGDRVTITCRASQDVNTAVAWYQQKPGKAPKLLIYS

ASFLYSGVPSRFSGSRSGTDFILTISSLQPEDFATYYCQQHYTTPPTFGQ

GTKVEIKRTVAAPSVFIFPPSDEQLKSGTASVVCLLNNFYPREAKVQNKV

DNALQSGNSQESVTEQDSKDSTYSLSSILTLSKADYEKHKVYACEVTHQG

LSSPVTKSFNRGEC

Anti-CD47 Antibodies

Ab-D1 (rt-Anti-CD47):

A rat anti-mouse CD47 antibody Ab-D1 having a rat IgG2b heavy chain constant region was sourced commercially from BioXcell (BE0270).

Expression and Purification

Plasmids encoding the heavy chain and light chain of target-binding antibodies were transfected into CHO cells for expression of antibodies using ExpiFectamine™ CHO Transfection Kit (ThermoFisher Scientific, Cat No: A29129) according to manufacturer's protocol. Total amount of plasmids used for transfection was 0.5 ug/ml CHO cell, with a ratio between heavy chain and light chain plasmids of 2:3. Six days after transfection, CHO cells were spun down and the media filtered, then loaded onto protein A beads (HiTrap Protein A HP, GE, Cat No: 17-0403-01) and eluted with 0.1 M Glycine (pH 3.0). The eluted antibody fractions were pooled and concentrated to 1 ml and buffer exchanged into PBS by size exclusion (ENrich Sec650, Bio-Rad, Cat No: 780-1650) before storage at −80° C.

Example 4. Preparation of CDN-A ADCs

Synthesis of CDN-A-Linker

Conjugation of Antibodies to CDN-A

Reduction of Antibody Disulfides:

Target-binding antibodies were first reduced with Tris-(2-carboxyethyl)-phosphine hydrochloride (TCEP) (2.3 molar equivalents of TCEP at room temperature for 1.5 hours, or 40 molar equivalents of TCEP at 37° C. for 2 hours. Excess TCEP was removed using a desalting column (HiTrap Desalting column, GE, Cat. No: 29048684).

Re-Oxidation of Hinge Cysteines:

The hinge cysteines of the reduced antibody were re-oxidized with 200 molar equivalent of dehydroascorbic acid (DHA, 0.5 M in DMSO) at 37° C. for 4 hours. Re-oxidation was verified using SDS-PAGE under non-reducing conditions. Excess DHA was removed via 30 Kd MWCO cutoff centrifugal filter (Amicon Ultra-15, Merck Millipore, Cat No: UFC903024).

Conjugation to CDN-A:

(Type I for reduced antibody) The reduced antibody reaction mixture was cooled at 4° C. for 20 min. CDN-A-Linker (4.8 molar equivalents to antibody) in histidine buffer (20 mM, pH 7.4) was added and incubated at 4° C. for 80 min. (Type II for re-oxidized antibody) The re-oxidized antibody was mixed with 10 molar equivalents of CDN-A-linker and incubated at room temperature for 4 hours. After conjugation, the reaction was quenched with N-acetyl cysteine, and the excess CDN-A-linker and N-acetyl cysteine were removed with a 5 ml desalting column (GE) under control of a FPLC system in PBS. The ADCs produced were concentrated and stored at 4° C.

DAR Measurement

To determine DAR of ADCs carrying CDN-A as CDN, OD260/OD280 ratios were measured on a UV spectrometer and compared to a standard curve generated using mixtures

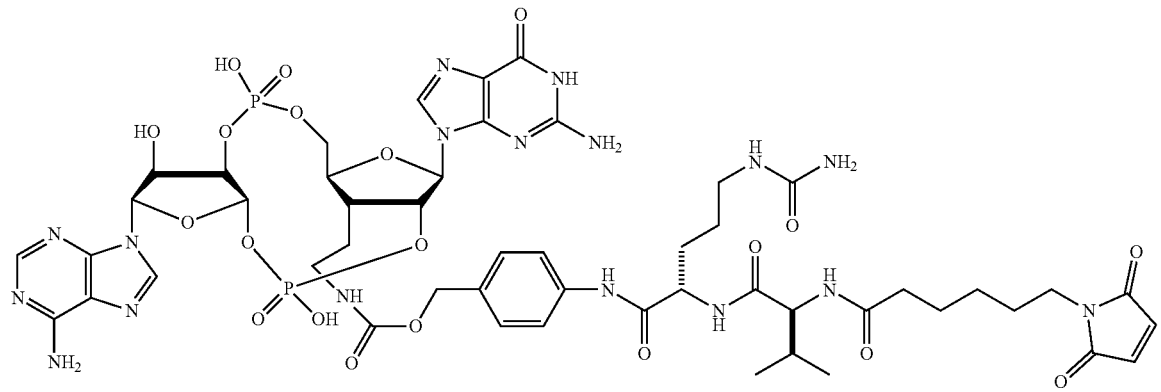

CDN-A (27 mg, 0.0385 mmol) is co-evaporated with Py. (3×3 ml) and dried under high vacuum before use. 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (54 mg, 0.0732 mmol, 2.0 eq.), HOBt (5.2 mg, 0.0385 mmol, 1.0 eq.) and DMF (2.5 ml) are added. With stirring, DIPEA (67 μl, 0.385 mmol, 10 eq.) is added. The mixture is stirred at room temperature under $N_2$ for 42 hours. The reaction mixture is diluted by a solvent mixture of ethyl acetate (25 ml), t-butyl methyl ether (75 ml) and acetic acid (30 μL, 0.521 mmol). The solid is collected by centrifugation and washing with t-butyl methyl ether (3×75 ml) to give 44 mg of crude. 20 mg of the crude is further purified by reverse phase column ($CH_3CN/H_2O$, 0.1% FA, 0% to 30%) to give desired product (7 mg, 31% yield, 97% pure). (MS: [M−1]⁻ 1298.2).

of CDN-A and antibody at known ratios. As shown in the following table, the DAR value of exemplary ADCs ranged from 1 to 6.3. The DAR value of ADCs using the Ab-A2 antibody (mu-anti-PDL1-cys) having an additional cysteine by substitution showed a greater DAR value than using the wild-type Ab-A1 antibody (mu-anti-PDL1).

TABLE 1

| Exemplary CDN-A ADCs | | | | |
|---|---|---|---|---|
| ADC ID | Ab ID | Ab Notes | CDN | DAR |
| ADC-IV | Ab-B1 | mu-anti-EGFR (BioXcell BE0279) | CDN-A | 1 |

TABLE 1-continued

Exemplary CDN-A ADCs

| ADC ID | Ab ID | Ab Notes | CDN | DAR |
|---|---|---|---|---|
| ADC-V | Ab-A3 | rt-anti-PDL1 (BioXcell BE0101) | CDN-A | 1 |
| ADC-VI | Ab-A2 | mu-anti-PDL1-cys | CDN-A | 2~4 |
| ADC-VII | Ab-B2 | mu-anti-EGFR-cys | CDN-A | 2 |
| ADC-VIII | Ab-B3 | hu-anti-EGFR | CDN-A | 6.3 |
| ADC-IX | Ab-B4 | hu-anti-EGFR-A/C,V/C | CDN-A | 3 |
| ADC-X | Ab-C1 | hu-anti-HER2 (trastuzumab) | CDN-A | 4.8 |
| ADC-XI | Ab-D1 | rt-anti-CD47 (BioXCell BE0270) | CDN-A | 2.5 |

Example 5. Preparation of CDN-B ADCs

Synthesis of 2,5-dioxopyrrolidin-1-yl 4-(pyridin-2-yldisulfaneyl)pentanoate (Linker I)

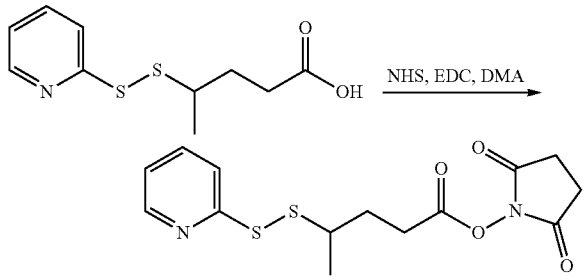

To a solution of 4-(pyridin-2-yldisulfaneyl) pentanoic acid (24 mg, 0.1 mmol) and NHS (14 mg, 0.12 mmol) in DMA is added EDC (HCl salt, 61 mg, 0.32 mmol). The solution is stirred at room temperature overnight. After filtration, the filtrate is concentrated and purified by column (MeOH/DCM=0% to 10%) to obtain 2,5-dioxopyrrolidin-1-yl 4-(pyridin-2-yldisulfaneyl)pentanoate as white solid (8 mg, 23.5%). (MS: $[M+1]^+$ 341.1).

Conjugation of Antibodies to CDN-B 0.2 ml of 3 mM solution of 2-amino-9-[(14S,15R,16R,17R,18S,19R,20R,21R)-20-(6-aminopurin-9-yl)-17,44,45-trihydroxy-44,45-dioxo-16-(2-sulfanylethyl)-38,39,40,41,42,43-hexaoxa-44,45diphosphatricyclooctadecan-21-yl]-1H-purin-6-one in phosphate buffer pH 6.0 was mixed with 0.2 ml of 2 mM 2,5-dioxopyrrolidin-1-yl 4-(pyridin-2-yldisulfaneyl)pentanoate in DMA. After incubation at room temperature overnight, 3.6 mg of target-binding antibody in 2 ml PBS was added and incubated at room temperature for another 2 hours. The mixture was concentrated and the conjugate was purified on a 5 ml desalting column controlled on a FPLC system equilibrated with PBS. The ADCs produced were concentrated and stored at 4° C.

DAR Measurement

To release CDN-B from ADCs, DTT was added to ADC to a final concentration of 10 mM, incubated at 95° C. for 5 min, and passed through a 30 KD cut-off filter. The filtrate was diluted and added to THP1-Lucia ISG cells permeabilized with 0.5 nM of Perfringolysin (PFO). 16 hours later, luciferase activity was measured, concentration of active compounds released from ADC and DAR values was calculated by comparing to standard curves. As shown in the following table, the DAR value of exemplary ADCs ranged from 0.33 to 1.66.

TABLE 2

Exemplary CDN-B ADCs

| ADC ID | Ab ID | Ab Notes | CDN | DAR |
|---|---|---|---|---|
| ADC-I | Ab-A1 | mu-anti-PDL1 | CDN-B | 1.66 |
| ADC-II | Ab-A3 | rt-anti-PDL1 (BioXcell BE0101) | CDN-B | 0.36 |
| ADC-III | Ab-B1 | mu-anti-EGFR (BioXcell BE0279) | CDN-B | 0.33 |

Example 6. Cellular Activity of CDN-A and CDN-B ADCs

IFN Stimulatory Activity

Two reporter cell lines, mouse macrophage RAW-Lucia ISG and human monocyte THP1-Lucia ISG were used to assess activity of ADCs. Both cell lines harbor IFN-stimulated response elements (ISRE) fused to an ISG54 minimal promoter. ADCs at different concentrations (0.3, 1.0, and/or 3 µM) were added to reporter cells and incubated for 16 h. Luciferase activity representing induction of interferon expression was compared to serial dilutions of a standard compound (cGAMP).

ADC-I through ADC-XI demonstrated effective interferon stimulatory activity of varying potencies, as summarized in Table 3. The reported "cGAMP equivalent" value is defined as the concentration of cGAMP (µM) that is required to induce the same level of response induced by 1 µM of ADC.

TABLE 3

Potency of IFN Stimulatory Activity in Reporter Cells

| ADC ID | mouse RAW-Lucia ISG (cGAMP equivalent) | human THP1-Lucia ISG (cGAMP equivalent) |
|---|---|---|
| ADC-I | 89 | 28 |
| ADC-II | 3.4 | 4.2 |
| ADC-III | ~7 | 0.58 |
| ADC-IV | ~10 | weak |
| ADC-V | ~10 | weak |
| ADC-VI | >100 | weak |
| ADC-VII | 3.1 | n.d. |
| ADC-VIII | 33 | n.d. |
| ADC-IX | 31 | n.d. |
| ADC-X | 10 | n.d. |
| ADC-XI | 3 | n.d. |

All of the ADCs demonstrated potent interferon stimulatory activity in the mouse RAW-Lucia ISG reporter assay (Table 3). ADC-I and ADC-VI were of the highest potency (FIGS. 1B and 6B, respectively), followed by ADC-VIII, ADC-IX (FIGS. 8B and 9B, respectively), then by ADC-IV, ADC-V, and ADC-X (FIGS. 4B, 5B, and 10, respectively), and then by ADC-III (FIG. 3B), ADC-II (FIG. IIB), and ADC-XI. As shown in FIGS. 3B, 4B, 5B, and 6B, treatment with the disclosed ADCs demonstrate synergism of interferon stimulatory activity when compared to treatment with the antibody alone, or the CDN alone, or a combined value of both the antibody and agonist potencies.

CDN-A antibody conjugates also demonstrated interferon stimulatory activity in a reporter assay using human monocyte THP1-Lucia ISG cells (Table 3). Of those tested, ADC-I was of the highest potency (FIG. 1C), followed by ADC-II (FIG. 1C), and ADC-III.

The activities of ADC-VIII and ADC-IX were further tested in a THP1-lucia ISG cell line stably expressing human EGFR. Both ADCs exhibited strong interferon-stimulatory activities in these cells (Table 4). The reported "cGAMP equivalent" value is defined as the concentration of cGAMP (nM) that is required to induce the same level of response induced by 1 nM of ADC. EC50 is half maximal effective concentration.

TABLE 4

Activity of ADC-VIII and ADC-IX in THPI-EGFR-lucia IS cells

| ADC ID | cGAMP equivalent | EC50 |
|---|---|---|
| ADC-VIII | 977 | 11.7 nM |
| ADC-IX | 912 | 8.2 nM |

Example 7. Antitumor Efficacy of CDN-A and CDN-B ADCs

Antitumor efficacy of selected ADCs was tested in mouse syngeneic tumor models B16-F10 metastatic melanoma, human EGFR-transfected B16F10 (B16F10-EGFR), and human HER2-transfected Lewis lung carcinoma (LLC1-HER2). Briefly, $10^6$ of log-phase tumor cells in 100 μL of PBS were injected subcutaneously into C57BL6 mice at their right flanks. Four to six days later, when tumor volumes were 50-100 mm$^3$, mice were regrouped according to their tumor sizes and treated intraperitoneally with 50 to 200 g of ADC, or with unconjugated antibody, unconjugated CDN, or mock PBS as controls (see figure legends for treatment details).

Tumor volumes and mice survival were monitored. ADC-IV, ADC-VI, ADC-VII, ADC-VIII, and ADC-IX demonstrated strong anti-tumor efficacy in both regression and survival and are potential candidates to treat human tumors. ADC-X was shown to slow tumor progression. ADC-I was also shown to slow tumor progression, but toxicity was observed.

Tumor Volume

In mice bearing B16F10 tumors, treatment with ADC-I (anti-PDL1-CDN-B) slowed tumor progression compared to mock, anti-PDL1 antibody alone, CDN-B alone, and the combination of anti-PDL1 antibody and unconjugated CDN-B (FIG. 1C).

In mice bearing B16F10-EGFR tumors, treatment with ADC-IV (anti-EGFR-CDN-A) slowed tumor progression and reduced tumor volume compared to mock treatment or treatment with anti-PDL1 antibody (FIGS. 4C and 4E). Comparative treatment with anti-EGFR antibody plus unconjugated CDN failed to stop tumor growth (FIG. 4C), suggesting improved efficacy when using an ADC for targeted CDN delivery. When ADC-IV was combined with anti-PDL1 antibody a complete suppression of tumor expansion was observed (FIG. 4E), suggesting improved efficacy when combining a CDN ADC with checkpoint inhibitors.

In mice bearing B16F10-EGFR tumors, ADC-VI (anti-PDL1-CDN-A) administered intraperitoneally at a dose of 200 μg (FIG. 6C) or intratumorally at a dose of 10 μg or 50 μg (FIG. 6D) prevented tumor expansion. Within two weeks after treatment with ADC-VI, B16F10-EGFR tumors showed complete remission, whereas treatment with the anti-PDL1 antibody alone or mock failed to stop tumor expansion.

In mice bearing B16F10-EGFR tumors, ADC-VII (anti-EGFR-CDN-A) led to a marked reduction of tumor expansion compared to mock treatment or treatment with anti-PDL1 antibody (FIGS. 7C and 7E). Comparative treatment with anti-EGFR antibody plus unconjugated CDN failed to stop tumor growth (FIG. 7C), suggesting improved efficacy when using an ADC for targeted CDN delivery. Enhancement of tumor suppression was observed when ADC-VII was combined with anti-PDL1 antibody, whereas treatment with anti-PDL1 antibody alone or mock failed to stop tumor expansion (FIG. 7E), suggesting improved efficacy when combining a CDN ADC with checkpoint inhibitors.

In mice bearing B16F10-EGFR tumors, ADC-VIII (anti-EGFR-CDN-A) led to a marked reduction of tumor expansion (FIG. 8C). This effect was enhanced when ADC-VIII was combined with anti-PDL1 antibody, whereas treatment with anti-PDL1 antibody alone or mock failed to stop tumor expansion, suggesting improved efficacy when combining a CDN ADC with checkpoint inhibitors.

In mice bearing B16F10-EGFR tumors, ADC-IX (anti-EGFR-CDN-A) led to a reduction of tumor expansion, and a similar effect was observed when ADC-IX was combined with anti-PD-L1 antibody (FIG. 9C). Treatment with anti-PDL1 antibody alone or mock failed to stop tumor expansion.

In mice bearing LLC1-HER2 tumors, ADC-X (anti-HER2-CDN-A) reduced tumor expansion in two separate mouse studies (FIGS. 10C and 10E), whereas treatment with the anti-PDL1 antibody alone or mock failed to stop tumor expansion. Comparative treatment with anti-HER2 antibody plus unconjugated CDN failed to stop tumor growth, suggesting improved efficacy when using an ADC for targeted CDN delivery. FIG. 10E further shows that intratumoral administration of ADC-X at a dose of 30 μg resulted in complete tumor remission.

Survival

The survival of mice bearing B16F10-EGFR or LLC1-HER2 tumors was monitored. Treatment with ADC-IV (anti-EGFR-CDN-A) increased the time of survival of B16F10-EGFR tumor bearing mice (3/5 at Day 37, FIG. 4D; 0/5 at Day 39, FIG. 4F) compared to treatment with anti-PDL1 antibody alone (0/5 at Day 26, FIG. 4D; 0/5 at Day 29, FIG. 4F), and mock (0/5 at Day 23, FIG. 4D; 0/5 at Day 20, FIG. 4F). Survival following ADC-IV treatment exceeded that of comparative treatment using anti-EGFR antibody plus unconjugated CDN (0/5 at Day 34, FIG. 4D), suggesting improved efficacy when using an ADC for targeted CDN delivery. A combination treatment of ADC-IV with anti-PDL1 antibody improved survival to 80% of mice (4/5 at Day 42), suggesting improved efficacy when combining a CDN ADC with checkpoint inhibitors.

Treatment with ADC-VI (anti-PDL1-CDN-A) administered intraperitoneally led to total survival of B16F10-EGFR tumor bearing mice (5/5 at Day 43), compared to treatment with the anti-PDL1 antibody alone (0/5 at Day 29), or mock (0/5 at Day 27) (FIG. 6D). Likewise, treatment of ADC-VI administered intratumorally led to total survival of the tumor bearing mice (FIG. 6F).

Treatment with ADC-VII (anti-EGFR-CDN-A) increased survival of B16F10-EGFR tumor bearing mice at endpoint (2/5 at Day 36, FIGS. 7D and 7F) compared to treatment with anti-PDL1 antibody alone (0/5 at Day 27, FIG. 7F), or mock (0/5 at Day 23, FIGS. 7D and 7F). Survival following ADC-VII treatment exceeded that of comparative treatment using anti-EGFR antibody plus unconjugated CDN (0/5 at Day 22, FIG. 7D), suggesting improved efficacy when using an ADC for targeted CDN delivery. A combination treatment of ADC-VII with anti-PDL1 antibody improved survival to 60% of mice (3/5 at Day 36, FIG. 7F) compared to ADC-VII, suggesting improved efficacy when combining a CDN ADC with checkpoint inhibitors.

Treatment with ADC-VIII (anti-EGFR-CDN-A) increased survival of B16F10-EGFR tumor bearing mice (1/5 at Day 35) compared to treatment with anti-PDL1 antibody alone (0/5 at Day 27), or mock (0/5 at Day 25) (FIG. 8D). Treatment with a combination of ADC-VIII and anti-PD-L1 antibody improved survival to 80% of mice (4/5 at Day 35), suggesting improved efficacy when combining a CDN ADC with checkpoint inhibitors.

Treatment with ADC-IX (anti-EGFR-CDN-A) increased survival of B16F10-EGFR tumor bearing mice (3/5 at Day 30) compared to treatment with anti-PDL1 antibody alone (0/5 at Day 23), or mock (0/5 at Day 19) (FIG. 9D). Treatment with a combination of ADC-IX and anti-PD-L1 antibody improved survival to 60% of mice (3/5 at Day 30), suggesting improved efficacy when combining a CDN ADC with checkpoint inhibitors.

Treatment with ADC-X (anti-HER2-CDN-A) increased the time of survival of LLC1-HER2 tumor bearing mice (0/5 at Day 41) compared to treatment with mock (0/5 at Day 32) (FIG. 10D). Survival time following ADC-X treatment exceeded that of comparative treatment using anti-HER2 antibody plus unconjugated CDN (0/5 at Day 32), suggesting improved efficacy when using an ADC for targeted CDN delivery.

The invention claimed is:

1. An antibody-drug conjugate (ADC) having the structure of Formula Ia:

Ab-[-L-D]$_n$      (Formula Ia)

wherein:

"D" represents a cyclic di-nucleotide (CDN) having the structure of Formula IIk:

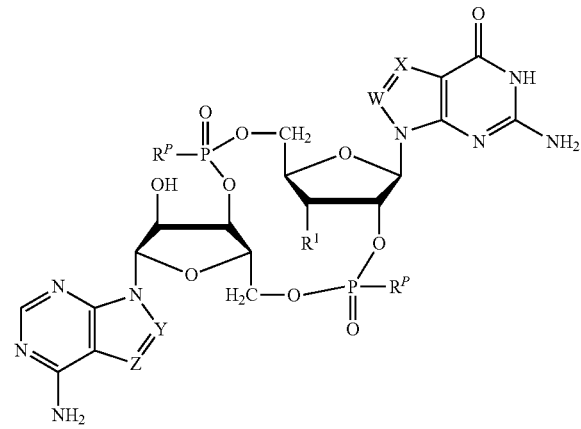

Formula IIk wherein

W, X, Y, and Z are independently CH or N;

R$^1$ is C$_{2-4}$alkyl substituted with an amino or C$_{1-6}$alkylamino group;

R$^P$ is, independently for each occurrence, hydroxyl, thiol, C$_{1-6}$alkyl, —BH$_3$, or —NR'R", wherein R' and R" are, independently for each occurrence, hydrogen or C$_{1-6}$alkyl optionally substituted with one or more groups selected from halogen, thiol, hydroxyl, carboxyl, C$_{1-6}$alkoxy, C$_{1-6}$hydroxyalkoxy, —OC(O)C$_{1-6}$alkyl, —N(H)C(O)C$_{1-6}$alkyl, -N(C$_{1-3}$alkyl)C(O)C$_{1-6}$alkyl, amino, C$_{1-6}$alkylamino, di(C$_{1-6}$alkyl)amino, oxo, and azido; or R' and R" on the same nitrogen together form a C$_{3-5}$heterocyclic ring;

or a pharmaceutically acceptable salt thereof;

"Ab" represents an antibody or binding fragment thereof which binds a target antigen;

"L" represents, independently for each occurrence, a linker linking one or more occurrences of D to Ab;

"n" represents the number of occurrences of D linked to Ab via the linker (L);

and wherein the CDN (D) is covalently bound to linker (L) at the amino, or C$_{1-6}$alkylamino group at the R$^1$ position of the CDN.

2. The ADC of claim 1, wherein D is a CDN having the structure of Formula IIm:

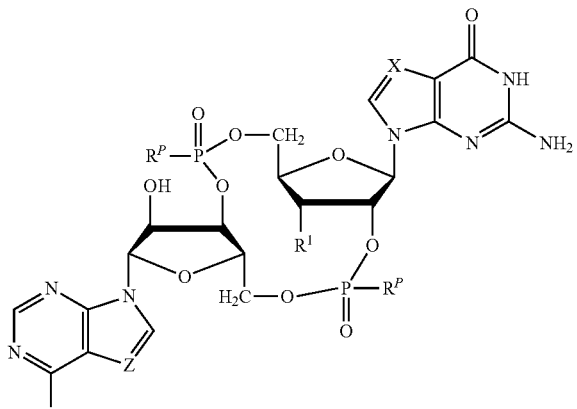

Formula IIm wherein

R$^1$ is ethyl substituted with an amino or C$_{1-6}$alkylamino group; and

R$^P$, independently for each occurrence, is hydroxyl or thiol;

or a pharmaceutically acceptable salt thereof.

3. The ADC of claim 2, wherein the ADC is derived from a structure of Formula IIn:

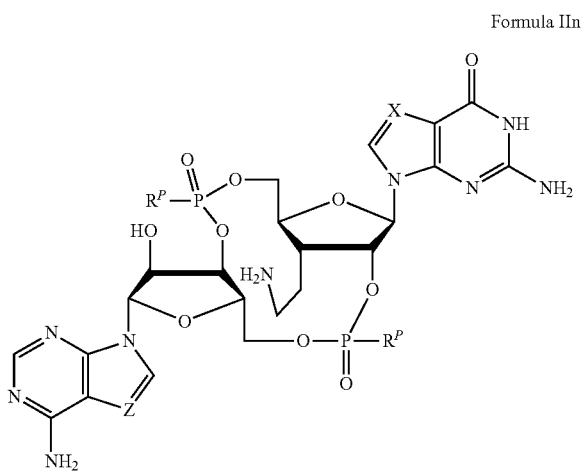

Formula IIn or a pharmaceutically acceptable salt thereof.

4. The ADC of claim 1, wherein the ADC has the structure of Formula III:

Formula III

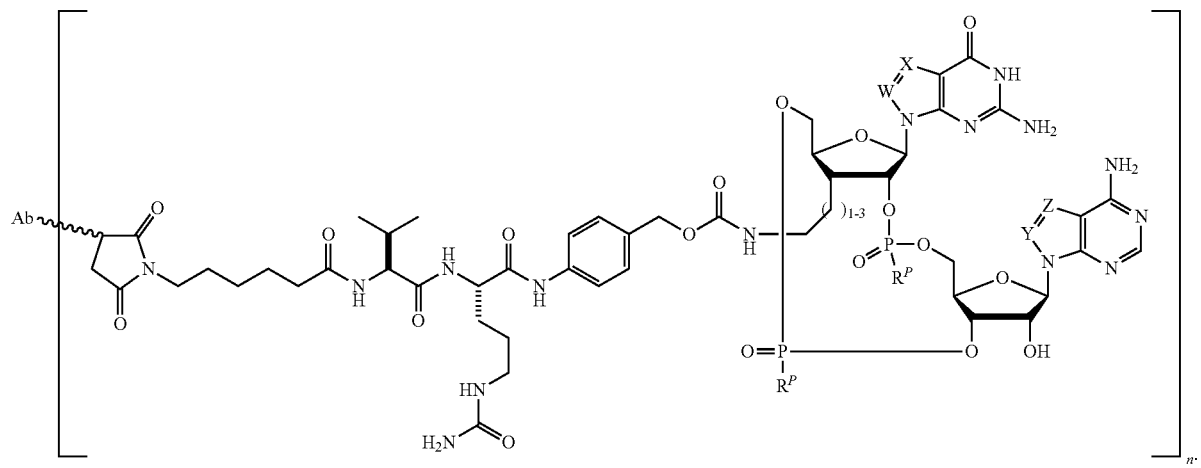

5. The ADC of claim 1, wherein $R^P$, independently for each occurrence, is hydroxyl or thiol.

6. The ADC of claim 1, wherein the ADC is derived from a CDN with the following structure:

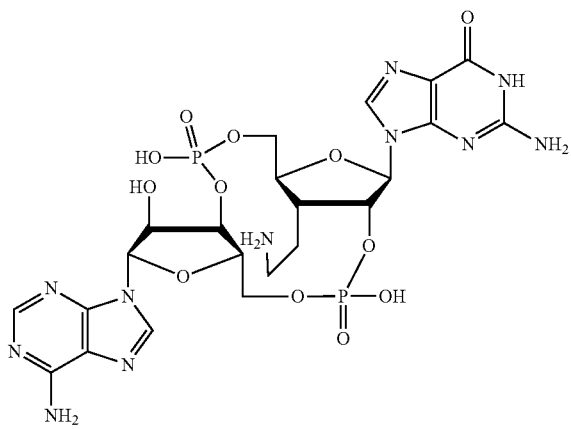

or a pharmaceutically acceptable salt thereof.

7. The ADC of claim 1, wherein L comprises a cleavable linker that is an acid-cleavable linker.

8. The ADC of claim 1, wherein L comprises a cleavable linker that is a reducible linker.

9. The ADC of claim 8, wherein the reducible linker is a disulfide linker.

10. The ADC of claim 1, wherein L comprises a cleavable linker that is an enzyme-cleavable linker.

11. The ADC of claim 10, wherein the enzyme-cleavable linker is selected from a polypeptide, tetrapeptide, dipeptide, and a β-glucuronide linker.

12. The ADC of claim 10, wherein the enzyme cleavable linker is cleavable by a lysosomal enzyme that is a cathepsin.

13. The ADC of claim 1, wherein L is coupled to Ab via a maleimide group, an activated disulfide, an active ester, a haloformate, an acid halide, an alkyl halide, or a benzyl halide.

14. The ADC of claim 1, having a covalent linkage formed between L and Ab with a thiol group or primary amino group on Ab.

15. The ADC of claim 1, wherein the ADC has the following structure:

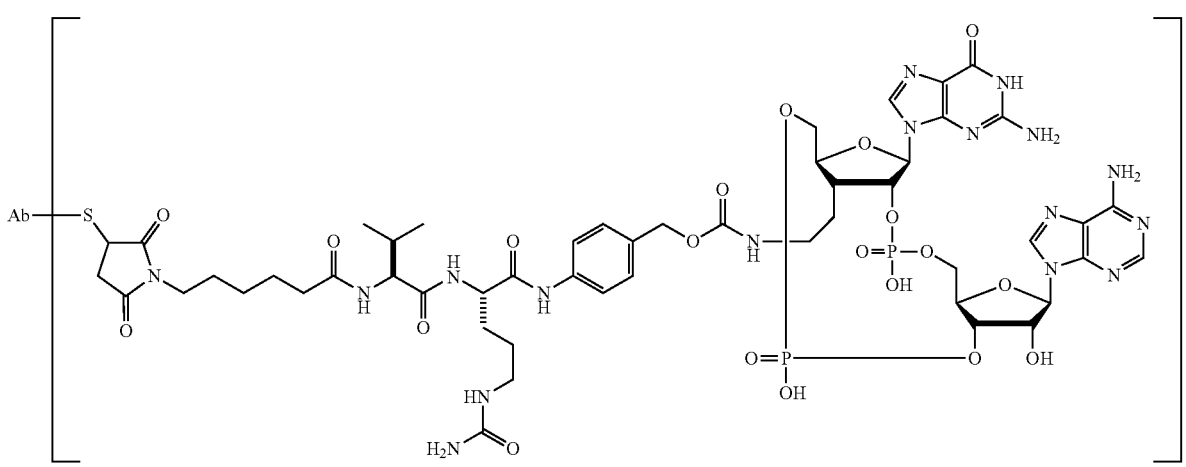

16. The ADC of claim 1, wherein n is 1, 2, 3, 4, 5, 6, 7, or 8.

17. The ADC of claim 1, wherein Ab is an antibody that binds to PD-L1, to an antigen that is a Growth Factor Receptor (GFR), to CD47, to an antigen preferentially expressed or overexpressed in cancer cells, or to an antigen derived from a microbe that infects human cells.

18. A pharmaceutical composition comprising the ADC of claim 1 and a pharmaceutically acceptable carrier.

19. A compound, wherein the compound is of Formula IIk:

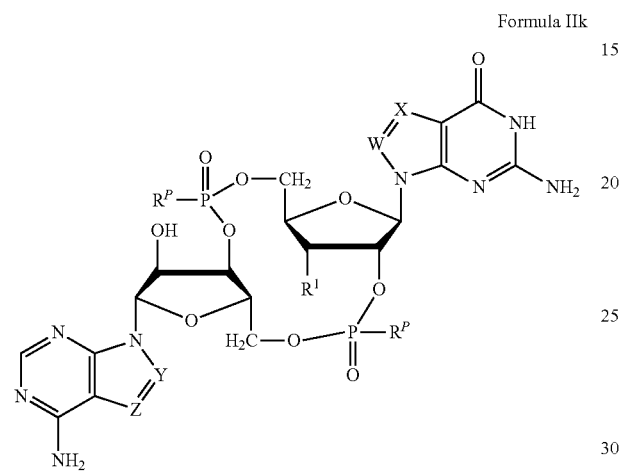

Formula IIk wherein
W, X, Y, and Z are independently CH or N;
$R^1$ is ethyl substituted with an amino or $C_{1-6}$alkylamino group;
$R^P$ is, independently for each occurrence, hydroxyl, thiol, $C_{1-6}$alkyl, —$BH_3$, or —NR'R", wherein R' and R" are, independently for each occurrence, hydrogen or $C_{1-6}$alkyl optionally substituted with one or more groups selected from halogen, thiol, hydroxyl, carboxyl, $CC_{1-6}$alkyl, $C_{1-6}$hydroxyalkoxy, —OC(O)$C_{1-6}$alkyl, —N(H)C(O)$C_{1-6}$alkyl, -N(Ci$_{1-3}$alkyl)C(O)$C_{1-6}$alkyl, amino, $C_{1-6}$alkylamino, di($C_{1-6}$alkyl)amino, oxo, and azido; or R' and R" on the same nitrogen together form a $C_{3-5}$ heterocyclic ring;
or a pharmaceutically acceptable salt thereof.

20. The compound of claim 19, wherein $R^P$, independently for each occurrence, is hydroxyl or thiol.

21. The compound of claim 19, wherein Y and W are both CH.

22. The compound of claim 19, wherein X and Z are both N.

23. The compound of claim 19, wherein $R^1$ is ethyl substituted with an amino group.

24. The compound of claim 19, wherein $R^1$ is ethyl substituted with a $C_{1-6}$ alkylamino group.

25. The compound of claim 19, wherein both occurrences of $R^P$ are hydroxyl.

26. The compound of claim 19, wherein the compound is

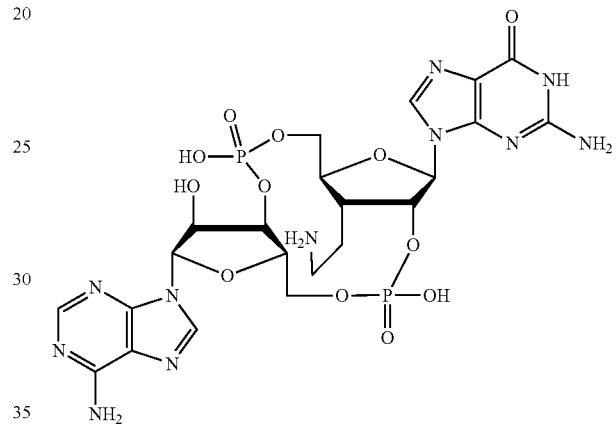

or a pharmaceutically acceptable salt thereof.

27. The ADC of claim 5, wherein both occurrences of $R^P$ are hydroxyl.

28. A pharmaceutical composition comprising the ADC of claim 6 and a pharmaceutically acceptable carrier.

* * * * *

UNITED STATES PATENT AND TRADEMARK OFFICE
CERTIFICATE OF CORRECTION

PATENT NO. : 11,033,635 B2
APPLICATION NO. : 16/933845
DATED : June 15, 2021
INVENTOR(S) : Zhijian Chen et al.

Page 1 of 1

It is certified that error appears in the above-identified patent and that said Letters Patent is hereby corrected as shown below:

In the Claims

At Column 139, Claim number 1, Line number 45, please change:
"thiol, $C_{1-6}$alkyl, -$BH_3$, or -NR'R", wherein R' and"

To:
--thiol, $C_{1-6}$alkyl, -$BH_3^-$, or -NR'R", wherein R' and--

At Column 139, Claim number 1, Line number 64, please change:
"(L) at the amino, or $C_{1-6}$alkylamino group at the $R^1$"

To:
--(L) at the amino or $C_{1-6}$alkylamino group at the $R^1$--

At Column 143, Claim number 19, Line number 38, please change:
"thiol, $C_{1-6}$alkyl, -$BH_3$, or -NR'R", wherein R' and"

To:
--thiol, $C_{1-6}$alkyl, -$BH_3^-$, or -NR'R", wherein R' and--

Signed and Sealed this
Seventeenth Day of August, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 21

<210> SEQ ID NO 1
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 3
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

```
Ile Ser Lys Pro Lys Gly Ser Val Arg Ala Pro Gln Val Tyr Val Leu
            340                 345                 350

Pro Pro Pro Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
            435                 440                 445

<210> SEQ ID NO 4
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Phe Leu Gly Gly Pro Cys
225                 230                 235                 240

Val Phe Ile Phe Pro Pro Lys Ile Lys Asp Val Leu Met Ile Ser Leu
                245                 250                 255
```

```
Ser Pro Ile Val Thr Cys Val Val Asp Val Ser Glu Asp Pro
            260             265             270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

<210> SEQ ID NO 5
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175
```

```
Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

```
<210> SEQ ID NO 6
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 6

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115
```

```
<210> SEQ ID NO 7
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 7

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105
```

```
<210> SEQ ID NO 8
<211> LENGTH: 449
<212> TYPE: PRT
<213> ORGANISM: Artificial Sequence
```

<220> FEATURE:
<223> OTHER INFORMATION: Synthetic polypeptide

<400> SEQUENCE: 8

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Phe Leu Gly Gly Pro
225                 230                 235                 240

Cys Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400
```

Asp Ser Asp Gly Ser Tyr Phe Met Tyr Ser Lys Leu Arg Val Glu Lys
            405                 410                 415

Lys Asn Trp Val Glu Arg Asn Ser Tyr Ser Cys Ser Val Val His Glu
        420                 425                 430

Gly Leu His Asn His His Thr Thr Lys Ser Phe Ser Arg Thr Pro Gly
        435                 440                 445

Lys

<210> SEQ ID NO 9
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 9

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 10
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 10

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
            115

<210> SEQ ID NO 11
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 11

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 12
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 12

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly

```
            100                 105                 110
Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 13
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 13

Asp Ile Leu Leu Thr Gln Ser Pro Val Ile Leu Ser Val Ser Pro Gly
1               5                   10                  15
```

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 14

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Cys
        115

<210> SEQ ID NO 15
<211> LENGTH: 107
<212> TYPE: PRT
<213> ORGANISM: Artificial Sequence

```
<220> FEATURE:
<223> OTHER INFORMATION: Synthetic polypeptide

<400> SEQUENCE: 15

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 16
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 16

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Cys Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

```
            225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 17
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 17

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Cys Thr Lys Ser
        195                 200                 205

Phe Asn Arg Gly Glu Cys
    210

<210> SEQ ID NO 18
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 19
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys

```
                100                 105

<210> SEQ ID NO 20
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 21
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```